US007291723B2

(12) United States Patent
Stapleton et al.

(10) Patent No.: US 7,291,723 B2
(45) Date of Patent: Nov. 6, 2007

(54) GB VIRUS C AND METHODS OF TREATING VIRAL INFECTIONS

(75) Inventors: Jack T. Stapleton, Iowa City, IA (US); Jinhua Xiang, Iowa City, IA (US); Sarah George, St. Louis, MO (US)

(73) Assignee: University of Iowa Research Foundation, Iowa City, IA (US)

( * ) Notice: Subject to any disclaimer, the term of this patent is extended or adjusted under 35 U.S.C. 154(b) by 492 days.

(21) Appl. No.: 10/693,258

(22) Filed: Oct. 24, 2003

(65) Prior Publication Data

US 2005/0119472 A1  Jun. 2, 2005

Related U.S. Application Data

(60) Provisional application No. 60/421,408, filed on Oct. 24, 2002.

(51) Int. Cl.
*C07H 21/04* (2006.01)

(52) U.S. Cl. .............................. 536/23.72; 424/189.1; 424/218.1; 435/69.1; 435/320.1; 536/23.1

(58) Field of Classification Search ...................... None
See application file for complete search history.

(56) References Cited

U.S. PATENT DOCUMENTS

| | | | |
|---|---|---|---|
| 5,620,896 A | 4/1997 | Herrmann et al. | 435/320.1 |
| 5,766,840 A | 6/1998 | Kim et al. | 435/5 |
| 5,766,916 A | 6/1998 | Belyaev et al. | 435/219 |
| 5,824,507 A | 10/1998 | Kim et al. | 435/69.3 |
| 5,849,532 A | 12/1998 | Kim et al. | 435/69.3 |
| 5,856,134 A | 1/1999 | Kim et al. | 435/69.3 |
| 5,859,230 A | 1/1999 | Kim et al. | 536/24.33 |
| 5,874,563 A | 2/1999 | Kim et al. | 536/23.72 |
| 5,958,895 A | 9/1999 | Pachuk et al. | 514/44 |
| 5,981,172 A | 11/1999 | Simons et al. | 435/5 |
| 6,004,799 A | 12/1999 | Luciw et al. | 435/236 |
| 6,156,495 A | 12/2000 | Pilot-Matias et al. | 435/5 |
| 6,870,043 B2 * | 3/2005 | Xiang et al. | 536/23.72 |
| 2003/0170870 A1 | 9/2003 | Xiang et al. | 435/235.1 |

OTHER PUBLICATIONS

Xiang, J., et al., "Effect of Coinfection with GB Virus C on Survival Among Patients with HIV Infection", *N. Engl. J. Med.*, vol. 345, No. 10 (Sep. 6, 2001), 707-714.
Xiang, J., et al., "Full-Length GB Virus C (Hepatitis G Virus) RNA Transcripts Are Infections in Primary CD4-Positive T Cells", *Journal of Virology*, vol. 74, No. 19 (Oct. 2000) 9125-9133.
Akiyoshi, et al., "Intraspousal Transmission of GB Virus C/Hepatitis G Virus in an Hepatitis C Virus Hyperendemic Area in Japan," *Am. J. Gastroenterol.*, 94(6):1627-1631, 1999.
Asada, et al., "Human Herpesvirus 6 Infects Dendritic Cells and Suppresses Human Immunodeficiency Virus Type 1 Replication in Coinfected Cultures," *J. Virol.* 73(5):4019-4028, 1999.
Beard, et al., "An Infectious Molecular Clone of a Japanese Genotype 1b Hepatitis C Virus," *Hepatology*, 30(1):316-324, 1999.

Birkenmeyer, et al., "Isolation of a GB Virus-Related Genome From a Chimpanzee," *J. Med. Virol.*, 56:44-51, 1998.
Bukh, et al., "Experimental Infection of Chimpanzees with Hepatitis G Virus and Genetic Analysis of the Virus," *J. Inf. Dis.*, 177:855-862, 1998.
Bukh, et al., "Toward a Surrogate Model for Hepatitis C Virus: An Infectious Molecular Clone of the GB Virus-B Hepatitis Agent," *Virol.*, 262:470-478, 1999.
Cohen, et al., "Hepatitis A Virus cDNA and Its RNA Transcripts Are Infectious in Cell Culture," *J. Virol.*, 61(10):3035-3039, 1987.
Dawson, et al., "Prevalence Studies of GB Virus-C Infection Using Reverse Transcriptase-Polymerase Chain Reaction," *J. Med. Virol.*, 50:97-103, 1996.
de Martino, et al., "Hepatitis G Virus Infection in Human Immunodeficiency Virus Type 1-Infected Mothers and Their Children," *J. Infect. Dis.*, 178:862-865, 1998.
Deacon, et al., "Genomic Structures of an Attenuated Quasi Species of HIV-1 from a Blood Transfusion Donor and Recipients," *Science*, 270:988-991, 1995.
Dickens, et al., "GB Virus C, Hepatitis G Virus, or Human Orphan Flavivirus?" *Hepatology*, 25(5):1285-1286, 1997.
Easterbrook, "Long-term Non-Progression in HIV Infection: Definitions and Epidemiological Issues," *J. Infect,.* 38:71-73, 1999.
Elvander, et al., "An Experimental Study of a Concurrent Primary Infection with Bovine Respiratory Syncytial Virus (BRSV) and Bovine Viral Diarrhoea Virus (BVDV) in Calves," *Acta. Vet.Scand,.* 39:251-264, 1998.
Emerson, et al., "cDNA Clone of Hepatitis A Virus Encoding a Virulent Virus: Induction of Viral Hepatitis by Direct Nucleic Acid Transfection of Marmosets," *J. Virol.*, 66(11):6649-6654, 1992.
Feucht, et al., "Distribution of Hepatitis G Viremia and Antibody Response to Recombinant Proteins With Special Regard to Risk Factors in 709 Patients," *Hepatology*, 26(2):491-494, 1997.
Fogeda, et al.,. In Vitro Infection of Human Peripheral Blood Mononuclear Cells by GB Virus C/Hepatitis G Virus, *J. Virol.* 73(5):4052-4061, 1999.
Gale, Jr,. et al., "Control of PKR Protein Kinase by Hepatitis C Virus Nonstructural 5A Protein: Molecular Mechanisms of Kinase Regulation," *Mol. Cell.Biol.* 18(9):5208-5218, 1998.
Gutierrez, et al., "Seroprevalence of GB Virus C and Persistence of RNA and Antibody," *J. Med. Virol.*, 53:167-173, 1997.
Hong, et al., "Generation of Transmissible Hepatitis C Virions from a Molecular Clone in Chimpanzees," *Virology*, 256:36-44, 1999.
Kolykhalov, et al., "Transmission of Hepatitis C by Intrahepatic Inoculation with Transcribed RNA," *Science*, 277:570-574, 1997.
Laskus, et al., "Detection of Hepatitis G Virus Replication Sites by Using Highly Strand-Specific Tth-Based Reverse Transcriptase PCR," *J. Virol.*, 72(4):3072-3075, 1998.
Leary, et al., "Sequence and Genomic Organization of GBV-C: A Novel Member of the Flaviviridae Associated With Human Non-A-E Hepatitis," *J. Med. Virol.*, 48:60-67, 1996.

(Continued)

*Primary Examiner*—Bruce R. Campell
*Assistant Examiner*—Michelle Horning
(74) *Attorney, Agent, or Firm*—Fullbright & Jaworski, LLP

(57) ABSTRACT

The present application provides GB virus C sequences (GBV-C or hepatitis G virus) and methods of using the sequences.

14 Claims, 44 Drawing Sheets

OTHER PUBLICATIONS

Lefrère, et al., "Carriage of GB Virus C/Hepatitis G Virus RNA Is Associated with a Slower Immunologic, Virologic, and Clinical Progression of Human Immunodeficiency Virus Disease in Coinfected Persons," *J.Infect.Dis.*, 179:783-789, 1999.

Melvin, et al., "Biophysical characterization of GB virus C from human plasma," *J. Virol. Methods*, 71:147-157, 1998.

Nerurkar, et al., "High Prevalence of GB Virus C/Hepatitis G Virus Infection Among Homosexual Men Infected With Human Immunodeficiency Virus Type 1: Evidence for Sexual Transmission," *J. Med. Virol.*, 56:123-127, 1998.

Okamoto, et al., "The entire nucleotide sequences of two GB virus C/hepatitis G virus isolates of distinct genotypes from Japan," *J. Gen. Virol.*, 78:737-745. 1997.

Pang et al., "Development of dengue virus replicons expressing HIV-1 gp120 and other heterologous genes: a potential future tool for dual vaccination against dengue virus and HIV," BMC Microbiology, 1(28):1-9, 2001.

Pessoa, et al., "Quantitation of Hepatitis G and C Viruses in the Liver: Evidence That Hepatitis G Virus Is Not Hepatotropic," *Hepatol.*, 27(3):877-880, 1998.

Pinto, et al., "Inhibition of Human Immunodeficiency Virus Type 1 Replication prior to Reverse Transcription by Influenza Virus Stimulation," *J. Virol.* 74(10):4505-4511, 2000.

Rowland-Jones, "Long-term Non-progression in HIV Infection: Clinico pathological Issues," *J.Infect.*, 38:67-70, 1999.

Sabin, et al., "Effect of Coinfection With Hepatitis G Virus on HIV Disease Progression in Hemophilic Men," *J.Acquir.Immune Defic. Syndr.*, 19:546-547, 1998.

Schmidt, et al., "Direct Detection of Hepatitis C Virus (HCV) RNA From Whole Blood, and Comparison With HCV RNA in Plasma and Peripheral Blood Monoclear Cells," *J. Med. Virol.*, 47:153-160, 1995.

Seipp, et al., "Hepatotropism of GB virus C (GBV-C): GBV-C replication in human hepatocytes and cells of human hepatoma cell lines," *J. Hepatol.*, 30:570-579, 1999.

Shimizu, "Replication of GB Virus C (Hepatitis G Virus) in Interferon-Resistant Daudi Cells," *J. Virol.*, 73(10):8411-8414, 1999.

Simons, et al., "Identification of two flavivirus-like genomes in the GB hepatitis agent," *Proc.Natl.Acad.Sci.*USA 92:34013405, 1995.

Simons, et al., "Translation Initiation in GB Viruses A and C: Evidence for Internal Ribosome Entry and Implications for Genome Organization," *J. Virol.*, 70(9):6126-6135, 1996.

Stapleton, et al., "Prospective Comparison of Whole-Blood- and Plasma-Based Hepatitis C Virus RNA Detection Systems: Improved Detection Using Whole Blood as the Source of Viral RNA," *J. Clin. Microbiol.*, 37(3):484-489, 1999.

Tacke, et al., "Humoral Immune Response to the E2 Protein of Hepatitis G Virus Is Associated With Long-Term Recovery From Infection and Reveals a High Frequency of Hepatitis G Virus Exposure Among Healthy Blood Donors," *Hepatol.*, 26(6):1626-1633, 1997.

Tanaka, et al., "Acute hepatitis caused by sexual or household transmission of GBV-C," *J. Hepatol.*, 27:1110-1112, 1997.

Taylor, et al., "Inhibition of the Interferon-Inducible Protein Kinase PKR by HCV E2 Protein," *Science*, 285:107-110, 1999.

Thomas, et al., "Association of Antibody to GB Virus C (Hepatitis G Virus) with Viral Clearance and Protection from Reinfection," *J.Infect.Dis.*, 177:539-542, 1998.

Toyoda, et al., "Comparison of Characteristics Between Patients With GB Virus C/Hepatitis G Virus (GBV-C/HGV) RNA and Those With GBV-C/HGV E2-Antibody in Patients With Hemophilia," *J.Med.Virol.*, 60:34-38, 2000.

Wu, et al., "Prevalence and Risk Factor Analysis of GBV-C/HGV Infection in Prostitutes," *J. Med. Virol.*, 52:83-85, 1997.

Wünschmann & Stapleton, "Fluorescence-Based Quantitative Methods for Detecting Human Immunodeficiency Virus Type 1-Induced Syncytia," *J.Clin.Microbiol.*, 38(8):3055-3060, 2000.

Wünschmann, et al., "Characterization of Hepatitis C Virus (HCV) and HCV E2 Interactions with CD81 and the Low-Density Lipoprotein Receptor," *J. Virol.*, 74(21):10055-10062, 2000.

Xiang, et al., "Characterization of Hepatitis G Virus (GB-C Virus) Particles: Evidence for a Nucleocapsid and Expression of Sequences Upstream of the E1 Protein," *J. Virol.*, 72(4):2738-2744, 1998.

Xiang, et al., "Full-Length GB Virus C (Hepatitis G Virus) RNA Transcripts Are Infectious in Primary CD4-Positive T Cells," *J. Virol.*, 74(19):9125-9133, 2000.

Xiang, et al., "Visualization and characterization of GB virus-C particles: evidence for a nucleocapsid," *J. Viral Hepat.*, 6(S1):16-22, 1999.

Yanagi, et al., "Transcripts from a single full-length cDNA clone of hepatits C virus are infectious when directly transfected into the liver of a chimpanzee," *Proc. Nat'l, Acad. Sci.*, 94:8738-8743, 1997.

Yanagi, et al., "Transcripts of a Chimeric cDNA Clone of Hepatitis C Virus Genotype 1b Are Infectious in Vivo," *Virology*, 244:161-172, 1998.

Gene Banc Accession #AF031827, Oct. 29, 1997.

Gene Banc Accession #AF031828, Oct. 29, 1997.

Gene Banc Accession #AF031829, Oct. 29, 1997.

Gene Banc Accession #AY196904, Dec. 13, 2002.

Gene Banc Accession #U94695, Mar. 19, 1997.

Liu et al.. "A competitive reverse transcription-polymerase chain reaction assay for quantitation of GB virus C/hepatitis G virus RNA that circumvents heteroduplex artifact" *Journal of Virological Methods* 79:149-159, 1999.

Venter et al. "Hepatitis G virus slows HIV," *Trends in Microbiology* 9:470, 2001.

* cited by examiner

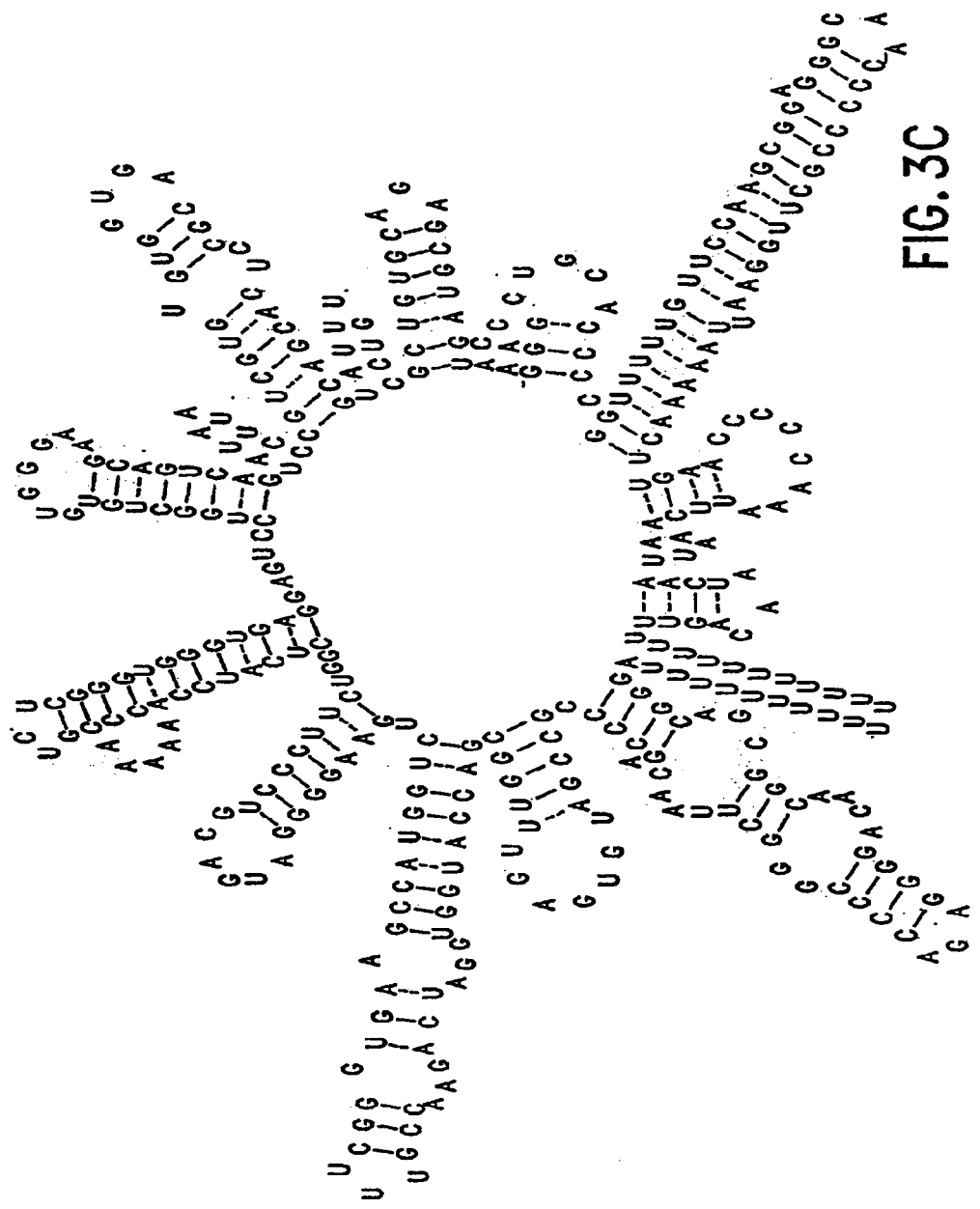

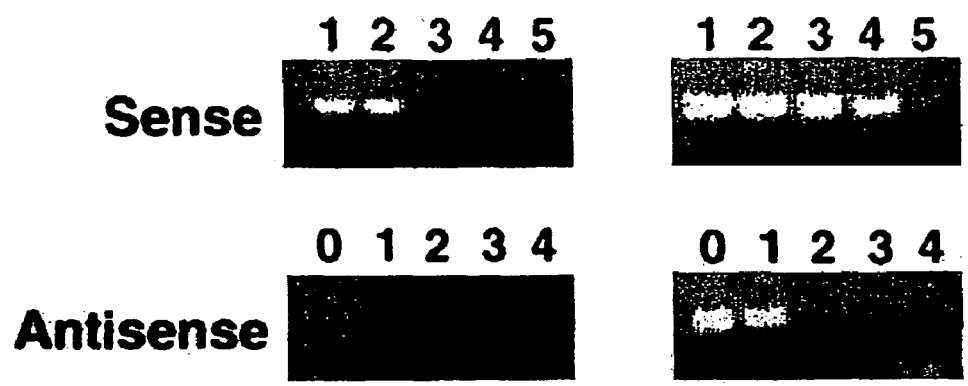
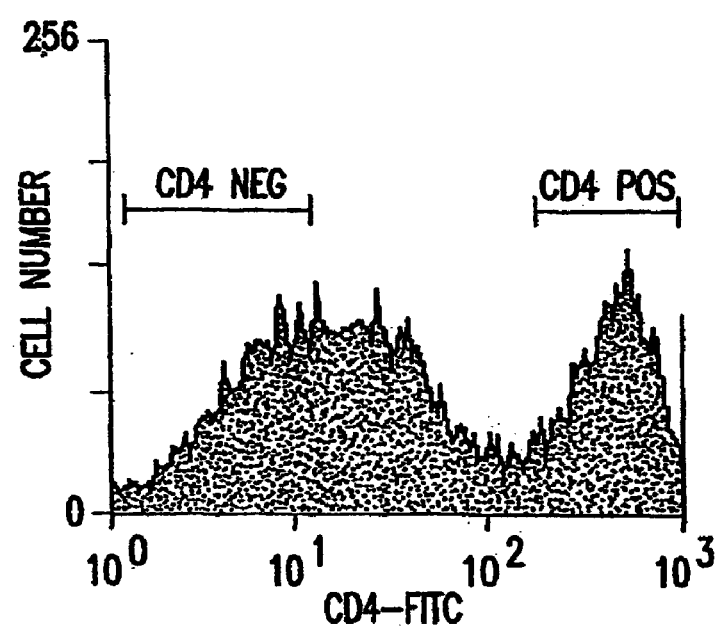
FIG.5

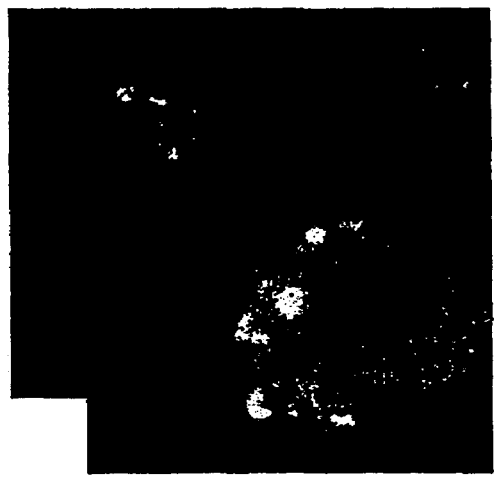
FIG.6A          FIG.6B
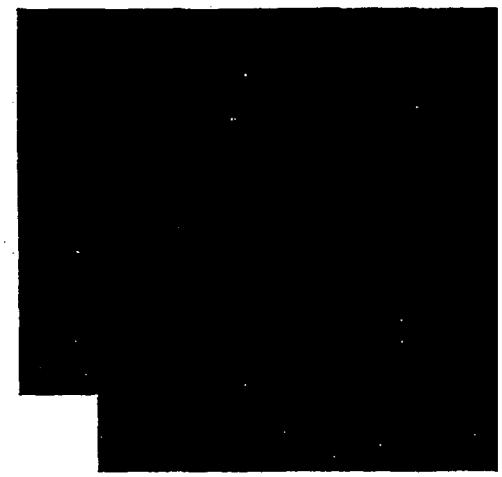
FIG.6C          FIG.6D

FIG. 13

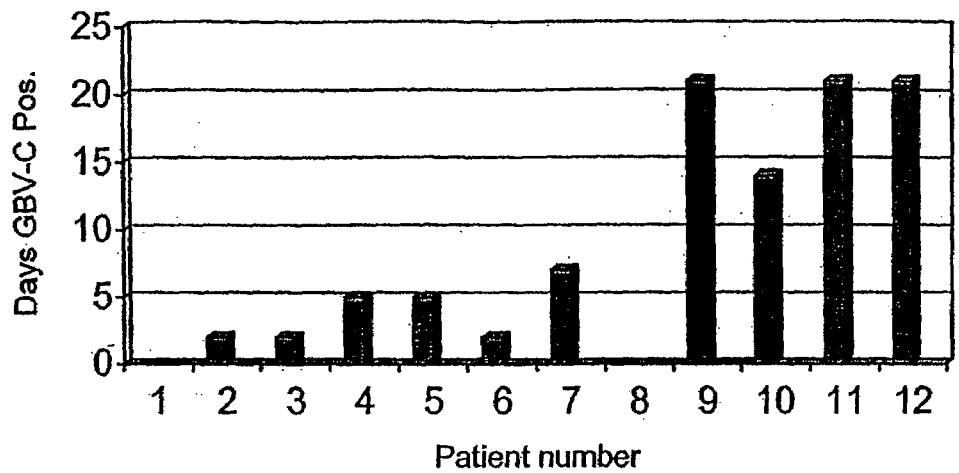
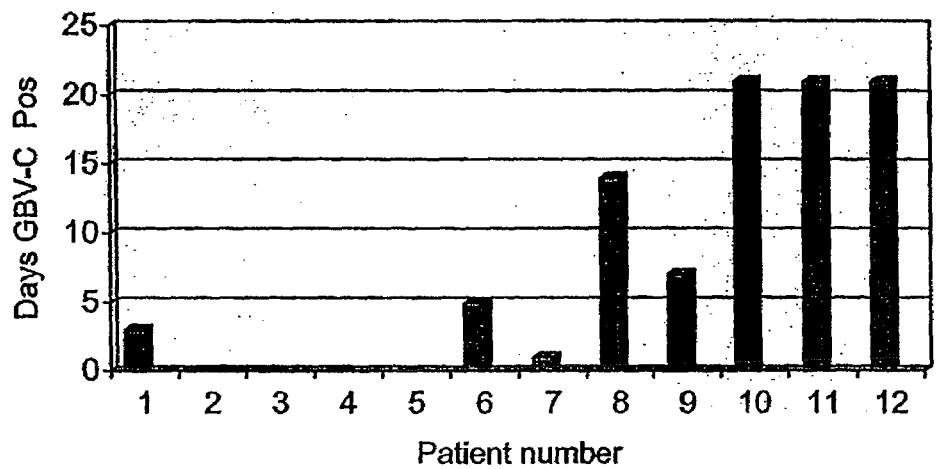
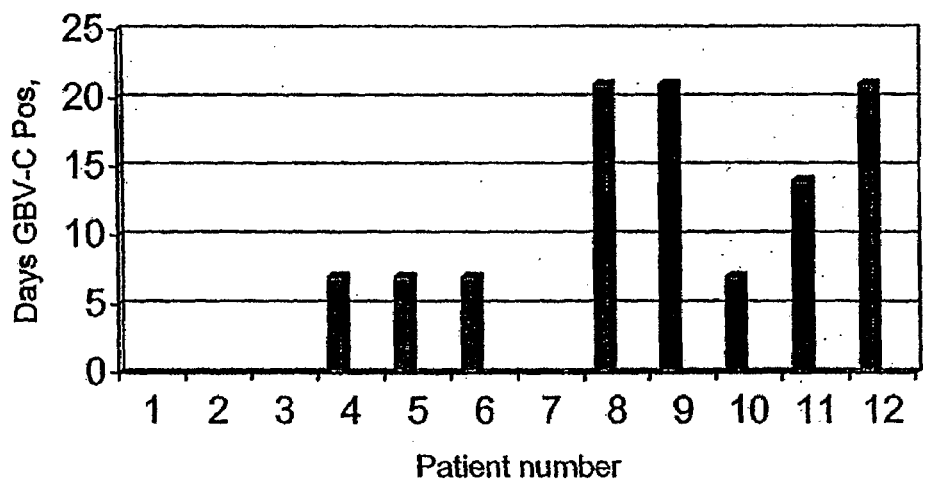
FIG. 16A-C

GBV-C phylogenetic relationships by protein coding region.

A 0.05

- 765_e1
- u44402_e1
- 121950_e1
- d90600_e1
- hgu63175_e1
- u36380_e1
- d87255_e1

B 0.05

- 765_e2
- u44402_e2
- d87255_e2_aa
- 121950_e2
- d90600_e2
- hgu63715_e2_seq
- u36380_e2

C 0.05

- 765_ns2
- 121950_ns2
- hgu63715_ns2
- u36380_ns2
- d90600_ns2
- u44402_ns2
- d87255_ns2

D 0.05

- 765_ns3
- d87255_ns3
- 121950_ns3
- u44402_ns3
- hgu63715_ns3
- u36380_ns3
- d90600_ns3

FIG. 23A-D

GBV-C phylogenetic relationships by protein coding region.

E 0.05
⊢⎯⎯⊣

- 765_ns4a_
- d87255_ns4a_
- u44402_ns4a_
- 121950_ns4a
- hgu63715_ns4a_
- u36380_ns4a_
- d90600_ns4a_

F 0.05
⊢⎯⎯⊣

- 765_ns5a
- d87255_ns5a_
- 121950_ns5a_
- u44402_ns5a_
- hgu63715_ns5a_
- d90600_ns5a_

G 0.05
⊢⎯⎯⊣

- 765_ns5b_
- u44402_ns5b_
- 121950_ns5b_
- d90600_ns5b_
- d87255_ns5b_
- hgu63715_ns5b_

FIG. 23E-G

```
121950  VALVNREPKVDEVQVGYVWDLWEWIMRQVRMVMARLRALCPVVSLPLWHCGEGWSGE
765     ----------------------------------------------------------

121950  WLLDGHVESRCLCGCVITGDVLNGQLKDPVYSTKLCRHYWMGTVPVNMLGYGETSPLLA
765     ----------------------------------------------------------

121950  SDTPKVVPFGTSGWAEVVVTPTHVVIRRTSAYKLLRQQILSAAVAEPYYVDGIPVSWDADA
765     ----------------------------------------------------------

121950  RAPAMVYGPGQSVTIDGERYTLPHQLRLRNVAPSEVSSEVSIDIGTETEDSELTEADLPPA
765     ----------------------------------------------------------

121950  AAALQAIENAARILEPHIDVIMEDCSTPSLCGSSREMPVWGEDIPRTPSPALISVTESSPDE
765     ----------------------------------------------------------

121950  KTPSVSSSQEDTPSSDSFEVIQESETAEGEESVFNVALSVLKALFPQSDATRKLTVKMSCC
765     ----------------------------------------------------------

121950  VEKSVTRFFSLGLTVADVASLCEMEIQNHTAYCDKVRTPLELQVGCLVGNELT
765     ----------------------------------------------------------
```

```
AA  2457   AF121950   FQYTPNQRIREMLKL
           AY196904   -------------VK-----

AA  2791   AF121950   GIPGAFPLSPPYMGVV
           AY196904   ----G-SP---F-----
```

FIG. 34B

```
121950  VALVNREPKVDEVQVGYVWDLWEWIMRQVRMVMARLRALCPVVSLPLWHCGEGWSGE
196904  ---------------------------------------------------------

121950  WLLDGHVESRCLCGCVITGDVLNGQLKDPVYSTKLCRHYWMGTVPVNMLGYGETSPLLA
196904  ---------------------------E-------------------------------

121950  SDTPKVVPFGTSGWAEVVVTPTHVVIRRTSAYKLLRQQILSAAVAEPYYVDGIPVSWDADA
196904  -------------------------------------------------------------

|Region homologous to the HCV ISDR|
121950  RAPAMVYGPGQSVTIDGERYTLPHQLRLRNVAPSEVSSEVSIDIGTETEDSELTEADLPPA
196904  ----------------------------------MT-L-----------------------

121950  AAALQAIENAARILEPHIDVIMEDCSTPSLCGSSREMPVWGEDIPRTPSPALISVTESSPDE
196904  ---------------L------------------------G------------------S--

121950  KTPSVSSSQEDTPSSDSFEVIQESETAEGEESVFNVALSVLKALFPQSDATRKLTVKMSCC
196904  -------------------------------------------------------------

121950  VEKSVTRFFSLGLTVADVASLCEMEIQNHTAYCDKVRTPLELQVGCLVGNELT
196904  A----------------------------------------------------
```

FIG. 34C

SEQUENCE LISTING

<160> NUMBER OF SEQ ID NOS: 44

<210> SEQ ID NO 1
<211> LENGTH: 9395
<212> TYPE: DNA
<213> ORGANISM: Hepatitis G virus

<400> SEQUENCE: 1

```
tgacgtgggg gggttgatcc ccccccccg gcactgggtg caagccccat aaaccgacgc      60
ctatctaagt agacgcaatg actcggcgcc gactcggcga ccggccaaaa ggtggtggat     120
gggtggtgac agggttggta ggtcgtaaat cccggtcatc ctggtagcca ctataggtgg    180
gtcttaagag aaggtcaaga ctcctcttgt gcctgcggcg agaccgcgca cggtccacag    240
gtgctggccc taccggtgtg aataaggggcc cgacgtcagg ctcgtcgtta aaccgagccc   300
gtcacccacc tgggcaaacg acgcccacgt acggtccacg tcgcccttca atgtctctct    360
tgaccaatag gtttatccgg cgagttgaca aggaccagtg ggggccgggg gttatgggga    420
aggaccccaa accctgccct tcccggtggg ccgggaaatg catgggccca cccagctccg    480
cggcggcctg cagccggggt agcccaagaa tccttcgggt gagggcgggt ggcatttctc    540
ttttctatac catcatggca gtccttctgc tccttctcgt ggttgaggcc ggggccattc    600
tggccccggc cacccacgct tgtcgagcga atgggcaata tttcctcaca aattgctgtg    660
ccccggaaga catcgggttc tgcctggaag gcggatgcct ggtggccctg gggtgcacgg    720
tttgcaccga ccgttgctgg ccactgtatc aggcgggttt ggctgtgcgg cctggcaagt    780
ccgcggccca gctcgttggg gaactgggga gcctgtacgg gcccttgtcg gtctcggctt    840
acgtagccgg gatcctgggt ctgggcgagg tttactccgg ggtcctgaca gttggtgttg    900
cgttgaggcg ccgggtctac ctgatgccca acctgaagtg tgcagtagaa tgtgacgtta    960
agtggggaag tgagttttgg agatggactg agcagttggc ctccaattac tggattttgg   1020 aataccttg gaaagtccca tttgaattt ggagaggagt gatgagcctg acccctctgt     1080
tggtttgggt ggccgcattg cttttgctgg agcaacggat tgtcatggtt ttcctgctgg    1140
tgacgatggc ggggatgttg caaggcgccc ccgcctccgt ttggggtcc cgcccctttg    1200 actacgggtt gaagtggcag tcatgctcct gcagggctaa cgggtcgcgt attcccactg    1260
```

```
gggagagggt gtgggatcga gggaatgtca cgctcttgtg tgactgcccc aacggcccct    1320
gggtttgggt cccggccttt tgccaggcgg ttgggtgggg cgaccccatc acccattgga    1380
gccacggaca aaaccagtgg cccctatcat gcccccaata tgtctatggg tctgtgtccg    1440
taacgtgcgt gtggggttcc gtgtcttggt ttgcctcgac cggcggtcgt gattcgaaga    1500
tcgatgtgtg gagtttggtg ccggttggat ctgccagctg caccatagcc gctctagggt    1560
catcggatcg cgacacggtg gttgagctct ccgagtgggg agtcccgtgc gtaacgtgta    1620
ttctggaccg tcggcctgct tcatgtggca cctgtgtgcg ggactgctgg cccgaaaccg    1680
ggtcggttag attcccttc catcggtgcg gcacggggcc tcggctgaca aaggacttgg    1740
aagctgtgcc cttcgtcaac aggacaactc ccttcaccat aaggggcccc ctgggcaacc    1800
aggggagagg caacccggtg cggtcgcccc tgggttttgg gtcctacacc atgaccaaga    1860
tccgggattc cctgcatttg gtgaaatgtc ccacaccagc catagagcct ccgactggaa    1920
cgttcgggtt cttccccgga gtcccgccca ttaacaactg catgccgcta ggcacggaag    1980
tgtctgaggc attgggcgga gctgggctta cgggggggtt ctacgagcct ctggttcgca    2040
ggtgttcgga gctgatggga cgccgaaatc cggtttgccc gggtacgca tggctgtcct    2100 ctggtagacc tgacgggttc atacacgtcc aggggcacct gcaggaggtg gatgcgggca    2160
acttcatccc tcctccacgc tggttgctct tggattttgt atttgtcctg ctctatctga    2220
tgaagctggc tgaggcacgg ttggtcccgt tgatcttgct tctgctgtgg tggtgggtga    2280
accagttggc ggttctagga ctgccggctg tggacgctgc cgtggcgggt gaagttttg     2340 cgggccctgc cttgtcatgg tgtttgggcc ttcccactgt cagtatgata ctaggtctag    2400
caaacctggt gttgtacttt cggtggatgg gccctcagcg cctcatgttc ctcgtgtttgt   2460 ggaagctcgc tcggggagct ttcccgctgg cacttttgat ggggatttcg gcgacccgcg    2520
ggcgcacctc tgtgctcggg gccgagttct gcttcgatgt cacattcgag gtggacactt    2580
cggtgttggg ctgggtggtg ccagcgtgg tggcttgggc catagcgctc ctgagctcaa     2640
tgagcgcagg ggggtggaag cacaaggccg tgatctatag gacgtggtgt aaagggtacc    2700
aggctgtgcg ccagagggtg gtgcggagcc ccctcgggga ggggcgtcct accaagcttc    2760
tgacgttcgc ctggtgcttg gcctcataca tctggccgga tgctgtgatg atggtggtgg    2820
tggccttggt cctcctcttc ggcctgttcg acgcactgga ctgggccctg gaggagctcc    2880
tggtctcccg gccctcgtta cggcgactgg cacgggtggt tgagtgctgt gtgatggcgg    2940
gcgagaaggc caccaccatc cgactggtct ccaagatgtg cgcaagaggg gcctacctgt    3000
ttgaccacat gggctctttc tcgcgcgctg tcaaggagcg cttgttggaa tgggacgcgg    3060 cttttggagcc cttgtcattc actaggacgg actgtcgcat catcagagat gccgcgagga    3120
ccctgtcctg cggacagtgc gtcatgggtt tacccgtggt agcacggcgc ggtgatgagg    3180
ttctcatcgg cgtctttcag gatgtgaatc atttgcctcc cggtttgtc ccgactgcac      3240 cagttgtcat ccgtcggtgc ggaaagggct tcctgggggt cacgaaggca gccttgacag    3300
gtagggatcc tgacttacat ccagggaacg tcatggtgtt ggggacggct acgtcacgaa    3360
gcatgggcac atgtctgaat ggcctgctgt tcacaacttt ccatgggct tcatcccgaa     3420 ccatcgccac gcccgtgggg gcccttaatc ccaggtggtg gtcagccagt gatgacgtca    3480
cggtgtaccc gcttccagat ggggcaactt cgttgacgcc ctgcacttgc caggcggagt    3540
cctgttgggt tattagatcc gacgggcctt tgtgccatgg cttgagcaag ggggacaagg    3600
ttgagctgga tgtggccatg gaggtctctg acttccgtgg ttcgtctggt tcaccggtcc    3660
```

-continued

```
tttgcgacaa agggcacgca gtaagaatgc tcgtgtcagt gctccactct ggcggcaggg      3720
ttactgcggc gcgattcact aggccgtgga ctcaagtacc aacagatgcc aagactacca      3780
cagaaccccc tccggtgccg gcaaaaggag ttttcaagga ggccccgttg tttatgccta      3840
cgggggcggg aaagagcacc cgcgtaccgt tggagtacgg caacatgggc cacaaggtct      3900
tgatcttgaa cccgtcggta gctaccgtga gggccatggg cccatacatg gagcggctgg      3960
cggggaaaca ccccagtatt tactgtggcc atgacaccac tgctttcaca aggatcactg      4020
actcgcccct tacgtattcc acttacgaaa gttttttggc caaccctagg cagatgctga      4080
ggggtgtgtc ggtggtcatt tgtgacgagt gccacagtca tgactcaact gtgttgttgg      4140
gcattgggcg tgtcagggag ctggcgcgag gatgtggagt gcaattggtg ctctacgcca      4200
ctgccacccc tcccggatcc ccgatgaccc agcacccatc aatcattgag acaaaactgg      4260
acgtgggaga gatcccctte tatgggcatg catacctct tgagcggatg cggaccggaa       4320
ggcatctcgt attctgccac tccaaggctg agtgcgagcg cctggcgggc cagttttcgg      4380
ctaggggggt aaatgccatc gcctattaca gggggaaaga cagttctatc atcaaagatg      4440
gagacctggt ggtgtgtgct acagacgcac tatccactgg gtacactggg aacttcgatt      4500
ctgtcaccga ttgtgggtta gtggtggagg aggtcgtcga ggtgacccct tgatcccacca     4560 ttaccatctc cctgcgcacg gtgcccgcgt cggctgaact gtcgatgcag cggcgaggac      4620
gcacgggtag gggcaggtct gggcgctact actacgcggg ggtcggcaag gcccctgctg     4680
gtgtggtgcg ctcaggtcct gtctggtcgg cggtggaagc cggtgtgacc tggtacggaa      4740
tggaacctga cctgacagca aacctactga gactttacga caactgccct tacaccgcag      4800
ccgtcgcagc tgacattggg gaagccgcg tgttcttttc ggggcttgcc ccgttgagga       4860
tgcatcccga tgttagctgg gcaaaagttc gcggcgtcaa ctggcccttc ctggtgggtg     4920
ttcagcggac catgtgccgg gaaacactgt ctccccggccc atcggatgac ccccagtggg    4980
caggtctgaa gggcccgaat cctgtcccac tcctgctgag gtggggcaat gatttaccat     5040
ctaaagtggc cggccatcac atcgtggacg acctggtccg taggctcggg gtggcggagg    5100
gttacgtccg ctgcgatgcg ggacccatct tgatggtggg cctcgctatt gcggggggca    5160
tgatctatgc gtcatacacc gggtctctcg tggtggttac agactgggat gtgaaggggg    5220
gtggcagccc cctttatcgg catggagacc aggccacgcc ccagccggtt gtgcaggtcc    5280
ccccggtaga ccatcggccg gggggagagt ctgcgccatc ggatgccaac acagtgacag    5340
atgcggtggc ggccatccag gtggattgcg attggtcagt catgaccctg tcgatcgggg   5400
aagtgctgtc cttggcccag gctaagacgg ccgaggccta cgcagctacc accaagtggc    5460
ttgctggctg ctacacgggg acgcgggccg tccccactgt ttcaattgtt gacaagctct    5520
tcgccggggg ctgggcggcg gtggtaggcc attgccacag tgtaatagct gcggcagtgg    5580
cggcctatgg ggcttctagg agccctccat tggctgctgc cgcttcctac ctcatgggt    5640 tgggcgtcgg aggcaacgcg caaacccgct tagcctccgc tctcctacta ggggccgctg     5700
ggaccgctct gggcacgcct gtcgtggggt taaccatggc gggcgcgttc atgggaagtg     5760
ctagcgtctc cccctccttg gtcaccattt tactgggggc cgtgggggc tgggagggcg     5820 tggtgaatgc ggctagcctt gtcttcgact ttatggcggg gaaactatca tcagaagatc    5880
tgtggtatgc catcccagtg ctaaccagtc cgggggcagg acttgcgggg atcgccctcg    5940
ggttggtgtt gtactcagct aacaactctg gcactaccac ttggttgaac cgtctgctga    6000
```

```
ctacattgcc aaggtcctca tgcatccctg acagttactt tcagcaggcc gattactgtg   6060
acaaggtctc agctgtgctc cgacgcttga gcctcactcg caccgtggtt gccctggtca   6120
acagggagcc taaggtggat gaggttcagg tggggtacgt ctgggacttg tgggagtgga   6180
tcatgcgtca agtgcgcatg gtgatggcca gacttcgggc cctctgcccc gtggtgtcat   6240
tacccttatg gcactgcggg gaggggtggt ccggagaatg gttgttggac ggccatgttg   6300
agagtcgttg tctttgtggt tgcgtgatca ccggtgatgt tttgaatggg caactcaaag   6360
atccagttta ctctaccaag ctgtgcaggc attattggat ggggacagtc cctgtgaaca   6420
tgctgggcta tggcgagacg tcgccttttgc tcgcctcaga caccccgaag gtggtaccat   6480
tcgggacgtc tgggtgggct gaggtggtgg tgaccctac ccacgttgtg atcaggcgaa   6540
catccgccta caaactgctg cgccagcaaa tcctgtcggc tgctgttgct gagccctatt   6600
acgtcgacgg cataccggtc tcatgggacg cggacgcgcg agcgcctgcc atggtctatg   6660
gccctgggca aagtgtcacc attgacgggg aacgctacac ccttccgcat caactgcggc   6720
ttaggaatgt ggcgccctct gaggtgtcat ccgaggtgtc cattgacatt gggacggaga   6780
ctgaagactc agaactgact gaggccgacc tgccgccggc ggctgcagcc cttcaggcta   6840
tcgagaatgc tgcgagaatt cttgaacctc acatagatgt catcatggaa gattgcagta   6900
caccctctct ttgtgggagt agccgagaga tgcctgtgtg gggagaagac ataccccgca   6960
ctccatcgcc agcacttatc tcggttactg agagcagccc agatgagaag accccgtcgg   7020
tgtcttcctc gcaggaggat accccgtctt ctgactcatt cgaggtcatc caagagtccg   7080
agacagccga aggggaggaa agcgtcttca acgtggctct ttccgtacta aaagccttgt   7140
ttccacagag cgatgccaca agaaagctta ccgttaagat gtcatgctgt gttgagaaga   7200
gcgtaacacg cttcttttca ttgggattga cggtcgctga cgtggcaagc ctgtgtgaga   7260
tggaaatcca gaaccataca gcctattgtg acaaggtgcg cactccgctt gaattgcagg   7320
ttgggtgctt ggtgggcaat gaacttacct ttgaatgtga caagtgtgag gctaggcaag   7380
agaccttggc ttccttctct tacatttggt ctggggtgcc actgacgagg gccactccgg   7440
ccaagccccc tgtggtgagg ccggttggct ccttgctggt ggccgacacc accaaggtgt   7500
atgtcaccaa cccggacaat gttgggagaa gagttgacaa ggttaccttc tggcgtgccc   7560
ctagggttca tgacaaattc ctcgtggact ccatagagcg cgctaagagg gcagctcaag   7620
cctgcctaag catgggttac acttatgagg aggcaataag gactgtaagg ccacatgctg   7680
ccatgggctg gggatctaag gtgtcggtca aggacctcgc cacccctgcg gggaagatgg   7740
ctgtccatga ccggctccag gagatacttg aagggacgcc agtcccctttt actcttactg   7800
tgaaaaagga agtgttcttc aaagaccgaa aggaagagaa ggcccccgcc ctcattgtgt   7860
tcccccccct ggacttccgg atagctgaaa agcttattct gggagaccct ggacgggtag   7920
ccaaggcggt gttggggggg gcctacgcct tccagtacac cccaaatcag cgaattaggg   7980
agatgctcaa actgtgggaa tcaaagaaga caccatgcgc catctgtgtg gacgccacat   8040
gcttcgacag tagcataact gaagaggacg tggcgctgga gacagagctt tatgccctgg   8100
cttcagacca tccagaatgg gtgcgtgccc tggggaaata ctatgcctct ggcacaatgg   8160
taaccccga gggggtgcca gtgggtgaga ggtattgtag atcctcaggg gtcttgacca   8220
ccagtgcgag caactgcttg acttgctata tcaaggtgaa agccgcctgt gagagggtgg   8280
ggctgaaaaa tgtctcgctc ctcatcgctg gcgatgactg tttgatcata tgcgaacggc   8340
ctgtgtgcga tcctagcgac gctttgggca gagccctggc gagctacggg tacgcatgcg   8400
```

```
agccttcgta tcatgcatca ctggacacgg cccccttctg ctccacttgg ctagctgagt    8460
gcaatgcaga tgggaaacgc catttcttcc tgaccacgga ctttcggagg cccctcgctc    8520
gcatgtcgag cgagtacagt gacccaatgg cttcggccat cggttacatc tcctatacc     8580 cttggcatcc tatcacacgg tgggtcatca tccctcacgt gctcacctgc gcgtttaggg    8640
gtggtggcac accgtctgat cctgtgtggt gccaggtaca tggtaattac tacaagtttc    8700
cactggacaa actgcctaac atcatcgtgg ccctccacgg accagcagcg ttgagggtta    8760
ccgcagacac aactaagaca aaaatggagg ctggcaaggt gctgagcgac ctcaagctcc    8820
ctggcctagc agtccaccgg aagaaggccg gggcattgcg aacgcgtatg ctccggtcgc    8880
gcggttgggc tgagttggct aggggggctgt tgtggcgtcc aggcctgcgg cttccccctc    8940
cggagattgc tggtatcccc ggggggtttcc ccctttcccc ccctatatg ggggtggttc    9000 atcaattgga tttcacaagc cagaggagtc gctggcggtg gttggggttc ttagccctgc    9060
tcatcgtagc cctcttcggg tgaactaaat tcatctgttg cggcaaggtc cggtgactga    9120
tcatcactgg aggaggttcc cgccctcccc gccccagggg tctccccgct ggtaaaaag     9180 ggcccggcct tgggaggcat ggtggttact aaccccctgg cagggtcaaa gcctgatggt    9240
gctaatgcac tgccacttcg gtggcgggtc gctaccttat agcgtaatcc gtgactacgg    9300
gctgctcgca gagccctccc cggatggggc acagtgcact gtgatctgaa ggggtgcacc    9360
ccggtaagag ctcggcccaa aggccgggtt ctact                               9395
```

<210> SEQ ID NO 2
<211> LENGTH: 2910
<212> TYPE: PRT
<213> ORGANISM: Hepatitis G virus

<400> SEQUENCE: 2

Met Ser Leu Leu Thr Asn Arg Phe Ile Arg Arg Val Asp Lys Asp Gln
1               5                   10                  15

Trp Gly Pro Gly Val Met Gly Lys Asp Pro Lys Pro Cys Pro Ser Arg
            20                  25                  30

Trp Ala Gly Lys Cys Met Gly Pro Pro Ser Ala Ala Ala Cys Ser
        35                  40                  45

Arg Gly Ser Pro Arg Ile Leu Arg Val Arg Ala Gly Gly Ile Ser Leu
    50                  55                  60

Phe Tyr Thr Ile Met Ala Val Leu Leu Leu Leu Val Val Glu Ala
65                  70                  75                  80

Gly Ala Ile Leu Ala Pro Ala Thr His Ala Cys Arg Ala Asn Gly Gln
                85                  90                  95

Tyr Phe Leu Thr Asn Cys Cys Ala Pro Glu Asp Ile Gly Phe Cys Leu
            100                 105                 110

Glu Gly Gly Cys Leu Val Ala Leu Gly Cys Thr Val Cys Thr Asp Arg
        115                 120                 125

Cys Trp Pro Leu Tyr Gln Ala Gly Leu Ala Val Arg Pro Gly Lys Ser
    130                 135                 140

Ala Ala Gln Leu Val Gly Glu Leu Gly Ser Leu Tyr Gly Pro Leu Ser
145                 150                 155                 160

Val Ser Ala Tyr Val Ala Gly Ile Leu Gly Leu Gly Glu Val Tyr Ser
                165                 170                 175

Gly Val Leu Thr Val Gly Val Ala Leu Arg Arg Arg Val Tyr Leu Met
            180                 185                 190

-continued

```
Pro Asn Leu Lys Cys Ala Val Glu Cys Asp Val Lys Trp Gly Ser Glu
        195                 200                 205

Phe Trp Arg Trp Thr Glu Gln Leu Ala Ser Asn Tyr Trp Ile Leu Glu
    210                 215                 220

Tyr Leu Trp Lys Val Pro Phe Glu Phe Trp Arg Gly Val Met Ser Leu
225                 230                 235                 240

Thr Pro Leu Leu Val Trp Val Ala Ala Leu Leu Leu Glu Gln Arg
                245                 250                 255

Ile Val Met Val Phe Leu Leu Val Thr Met Ala Gly Met Leu Gln Gly
                260                 265                 270

Ala Pro Ala Ser Val Leu Gly Ser Arg Pro Phe Asp Tyr Gly Leu Lys
        275                 280                 285

Trp Gln Ser Cys Ser Cys Arg Ala Asn Gly Ser Arg Ile Pro Thr Gly
        290                 295                 300

Glu Arg Val Trp Asp Arg Gly Asn Val Thr Leu Leu Cys Asp Cys Pro
305                 310                 315                 320

Asn Gly Pro Trp Val Trp Val Pro Ala Phe Cys Gln Ala Val Gly Trp
                325                 330                 335

Gly Asp Pro Ile Thr His Trp Ser His Gly Gln Asn Gln Trp Pro Leu
                340                 345                 350

Ser Cys Pro Gln Tyr Val Tyr Gly Ser Val Ser Val Thr Cys Val Trp
        355                 360                 365

Gly Ser Val Ser Trp Phe Ala Ser Thr Gly Gly Arg Asp Ser Lys Ile
        370                 375                 380

Asp Val Trp Ser Leu Val Pro Val Gly Ser Ala Ser Cys Thr Ile Ala
385                 390                 395                 400

Ala Leu Gly Ser Ser Asp Arg Asp Thr Val Val Glu Leu Ser Glu Trp
                405                 410                 415

Gly Val Pro Cys Val Thr Cys Ile Leu Asp Arg Arg Pro Ala Ser Cys
                420                 425                 430

Gly Thr Cys Val Arg Asp Cys Trp Pro Glu Thr Gly Ser Val Arg Phe
        435                 440                 445

Pro Phe His Arg Cys Gly Thr Gly Pro Arg Leu Thr Lys Asp Leu Glu
        450                 455                 460

Ala Val Pro Phe Val Asn Arg Thr Thr Pro Phe Thr Ile Arg Gly Pro
465                 470                 475                 480

Leu Gly Asn Gln Gly Arg Gly Asn Pro Val Arg Ser Pro Leu Gly Phe
                485                 490                 495

Gly Ser Tyr Thr Met Thr Lys Ile Arg Asp Ser Leu His Leu Val Lys
        500                 505                 510

Cys Pro Thr Pro Ala Ile Glu Pro Pro Thr Gly Thr Phe Gly Phe Phe
        515                 520                 525

Pro Gly Val Pro Pro Ile Asn Asn Cys Met Pro Leu Gly Thr Glu Val
        530                 535                 540

Ser Glu Ala Leu Gly Gly Ala Gly Leu Thr Gly Phe Tyr Glu Pro
545                 550                 555                 560

Leu Val Arg Arg Cys Ser Glu Leu Met Gly Arg Asn Pro Val Cys
                565                 570                 575

Pro Gly Tyr Ala Trp Leu Ser Ser Gly Arg Pro Asp Gly Phe Ile His
                580                 585                 590

Val Gln Gly His Leu Gln Glu Val Asp Ala Gly Asn Phe Ile Pro Pro
        595                 600                 605

Pro Arg Trp Leu Leu Leu Asp Phe Val Phe Val Leu Leu Tyr Leu Met
```

```
                610                 615                 620
Lys Leu Ala Glu Ala Arg Leu Val Pro Leu Ile Leu Leu Leu Trp
625                 630                 635                 640

Trp Trp Val Asn Gln Leu Ala Val Leu Gly Leu Pro Ala Val Asp Ala
                645                 650                 655

Ala Val Ala Gly Glu Val Phe Ala Gly Pro Ala Leu Ser Trp Cys Leu
                660                 665                 670

Gly Leu Pro Thr Val Ser Met Ile Leu Gly Leu Ala Asn Leu Val Leu
                675                 680                 685

Tyr Phe Arg Trp Met Gly Pro Gln Arg Leu Met Phe Leu Val Leu Trp
690                 695                 700

Lys Leu Ala Arg Gly Ala Phe Pro Leu Ala Leu Leu Met Gly Ile Ser
705                 710                 715                 720

Ala Thr Arg Gly Arg Thr Ser Val Leu Gly Ala Glu Phe Cys Phe Asp
                725                 730                 735

Val Thr Phe Glu Val Asp Thr Ser Val Leu Gly Trp Val Val Ala Ser
                740                 745                 750

Val Val Ala Trp Ala Ile Ala Leu Leu Ser Ser Met Ser Ala Gly Gly
                755                 760                 765

Trp Lys His Lys Ala Val Ile Tyr Arg Thr Trp Cys Lys Gly Tyr Gln
                770                 775                 780

Ala Val Arg Gln Arg Val Val Arg Ser Pro Leu Gly Glu Gly Arg Pro
785                 790                 795                 800

Thr Lys Leu Leu Thr Phe Ala Trp Cys Leu Ala Ser Tyr Ile Trp Pro
                805                 810                 815

Asp Ala Val Met Met Val Val Val Ala Leu Val Leu Leu Phe Gly Leu
                820                 825                 830

Phe Asp Ala Leu Asp Trp Ala Leu Glu Glu Leu Leu Val Ser Arg Pro
                835                 840                 845

Ser Leu Arg Arg Leu Ala Arg Val Val Glu Cys Cys Val Met Ala Gly
                850                 855                 860

Glu Lys Ala Thr Thr Ile Arg Leu Val Ser Lys Met Cys Ala Arg Gly
865                 870                 875                 880

Ala Tyr Leu Phe Asp His Met Gly Ser Phe Ser Arg Ala Val Lys Glu
                885                 890                 895

Arg Leu Leu Glu Trp Asp Ala Ala Leu Glu Pro Leu Ser Phe Thr Arg
                900                 905                 910

Thr Asp Cys Arg Ile Ile Arg Asp Ala Ala Arg Thr Leu Ser Cys Gly
                915                 920                 925

Gln Cys Val Met Gly Leu Pro Val Val Ala Arg Gly Asp Glu Val
                930                 935                 940

Leu Ile Gly Val Phe Gln Asp Val Asn His Leu Pro Pro Gly Phe Val
945                 950                 955                 960

Pro Thr Ala Pro Val Val Ile Arg Arg Cys Gly Lys Gly Phe Leu Gly
                965                 970                 975

Val Thr Lys Ala Ala Leu Thr Gly Arg Asp Pro Asp Leu His Pro Gly
                980                 985                 990

Asn Val Met Val Leu Gly Thr Ala Thr Ser Arg Ser Met Gly Thr Cys
                995                 1000                1005

Leu Asn Gly Leu Leu Phe Thr Thr Phe His Gly Ala Ser Ser Arg Thr
                1010                1015                1020

Ile Ala Thr Pro Val Gly Ala Leu Asn Pro Arg Trp Trp Ser Ala Ser
1025                1030                1035                1040
```

-continued

```
Asp Asp Val Thr Val Tyr Pro Leu Pro Asp Gly Ala Thr Ser Leu Thr
            1045                1050                1055

Pro Cys Thr Cys Gln Ala Glu Ser Cys Trp Val Ile Arg Ser Asp Gly
            1060                1065                1070

Ala Leu Cys His Gly Leu Ser Lys Gly Asp Lys Val Glu Leu Asp Val
            1075                1080                1085

Ala Met Glu Val Ser Asp Phe Arg Gly Ser Gly Ser Pro Val Leu
            1090                1095            1100

Cys Asp Lys Gly His Ala Val Arg Met Leu Val Ser Val Leu His Ser
1105                1110                1115                1120

Gly Gly Arg Val Thr Ala Ala Arg Phe Thr Arg Pro Trp Thr Gln Val
                1125                1130                1135

Pro Thr Asp Ala Lys Thr Thr Thr Glu Pro Pro Val Pro Ala Lys
            1140                1145                1150

Gly Val Phe Lys Glu Ala Pro Leu Phe Met Pro Thr Gly Ala Gly Lys
            1155                1160                1165

Ser Thr Arg Val Pro Leu Glu Tyr Gly Asn Met Gly His Lys Val Leu
    1170                1175                1180

Ile Leu Asn Pro Ser Val Ala Thr Val Arg Ala Met Gly Pro Tyr Met
1185                1190                1195                1200

Glu Arg Leu Ala Gly Lys His Pro Ser Ile Tyr Cys Gly His Asp Thr
                1205                1210                1215

Thr Ala Phe Thr Arg Ile Thr Asp Ser Pro Leu Thr Tyr Ser Thr Tyr
            1220                1225                1230

Gly Arg Phe Leu Ala Asn Pro Arg Gln Met Leu Arg Gly Val Ser Val
            1235                1240                1245

Val Ile Cys Asp Glu Cys His Ser His Asp Ser Thr Val Leu Leu Gly
            1250                1255                1260

Ile Gly Arg Val Arg Glu Leu Ala Arg Gly Cys Gly Val Gln Leu Val
1265                1270                1275                1280

Leu Tyr Ala Thr Ala Thr Pro Pro Gly Ser Pro Met Thr Gln His Pro
            1285                1290                1295

Ser Ile Ile Glu Thr Lys Leu Asp Val Gly Glu Ile Pro Phe Tyr Gly
            1300                1305                1310

His Gly Ile Pro Leu Glu Arg Met Arg Thr Gly Arg His Leu Val Phe
            1315                1320                1325

Cys His Ser Lys Ala Glu Cys Glu Arg Leu Ala Gly Gln Phe Ser Ala
            1330                1335                1340

Arg Gly Val Asn Ala Ile Ala Tyr Tyr Arg Gly Lys Asp Ser Ser Ile
1345                1350                1355                1360

Ile Lys Asp Gly Asp Leu Val Val Cys Ala Thr Asp Ala Leu Ser Thr
            1365                1370                1375

Gly Tyr Thr Gly Asn Phe Asp Ser Val Thr Asp Cys Gly Leu Val Val
            1380                1385                1390

Glu Glu Val Val Glu Val Thr Leu Asp Pro Thr Ile Thr Ile Ser Leu
            1395                1400                1405

Arg Thr Val Pro Ala Ser Ala Glu Leu Ser Met Gln Arg Arg Gly Arg
    1410                1415                1420

Thr Gly Arg Gly Arg Ser Gly Arg Tyr Tyr Tyr Ala Gly Val Gly Lys
1425                1430                1435                1440

Ala Pro Ala Gly Val Val Arg Ser Gly Pro Val Trp Ser Ala Val Glu
            1445                1450                1455
```

-continued

```
Ala Gly Val Thr Trp Tyr Gly Met Glu Pro Asp Leu Thr Ala Asn Leu
            1460                1465                1470
Leu Arg Leu Tyr Asp Asn Cys Pro Tyr Thr Ala Ala Val Ala Ala Asp
        1475                1480                1485
Ile Gly Glu Ala Ala Val Phe Phe Ser Gly Leu Ala Pro Leu Arg Met
    1490                1495                1500
His Pro Asp Val Ser Trp Ala Lys Val Arg Gly Val Asn Trp Pro Phe
1505                1510                1515                1520
Leu Val Gly Val Gln Arg Thr Met Cys Arg Glu Thr Leu Ser Pro Gly
            1525                1530                1535
Pro Ser Asp Asp Pro Gln Trp Ala Gly Leu Lys Gly Pro Asn Pro Val
        1540                1545                1550
Pro Leu Leu Leu Arg Trp Gly Asn Asp Leu Pro Ser Lys Val Ala Gly
    1555                1560                1565
His His Ile Val Asp Asp Leu Val Arg Arg Leu Gly Val Ala Glu Gly
1570                1575                1580
Tyr Val Arg Cys Asp Ala Gly Pro Ile Leu Met Val Gly Leu Ala Ile
1585                1590                1595                1600
Ala Gly Gly Met Ile Tyr Ala Ser Tyr Thr Gly Ser Leu Val Val Val
            1605                1610                1615
Thr Asp Trp Asp Val Lys Gly Gly Ser Pro Leu Tyr Arg His Gly
        1620                1625                1630
Asp Gln Ala Thr Pro Gln Pro Val Val Gln Val Pro Pro Val Asp His
    1635                1640                1645
Arg Pro Gly Gly Glu Ser Ala Pro Ser Asp Ala Asn Thr Val Thr Asp
1650                1655                1660
Ala Val Ala Ala Ile Gln Val Asp Cys Asp Trp Ser Val Met Thr Leu
1665                1670                1675                1680
Ser Ile Gly Glu Val Leu Ser Leu Ala Gln Ala Lys Thr Ala Glu Ala
            1685                1690                1695
Tyr Ala Ala Thr Thr Lys Trp Leu Ala Gly Cys Tyr Thr Gly Thr Arg
        1700                1705                1710
Ala Val Pro Thr Val Ser Ile Val Asp Lys Leu Phe Ala Gly Gly Trp
    1715                1720                1725
Ala Ala Val Val Gly His Cys His Ser Val Ile Ala Ala Ala Val Ala
1730                1735                1740
Ala Tyr Gly Ala Ser Arg Ser Pro Pro Leu Ala Ala Ala Ala Ser Tyr
1745                1750                1755                1760
Leu Met Gly Leu Gly Val Gly Gly Asn Ala Gln Thr Arg Leu Ala Ser
            1765                1770                1775
Ala Leu Leu Leu Gly Ala Ala Gly Thr Ala Leu Gly Thr Pro Val Val
        1780                1785                1790
Gly Leu Thr Met Ala Gly Ala Phe Met Gly Ser Ala Ser Val Ser Pro
    1795                1800                1805
Ser Leu Val Thr Ile Leu Leu Gly Ala Val Gly Gly Trp Glu Gly Val
1810                1815                1820
Val Asn Ala Ala Ser Leu Val Phe Asp Phe Met Ala Gly Lys Leu Ser
1825                1830                1835                1840
Ser Glu Asp Leu Trp Tyr Ala Ile Pro Val Leu Thr Ser Pro Gly Ala
            1845                1850                1855
Gly Leu Ala Gly Ile Ala Leu Gly Leu Val Leu Tyr Ser Ala Asn Asn
        1860                1865                1870
Ser Gly Thr Thr Thr Trp Leu Asn Arg Leu Leu Thr Thr Leu Pro Arg
```

-continued

```
                1875                1880                1885
Ser Ser Cys Ile Pro Asp Ser Tyr Phe Gln Gln Ala Asp Tyr Cys Asp
    1890                1895                1900
Lys Val Ser Ala Val Leu Arg Arg Leu Ser Leu Thr Arg Thr Val Val
1905                1910                1915                1920
Ala Leu Val Asn Arg Glu Pro Lys Val Asp Glu Val Gln Val Gly Tyr
                1925                1930                1935
Val Trp Asp Leu Trp Glu Trp Ile Met Arg Gln Val Arg Met Val Met
                    1940                1945                1950
Ala Arg Leu Arg Ala Leu Cys Pro Val Val Ser Leu Pro Leu Trp His
        1955                1960                1965
Cys Gly Glu Gly Trp Ser Gly Glu Trp Leu Leu Asp Gly His Val Glu
    1970                1975                1980
Ser Arg Cys Leu Cys Gly Cys Val Ile Thr Gly Asp Val Leu Asn Gly
1985                1990                1995                2000
Gln Leu Lys Asp Pro Val Tyr Ser Thr Lys Leu Cys Arg His Tyr Trp
                2005                2010                2015
Met Gly Thr Val Pro Val Asn Met Leu Gly Tyr Gly Glu Thr Ser Pro
                2020                2025                2030
Leu Leu Ala Ser Asp Thr Pro Lys Val Val Pro Phe Gly Thr Ser Gly
                2035                2040                2045
Trp Ala Glu Val Val Thr Pro Thr His Val Val Ile Arg Arg Thr
        2050                2055                2060
Ser Ala Tyr Lys Leu Leu Arg Gln Gln Ile Leu Ser Ala Ala Val Ala
2065                2070                2075                2080
Glu Pro Tyr Tyr Val Asp Gly Ile Pro Val Ser Trp Asp Ala Asp Ala
                2085                2090                2095
Arg Ala Pro Ala Met Val Tyr Gly Pro Gly Gln Ser Val Thr Ile Asp
                2100                2105                2110
Gly Glu Arg Tyr Thr Leu Pro His Gln Leu Arg Leu Arg Asn Val Ala
            2115                2120                2125
Pro Ser Glu Val Ser Ser Glu Val Ser Ile Asp Ile Gly Thr Glu Thr
    2130                2135                2140
Glu Asp Ser Glu Leu Thr Glu Ala Asp Leu Pro Ala Ala Ala Ala
2145                2150                2155                2160
Leu Gln Ala Ile Glu Asn Ala Ala Arg Ile Leu Glu Pro His Ile Asp
            2165                2170                2175
Val Ile Met Glu Asp Cys Ser Thr Pro Ser Leu Cys Gly Ser Ser Arg
        2180                2185                2190
Glu Met Pro Val Trp Gly Glu Asp Ile Pro Arg Thr Pro Ser Pro Ala
        2195                2200                2205
Leu Ile Ser Val Thr Glu Ser Ser Pro Asp Glu Lys Thr Pro Ser Val
    2210                2215                2220
Ser Ser Ser Gln Glu Asp Thr Pro Ser Ser Asp Ser Phe Glu Val Ile
2225                2230                2235                2240
Gln Glu Ser Glu Thr Ala Glu Gly Glu Glu Ser Val Phe Asn Val Ala
                2245                2250                2255
Leu Ser Val Leu Lys Ala Leu Phe Pro Gln Ser Asp Ala Thr Arg Lys
                2260                2265                2270
Leu Thr Val Lys Met Ser Cys Cys Val Glu Lys Ser Val Thr Arg Phe
            2275                2280                2285
Phe Ser Leu Gly Leu Thr Val Ala Asp Val Ala Ser Leu Cys Glu Met
        2290                2295                2300
```

```
Glu Ile Gln Asn His Thr Ala Tyr Cys Asp Lys Val Arg Thr Pro Leu
2305                2310                2315                2320

Glu Leu Gln Val Gly Cys Leu Val Gly Asn Glu Leu Thr Phe Glu Cys
            2325                2330                2335

Asp Lys Cys Glu Ala Arg Gln Glu Thr Leu Ala Ser Phe Ser Tyr Ile
        2340                2345                2350

Trp Ser Gly Val Pro Leu Thr Arg Ala Thr Pro Ala Lys Pro Pro Val
    2355                2360                2365

Val Arg Pro Val Gly Ser Leu Leu Val Ala Asp Thr Thr Lys Val Tyr
2370                2375                2380

Val Thr Asn Pro Asp Asn Val Gly Arg Arg Val Asp Lys Val Thr Phe
2385                2390                2395                2400

Trp Arg Ala Pro Arg Val His Asp Lys Phe Leu Val Asp Ser Ile Glu
            2405                2410                2415

Arg Ala Lys Arg Ala Ala Gln Ala Cys Leu Ser Met Gly Tyr Thr Tyr
            2420                2425                2430

Glu Glu Ala Ile Arg Thr Val Arg Pro His Ala Ala Met Gly Trp Gly
            2435                2440                2445

Ser Lys Val Ser Val Lys Asp Leu Ala Thr Pro Ala Gly Lys Met Ala
    2450                2455                2460

Val His Asp Arg Leu Gln Glu Ile Leu Glu Gly Thr Pro Val Pro Phe
2465                2470                2475                2480

Thr Leu Thr Val Lys Lys Glu Val Phe Phe Lys Asp Arg Lys Glu Glu
            2485                2490                2495

Lys Ala Pro Arg Leu Ile Val Phe Pro Pro Leu Asp Phe Arg Ile Ala
            2500                2505                2510

Glu Lys Leu Ile Leu Gly Asp Pro Gly Arg Val Ala Lys Ala Val Leu
    2515                2520                2525

Gly Gly Ala Tyr Ala Phe Gln Tyr Thr Pro Asn Gln Arg Ile Arg Glu
    2530                2535                2540

Met Leu Lys Leu Trp Glu Ser Lys Lys Thr Pro Cys Ala Ile Cys Val
2545                2550                2555                2560

Asp Ala Thr Cys Phe Asp Ser Ser Ile Thr Glu Glu Asp Val Ala Leu
            2565                2570                2575

Glu Thr Glu Leu Tyr Ala Leu Ala Ser Asp His Pro Glu Trp Val Arg
            2580                2585                2590

Ala Leu Gly Lys Tyr Tyr Ala Ser Gly Thr Met Val Thr Pro Glu Gly
    2595                2600                2605

Val Pro Val Gly Glu Arg Tyr Cys Arg Ser Ser Gly Val Leu Thr Thr
2610                2615                2620

Ser Ala Ser Asn Cys Leu Thr Cys Tyr Ile Lys Val Lys Ala Ala Cys
2625                2630                2635                2640

Glu Arg Val Gly Leu Lys Asn Val Ser Leu Leu Ile Ala Gly Asp Asp
            2645                2650                2655

Cys Leu Ile Ile Cys Glu Arg Pro Val Cys Asp Pro Ser Asp Ala Leu
            2660                2665                2670

Gly Arg Ala Leu Ala Ser Tyr Gly Tyr Ala Cys Glu Pro Ser Tyr His
            2675                2680                2685

Ala Ser Leu Asp Thr Ala Pro Phe Cys Ser Thr Trp Leu Ala Glu Cys
    2690                2695                2700

Asn Ala Asp Gly Lys Arg His Phe Phe Leu Thr Thr Asp Phe Arg Arg
2705                2710                2715                2720
```

-continued

```
Pro Leu Ala Arg Met Ser Ser Glu Tyr Ser Asp Pro Met Ala Ser Ala
            2725                2730                2735

Ile Gly Tyr Ile Leu Leu Tyr Pro Trp His Pro Ile Thr Arg Trp Val
            2740            2745                2750

Ile Ile Pro His Val Leu Thr Cys Ala Phe Arg Gly Gly Thr Pro
            2755            2760            2765

Ser Asp Pro Val Trp Cys Gln Val His Gly Asn Tyr Tyr Lys Phe Pro
2770            2775            2780

Leu Asp Lys Leu Pro Asn Ile Ile Val Ala Leu His Gly Pro Ala Ala
2785            2790            2795            2800

Leu Arg Val Thr Ala Asp Thr Lys Thr Lys Met Glu Ala Gly Lys
            2805            2810            2815

Val Leu Ser Asp Leu Lys Leu Pro Gly Leu Ala Val His Arg Lys Lys
            2820            2825            2830

Ala Gly Ala Leu Arg Thr Arg Met Leu Arg Ser Arg Gly Trp Ala Glu
            2835            2840            2845

Leu Ala Arg Gly Leu Leu Trp Arg Pro Gly Leu Arg Leu Pro Pro Pro
            2850            2855            2860

Glu Ile Ala Gly Ile Pro Gly Gly Phe Pro Leu Ser Pro Pro Tyr Met
2865            2870            2875            2880

Gly Val Val His Gln Leu Asp Phe Thr Ser Gln Arg Ser Arg Trp Arg
            2885            2890            2895

Trp Leu Gly Phe Leu Ala Leu Leu Ile Val Ala Leu Phe Gly
            2900            2905            2910

<210> SEQ ID NO 3
<211> LENGTH: 36
<212> TYPE: DNA
<213> ORGANISM: Artificial Sequence
<220> FEATURE:
<223> OTHER INFORMATION: A synthetic primer.

<400> SEQUENCE: 3
tcatggtggc gaataaaagc cccagaaacc gacgcc                                36

<210> SEQ ID NO 4
<211> LENGTH: 16
<212> TYPE: DNA
<213> ORGANISM: Artificial Sequence
<220> FEATURE:
<223> OTHER INFORMATION: A synthetic primer.

<400> SEQUENCE: 4
tcatggtggc gaataa                                                      16

<210> SEQ ID NO 5
<211> LENGTH: 24
<212> TYPE: DNA
<213> ORGANISM: Artificial Sequence
<220> FEATURE:
<223> OTHER INFORMATION: A synthetic primer.

<400> SEQUENCE: 5
tactgcartc ytccatgatg acat                                             24

<210> SEQ ID NO 6
<211> LENGTH: 22
<212> TYPE: DNA
<213> ORGANISM: Artificial Sequence
<220> FEATURE:
<223> OTHER INFORMATION: A synthetic primer.
```

```
<400> SEQUENCE: 6
atggtytayg gycctggvca aa                                              22

<210> SEQ ID NO 7
<211> LENGTH: 23
<212> TYPE: DNA
<213> ORGANISM: Artificial Sequence
<220> FEATURE:
<223> OTHER INFORMATION: A synthetic primer.

<400> SEQUENCE: 7
ttcaagaatc ctcgcagcat tct                                             23

<210> SEQ ID NO 8
<211> LENGTH: 20
<212> TYPE: DNA
<213> ORGANISM: Artificial Sequence
<220> FEATURE:
<223> OTHER INFORMATION: A synthetic primer.

<400> SEQUENCE: 8
ctggvcaaag ygtyaccatt                                                 20

<210> SEQ ID NO 9
<211> LENGTH: 20
<212> TYPE: DNA
<213> ORGANISM: Hepatitis G virus

<400> SEQUENCE: 9
taccggtgtg aataagggcc                                                 20

<210> SEQ ID NO 10
<211> LENGTH: 17
<212> TYPE: DNA
<213> ORGANISM: Hepatitis G virus

<400> SEQUENCE: 10
cgtcgtttgc ccaggtg                                                    17

<210> SEQ ID NO 11
<211> LENGTH: 25
<212> TYPE: DNA
<213> ORGANISM: Hepatitis G virus

<400> SEQUENCE: 11
ctcgtcgtta aaccgagccc gtcac                                           25

<210> SEQ ID NO 12
<211> LENGTH: 24
<212> TYPE: DNA
<213> ORGANISM: Artificial Sequence
<220> FEATURE:
<223> OTHER INFORMATION: A synthetic primer.

<400> SEQUENCE: 12
tactgcartc ytccatgatg acat                                            24

<210> SEQ ID NO 13
<211> LENGTH: 22
<212> TYPE: DNA
<213> ORGANISM: Artificial Sequence
<220> FEATURE:
<223> OTHER INFORMATION: A synthetic primer.
```

```
<400> SEQUENCE: 13
atggtytayg gycctggvca aa                                              22

<210> SEQ ID NO 14
<211> LENGTH: 23
<212> TYPE: DNA
<213> ORGANISM: Artificial Sequence
<220> FEATURE:
<223> OTHER INFORMATION: A synthetic primer.

<400> SEQUENCE: 14
ttcaagaatc ctcgcagcat tct                                             23

<210> SEQ ID NO 15
<211> LENGTH: 20
<212> TYPE: DNA
<213> ORGANISM: Artificial Sequence
<220> FEATURE:
<223> OTHER INFORMATION: A synthetic primer.

<400> SEQUENCE: 15
ctggvcaaag ygtyaccatt                                                 20

<210> SEQ ID NO 16
<211> LENGTH: 20
<212> TYPE: DNA
<213> ORGANISM: Hepatitis G virus

<400> SEQUENCE: 16
taccggtgtg aataagggcc                                                 20

<210> SEQ ID NO 17
<211> LENGTH: 17
<212> TYPE: DNA
<213> ORGANISM: Hepatitis G virus

<400> SEQUENCE: 17
cgtcgtttgc ccaggtg                                                    17

<210> SEQ ID NO 18
<211> LENGTH: 25
<212> TYPE: DNA
<213> ORGANISM: Hepatitis G virus

<400> SEQUENCE: 18
ctcgtcgtta aaccgagccc gtcac                                           25

<210> SEQ ID NO 19
<211> LENGTH: 9309
<212> TYPE: DNA
<213> ORGANISM: Hepatitis G virus

<400> SEQUENCE: 19
aagccccaga aaccgacgcc tatctaagta gacgcaatga ctcggcgccg actcggcgac      60
cggccaaaag gtggtggatg ggtgatgaca gggttggtag gtcgtaaatc ccggtcatcc     120
tggtagccac tataggtggg tcttaagaga aggttaagat tcctcttgtg cctgcggcga     180
gaccgcgcac ggtccacagg tgttggccct accggtgtga ataagggccc gacgtcaggc     240
tcgtcgttaa accgagcccg ttacccacct gggcaaacga cgcccacgta cggtccacgt     300
cgcccttcaa tgtctctctt gaccaatagg cttagccggc gagttgacaa ggaccagtgg     360
gggccggggg ctatggagat ggactccaag tcctgccctt cccggtgggg cgggaaatgc     420
```

-continued

```
atggggccac ccagctccgc ggcggcctgc agccggggta gcccaagaac ccttcgggtg    480
agggcgggtg gcattttcct tttctatacc atcatggcag tccttctgct ccttctcgtg    540
gttgaggccg gggccatttt agccccggcc acccacgctt gtcgagcgaa tgggcaatac    600
ttccttacaa attgttgcgc cccggaggac atcgggttct gcctggaagg tggatgcctg    660
gtggccttgg gatgcacagt ttgcactgac caatgctggc cactgtatca ggcgggtttg    720
gctgtgcggc ctggcaagtc cgcggcccaa ctggtggggg agctgggtag cctatacggg    780
cccttgtcgg tctcggccta cgtggctggg atcctgggcc tgggcgaggt ttactcgggt    840
gtcctaacgg tgggcgtcgc gttgacgcgt cgggtctacc cggtgcccaa cctgacgtgt    900
gcagtagagt gtgagcttaa gtgggaaagt gagttttgga gatggactga acagttggcc    960
tccaattact ggattctgga ataccttcgg aaggtcccat ttgacttctg gagggcgtg   1020 atgagcctga cccctctgtt ggtctgtgtg ccgctctgc tgctgcttga caaaggatt    1080 gttatggtct tcctgctggt gaccatggcc gggatgtcgc aaggcgcccc tgcttcggtt    1140
ttggggtcac gcccctttga ctacgggttg acttggcaga cctgctcttg caaggcgaac    1200
ggctcacgca ttccgactgg ggaaaaggtg tgggaccgcg ggaatgtcac gcttctgtgt    1260
gattgcccca acggaccatg ggtgtggtta ccggcttct gccaagcagt tggctgggt    1320 gatcctatca cccattggag ccacggacaa atcggtggc ccctctcatg ccctcagtat    1380
gtctatgggt ctgtttcagt cacttgcgtg tgggctccg cgtcttggtt tgcctccact    1440
ggtggacgcg attcgaagat cgatgtgtgg agtttggtgc cagttggttc tgccacttgc    1500
accatagccg ctctcgggtc gtcggaccgc gatacggtgg tggagctctc cgagtggggg    1560
gtcccgtgcg tgacgtgcat tctggatcgt cggcctgcct cctgcggcac ctgtgtgagg    1620
gactgctggc ccgagactgg gtcggtcaga ttcccattcc ataggtgtgg cacggggcct    1680
cggctgacaa aggacttgga agctgtgccc ttcgtcaata ggacaactcc cttcaccatt    1740
aggggggcct ctgggcaacca gggccgaggc aaccggtgc ggtcgccctt gggttttggg    1800
tcctacacca tgaccaagat ccgagacacc ctacatttgg tgaaatgtcc cacaccagcc    1860
attgagcctc ccaccgggac gtttgggttc ttcccgggga cgccgccct caacaactgc    1920 atgcttctag gcacggaagt gtctgaggca ctcggcgggg ctggtctcac gggggtttc    1980 tatgaacccc tggtgcgcag tgttcggag ctgatgggac gccgaaatcc ggtttgtccg    2040 gggttttgcat ggctctcctc gggcaggcct gatgggttca tacatgtcca gggccacttg    2100
caggaggtgg atgcaggcaa cttcattccg ccccccgcgct ggctgctctt ggactttgta    2160
tttgtcctgt atacctgat gaagctggct gaggctcgt tggtcccgct gatcttgctt    2220
ctgctgtggt ggtgggtgaa ccagctggcg gttttaggac tgccggctgt ggacgccgcc    2280
gtagcaggtg aggtctttgc gggccctgcc ctgtcctggt gtctgggact cccgactgtc    2340
agtatgatac tgggtctagc aaacctggtg ttgtacttta gatggctggg accccaacgc    2400
cttatgttcc ttgtgttgtg gaagctcgct cggggagctt tccgctggc acttctgatg    2460 gggatttcgg cgactcgcgg gcgcacctcc gtgctcgggg ccgagttctg cttcgatgct    2520
acattcgagg tggacactc ggtgttgggc tgggtggtgg ccagcgtggt ggcttgggcc    2580
atagcgctcc tgagctcgat gagcgcaggg gggtggaggc acaaagccgt gatctatagg    2640
acgtggtgta aagggtacca ggctatacgc cagagagtgg ttcggagccc cttcggggag    2700
gggcgaccta ctaagcctct gacttcgct tggtgcttgg cctcgtacat ctggccggat    2760
```

```
gctgtgatga tggtggtggt cgccttggtc ttactctttg gcctgttcga tgcgttggac    2820
tgggctttgg aggagatctt ggtgtcccgg ccctcgttgc gccgtttggc tcgggtgatc    2880
gagtgctgtg tgatggcggg tgagaaggcc acaactgtcc ggctggtctc caagatgtgc    2940
gcgagagggg cctacttgtt cgatcatatg ggctcatttt cgcgcgctgt caaggagcgc    3000
ctgttggagt gggacgcggc tcttgaacct ctgtcattca ctaggacgga ctgtcgcatt    3060
ataagagatg ccgctaggac tttgtcttgc ggacagtgcg tcatgggctt gcccgtggta    3120
gcgcgccgtg gagatgaggt tctcatcggc gtcttccagg atgtgaatca tttgcctcct    3180
gggtttgtcc caaccgcacc agttgtcatc cggcggtgcg gaaagggttt cctaggggtc    3240
acaaaggctg ccttgacggg tcgggatcct gacttacatc caggaaacgt catggtgttg    3300
gggacggcaa cgtcgcgaag catgggaaca tgtctgaacg gcctgttgtt cacgaccttc    3360
catgggcttt catcccgaac catcgccacg cccgtggggg cccttaaccc taggtggtgg    3420
tccgccagtg atgacgtcac ggtgtatccg cttccagatg gggcgacttc gttgacacct    3480
tgcacttgcc aagctgagtc ctgttgggtc atcagatctg acggggcttt atgccatggc    3540
ttgagcaagg gggacaaggt agagctggat gtagctatgg aggtctctga cttccgtggt    3600
tcgtccggct cgccggtcct gtgcgacgaa gggcacgcag taggaatgct cgtgtcagtg    3660
ctccattcgg cggagaagt caccgcggct cgatttacta gggcgtggac ccaagttcca    3720
actgacgcca aaaccaccac tgaccccccct ccggtgccgg caaaaggagt tttcaaagag    3780
gcccccgttgt ttatgcctac gggagcggga aagagcactc gcgtcccgtt ggagtacggc    3840
aacatggggc acaaggtctt gattttgaac ccctcggtcg ctactgtgcg ggccatgggc    3900
ccctacatgg agcggctggc gggcaaacat ccaagcattt actgtggaca tgacaccact    3960
gctttcacga ggatcactga ctcccccta acgtattcta cctatgggag gttttagcc     4020
aaccctaggc agatgctacg gggtgtatcg gtggtcatct gtgatgagtg ccacagccat    4080
gactcaaccg tgctgctggg cattgggagg gtccgggagc tggcgcgtgg gtgtggagtg    4140
caactggtgc tctacgctac cgccacgcct cctggttccc ccatgacaca gcaccccttct   4200
ataattgaga caaagctgga tgtgggtgag atccccttt atgggcatgg cataccccctc    4260
gaacggatgc gaaccgggag gcatctcgta ttctgccatt ccaaggctga gtgtgagcgc    4320
cttgccggcc agttctccgc gagggggta aatgctattg cttattatag ggggaaagac    4380
agttccatca ttcaggacgg agacctagtg gtgtgcgcca ctgacgcact ttccaccggg    4440
tatactggga atttttgattc tgtcaccgat tgtgggttgg tggtggagga ggtcgttgag    4500
gtgacccttg atcccaccat taccatctcc ctgcgaacag tgcctgcttc ggctgaattg    4560
tcgatgcaga gacgaggacg cacgggtagg gcaggtctg ggcgctacta ctacgcgggg     4620
gtgggcaaag cccccgctgg ggtggtgcgc tcaggtcctg tctggtcggc ggtgaagcc     4680
ggagtgacct ggtacggaat ggaacctgac ctgacagcta acctattgag actttacgac    4740
gactgccctt acaccgcagc cgtcgcagct gacattggag aggccgcggt gttcttctcc    4800
gggctcgccc cgttgaggat gcaccccgat gttagctggg caaaagttcg cggcgtcaac    4860
tggcccctct tggtgggtgt tcagcggacc atgtgccggg aaacactgtc tcctggtcca    4920
tcggatgacc cccaatgggc aggtctgaag ggcccgaatc ctgtcccact actgctgagg    4980
tggggcaatg atttaccatc taaagtggcc ggccatcaca tagtggacga cctggtccgt    5040
agactcggtg tggcgagggg ttatgtccgc tgcgatgcgg ggcgatctt gatggtcggt    5100
ctcgctatcg cggggggat gatctacgcg tcatacaccg ggtccatagt ggtggtgaca    5160
```

-continued

```
gactgggatg tgaaggggg tggcgccccc ctttatcggc atggagacca ggccacgcca    5220
caaccggtgg tgcaggtccc cccggtagac catcggccgg gggggagtc tgcgccatcg    5280 gacgccaaga cagtgacaga tgcggtggca gccatccagg tggattgcga ttggtcagtt    5340
atgactctgt cgatcggaga agtactgtcc ttggctcagg ctaagacggc cgaggcctac    5400
acagcaaccg ccaagtggct tgctggctgc tatacgggga cgcggccgt ccccactgtt    5460 tcaattgttg acaagctctt cgccggaggg tgggcggccg tggtgggcca ttgccacagc    5520
gtaatagctg cggcggtggc ggcctacggg gcttctagga gccgccgtt ggcagccgcg    5580 gcttcctacc tgatggggtt gggcgtcgga ggcaacgccc aaacgcgttt ggcatctgcc    5640
ctcctattgg gggctgctgg gaccgccctg ggtactccgg ttgtgggttt gaccatggct    5700
ggggcattca tgggggtgc tagcgtctcc ccctctctgg tcaccatcct gttggggcc    5760 gtgggaggct gggagggcgt tgtcaatgcg gcaagccttg tctttgactt catggcgggg    5820
aaactttcat cagaagattt gtggtatgct atcccggtgc tgaccagtcc ggggcgggc    5880 ctcgcgggga tcgcccttgg actggttctg tactcagcta acaactctgg cactaccact    5940
tggctgaacc gtctgctgac gacgttgcca aggtcttcat gcatccctga cagttacttt    6000
cagcaggccg actactgtga caaagtctca gctgtgctcc gccgtttgag ccttacccgc    6060
actgtggttg ccctggtcaa cagggagccc aaggtggatg aggttcaggt ggggtacgtc    6120
tgggacctgt gggagtggat catgcgccag gtgcgcatgg tcatggctag actcagggcc    6180
ctctgccccg tggtgtcgct gcctttgtgg cactgcgggg aggggtggtc tggggaatgg    6240
ctgttggacg gccatgttga gagtcgctgc ctttgtggct gcgtgatcac cggcgatgtt    6300
ctgaatgggc aactcaaaga accagtttac tctaccaagc tgtgccggca ctattggatg    6360
gggactgttc ctgtgaacat gctgggctat ggtgagacgt cgcctctctt ggcttctgac    6420
accccgaagg tggtaccttt cgggacgtct ggctgggctg aggtggtggt gaccccctacc    6480 cacgtagtga tcaggaggac ctccgcctat aagttgctgc gccagcaaat cctatcggct    6540
gctgtagctg agccctatta cgtcgacggc attccggtct cgtgggacgc ggacgcgcga    6600
gcgcccgcca tggtctatgg ccctgggcaa agtgttacca ttgacgggga gcgctacacc    6660
ttgcctcacc agttgaggct taggaacgtg gcgccctctg aggtttcatc cgagatgacc    6720
attgaccttg gacggagac tgaagattca gaactgactg aagccgatct gccgccggcg    6780
gctgcagccc tccaggcgat cgagaatgct gcgaggattc tcgagccgct cattgatgtc    6840
atcatggagg actgtagtac accctctctt tgtggtagta gccgagagat gcctgtgtgg    6900
ggaggagaca tcccccgcac tccatcgcca gcacttatct cggttactga gagcagctca    6960
gatgagaaga ccccgtcggt gtcctcttcg caggaggata ccccgtcctc agactcattc    7020
gaggtcatcc aagagtccga gacagccgag gggaggaaa gtgtcttcaa cgtggctctt    7080
tccgtactaa aagccttatt tccacagagc gacgcgacca ggaagctcac cgtcaagatg    7140
tcatgctgtg ctgaaaagag cgtcacacgt ttttttttcat tagggctgac ggtggctgat    7200
gttgctagcc tgtgtgagat ggagattcag aaccatacag cctattgtga caaggtgcgc    7260
actccgcttg aattgcaggt tgggtgcttg tgggcaatg aacttacctt tgaatgtgac    7320
aagtgtgagg ctaggcaaga cttttggcc tccttctcct catctggtc tggtgtgccg    7380 ctaacgcggg ccacgccggc caagccccct gtggtgaggc cggttggttc tttgttggtg    7440
gccgacacta ccaaagtgta tgttaccaat ccggacaatg tgggaaggag ggtggacaag    7500
```

```
gtgaccttct ggcgcgctcc tagggttcat gacaaatatc ttgtggactc tatcgagcgg    7560
gctaagaggg ctgctcaagc ctgcctaagc atgggttaca cttatgagga agcaataagg    7620
actgtaaggc cacatgctgc catgggctgg ggatctaagg tgtcggtcaa agacttggcc    7680 accectgcgg ggaagatggc tgtccacgat cgacttcagg agatacttga agggactccg    7740
gtccccttta cccttactgt gaaaaaggag gtgttcttca agaccgaaa ggaggagaag     7800 gccectcgcc tcattgtgtt cccccccctg gacttccgga tagctgaaaa gcttatcctg    7860
ggagacccgg ggcgggtagc caaggcggtg ttggggggggg cttacgcctt ccagtacacc   7920
ccaaaccagc gagttaagga gatgctcaaa ctgtgggagt ccaaaaaaac ccttgcgcc     7980 atctgcgtgg acgccacgtg cttcgacagt agcattactg aagaggacgt ggccttagag    8040
acagagctat atgctctggc ctctgaccat ccagaatggg tgcgagccct tgggaaatac    8100
tatgcttcag gcaccatggt caccccagaa ggggtgcccg ttggtgagag gtattgtaga    8160
tcctcagggg tcttgacaac cagtgcgagc aattgcttga catgctacat caaggtggaa    8220
gccgcctgtg agagggtggg tctgaaaaat gtctcactcc tcattgctgg cgatgactgt    8280
ttgatcatat gtgagcggcc agtttgcgac cctagcgacg ctctgggcag agccctggct    8340
agctatgggt acgcatgcga gccctcatat catgcatcat tggacacggc ccccttctgc    8400
tccacttggc ttgccgagtg taatgcagat gggaagcgcc atttcttcct gacaacggac    8460
ttccggaggg cgctcgctcg catgtcgagc gagtatagtg acccgatggc ttcggccatc    8520
ggttacatcc tcctttatcc ttggcatccc atcacacggt gggtcatcat cccccacgtg    8580
ctaacatgcg cgtttagggg tggtggtaca ccgtctgatc cggtttggtg ccaagtacat    8640
ggtaattact acaagtttcc actggacaaa ctgcctaaca tcatcgtggc cctccacgga    8700
ccagcagcgt tgagggttac cgcagacaca actaagacaa aaatggaggc cggtaaggtc    8760
ttaagcgacc tcaagctccc tggcttagcg gtccaccgta agaaggccgg ggcactgcgt    8820
acgcgcatgc tccgttcgcg cggttgggcc gagttggcta ggggcctgtt gtggcatcca    8880
ggcctacggc tccctccccc tgagattgct ggtatcccg ggggtttccc ctctccccc     8940 ccctttatgg gggtggttca tcaattggat ttcacaagcc agaggagtcg ctggcggggg    9000 ttggggggtct tagccctgct catcgtggcc ctcttcgggt gaactaaatt catctgttgc    9060
ggcaaggtct ggtgactgat catcaccgga ggaggttccc gccctccccg ccccagggggt   9120 ctccccgctg ggtaaaaagg gcccggcctt gggaggcatg gtggttacta accccctggc    9180
agggtcaaag cctgatggtg ctaatgcact gccacttcgg tggcgggtcg ctaccttata    9240
gcgtaatccg tgactacggg ctgctcgcag agccctcccc ggatggggca cagtgcactg    9300
tgatctgaa                                                            9309

<210> SEQ ID NO 20
<211> LENGTH: 2842
<212> TYPE: PRT
<213> ORGANISM: Hepatitis G virus

<400> SEQUENCE: 20

Met Ala Val Leu Leu Leu Leu Val Val Glu Ala Gly Ala Ile Leu
 1               5                  10                  15

Ala Pro Ala Thr His Ala Cys Arg Ala Asn Gly Gln Tyr Phe Leu Thr
                20                  25                  30

Asn Cys Cys Ala Pro Glu Asp Ile Gly Phe Cys Leu Glu Gly Gly Cys
        35                  40                  45
```

-continued

```
Leu Val Ala Leu Gly Cys Thr Val Cys Thr Asp Gln Cys Trp Pro Leu
 50              55              60
Tyr Gln Ala Gly Leu Ala Val Arg Pro Gly Lys Ser Ala Ala Gln Leu
 65              70              75              80
Val Gly Glu Leu Gly Ser Leu Tyr Gly Pro Leu Ser Val Ser Ala Tyr
             85              90              95
Val Ala Gly Ile Leu Gly Leu Gly Glu Val Tyr Ser Gly Val Leu Thr
            100             105             110
Val Gly Val Ala Leu Thr Arg Arg Val Tyr Pro Val Pro Asn Leu Thr
            115             120             125
Cys Ala Val Glu Cys Glu Leu Lys Trp Glu Ser Phe Trp Arg Trp
 130             135             140
Thr Glu Gln Leu Ala Ser Asn Tyr Trp Ile Leu Glu Tyr Leu Trp Lys
145             150             155             160
Val Pro Phe Asp Phe Trp Arg Gly Val Met Ser Leu Thr Pro Leu Leu
            165             170             175
Val Cys Val Ala Ala Leu Leu Leu Glu Gln Arg Ile Val Met Val
            180             185             190
Phe Leu Leu Val Thr Met Ala Gly Met Ser Gln Gly Ala Pro Ala Ser
            195             200             205
Val Leu Gly Ser Arg Pro Phe Asp Tyr Gly Leu Thr Trp Gln Thr Cys
210             215             220
Ser Cys Lys Ala Asn Gly Ser Arg Ile Pro Thr Gly Glu Lys Val Trp
225             230             235             240
Asp Arg Gly Asn Val Thr Leu Leu Cys Asp Cys Pro Asn Gly Pro Trp
            245             250             255
Val Trp Leu Pro Ala Phe Cys Gln Ala Val Gly Trp Gly Asp Pro Ile
            260             265             270
Thr His Trp Ser His Gly Gln Asn Arg Trp Pro Leu Ser Cys Pro Gln
            275             280             285
Tyr Val Tyr Gly Ser Val Ser Val Thr Cys Val Trp Gly Ser Ala Ser
290             295             300
Trp Phe Ala Ser Thr Gly Gly Arg Asp Ser Lys Ile Asp Val Trp Ser
305             310             315             320
Leu Val Pro Val Gly Ser Ala Thr Cys Thr Ile Ala Ala Leu Gly Ser
            325             330             335
Ser Asp Arg Asp Thr Val Val Glu Leu Ser Glu Trp Gly Val Pro Cys
            340             345             350
Val Thr Cys Ile Leu Asp Arg Arg Pro Ala Ser Cys Gly Thr Cys Val
            355             360             365
Arg Asp Cys Trp Pro Glu Thr Gly Ser Val Arg Phe Pro Phe His Arg
370             375             380
Cys Gly Thr Gly Pro Arg Leu Thr Lys Asp Leu Glu Ala Val Pro Phe
385             390             395             400
Val Asn Arg Thr Thr Pro Phe Thr Ile Arg Gly Pro Leu Gly Asn Gln
            405             410             415
Gly Arg Gly Asn Pro Val Arg Ser Pro Leu Gly Phe Gly Ser Tyr Thr
            420             425             430
Met Thr Lys Ile Arg Asp Thr Leu His Leu Val Lys Cys Pro Thr Pro
            435             440             445
Ala Ile Glu Pro Pro Thr Gly Thr Phe Gly Phe Phe Pro Gly Thr Pro
450             455             460
Pro Leu Asn Asn Cys Met Leu Leu Gly Thr Glu Val Ser Glu Ala Leu
```

-continued

```
            465                 470                 475                 480
Gly Gly Ala Gly Leu Thr Gly Gly Phe Tyr Glu Pro Leu Val Arg Arg
                    485                 490                 495
Cys Ser Glu Leu Met Gly Arg Arg Asn Pro Val Cys Pro Gly Phe Ala
                500                 505                 510
Trp Leu Ser Ser Gly Arg Pro Asp Gly Phe Ile His Val Gln Gly His
            515                 520                 525
Leu Gln Glu Val Asp Ala Gly Asn Phe Ile Pro Pro Arg Trp Leu
    530                 535                 540
Leu Leu Asp Phe Val Phe Val Leu Leu Tyr Leu Met Lys Leu Ala Glu
545                 550                 555                 560
Ala Arg Leu Val Pro Leu Ile Leu Leu Leu Trp Trp Val Asn
                565                 570                 575
Gln Leu Ala Val Leu Gly Leu Pro Ala Val Asp Ala Val Ala Gly
            580                 585                 590
Glu Val Phe Ala Gly Pro Ala Leu Ser Trp Cys Leu Gly Leu Pro Thr
            595                 600                 605
Val Ser Met Ile Leu Gly Leu Ala Asn Leu Val Leu Tyr Phe Arg Trp
    610                 615                 620
Leu Gly Pro Gln Arg Leu Met Phe Leu Val Leu Trp Lys Leu Ala Arg
625                 630                 635                 640
Gly Ala Phe Pro Leu Ala Leu Leu Met Gly Ile Ser Ala Thr Arg Gly
                645                 650                 655
Arg Thr Ser Val Leu Gly Ala Glu Phe Cys Phe Asp Ala Thr Phe Glu
                660                 665                 670
Val Asp Thr Ser Val Leu Gly Trp Val Val Ala Ser Val Val Ala Trp
            675                 680                 685
Ala Ile Ala Leu Leu Ser Ser Met Ser Ala Gly Gly Trp Arg His Lys
        690                 695                 700
Ala Val Ile Tyr Arg Thr Trp Cys Lys Gly Tyr Gln Ala Ile Arg Gln
705                 710                 715                 720
Arg Val Val Arg Ser Pro Phe Gly Glu Gly Arg Pro Thr Lys Pro Leu
                725                 730                 735
Thr Phe Ala Trp Cys Leu Ala Ser Tyr Ile Trp Pro Asp Ala Val Met
            740                 745                 750
Met Val Val Ala Leu Val Leu Phe Gly Leu Phe Asp Ala Leu
        755                 760                 765
Asp Trp Ala Leu Glu Glu Ile Leu Val Ser Arg Pro Ser Leu Arg Arg
    770                 775                 780
Leu Ala Arg Val Ile Glu Cys Cys Val Met Ala Gly Glu Lys Ala Thr
785                 790                 795                 800
Thr Val Arg Leu Val Ser Lys Met Cys Ala Arg Gly Ala Tyr Leu Phe
                805                 810                 815
Asp His Met Gly Ser Phe Ser Arg Ala Val Lys Glu Arg Leu Leu Glu
            820                 825                 830
Trp Asp Ala Ala Leu Glu Pro Leu Ser Phe Thr Arg Thr Asp Cys Arg
            835                 840                 845
Ile Ile Arg Asp Ala Ala Arg Thr Leu Ser Cys Gly Gln Cys Val Met
    850                 855                 860
Gly Leu Pro Val Ala Arg Arg Gly Asp Glu Val Leu Ile Gly Val
865                 870                 875                 880
Phe Gln Asp Val Asn His Leu Pro Pro Gly Phe Val Pro Thr Ala Pro
                885                 890                 895
```

-continued

```
Val Val Ile Arg Arg Cys Gly Lys Gly Phe Leu Gly Val Thr Lys Ala
            900                 905                 910
Ala Leu Thr Gly Arg Asp Pro Asp Leu His Pro Gly Asn Val Met Val
            915                 920                 925
Leu Gly Thr Ala Thr Ser Arg Ser Met Gly Thr Cys Leu Asn Gly Leu
            930                 935                 940
Leu Phe Thr Thr Phe His Gly Ala Ser Ser Arg Thr Ile Ala Thr Pro
945                 950                 955                 960
Val Gly Ala Leu Asn Pro Arg Trp Trp Ser Ala Ser Asp Asp Val Thr
            965                 970                 975
Val Tyr Pro Leu Pro Asp Gly Ala Thr Ser Leu Thr Pro Cys Thr Cys
            980                 985                 990
Gln Ala Glu Ser Cys Trp Val Ile Arg Ser Asp Gly Ala Leu Cys His
            995                 1000                1005
Gly Leu Ser Lys Gly Asp Lys Val Glu Leu Asp Val Ala Met Glu Val
            1010                1015                1020
Ser Asp Phe Arg Gly Ser Ser Gly Ser Pro Val Leu Cys Asp Glu Gly
1025                1030                1035                1040
His Ala Val Gly Met Leu Val Ser Val Leu His Ser Ala Gly Glu Val
            1045                1050                1055
Thr Ala Ala Arg Phe Thr Arg Ala Trp Thr Gln Val Pro Thr Asp Ala
            1060                1065                1070
Lys Thr Thr Thr Asp Pro Pro Val Pro Ala Lys Gly Val Phe Lys
            1075                1080                1085
Glu Ala Pro Leu Phe Met Pro Thr Gly Ala Gly Lys Ser Thr Arg Val
            1090                1095                1100
Pro Leu Glu Tyr Gly Asn Met Gly His Lys Val Leu Ile Leu Asn Pro
1105                1110                1115                1120
Ser Val Ala Thr Val Arg Ala Met Gly Pro Tyr Met Glu Arg Leu Ala
            1125                1130                1135
Gly Lys His Pro Ser Ile Tyr Cys Gly His Asp Thr Thr Ala Phe Thr
            1140                1145                1150
Arg Ile Thr Asp Ser Pro Leu Thr Tyr Ser Thr Tyr Gly Arg Phe Leu
            1155                1160                1165
Ala Asn Pro Arg Gln Met Leu Arg Gly Val Ser Val Ile Cys Asp
            1170                1175                1180
Glu Cys His Ser His Asp Ser Thr Val Leu Leu Gly Ile Gly Arg Val
1185                1190                1195                1200
Arg Glu Leu Ala Arg Gly Cys Gly Val Gln Leu Val Leu Tyr Ala Thr
            1205                1210                1215
Ala Thr Pro Pro Gly Ser Pro Met Thr Gln His Pro Ser Ile Ile Glu
            1220                1225                1230
Thr Lys Leu Asp Val Gly Glu Ile Pro Phe Tyr Gly His Gly Ile Pro
            1235                1240                1245
Leu Glu Arg Met Arg Thr Gly Arg His Leu Val Phe Cys His Ser Lys
            1250                1255                1260
Ala Glu Cys Glu Arg Leu Ala Gly Gln Phe Ser Ala Arg Gly Val Asn
1265                1270                1275                1280
Ala Ile Ala Tyr Tyr Arg Gly Lys Asp Ser Ser Ile Ile Gln Asp Gly
            1285                1290                1295
Asp Leu Val Val Cys Ala Thr Asp Ala Leu Ser Thr Gly Tyr Thr Gly
            1300                1305                1310
```

```
Asn Phe Asp Ser Val Thr Asp Cys Gly Leu Val Val Glu Glu Val Val
        1315                1320                1325

Glu Val Thr Leu Asp Pro Thr Ile Thr Ile Ser Leu Arg Thr Val Pro
    1330                1335                1340

Ala Ser Ala Glu Leu Ser Met Gln Arg Gly Arg Thr Gly Arg Gly
1345                1350                1355                1360

Arg Ser Gly Arg Tyr Tyr Tyr Ala Gly Val Gly Lys Ala Pro Ala Gly
        1365                1370                1375

Val Val Arg Ser Gly Pro Val Trp Ser Ala Val Glu Ala Gly Val Thr
            1380                1385                1390

Trp Tyr Gly Met Glu Pro Asp Leu Thr Ala Asn Leu Leu Arg Leu Tyr
        1395                1400                1405

Asp Asp Cys Pro Tyr Thr Ala Ala Val Ala Ala Asp Ile Gly Glu Ala
    1410                1415                1420

Ala Val Phe Phe Ser Gly Leu Ala Pro Leu Arg Met His Pro Asp Val
1425                1430                1435                1440

Ser Trp Ala Lys Val Arg Gly Val Asn Trp Pro Leu Leu Val Gly Val
        1445                1450                1455

Gln Arg Thr Met Cys Arg Glu Thr Leu Ser Pro Gly Pro Ser Asp Asp
        1460                1465                1470

Pro Gln Trp Ala Gly Leu Lys Gly Pro Asn Pro Val Pro Leu Leu Leu
        1475                1480                1485

Arg Trp Gly Asn Asp Leu Pro Ser Lys Val Ala Gly His His Ile Val
        1490                1495                1500

Asp Asp Leu Val Arg Arg Leu Gly Val Ala Glu Gly Tyr Val Arg Cys
1505                1510                1515                1520

Asp Ala Gly Pro Ile Leu Met Val Gly Leu Ala Ile Ala Gly Gly Met
        1525                1530                1535

Ile Tyr Ala Ser Tyr Thr Gly Ser Ile Val Val Thr Asp Trp Asp
        1540                1545                1550

Val Lys Gly Gly Gly Ala Pro Leu Tyr Arg His Gly Asp Gln Ala Thr
        1555                1560                1565

Pro Gln Pro Val Val Gln Val Pro Pro Val Asp His Arg Pro Gly Gly
    1570                1575                1580

Glu Ser Ala Pro Ser Asp Ala Lys Thr Val Thr Asp Ala Val Ala Ala
1585                1590                1595                1600

Ile Gln Val Asp Cys Asp Trp Ser Val Met Thr Leu Ser Ile Gly Glu
        1605                1610                1615

Val Leu Ser Leu Ala Gln Ala Lys Thr Ala Glu Ala Tyr Thr Ala Thr
        1620                1625                1630

Ala Lys Trp Leu Ala Gly Cys Tyr Thr Gly Thr Arg Ala Val Pro Thr
        1635                1640                1645

Val Ser Ile Val Asp Lys Leu Phe Ala Gly Gly Trp Ala Ala Val Val
        1650                1655                1660

Gly His Cys His Ser Val Ile Ala Ala Val Ala Ala Tyr Gly Ala
1665                1670                1675                1680

Ser Arg Ser Pro Pro Leu Ala Ala Ala Ala Ser Tyr Leu Met Gly Leu
            1685                1690                1695

Gly Val Gly Gly Asn Ala Gln Thr Arg Leu Ala Ser Ala Leu Leu Leu
        1700                1705                1710

Gly Ala Ala Gly Thr Ala Leu Gly Thr Pro Val Val Gly Leu Thr Met
        1715                1720                1725

Ala Gly Ala Phe Met Gly Gly Ala Ser Val Ser Pro Ser Leu Val Thr
```

```
                    1730              1735              1740
Ile Leu Leu Gly Ala Val Gly Gly Trp Glu Gly Val Val Asn Ala Ala
1745              1750              1755              1760

Ser Leu Val Phe Asp Phe Met Ala Gly Lys Leu Ser Ser Glu Asp Leu
                    1765              1770              1775

Trp Tyr Ala Ile Pro Val Leu Thr Ser Pro Gly Ala Gly Leu Ala Gly
                    1780              1785              1790

Ile Ala Leu Gly Leu Val Leu Tyr Ser Ala Asn Asn Ser Gly Thr Thr
                    1795              1800              1805

Thr Trp Leu Asn Arg Leu Leu Thr Thr Leu Pro Arg Ser Ser Cys Ile
                    1810              1815              1820

Pro Asp Ser Tyr Phe Gln Gln Ala Asp Tyr Cys Asp Lys Val Ser Ala
1825              1830              1835              1840

Val Leu Arg Arg Leu Ser Leu Thr Arg Thr Val Ala Leu Val Asn
                    1845              1850              1855

Arg Glu Pro Lys Val Asp Glu Val Gln Val Gly Tyr Val Trp Asp Leu
                    1860              1865              1870

Trp Glu Trp Ile Met Arg Gln Val Arg Met Val Met Ala Arg Leu Arg
                    1875              1880              1885

Ala Leu Cys Pro Val Val Ser Leu Pro Leu Trp His Cys Gly Glu Gly
                    1890              1895              1900

Trp Ser Gly Glu Trp Leu Leu Asp Gly His Val Glu Ser Arg Cys Leu
1905              1910              1915              1920

Cys Gly Cys Val Ile Thr Gly Asp Val Leu Asn Gly Gln Leu Lys Glu
                    1925              1930              1935

Pro Val Tyr Ser Thr Lys Leu Cys Arg His Tyr Trp Met Gly Thr Val
                    1940              1945              1950

Pro Val Asn Met Leu Gly Tyr Gly Glu Thr Ser Pro Leu Leu Ala Ser
                    1955              1960              1965

Asp Thr Pro Lys Val Val Pro Phe Gly Thr Ser Gly Trp Ala Glu Val
                    1970              1975              1980

Val Val Thr Pro Thr His Val Val Ile Arg Arg Thr Ser Ala Tyr Lys
1985              1990              1995              2000

Leu Leu Arg Gln Gln Ile Leu Ser Ala Ala Val Ala Glu Pro Tyr Tyr
                    2005              2010              2015

Val Asp Gly Ile Pro Val Ser Trp Asp Ala Asp Ala Arg Ala Pro Ala
                    2020              2025              2030

Met Val Tyr Gly Pro Gly Gln Ser Val Thr Ile Asp Gly Glu Arg Tyr
                    2035              2040              2045

Thr Leu Pro His Gln Leu Arg Leu Arg Asn Val Ala Pro Ser Glu Val
                    2050              2055              2060

Ser Ser Glu Met Thr Ile Asp Leu Gly Thr Glu Thr Glu Asp Ser Glu
2065              2070              2075              2080

Leu Thr Glu Ala Asp Leu Pro Pro Ala Ala Ala Leu Gln Ala Ile
                    2085              2090              2095

Glu Asn Ala Ala Arg Ile Leu Glu Pro Leu Ile Asp Val Ile Met Glu
                    2100              2105              2110

Asp Cys Ser Thr Pro Ser Leu Cys Gly Ser Ser Arg Glu Met Pro Val
                    2115              2120              2125

Trp Gly Gly Asp Ile Pro Arg Thr Pro Ser Pro Ala Leu Ile Ser Val
                    2130              2135              2140

Thr Glu Ser Ser Ser Asp Glu Lys Thr Pro Ser Val Ser Ser Ser Gln
2145              2150              2155              2160
```

```
Glu Asp Thr Pro Ser Ser Asp Ser Phe Glu Val Ile Gln Ser Glu
            2165                2170                2175

Thr Ala Glu Gly Glu Glu Ser Val Phe Asn Val Ala Leu Ser Val Leu
        2180                2185                2190

Lys Ala Leu Phe Pro Gln Ser Asp Ala Thr Arg Lys Leu Thr Val Lys
        2195                2200                2205

Met Ser Cys Cys Ala Glu Lys Ser Val Thr Arg Phe Phe Ser Leu Gly
    2210                2215                2220

Leu Thr Val Ala Asp Val Ala Ser Leu Cys Glu Met Glu Ile Gln Asn
2225                2230                2235                2240

His Thr Ala Tyr Cys Asp Lys Val Arg Thr Pro Leu Glu Leu Gln Val
            2245                2250                2255

Gly Cys Leu Val Gly Asn Glu Leu Thr Phe Glu Cys Asp Lys Cys Glu
        2260                2265                2270

Ala Arg Gln Glu Thr Leu Ala Ser Phe Ser Tyr Ile Trp Ser Gly Val
        2275                2280                2285

Pro Leu Thr Arg Ala Thr Pro Ala Lys Pro Pro Val Val Arg Pro Val
    2290                2295                2300

Gly Ser Leu Leu Val Ala Asp Thr Thr Lys Val Tyr Val Thr Asn Pro
2305                2310                2315                2320

Asp Asn Val Gly Arg Arg Val Asp Lys Val Thr Phe Trp Arg Ala Pro
        2325                2330                2335

Arg Val His Asp Lys Tyr Leu Val Asp Ser Ile Glu Arg Ala Lys Arg
        2340                2345                2350

Ala Ala Gln Ala Cys Leu Ser Met Gly Tyr Thr Tyr Glu Glu Ala Ile
        2355                2360                2365

Arg Thr Val Arg Pro His Ala Ala Met Gly Trp Gly Ser Lys Val Ser
    2370                2375                2380

Val Lys Asp Leu Ala Thr Pro Ala Gly Lys Met Ala Val His Asp Arg
2385                2390                2395                2400

Leu Gln Glu Ile Leu Glu Gly Thr Pro Val Pro Phe Thr Leu Thr Val
        2405                2410                2415

Lys Lys Glu Val Phe Phe Lys Asp Arg Lys Glu Glu Lys Ala Pro Arg
        2420                2425                2430

Leu Ile Val Phe Pro Pro Leu Asp Phe Arg Ile Ala Glu Lys Leu Ile
        2435                2440                2445

Leu Gly Asp Pro Gly Arg Val Ala Lys Ala Val Leu Gly Gly Ala Tyr
    2450                2455                2460

Ala Phe Gln Tyr Thr Pro Asn Gln Arg Val Lys Glu Met Leu Lys Leu
2465                2470                2475                2480

Trp Glu Ser Lys Lys Thr Pro Cys Ala Ile Cys Val Asp Ala Thr Cys
            2485                2490                2495

Phe Asp Ser Ser Ile Thr Glu Glu Asp Val Ala Leu Glu Thr Glu Leu
        2500                2505                2510

Tyr Ala Leu Ala Ser Asp His Pro Glu Trp Val Arg Ala Leu Gly Lys
        2515                2520                2525

Tyr Tyr Ala Ser Gly Thr Met Val Thr Pro Glu Gly Val Pro Val Gly
    2530                2535                2540

Glu Arg Tyr Cys Arg Ser Ser Gly Val Leu Thr Thr Ser Ala Ser Asn
2545                2550                2555                2560

Cys Leu Thr Cys Tyr Ile Lys Val Glu Ala Ala Cys Glu Arg Val Gly
            2565                2570                2575
```

```
Leu Lys Asn Val Ser Leu Leu Ile Ala Gly Asp Asp Cys Leu Ile Ile
            2580                2585                2590

Cys Glu Arg Pro Val Cys Asp Pro Ser Asp Ala Leu Gly Arg Ala Leu
        2595                2600                2605

Ala Ser Tyr Gly Tyr Ala Cys Glu Pro Ser Tyr His Ala Ser Leu Asp
    2610                2615                2620

Thr Ala Pro Phe Cys Ser Thr Trp Leu Ala Glu Cys Asn Ala Asp Gly
2625                2630                2635                2640

Lys Arg His Phe Phe Leu Thr Thr Asp Phe Arg Arg Ala Leu Ala Arg
            2645                2650                2655

Met Ser Ser Glu Tyr Ser Asp Pro Met Ala Ser Ala Ile Gly Tyr Ile
        2660                2665                2670

Leu Leu Tyr Pro Trp His Pro Ile Thr Arg Trp Val Ile Ile Pro His
    2675                2680                2685

Val Leu Thr Cys Ala Phe Arg Gly Gly Gly Thr Pro Ser Asp Pro Val
2690                2695                2700

Trp Cys Gln Val His Gly Asn Tyr Tyr Lys Phe Pro Leu Asp Lys Leu
2705                2710                2715                2720

Pro Asn Ile Ile Val Ala Leu His Gly Pro Ala Ala Leu Arg Val Thr
            2725                2730                2735

Ala Asp Thr Thr Lys Thr Lys Met Glu Ala Gly Lys Val Leu Ser Asp
        2740                2745                2750

Leu Lys Leu Pro Gly Leu Ala Val His Arg Lys Lys Ala Gly Ala Leu
    2755                2760                2765

Arg Thr Arg Met Leu Arg Ser Arg Gly Trp Ala Glu Leu Ala Arg Gly
    2770                2775                2780

Leu Leu Trp His Pro Gly Leu Arg Leu Pro Pro Pro Glu Ile Ala Gly
2785                2790                2795                2800

Ile Pro Gly Gly Phe Pro Ser Pro Pro Phe Met Gly Val Val His
            2805                2810                2815

Gln Leu Asp Phe Thr Ser Gln Arg Ser Arg Trp Arg Gly Leu Gly Val
        2820                2825                2830

Leu Ala Leu Leu Ile Val Ala Leu Phe Gly
    2835                2840

<210> SEQ ID NO 21
<211> LENGTH: 414
<212> TYPE: PRT
<213> ORGANISM: Hepatitis G virus

<400> SEQUENCE: 21

Val Ala Leu Val Asn Arg Glu Pro Lys Val Asp Glu Val Gln Val Gly
1               5                   10                  15

Tyr Val Trp Asp Leu Trp Glu Trp Ile Met Arg Gln Val Arg Met Val
            20                  25                  30

Met Ala Arg Leu Arg Ala Leu Cys Pro Val Val Ser Leu Pro Leu Trp
        35                  40                  45

His Cys Gly Glu Gly Trp Ser Gly Glu Trp Leu Leu Asp Gly His Val
    50                  55                  60

Glu Ser Arg Cys Leu Cys Gly Cys Val Ile Thr Gly Asp Val Leu Asn
65                  70                  75                  80

Gly Gln Leu Lys Glu Pro Val Tyr Ser Thr Lys Leu Cys Arg His Tyr
                85                  90                  95

Trp Met Gly Thr Val Pro Val Asn Met Leu Gly Tyr Gly Glu Thr Ser
            100                 105                 110
```

-continued

```
Pro Leu Leu Ala Ser Asp Thr Pro Lys Val Val Pro Phe Gly Thr Ser
            115                 120                 125
Gly Trp Ala Glu Val Val Thr Pro Thr His Val Val Ile Arg Arg
    130                 135                 140
Thr Ser Ala Tyr Lys Leu Leu Arg Gln Gln Ile Leu Ser Ala Ala Val
145                 150                 155                 160
Ala Glu Pro Tyr Tyr Val Asp Gly Ile Pro Val Ser Trp Asp Ala Asp
                165                 170                 175
Ala Arg Ala Pro Ala Met Val Tyr Gly Pro Gly Gln Ser Val Thr Ile
            180                 185                 190
Asp Gly Glu Arg Tyr Thr Leu Pro His Gln Leu Arg Leu Arg Asn Val
        195                 200                 205
Ala Pro Ser Glu Val Ser Ser Glu Met Thr Ile Asp Leu Gly Thr Glu
    210                 215                 220
Thr Glu Asp Ser Glu Leu Thr Glu Ala Asp Leu Pro Pro Ala Ala Ala
225                 230                 235                 240
Ala Leu Gln Ala Ile Glu Asn Ala Ala Arg Ile Leu Glu Pro Leu Ile
                245                 250                 255
Asp Val Ile Met Glu Asp Cys Ser Thr Pro Ser Leu Cys Gly Ser Ser
            260                 265                 270
Arg Glu Met Pro Val Trp Gly Gly Asp Ile Pro Arg Thr Pro Ser Pro
        275                 280                 285
Ala Leu Ile Ser Val Thr Glu Ser Ser Asp Glu Lys Thr Pro Ser
    290                 295                 300
Val Ser Ser Ser Gln Glu Asp Thr Pro Ser Ser Asp Ser Phe Glu Val
305                 310                 315                 320
Ile Gln Glu Ser Glu Thr Ala Glu Gly Glu Glu Ser Val Phe Asn Val
                325                 330                 335
Ala Leu Ser Val Leu Lys Ala Leu Phe Pro Gln Ser Asp Ala Thr Arg
            340                 345                 350
Lys Leu Thr Val Lys Met Ser Cys Cys Ala Glu Lys Ser Val Thr Arg
        355                 360                 365
Phe Phe Ser Leu Gly Leu Thr Val Ala Asp Val Ala Ser Leu Cys Glu
    370                 375                 380
Met Glu Ile Gln Asn His Thr Ala Tyr Cys Asp Lys Val Arg Thr Pro
385                 390                 395                 400
Leu Glu Leu Gln Val Gly Cys Leu Val Gly Asn Glu Leu Thr
                405                 410

<210> SEQ ID NO 22
<211> LENGTH: 414
<212> TYPE: PRT
<213> ORGANISM: Hepatitis G virus

<400> SEQUENCE: 22

Val Ala Leu Val Asn Arg Glu Pro Lys Val Asp Glu Val Gln Val Gly
 1               5                  10                  15
Tyr Val Trp Asp Leu Trp Glu Trp Ile Met Arg Gln Val Arg Met Val
                20                  25                  30
Met Ala Arg Leu Arg Ala Leu Cys Pro Val Val Ser Leu Pro Leu Trp
            35                  40                  45
His Cys Gly Glu Gly Trp Ser Gly Glu Trp Leu Leu Asp Gly His Val
        50                  55                  60
Glu Ser Arg Cys Leu Cys Gly Cys Val Ile Thr Gly Asp Val Leu Asn
```

```
                65                  70                  75                  80
            Gly Gln Leu Lys Asp Pro Val Tyr Ser Thr Lys Leu Cys Arg His Tyr
                            85                  90                  95
            Trp Met Gly Thr Val Pro Val Asn Met Leu Gly Tyr Gly Glu Thr Ser
                        100                 105                 110
            Pro Leu Leu Ala Ser Asp Thr Pro Lys Val Val Pro Phe Gly Thr Ser
                        115                 120                 125
            Gly Trp Ala Glu Val Val Thr Pro Thr His Val Val Ile Arg Arg
                    130                 135                 140
            Thr Ser Ala Tyr Lys Leu Leu Arg Gln Gln Ile Leu Ser Ala Ala Val
            145                 150                 155                 160
            Ala Glu Pro Tyr Tyr Val Asp Gly Ile Pro Val Ser Trp Asp Ala Asp
                            165                 170                 175
            Ala Arg Ala Pro Ala Met Val Tyr Gly Pro Gly Gln Ser Val Thr Ile
                        180                 185                 190
            Asp Gly Glu Arg Tyr Thr Leu Pro His Gln Leu Arg Leu Arg Asn Val
                        195                 200                 205
            Ala Pro Ser Glu Val Ser Ser Glu Val Ser Ile Asp Ile Gly Thr Glu
                    210                 215                 220
            Thr Glu Asp Ser Glu Leu Thr Glu Ala Asp Leu Pro Ala Ala Ala
            225                 230                 235                 240
            Ala Leu Gln Ala Ile Glu Asn Ala Ala Arg Ile Leu Glu Pro His Ile
                            245                 250                 255
            Asp Val Ile Met Glu Asp Cys Ser Thr Pro Ser Leu Cys Gly Ser Ser
                        260                 265                 270
            Arg Glu Met Pro Val Trp Gly Glu Asp Ile Pro Arg Thr Pro Ser Pro
                        275                 280                 285
            Ala Leu Ile Ser Val Thr Glu Ser Ser Pro Asp Glu Lys Thr Pro Ser
                    290                 295                 300
            Val Ser Ser Ser Gln Glu Asp Thr Pro Ser Ser Asp Ser Phe Glu Val
            305                 310                 315                 320
            Ile Gln Glu Ser Glu Thr Ala Glu Gly Glu Glu Ser Val Phe Asn Val
                            325                 330                 335
            Ala Leu Ser Val Leu Lys Ala Leu Phe Pro Gln Ser Asp Ala Thr Arg
                        340                 345                 350
            Lys Leu Thr Val Lys Met Ser Cys Cys Val Glu Lys Ser Val Thr Arg
                        355                 360                 365
            Phe Phe Ser Leu Gly Leu Thr Val Ala Asp Val Ala Ser Leu Cys Glu
                    370                 375                 380
            Met Glu Ile Gln Asn His Thr Ala Tyr Cys Asp Lys Val Arg Thr Pro
            385                 390                 395                 400
            Leu Glu Leu Gln Val Gly Cys Leu Val Gly Asn Glu Leu Thr
                            405                 410

<210> SEQ ID NO 23
<211> LENGTH: 97
<212> TYPE: DNA
<213> ORGANISM: Hepatitis G virus

<400> SEQUENCE: 23
tctgggcaaa gtgtcaccat tgacggggag cgctacacct tgccgcacca gttgcggctc        60
aggaacgtgg cgccctctga ggtttcatcc gaggtgt                                  97

<210> SEQ ID NO 24
```

```
<211> LENGTH: 97
<212> TYPE: DNA
<213> ORGANISM: Hepatitis G virus

<400> SEQUENCE: 24
tctgggcaaa gcgttaccat tgacggggag cgctacacct tgccgcacca gttgcggctc    60
aggaacgtga cgccctctga ggtttcatcc gaggtgt                             97

<210> SEQ ID NO 25
<211> LENGTH: 97
<212> TYPE: DNA
<213> ORGANISM: Hepatitis G virus

<400> SEQUENCE: 25
tctgggcaaa gtgtcaccat tgacggggag cgctacacct tgccgcacca gttgcggctc    60
aggaacgtgg cgccctctga ggtttcatcc gaggtgt                             97

<210> SEQ ID NO 26
<211> LENGTH: 97
<212> TYPE: DNA
<213> ORGANISM: Hepatitis G virus

<400> SEQUENCE: 26
tctgggcaaa gcgttaccat tgacggggag cgctacacct tgccgcacca gttgcggctc    60
aggaacgtgg cgccctctga ggtttcatcc gaggtgt                             97

<210> SEQ ID NO 27
<211> LENGTH: 97
<212> TYPE: DNA
<213> ORGANISM: Hepatitis G virus

<400> SEQUENCE: 27
tctgggcaaa gcgttaccat tgacggggag cgctacacct tgccccacca gctgaggctt    60
aggaacgtgg cgccctctga ggtttcatcc gaggtgt                             97

<210> SEQ ID NO 28
<211> LENGTH: 97
<212> TYPE: DNA
<213> ORGANISM: Hepatitis G virus

<400> SEQUENCE: 28
tctggacaaa gtgtcaccat tgacggggag cgctacacct tgccccacca gctgaggctt    60
aggaacgtgg cgccctctga ggtttcatcc gaggtgt                             97

<210> SEQ ID NO 29
<211> LENGTH: 97
<212> TYPE: DNA
<213> ORGANISM: Hepatitis G virus

<400> SEQUENCE: 29
tctgggcaaa gtgttaccat tgacggggag cgctacacct tgccccacca gctgaggctt    60
aggaacgtgg cgccctctga ggtttcatcc gaggtgt                             97

<210> SEQ ID NO 30
<211> LENGTH: 97
<212> TYPE: DNA
<213> ORGANISM: Hepatitis G virus

<400> SEQUENCE: 30
tctgggcaaa gtgtcaccat tgacggggag cgctacacct tgccccacca gctgaggctt    60
```

```
aggaacgtgg cgccctctga ggtttcatcc gaggtgt                              97

<210> SEQ ID NO 31
<211> LENGTH: 97
<212> TYPE: DNA
<213> ORGANISM: Hepatitis G virus

<400> SEQUENCE: 31
tctgggcaaa gcgtcaccat tgacggggag cgctacacct tgccccacca gctgaggctt    60
aggaacgtgg cgccctctga ggtttcatcc gaggtgt                              97

<210> SEQ ID NO 32
<211> LENGTH: 97
<212> TYPE: DNA
<213> ORGANISM: Hepatitis G virus

<400> SEQUENCE: 32
ccatagacat tgggacggag actgaggatt cagaactgac tgaggctgac ctgccgccgg    60
cagctgcggc cctccaggcg atcgagaatg ctgcgag                              97

<210> SEQ ID NO 33
<211> LENGTH: 97
<212> TYPE: DNA
<213> ORGANISM: Hepatitis G virus

<400> SEQUENCE: 33
ccatagacat tgggacggag actgaggatt cagaactgac tgaggctgac ctgtcgccgg    60
cagctgcggc cctccaggcg atcgagaatg ctgcgag                              97

<210> SEQ ID NO 34
<211> LENGTH: 97
<212> TYPE: DNA
<213> ORGANISM: Hepatitis G virus

<400> SEQUENCE: 34
ccatagacat tgggacggag actgaggatt cagaactgac tgaggctgac ctgccgccgg    60
cagccgcggc cctccaggcg atcgagaatg ctgcgag                              97

<210> SEQ ID NO 35
<211> LENGTH: 97
<212> TYPE: DNA
<213> ORGANISM: Hepatitis G virus

<400> SEQUENCE: 35
ccatagacat tgggacggag actgaggatt cagaactgac tgaggctgac ctgccgccgg    60
cagctgcggc cctccaggcg atcgagaatg ctgcgag                              97

<210> SEQ ID NO 36
<211> LENGTH: 97
<212> TYPE: DNA
<213> ORGANISM: Hepatitis G virus

<400> SEQUENCE: 36
ccattgacat tgggacggag actgaagact cagaactgac tgaggccgat ctgccgccgg    60
cggctgctgc tctccaagcg attgagaatg ctgcgag                              97

<210> SEQ ID NO 37
<211> LENGTH: 97
<212> TYPE: DNA
```

```
<213> ORGANISM: Hepatitis G virus

<400> SEQUENCE: 37
ccattgacat tgggacggag actgaagact cagaactgac tgaggccgat ctgccgccgg      60
cggctgctgc tctccaagcg attgagaatg ctgcgag                              97

<210> SEQ ID NO 38
<211> LENGTH: 97
<212> TYPE: DNA
<213> ORGANISM: Hepatitis G virus

<400> SEQUENCE: 38
ccattgacat tgggacggag actgaagact cagaactgac tgaggccgat ctgccgccgg      60
cggctgctgc tctccaagcg attgagaatg ctgcgag                              97

<210> SEQ ID NO 39
<211> LENGTH: 97
<212> TYPE: DNA
<213> ORGANISM: Hepatitis G virus

<400> SEQUENCE: 39
ccattgacat tgggacggag actgaagact cagaactgac tgaggccgat ctgccgccgg      60
cggctgctgc tctccaagcg attgagaatg ctgcgag                              97

<210> SEQ ID NO 40
<211> LENGTH: 97
<212> TYPE: DNA
<213> ORGANISM: Hepatitis G virus

<400> SEQUENCE: 40
ccattgacat tgggacggag actgaagact cagaactgac tgaggccgat ctgccgccgg      60
cggctgctgc tctccaagcg attgagaatg ctgcgag                              97

<210> SEQ ID NO 41
<211> LENGTH: 15
<212> TYPE: PRT
<213> ORGANISM: Hepatitis G virus

<400> SEQUENCE: 41

Phe Gln Tyr Thr Pro Asn Gln Arg Ile Arg Glu Met Leu Lys Leu
 1               5                  10                  15

<210> SEQ ID NO 42
<211> LENGTH: 15
<212> TYPE: PRT
<213> ORGANISM: Hepatitis G virus

<400> SEQUENCE: 42

Phe Gln Tyr Thr Pro Asn Gln Arg Val Lys Glu Met Leu Lys Leu
 1               5                  10                  15

<210> SEQ ID NO 43
<211> LENGTH: 16
<212> TYPE: PRT
<213> ORGANISM: Hepatitis G virus

<400> SEQUENCE: 43

Gly Ile Pro Gly Ala Phe Pro Leu Ser Pro Pro Tyr Met Gly Val Val
 1               5                  10                  15

<210> SEQ ID NO 44
```

```
<211> LENGTH: 16
<212> TYPE: PRT
<213> ORGANISM: Hepatitis G virus

<400> SEQUENCE: 44

Gly Ile Pro Gly Gly Phe Ser Pro Ser Pro Pro Phe Met Gly Val Val
1               5                   10                  15
```

GB VIRUS C AND METHODS OF TREATING VIRAL INFECTIONS

CLAIM OF PRIORITY

This application claims priority under 35 U.S.C. § 119(e) from U.S. Provisional Application Ser. No. 60/421,408, filed Oct. 24, 2002, which is incorporated by reference herein.

U.S. application Ser. No. 09/828,498, PCT Application Number PCT/US01/11389, U.S. provisional patent application Ser. No. 60/253,390, filed Nov. 27, 2000, U.S. provisional patent application Ser. No. 60/195,597, filed on Apr. 6, 2000, are incorporated by reference herein.

STATEMENT OF GOVERNMENT RIGHTS

The invention was made with the support of NIH Grant numbers R01AA12671 and AI 250478. The U.S. Government has certain rights in the invention.

BACKGROUND OF THE INVENTION

I. Field of the Invention

The present invention relates generally to the fields of molecular biology and virology. More particularly, it concerns an infectious clone of GBV-C, which can be used in treatment of other related hepatitis viruses infections and HIV, as well as broader uses in therapeutic and preventative therapies.

II. Description of Related Art

A. GB Virus Type C

Hepatitis C virus (HCV) is responsible for causing hepatitis C, a disease that chronically affects approximately four million Americans, many of whom may develop liver disease. Hepatitis C annually accounts for as many as 1,000 liver transplants in the United States and between 8,000 and 10,000 deaths. There is no vaccine or preventative treatment against HCV infection and treatment regimens may cause unwanted side effects.

GB virus type C (GBV-C), also known as hepatitis G virus (HGV), is a recently described virus whose genomic organization and nucleotide sequence places it in the Flavivirus family (Robertson et al., 1998). It is the most closely related human virus to HCV (Leary et al., 1996; Linnen et al., 1996; Simons et al., 1995), a major, worldwide pathogen (Robertson et al., 1998). It has been suggested that these viruses should be classified together with non-human GB-hepatitis agents as the hepacivirus genus. Both GBV-C and HCV appear to utilize the LDL receptor for viral entry (Agnello et al., 1999). Thus, comparison of GBV-C and HCV may provide insight into the reasons why HCV does not appear to replicate as efficiently in cell culture as GBV-C, and why GBV-C is cleared more efficiently by the host immune response than HCV (Gutierrez et al., 1997; Thomas et al., 1998; Toyoda et al., 2000).

Although GBV-C was originally associated with post-transfusion hepatitis in humans (Linnen et al., 1996), subsequent epidemiological studies indicated that it does not cause acute or chronic hepatitis (Alter et al., 1997a; Alter et al., 1997b). In addition, experimental GBV-C infection of chimpanzees was not associated with acute hepatitis (Bukh et al., 1998).

Persistent GBV-C viremia (as detected by RT-PCR) is common, with 0.9% to 3% of healthy U.S. blood donors and approximately 20%-30% of patients with HCV infection persistently infected with GBV-C (Dawson et al., 1996; Feucht et al., 1997; Guitierrez et al., 1997; Simons et al., 1995a; Simons et al., 1995b; Tacke et al., 1997). Following infection, about 80% of people clear their viremia, concomitantly developing antibody to the GBV-C E2 protein (Feucht et al., 1997; Gutierrez et al., 1997; Thomas et al., 1998). Thus, it is estimated that approximately 20% of infected people remain viremic for long periods of time. GBV-C appears to be transmitted primarily by parenteral exposure (Simons et al., 1995), although there are data suggesting that sexual and/or household transmission of GBV-C infection may occur (Akiyoshi et al., 1999; de Martino et al., 1998; Nerurkar et al., 1998; Tanaka et al., 1997; Wu et al., 1997).

B. GBV-C and HIV

Recently, GBV-C has been investigated in the context of HIV infection. The course of HIV-1 infection is extremely variable among infected individuals, although the reasons for this observation are incompletely understood. Individuals whose HIV disease progresses slowly are often called long-term non-progressors (LTNPs). The prevalence of LTNPs varies from 1% to 25% of infected people, depending upon the definition used (reviewed in Easterbrook, 1999). There are no specific clinical criteria for LTNP; however, non-progression generally implies the absence of HIV-related clinical disease 10 or more years following infection and an absolute CD4 count of $\geq 500$ cells/mm$^3$ (Easterbrook, 1999). Evaluation of LTNP's has identified HIV isolates with deletions in key replicative genes (Deacon et al., 1995) and host genetic factors, including specific HLA haplotypes (reviewed in reference Rowland-Jones, 1999) or, in some individuals, polymorphisms that result in absent or reduced expression of HIV co-receptors (Huang et al., 1996). However, these findings are uncommon and thought to account for no more than one-third of LTNP's (Rowland-Jones, 1999).

Persistent GBV-C infection is common in humans, with infection rates of approximately 1.8% in healthy blood donors, 15% in HCV positive people (Dawson et al., 1996), and 35%-40% in HIV positive individuals. GBV-C infection can persist for decades in the absence of any clinical morbidity or mortality. Among immune-competent individuals, it is estimated that 60% to 75% of GBV-C-infected people clear the infection, concomitantly developing antibodies to the envelope glycoprotein E2 (Thomas et al., 1998). GBV-C has been propagated in cultures of peripheral blood mononuclear cells (PBMC's) (Fogeda et al., 1999).

In 1998, Toyoda et al. found that hemophiliacs co-infected with HIV and GBV-C (also known as hepatitis G virus, HGV, or GBVC-HGV) had a lower plasma HIV RNA concentration and a lower incidence of AIDS diagnoses compared to those infected with HIV alone (Toyoda et al., 1998), although the differences were not statistically significant. In contrast, Sabin and colleagues found an increased rate of AIDS and death in hemophiliacs "exposed" to GBV-C (Sabin et al., 1998) compared to non-exposed individuals. This study included HIV-positive subjects who were either GBV-C viremic as determined by detection of GBV-C RNA in plasma, or HIV-infected people who were not viremic but were anti-GBV-C E2 antibody-positive. Although the mortality rate was higher among the GBV-C "exposed" individuals, the results were not statistically significant. Looking at HIV-infected persons, Lefrère and colleagues reported a significant delay in the rate of CD4+ T cell decline, development of AIDS, and death in 23 HIV-positive individuals with GBV-C viremia compared to 72 HIV-infected people without GBV-C viremia (Lefrère et al., 1999). In this study, HIV-infected individuals who were also GBV-C-positive were compared to HIV-infected individuals who were GBV-C-negative. When these subjects were matched by age, sex, baseline HIV RNA load, and baseline CD4 T cell count, HIV disease progression appeared to be worse in GBV-C-negative subjects.

Human herpesvirus 6 suppresses HIV replication in CD4+ T cells and dendritic cells (Asada et al., 1999), and recently, Pinto et al. demonstrated induction of in vitro anti-HIV activity by influenza virus (Pinto et al., 2000). Pinto and colleagues demonstrated that this anti-HIV activity was inhibited in part by anti-interferon alpha (γ-IFN) antibodies. GBV-C and its close relative HCV are unusual among human RNA viruses in that they cause persistent infection without a DNA intermediate or known latent stage in their replication cycle. Although the mechanism by which GBV-C is able to persist in vivo is unknown, there are some suggestive data potentially explaining HCV persistence. Two HCV proteins (the envelope glycoprotein E2 and the nonstructural protein NS5a) interact and inhibit an interferon-induced, RNA dependent protein kinase (PKR) (Gale et al., 1998; Taylor et al., 1999). PKR is one of several enzymes induced by γ-IFN, and one of the activities of PKR is to inhibit viral protein synthesis. Since GBV-C and HCV contain numerous predicted stem-loop structures in their positive sense RNA genomes, and replicate via a negative sense RNA intermediate, both viruses would potentially induce γ-IFN in PBMC cultures by presenting double stranded RNA in the cytoplasm of the cell. There appears to be an animal model supportive of this hypothesis. Two reports suggest that bovine viral diarrhea virus (BVDV; a flavivirus related to GBV-C) induces γ-IFN in cattle (Rinaldo, et at, 1976), and BVDV infection ameliorates experimental bovine respiratory syncytial virus infection in calves (Elvander et al., 1998).

During progressive human immunodeficiency virus type 1 (HIV-1) infection, the virus-specific immune responses of an infected subject gradually deteriorate, leading to the development of acquired immunodeficiency syndrome (AIDS). Most infected patients do not exhibit overt clinical manifestations of the disease for six to ten years following initial infection, however, most individuals infected with HIV eventually die from conditions or infections that the individual's immune system is no longer equipped to fight. While treatment for AIDS has been forthcoming, no effective cure has been reported. Thus, preventative and treatment options against HIV infection and the development of AIDS remain highly desirable. Use of GBV-C is advantageous because of the relative innocuousness of the virus.

C. Infectious Nucleic Acids

Full length cDNAs or RNA transcripts of several RNA viruses including hepatitis A virus, GBV-B, and HCV are infectious in cell culture or animal inoculation studies (Beard et al., 1999; Bukh et al., 1999; Cohen et al., 1987; Emerson et al., 1992; Hong et al., 1999; Kolykhalov et al., 1997; Yanagi et al., 1997; Yanagi et al., 1998). These infectious clones are useful for genetic studies and allow a precise method for evaluating evolution of viruses that normally exist in molecular quasispecies. Although several infectious HCV clones have been described, all of these rely upon inoculation of transcribed RNA into susceptible primate species, and none were shown to be infectious in vitro (Beard et al., 1999; Hong et al., 1999; Kolykhalov et al., 1997; Yanagi et al., 1997; Yanagi et al., 1998). Thus, these HCV infectious clones have only limited application (Beard et al., 1999; Hong et al., 1999; Kolykhalov et al., 1997; Yanagi et al., 1997; Yanagi et al., 1998).

SUMMARY OF THE INVENTION

The compositions and methods of the present invention take advantage of the discovery of an isolated and purified nucleic acid molecule encoding an infectious GBV-C.

"Isolated and purified" indicates the nucleic acid molecule is not part of an intact GBV-C virus. These nucleic acid molecules have been produced in the form of a DNA construct or expression construct, as well as an infectious full-length GBV-C RNA transcript expressed from the DNA construct (collectively referred to as "recombinant GBV-C"). A cDNA clone made from the full-length or a less-than full-length transcript is also contemplated within the scope of the invention.

A nucleic acid sequence of the entire GBV-C genome is represented by SEQ ID NO:19, which corresponds to Genbank accession number AY196904. The sequence is provided as a DNA sequence, however, it may also be an RNA sequence with the corresponding thymidines (T) being substituted with uracils (U). The protein sequence encoded by this nucleic acid sequence is represented in SEQ ID NO:20. While nucleic acid molecules comprising all of SEQ ID NO: 19 are contemplated, smaller transcripts and clones containing less than the full-length of GBV-C sequences are considered within the present invention; particularly useful are transcripts or clones containing less than the entire-GBV-C sequence but also capable of producing an infectious GBV-C virus particle. Such viral particles made by recombinant techniques would be considered "recombinant." Viruses isolated from serum, for example, whose genome has not been altered recombinantly are considered non-recombinant. While the present invention is directed at recombinant forms of GVB-C, in some methods of the invention, non-recombinant viruses may be used as recombinant viruses.

In some embodiments of the invention, infectious GBV-C nucleic acid molecules and GBV-C viral particles produced from these molecules contain heterologous nucleic acid sequences. These heterologous sequences encode non-GBV-C sequences. For example, the heterologous sequence could encode HCV sequences, such that a chimeric virus is produced. GBV-C can be used a viral vector to provide a cell with an exogenous nucleic acid sequence. Alternatively, the compositions of the invention may be used as a vaccine to evoke an immune response against either GBV-C or a polypeptide or polypeptides encoded by heterologous sequences in the GBV-C nucleic acid molecules. These heterologous sequences could encode any sequence with therapeutic, preventative, or diagnostic functions. They could encode for antisense sequences, ribozymes, peptides, or polypeptides. Furthermore, they could be derived from non-GBV-C viruses, prokaryotes, or eukaryotes, such as mammals, or even humans. Transcription of a heterologous sequence may be controlled by a regulatory region, such as a promoter and/or enhancer, that is from GBV-C or a heterologous region. In some cases, the control region may be endogenous to the host cell, or it may be the control region that is normally associated with the heterologous sequence. The promoter and enhancers for use with the present invention may be eukaryotic, such as from a mammal, or it may be prokaryotic, such as T3, T7, and Sp6, or viral. In a further embodiment, the infectious GBV-C nucleic acid molecule exhibits resistance to interferon.

The present invention is also directed to methods of preparing or producing an infectious GBV-C. In some embodiments, an infectious GBV-C is prepared by incubating a nucleic acid molecule containing GBV-C sequence under conditions effective to allow transcription of at least a portion of the GBV-C sequence, collecting the RNA transcript, and providing the RNA transcript to a cell. A cell, which can be a prokaryotic or eukaryotic cell, can be provided with the transcript by a number of ways, including transfection methods, which are well known to those of skill in the art. In other methods, the transfected cell is incubated in appropriate media with or without serum to allow the cell to live. In any of the methods of the present invention, the cell may be prokaryotic or eukaryotic; the cell may be a mammalian cell. In other examples, the cell is a lymphocyte, while in still further examples, the cell is a CD4+ lymphocyte cell. A lymphocyte cell may be a T cell or a B cell. In the methods of the present invention, after sufficient time to allow the virus to propagate has passed, the supernatant can be collected from the cell. Any of the compositions described above and herein may be used to prepare infectious GBV-C. Any and all progeny GBV-C particles produced using the method and compositions of the present invention are encompassed by the invention.

In further aspects of the present invention, methods of producing infectious GBV-C are provided. Such methods may be accomplished by providing to a cell any composition of the present invention such as an isolated and purified nucleic acid molecule encoding an infectious GBV-C, or a GBV-C produced from such a molecule. In some cases the molecule will further comprise a heterologous sequence, with or without a heterologous, exogenous, or endogenous promoter. This cell may then be incubated under conditions that will permit replication and/or integration of viral nucleic acid molecules encoding an infectious GBV-C. The transfected or infected cell will eventually produce viral particles that can be collected from the supernatant.

The methods of the present invention may also include the steps of taking the supernatant from an infected or transfected cell and contacting a second cell with the supernatant of the first infected or transfected cell; incubating the second cell under conditions to permit replication of a GBV-C viral genome; and collecting the supernatant from the second cell.

The invention includes methods of expressing a heterologous nucleic acid sequence by providing to a cell an isolated and purified nucleic acid molecule encoding an infectious GBV-C sequence and the heterologous nucleic acid sequence. These methods can be utilized in vitro or in vivo.

Because the compositions of the invention can comprise a heterologous sequence encoding a polypeptide, they can be used to produce an immune response as well as antibodies in a subject given these compositions. For example, methods of producing an immune response in a subject can be accomplished by administering to the subject an effective amount of an expression construct comprising GBV-C sequences and a heterologous nucleic acid sequence operably linked to a promoter, such that the heterologous nucleic acid sequence encodes a polypeptide that elicits an immune response against the polypeptide.

In other methods of the invention, HIV disease progression (AIDS) is inhibited or reduced in a subject infected with HIV. This can be accomplished by administering to the subject an effective amount of an isolated and purified nucleic acid molecule encoding an infectious GBV-C sequence. The nucleic acid molecule may be RNA or DNA, or it may be a virus produced by such an isolated and purified nucleic acid molecule. The molecule may also contain the sequence of SEQ ID NO:1, be 9.3-9.7 kb in length, or comprise a portion of SEQ ID NO:1. These methods may be implemented in conjunction with other AIDS treatments such as AZT, HAART, or at least one protease inhibitor. Alternatively, these methods can be used to prevent HIV infection in an uninfected subject as well. Such methods could be employed by administering an effective amount of an isolated and purified nucleic acid molecule encoding an infectious GBV-C to a subject. This could be used to prevent HIV infection of a person's CD4+ cell.

Other embodiments of the invention include methods of treating a subject infected with HIV comprising administering to a cell of the subject an effective amount of an infectious GBV-C comprising a heterologous nucleic acid sequence. The method may be practiced in vitro or in vivo. If cells are treated in vitro, they may then be placed in a subject. In some embodiments, a recombinant infectious GVB-C is employed, while in others non-recombinant GVB-C is employed.

Methods of treating a subject infected with HIV may be implemented according to the present invention by administering to the subject an effective amount of an expression construct comprising a GBV-C sequence, such that the subject is provided a therapeutic benefit. Other ways of practicing the treatment methods of the invention include administering to the subject other AIDS treatments before, after, or concurrently with the expression construct. In some embodiments, a cell infected with HIV is contacted with an isolated and purified nucleic acid molecule comprising a nucleic acid sequence of SEQ ID NO:1, such that all or part of a GBV-C polypeptide is expressed in the cell. The polypeptide may cause HIV replication to be inhibited. It is contemplated that the isolated and purified nucleic acid molecule may encode an infectious GBV-C and inhibit HIV replication in the HIV-infected cell. The cell may be in an animal, such as a human. It is further contemplated that the cell may be one typically infected by HIV such as a CD4+ cell. Traditional AIDS therapy such as AZT or a protease inhibitor or HAART may be implemented in combination with any of the treatment methods described herein.

In other embodiments, a subject may be evaluated for cytokine inductions. Cytokine levels in a subject may be assayed before and/or after exposure to an infectious GVB-C sequence. In some embodiments, IL-2, IL-1B, IL-8, or IL-15 may be assayed by techniques well known to those of skill in the art.

The cells of the various methods may be eukaryotic or prokaryotic. In some cases, the cells are mammalian. In other cases, the cells are lymphocytes or are PBMCs. Alternatively, the cells may be CD4+. In still further embodiments, the cell may be any cell that supports the infection and/or propagation of a GBV-C, such as HepG2, Daudi, MT-2, and PH5CH cells. Cells may also be sustained in culture or in an organism.

In any of the compositions or methods of the present invention, a heterologous sequence may be comprised within a nucleic acid molecule encoding GBV-C sequences. The heterologous sequence is any nucleic acid sequence that does not encode GBV-C sequences. It may encode more than one gene or regulatory region. A heterologous sequence may encode an untranslated RNA such as an antisense construct or ribozyme, or a polypeptide that has therapeutic, preventative, or diagnostic uses. It may also encode a selectable or screenable marker by itself or in conjunction with another heterologous coding region. The untranslated RNA or polypeptide may be derived from an eukaryote, prokaryote, or virus. Examples of RNA and polypeptides encoded by heterologous sequences are provided below, but the invention should not be limited to those examples.

It is also contemplated that the invention covers all subsequent generations of GBV-C produced using the compositions and methods of the present invention. For example, if an isolated and purified nucleic acid molecule encoding a GBV-C virus is introduced into a cell such that the cell produces infectious GBV-C particles (first generation), the invention covers not only the particles, but also the viruses produced from the first generation particles, which would include viruses from generations 2, 3, 4, 5, 6, 7, 8, 9, 10, 15, 20, and later.

In other embodiments of the invention, an effective amount of an infectious GVB-C may be administered to cells or a subject to induce expression of IL-2, IL-1B, IL-8, or IL-15. Alternatively, an effective amount of an infectious GBV-C may be administered to reduce or inhibit the expression of IL-13. It is contemplated that GBV-C may be administered to cells or a subject to alter the cytokines listing in FIG. 14.

In some embodiments of the invention, an infectious GBV-C can be used to inhibit or prevent apoptosis in a cell. An effective amount of GBV-C may be administered to a cell in vitro or in vivo to prevent or delay apoptosis.

The use of the word "a" or "an" when used in conjunction with the term "comprising" in the claims and/or the specification may mean "one," but it is also consistent with the meaning of "one or more," "at least one," and "one or more than one." Furthermore, where multiple steps of a method of process are cited, it is understood that the steps are not required to be performed in the particular order recited unless one of skill in the art is not be able to practice the method in a different order.

The DNA of the invention may encode GBV-C 765 (FIG. 7). The vaccine may also contain an immunological adjuvant. The terms "protein," "peptide" and "polypeptide" are used interchangeably herein.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 3A-D Phylogenetic relationship of the 3'ntr sequences of GBV-C, GBV-B and HCV (FIG. 3A). The predicted secondary structure of 3'ntr regions for GBV-C (FIG. 3B), GBV-B (FIG. 3C) and HCV (FIG. 3D) is shown.

FIG. 5 CD4 positive and CD4 negative cells were sorted and collected by flow cytometry. The bars represent the cell populations sorted for these experiments. RNA was extracted from equal numbers of CD4+ and CD4– cells, and the relative end-point dilution titer of sense and antisense GBV-C RNA was measured. The numbers represent the dilution titer ($Log_{10}$).

FIG. 6A-D GBV-C E2 expression in PBMCs. PBMCs were infected with supernatant from pass 4, and 24 h (FIG. 6A) and 96 h (FIG. 6B) post-infection, the cells were fixed and processed as described in Materials and Methods. GBV-C E2 expression was detected using a murine monoclonal anti-HGV E2 antibody as described in Materials and Methods. The same cells (24 hrs. post-infection) did not show specific cytoplasmic fluorescence when evaluated without the GBV-C E2 antibody (FIG. 6C), and mock infected PBMCs evaluated exactly the same as panel A and B did not demonstrate cytoplasmic fluorescence (FIG. 6D).

FIG. 13 Metabolic activity of cells infected with GBV-C. Peripheral blood mononuclear cells infected with GBV-C or mock-infected PBMCs were compared for metabolic activity by assaying for incorporation of $^{35}$S-methionine.

FIG. 16 (A) Culture of GBV-C/HIV coinfected patient PBMC's. Total days GBV-C RNA was detected in culture supernatant is shown for each patient. Patient 8 did not have enough PBMC's for culture without donor PBMC's. Patient 7 had GBV-C detected in supernatant in only one of two duplicate cultures. (B) Coculture of GBV-C/HIV coinfected patient PBMC's with equal numbers of donor PBMC's. Total days GBV-C RNA was detected in culture supernatant is shown for each patient. (C) Detection of GBV-C RNA in cell lysates from PBMC cultures in (A) and (B). The last date cell lysates had detectable GBV-C RNA in either culture method is shown.

FIG. 23A-G Comparison of the sequence of isolate 765 and other genotype 2 sequences are shown by their predicted coding regions (E1, E2, NS2, NS3, NS4, NS5A, and NS5B). Phylogenetic distances were determined using the Kimura method.

FIG. 25 Amino acid substitutions in NS5A region of GBV-C isolate 765 compared with isolate AF121950. Isolate 765 demonstrated prolonged replication in PBMC culture (up to 72 days, data not shown); whereas isolate AF 121950 did not replicate beyond 7 days in PBMC cultures.

FIG. 31 Selection of GBV-C nucleotide mutations in supernatant on day 14 (patient 8). A segment of the NS5A region is shown (Panel A=1-97, Panel B=98-194). The nucleotide sequence of the plasma GBV-C isolate is shown (4 clones) and compared to the sequence obtained from day 14 culture supernatant (5 clones).

and healthy donor PBMCs infected with patient serum from patient 12 (G– donor) were cultured with and without PHA/IL-2 supplementation in media for 14 days. GBV-C RNA concentrations measured in day 7 culture supernatant are shown. The results were consistent at day 14.

Figure 33:
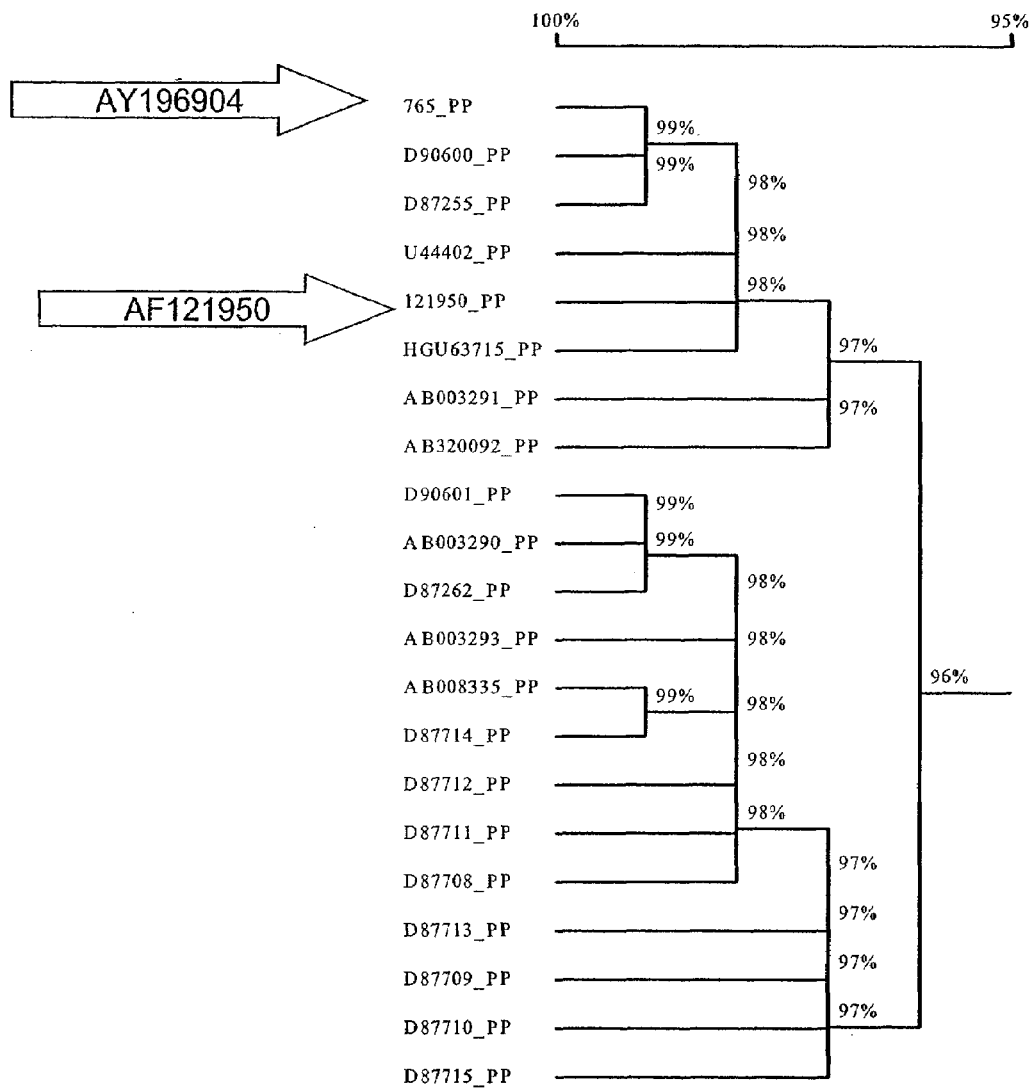

FIG. 33 Comparison of the predicted full-length polyprotein sequence of the isolate from patient 12 (GenBank #AY196904) with predicted polyprotein sequences of 20 full-length GBV-C RNA sequences. The phylogenetic tree was created using the Jukes-Cantor method and percentage homologies of the polyprotein sequences are shown. Isolates AY196904 (patient 12) and AF121950 (infectious clone) are highlighted, as these are the only isolates characterized for replication in PBMC culture.

FIG. 34 Amino acid polymorphisms in AY196904. Sixteen amino acids were identified in AY196904 that were not present in the other sequences (A). Comparing the isolate from patient 12 (AY196904) with the infectious clone (AF121950), 2 amino acid differences were identified in the NS5B region (panel B) similar to those related to RNA replication in HCV (Lohmann, Korner, Dobierzewska, & Bartenschlager 2001). Similarly, comparison of predicted NS5A amino acid sequences from AY196904 and AF121950 revealed differences in a region homologous to the HCV interferon-sensitivity determining region (panel C).

DESCRIPTION OF ILLUSTRATIVE EMBODIMENTS

While several full-length GBV-C sequences have been submitted to Genbank, the present invention provides a cDNA clone encoding full-length GBV-C RNA transcripts that are infectious in peripheral blood mononuclear cell (PBMC) cultures. Unlike most previous full-length HCV constructions, the present invention is not a product of a consensus sequence, but instead, an authentic GBV-C sequence obtained from direct amplification of viral RNA. Replication was demonstrated by serial passage of culture supernatants, expression of the envelope glycoprotein E2, RNA replication (positive and negative strand RNA synthesis), and the detection of viral particles by sucrose gradient centrifugation and immune electron microscopy.

Thus, the present invention concerns the discovery of an infectious GBV-C clone. GBV-C is the most closely related virus to HCV, the cause of hepatitis C.

It was recently reported that GBV-C infection in HIV-infected patients correlates with a delayed onset of HIV (LeFrere et al., 1999). This report, however, is in conflict with a previous study by Sabin et al. (Sabin et al., 1998). Thus, there existed confusion in the art at this time about whether or not there is a correlation between the onset of AIDS and a GBV-C infection. Furthermore, any evidence that did exist was merely correlative, as opposed to involving an evaluation of whether GBV-C was involved in the observed delay of HIV.

The experiments described herein demonstrate a correlation. Unlike the previously reported studies, only subjects with viremia, as demonstrated by the detection of GBV-C RNA by RT-PCR, were evaluated; people with GBV-C anti-E2 antibody were not included. The studies disclosed herein also show that GBV-C inhibits HIV replication, but they significantly extend the observation of a correlation and provide a mechanism by which GBV-C delays the onset of HIV. Since this study employed an infectious GBV-C clone, they further indicate the advantage of the GBV-C clones of the present invention. Therefore, an infectious GBV-C of the present invention can be implemented in preventative or therapeutic treatments for HIV infection and the development of AIDS.

I. GBV-C

Like other members of the Flaviviridae, GBV-C is a positive-strand RNA virus that encodes a single long open reading frame (Leary et al., 1996). As discussed above, it does not cause acute or chronic hepatitis, yet it is the family member most closely related to HCV, the cause of hepatitis C. While sequences of GBV-C have been previously reported, for example in U.S. Pat. No. 5,874,563, an infectious GBV-C clone has not been previously described.

The GBV-C polyprotein is predicted to be cleaved into two envelope proteins (E1 and E2), an RNA helicase, a trypsin-like serine protease, and an RNA-dependent RNA polymerase. A major difference between GBV-C and HCV is in the amino terminus of the polyprotein. In many isolates, this region is truncated, and no core (or nucleocapsid) protein is present (Simons et al., 1995; Xiang et al., 1999). In vitro translation experiments suggest that the AUG immediately upstream of the putative E1 protein is preferentially used to initiate translation, although there may be as many as four AUG's in frame with the polyprotein upstream of this AUG (Simons et al., 1996). In addition, the mutation frequency in codon position 1 and 2 of the region upstream of this AUG suggest that it is a non-coding region (Okamoto et al., 1997). These observations have led to speculation that GBV-C may not have a core protein or nucleocapsid (Dickens and Lenon, 1997; Simons et al., 1996). However, the inventors and others have shown that the sedimentation profiles of GBV-C particles are consistent with the presence of a nucleocapsid (Melvin et al., 2000; Xiang et al., 1998), and electron microscopy of plasma-derived GBV-C demonstrated enveloped particles with a nucleocapsid structure (Xiang et al., 1999). Although the amino acid composition of the nucleocapsid remains undefined, some infected individuals have antibody to a peptide representing amino acids upstream of the predicted E1 protein in frame with the polyprotein (Xiang et al., 1998). Thus, this region may encode the nucleocapsid.

Simons et al., 1996 demonstrated that the AUG codon at the amino terminus of putative E1 protein (AUG-554 in the isolate) was capable of initiating translation, whereas the upstream AUG's were not (Simons et al., 1996). In many isolates, the amino terminus of the predicted HGV polyprotein is truncated or absent (Leary et al., 1996; Linnen et al., 1996; Okamoto et al., 1997), and the frequency of polymorphisms in codon position 1 and 2 in the upstream ORF suggests that the region is not a coding region (Okamoto et al., 1997). Thus, it has been suggested that GBV-C may not have a core protein (Dickens and Lemon, 1997). It was previously shown that GBV-C particles have similar densities and sedimentation characteristics in sucrose and cesium chloride gradients as HCV (Xiang et al., 1998); subsequently particles of approximately 65 nm particle were shown with a 50 nm nucleocapsid structure (Xiang et al., 1999). In this study, two GBV-C particles types were identified with densities of 1.07 and 1.18 g/ml, consistent with virions and nucleocapsids respectively (Xiang et al., 1998). Furthermore, electron dense structures approximately 50-55 nm in size were visualized within the enveloped particle (FIG. 8). Thus, the data support previous work identifying a nucleocapsid for GBV-C. The truncation of the polyprotein upstream of AUG-554 would be abolished if most isolates did not contain a single nucleotide deletion at position 381. Given the fact that all sequences produced thus far utilized nested RT-PCR, this may represent a polymerase artifact. Nevertheless, propagation of GBV-C in culture should allow the production of sufficient virus for ultimate characterization of the protein content of the GBV-C nucleocapsid. With the exception of the 5' ntr region, the remaining GBV-C sequences are highly conserved among geographically diverse isolates. Although there is less than 50% sequence homology in the 3' ntr region between GBV-C, GBV-B and HCV, the predicted secondary structures of these viruses bear striking similarities. GBV-C does not include a polypyrimidine tract, but does have three stem-loop structures at the extreme 3' end (FIG. 3). This indicates that the polypyrimidine regions of HCV and GBV-B are not requirements of hepacivirus replication.

The site of GBV-C replication has not been clearly identified, but it appears that replication in the hepatocyte, if it occurs, is not the primary source of virus in infected individuals (Laskus et al., 1998; Pessoa et al., 1998; Seipp et al., 1999). Recently, there were reports that human peripheral blood mononuclear cells (PBMC's) and interferon-resistant Daudi cells are permissive for GBV-C replication (Fogeda et al., 1999; Shimizu, 1999). In addition, transient replication of GBV-C was described in MT-2 cells (a human T-cell line), and PH5CH (a human hepatocyte line immortalized with simian virus 40 large T antigen) (Seipp et al., 1999).

A. Polynucleotides

1. Infectious GBV-C

The present invention concerns infectious GBV-C polynucleotides or nucleic acid molecules, isolatable and purifiable from GBV-C or mammalian cells infected with GBV-C, indicating they are free from total viral genomic RNA and proteins and are capable of infecting cells and propagating infectious GBV-C particles. It is contemplated that an isolated and purified infectious GBV-C nucleic acid molecule may take the form of RNA or DNA. An infectious GBV-C nucleic acid molecule refers to an RNA or DNA molecule that is capable of yielding an infectious GBV-C particle from a transfected cell.

As used herein, the term "RNA transcript" refers to an RNA molecule that has been isolated free of total genomic viral RNA and virus proteins and that is the product of transcription from a nucleic acid molecule for which at least one strand is DNA. A "full-length RNA transcript" refers to an RNA transcript that is full-length when compared to the genomic coding region, for example of GBV-C. Therefore, a full-length GBV-C RNA transcript encoding the GBV-C genome refers to an RNA segment that contains GBV-C sequences capable of producing an infectious GBV-C, yet is isolated away from, or purified free from, total GBV-C viral genomic RNA and GBV-C proteins. Such a full-length transcript may encode for one or more polypeptides, as well as contain regions controlling the regulation, e.g., transcription, translation, and RNA stability, of these polypeptides.

As used in this application, the term "polynucleotide" refers to a nucleic acid molecule, RNA or DNA, that has been isolated free of total genomic nucleic acid. Therefore, a "polynucleotide encoding an infectious GBV-C" refers to a nucleic acid segment that contains GBV-C coding sequences, yet is isolated away from, or purified and free of, total viral genomic RNA and proteins; similarly, a "polynucleotide encoding full-length GBV-C" refers to a nucleic acid segment that contains full-length GBV-C coding sequences yet is isolated away from, or purified and free of, total viral genomic RNA and protein. Therefore, when the present application refers to the function or activity of an infectious GBV-C that is encoded by a GBV-C polynucleotide, it is meant that the polynucleotide encodes a molecule that has the ability to propagate an infectious GBV-C virus particle from a cell. It is contemplated that an infectious GBV-C polynucleotide may refer to a GBV-C RNA transcript that is able to propagate an infectious GBV-C virus particle after introduction to a cell or to a GBV-C expression construct, clone, or vector composed of double-stranded DNA or DNA/RNA hybrid that is similarly capable.

The term "cDNA" is intended to refer to DNA prepared using RNA as a template. The advantage of using a cDNA, as opposed to genomic RNA or an RNA transcript is stability and the ability to manipulate the sequence using recombinant DNA technology (See Maniatis, 1989; Ausubel, 1994). There may be times when the full or partial genomic sequence is preferred. Alternatively, cDNAs may be advantageous because it represents coding regions of a polypeptide and eliminates introns and other regulatory regions.

It also is contemplated that a given GBV-C from a given cell may be represented by natural variants or strains that have slightly different nucleic acid sequences but, nonetheless, encode the same viral polypeptides. Consequently, the present invention also encompasses derivatives of GBV-C with minimal amino acid changes in its viral proteins, but that possess the same activities.

The term "gene" is used for simplicity to refer to a functional protein, polypeptide, or peptide-encoding unit. As will be understood by those in the art, this functional term includes genomic sequences, cDNA sequences, and smaller engineered gene segments that express, or may be adapted to express, proteins, polypeptides, domains, peptides, fusion proteins, and mutants. The nucleic acid molecule encoding GBV-C may contain a contiguous nucleic acid sequence encoding one or more GBV-C genes and regulatory regions and be of the following lengths: about 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1010, 1020, 1030, 1040, 1050, 1060, 1070, 1080, 1090, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 5100, 5200, 5300, 5400, 5500, 5600, 5700, 5800, 5900, 6000, 6100, 6200, 6300, 6400, 6500, 6600, 6700, 6800, 6900, 7000, 7100, 7200, 7300, 7400, 7500, 7600, 7700, 7800, 7900, 8000, 8100, 8200, 8300, 8400, 8500, 8600, 8700, 8800, 8900, 9000, 9100, 9200, 9300, 9400, 9500, 9600, 9700, 9800, 9900, 10000, 10100, 10200, 10300, 10400, 10500, 10600, 10700, 10800, 10900, 11000, 11100, 11200, 11300, 11400, 11500, 11600, 11700, 11800, 11900, 12000 or more nucleotides, nucleosides, or base pairs. Such sequences may be identical or complementary to SEQ ID NO:1 or Genbank Accession number AF070476.

"Isolated substantially away from other coding sequences" means that the gene of interest forms part of the coding region of the nucleic acid segment, and that the segment does not contain large portions of naturally-occurring coding nucleic acid, such as large chromosomal fragments or other functional genes or cDNA coding regions. Of course, this refers to the nucleic acid segment as originally isolated, and does not exclude genes or coding regions later added to the segment by human manipulation.

In particular embodiments, the invention concerns isolated nucleic acid segments and recombinant vectors incorporating DNA sequences that encode GBV-C polypeptides or peptides that include within its amino acid sequence a contiguous amino acid sequence in accordance with, or essentially corresponding to GBV-C polypeptides.

In other embodiments, the invention concerns isolated nucleic acid segments and DNA recombinant vectors incorporating nucleic acid sequences that encode GBV-C polypeptides or peptides, particularly those necessary for infection, that include within its amino acid sequence a contiguous amino acid sequence in accordance with, or essentially corresponding to all strains of GBV-C polypeptides.

The nucleic acid segments used in the present invention, regardless of the length of the coding sequence itself, may be combined with other DNA or RNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol.

It is contemplated that the nucleic acid constructs of the present invention may encode full-length GBV-C or an infectious GBV-C, with or without heterologous sequences. A "heterologous" sequence refers to a sequence that is foreign or exogenous to the remaining sequence. A heterologous gene refers to a gene that is not found in nature adjacent to the sequences with which it is now placed.

In a non-limiting example, one or more nucleic acid constructs may be prepared that include a contiguous stretch of nucleotides identical to or complementary to GBV-C. A nucleic acid construct may be about 50, 60, 70, 80, 90, 100, 200, 300, 400, 500, 600, 700, 800, 900, 1,000, 2,000, 3,000, 4,000, 5,000, 6,000, 7,000, 8,000, 9,000, 10,000, 11,000, 12,000, 13,000, 14,000, 15,000, 20,000, 30,000, 50,000, 100,000, 250,000, about 500,000, 750,000, to about 1,000,000 nucleotides in length, as well as constructs of greater size, up to and including chromosomal sizes (including all intermediate lengths and intermediate ranges), given the advent of nucleic acids constructs such as a yeast artificial chromosome are known to those of ordinary skill in the art. It will be readily understood that "intermediate lengths" and "intermediate ranges," as used herein, means any length or range including or between the quoted values (i.e., all integers including and between such values). Non-limiting examples of intermediate lengths include about 11, about 12, about 13, about 16, about 17, about 18, about 19, etc.; about 21, about 22, about 23, etc.; about 31, about 32, etc.; about 51, about 52, about 53, etc.; about 101, about 102, about 103, etc.; about 151, about 152, about 153, about 97001, about 1,001, about 1002, about 50,001, about 50,002, about 750,001, about 750,002, about 1,000,001, about 1,000,002, etc. Non-limiting examples of intermediate ranges include about 3 to about 32, about 150 to about 500,001, about 3,032 to about 7,145, about 5,000 to about 15,000, about 20,007 to about 1,000,003, etc.

The nucleic acid segments used in the present invention encompass biologically functional equivalent GBV-C proteins and peptides. Such sequences may arise as a consequence of codon redundancy and functional equivalency that are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by human may be introduced through the application of site-directed mutagenesis techniques, e.g., to introduce improvements to the antigenicity of the protein or to test mutants in order to examine DNA binding activity at the molecular level.

2. Vectors Encoding Infectious GBV-C

The present invention encompasses the use of vectors to encode for an infectious GBV-C. The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques, which are described in Maniatis et al., 1988 and Ausubel et al., 1994.

The term "expression vector" or "expression construct" refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described infra. It is contemplated that the infectious GBV-C particles of the present invention may arise from a vector containing GBV-C sequence or RNA encoding GBV-C sequence into a cell. Either of these, or any other nucleic acid molecules of the present invention may be constructed with any of the following nucleic acid control sequences. Thus, the full-length RNA transcript may contain the benefit of recombinant DNA technology such that it contains exogenous control sequences or genes.

a. Promoters and Enhancers

A "promoter" is a control sequence that is a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" mean that a promoter is in a correct functional location and/or orientation in relation to a nucleic acid sequence to control transcriptional initiation and/or expression of that sequence. A promoter may or may not be used in conjunction with an "enhancer," which refers to a cis-acting regulatory sequence involved in the transcriptional activation of a nucleic acid sequence.

A promoter may be one naturally associated with a gene or sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. No. 4,683,202, U.S. Pat. No. 5,928,906). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the nucleic acid segment in the cell type, organelle, and organism chosen for expression. Those of skill in the art of molecular biology generally know the use of promoters, enhancers, and cell type combinations for protein expression, for example, see Sambrook et al. (1989). The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or exogenous, i.e., from a different source than GBV-C sequence. In some examples, a prokaryotic promoter is employed for use with in vitro transcription of a desired sequence. Prokaryotic promoters for use with many commercially available systems include T7, T3, and Sp6.

Table 1 lists several elements/promoters that may be employed, in the context of the present invention, to regulate the expression of a gene. This list is not intended to be exhaustive of all the possible elements involved in the promotion of expression but, merely, to be exemplary thereof. Table 2 provides examples of inducible elements, which are regions of a nucleic acid sequence that can be activated in response to a specific stimulus.

TABLE 1

Promoter and/or Enhancer

| Promoter/Enhancer | References |
| --- | --- |
| Immunoglobulin Heavy Chain | Banerji et al., 1983; Gilles et al., 1983; Grosschedl et al., 1985; Atchinson et al., 1986, 1987; Imler et al., 1987; Weinberger et al., 1984; Kiledjian et al., 1988; Porton et al.; 1990 |
| Immunoglobulin Light Chain | Queen et al., 1983; Picard et al., 1984 |
| T-Cell Receptor | Luria et al., 1987; Winoto et al., 1989; Redondo et al.; 1990 |
| HLA DQ a and/or DQ β | Sullivan et al., 1987 |
| β-Interferon | Goodbourn et al., 1986; Fujita et al., 1987; Goodbourn et al., 1988 |
| Interleukin-2 | Greene et al., 1989 |

TABLE 1-continued

Promoter and/or Enhancer

| Promoter/Enhancer | References |
| --- | --- |
| Interleukin-2 Receptor | Greene et al., 1989; Lin et al., 1990 |
| MHC Class II 5 | Koch et al., 1989 |
| MHC Class II HLA-DRa | Sherman et al., 1989 |
| β-Actin | Kawamoto et al., 1988; Ng et al.; 1989 |
| Muscle Creatine Kinase (MCK) | Jaynes et al., 1988; Horlick et al., 1989; Johnson et al., 1989 |
| Prealbumin (Transthyretin) | Costa et al., 1988 |
| Elastase I | Omitz et al., 1987 |
| Metallothionein (MTII) | Karin et al., 1987; Culotta et al., 1989 |
| Collagenase | Pinkert et al., 1987; Angel et al., 1987 |
| Albumin | Pinkert et al., 1987; Tronche et al., 1989, 1990 |
| α-Fetoprotein | Godbout et al., 1988; Campere et al., 1989 |
| γ-Globin | Bodine et al., 1987; Perez-Stable et al., 1990 |
| β-Globin | Trudel et al., 1987 |
| c-fos | Cohen et al., 1987 |
| c-HA-ras | Triesman, 1986; Deschamps et al., 1985 |
| Insulin | Edlund et al., 1985 |
| Neural Cell Adhesion Molecule (NCAM) | Hirsh et al., 1990 |
| $\alpha_1$-Antitrypain | Latimer et al., 1990 |
| H2B (TH2B) Histone | Hwang et al., 1990 |
| Mouse and/or Type I Collagen | Ripe et al., 1989 |
| Glucose-Regulated Proteins (GRP94 and GRP78) | Chang et al., 1989 |
| Rat Growth Hormone | Larsen et al., 1986 |
| Human Serum Amyloid A (SAA) | Edbrooke et al., 1989 |
| Troponin I (TN I) | Yutzey et al., 1989 |
| Platelet-Derived Growth Factor (PDGF) | Pech et al., 1989 |
| Duchenne Muscular Dystrophy | Klamut et al., 1990 |
| SV40 | Banerji et al., 1981; Moreau et al., 1981; Sleigh et al., 1985; Firak et al., 1986; Herr et al., 1986; Imbra et al., 1986; Kadesch et al., 1986; Wang et al., 1986; Ondek et al., 1987; Kuhl et al., 1987; Schaffner et al., 1988 |
| Polyoma | Swartzendruber et al., 1975; Vasseur et al., 1980; Katinka et al., 1980, 1981; Tyndell et al., 1981; Dandolo et al., 1983; de Villiers et al., 1984; Hen et al., 1986; Satake et al., 1988; Campbell and/or Villarreal, 1988 |
| Retroviruses | Kriegler et al., 1982, 1983; Levinson et al., 1982; Kriegler et al., 1983, 1984a, b, 1988; Bosze et al., 1986; Miksicek et al., 1986; Celander et al., 1987; Thiesen et al., 1988; Celander et al., 1988; Chol et al., 1988; Reisman et al., 1989 |
| Papilloma Virus | Campo et al., 1983; Lusky et al., 1983; Spandidos and/or Wilkie, 1983; Spalholz et al., 1985; Lusky et al., 1986; Cripe et al., 1987; Gloss et al., 1987; Hirochika et al., 1987; Stephens et al., 1987; Glue et al., 1988 |
| Hepatitis B Virus | Bulla et al., 1986; Jameel et al., 1986; Shaul et al., 1987; Spandau et al., 1988; Vannice et al., 1988 |
| Human Immunodeficiency Virus | Muesing et al., 1987; Hauber et al., 1988; Jakobovits et al., 1988; Feng et al., 1988; Takebe et al., 1988; Rosen et al., 1988; Berkhout et al., 1989; Laspia et al., 1989; Sharp et al., 1989; Braddock et al., 1989 |
| Cytomegalovirus (CMV) | Weber et al., 1984; Boshart et al., 1985; Foecking et al., 1986 |
| Gibbon Ape Leukemia Virus | Holbrook et al., 1987; Quinn et al., 1989 |

TABLE 2

Inducible Elements

| Element | Inducer | References |
|---|---|---|
| MT II | Phorbol Ester (TFA) Heavy metals | Palmiter et al., 1982; Haslinger et al., 1985; Searle et al., 1985; Stuart et al., 1985; Imagawa et al., 1987; Karin et al., 1987; Angel et al., 1987b; McNeall et al., 1989 |
| MMTV (mouse mammary tumor virus) | Glucocorticoids | Huang et al., 1981; Lee et al., 1981; Majors et al., 1983; Chandler et al., 1983; Lee et al., 1984; Ponta et al., 1985; Sakai et al., 1988 |
| β-Interferon | poly(rI)x poly(rc) | Tavernier et al., 1983 |
| Adenovirus 5 E2 | E1A | Imperiale et al., 1984 |
| Collagenase | Phorbol Ester (TPA) | Angel et al., 1987a |
| Stromelysin | Phorbol Ester (TPA) | Angel et al., 1987b |
| SV40 | Phorbol Ester (TPA) | Angel et al., 1987b |
| Murine MX Gene | Interferon, Newcastle Disease Virus | Hug et al., 1988 |
| GRP78 Gene | A23187 | Resendez et al., 1988 |
| α-2-Macroglobulin | IL-6 | Kunz et al., 1989 |
| Vimentin | Serum | Rittling et al., 1989 |
| MHC Class I Gene H-2κb | Interferon | Blanar et al., 1989 |
| HSP70 | E1A, SV40 Large T Antigen | Taylor et al., 1989, 1990a, 1990b |
| Proliferin | Phorbol Ester-TPA | Mordacq et al., 1989 |
| Tumor Necrosis Factor | PMA | Hensel et al., 1989 |
| Thyroid Stimulating Hormone α Gene | Thyroid Hormone | Chatterjee et al., 1989 |

The identity of tissue-specific promoters or elements, as well as assays to characterize their activity, is well known to those of skill in the art. Examples of such regions include the human LIMK2 gene (Nomoto et al. 1999), the somatostatin receptor 2 gene (Kraus et al., 1998), murine epididymal retinoic acid-binding gene (Lareyre et al., 1999), human CD4 (Zhao-Emonet et al., 1998), mouse alpha2 (XI) collagen (Tsumaki, et al., 1998), D1A dopamine receptor gene (Lee, et al., 1997), insulin-like growth factor II (Wu et al., 1997), human platelet endothelial cell adhesion molecule-1 (Almendro et al., 1996).

b. Initiation Signals and Internal Ribosome Binding Sites

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments of the invention, the use of internal ribosome entry sites (IRES) elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819).

c. Multiple Cloning Sites

Vectors can include a multiple cloning site (MCS), which is a nucleic acid region that contains multiple restriction enzyme sites, any of which can be used in conjunction with standard recombinant technology to digest the vector. (See Carbonelli et al., 1999, Levenson et al., 1998, and Cocea, 1997) "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

d. Splicing Sites

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression. (See Chandler et al., 1997).

e. Termination Signals

The vectors or constructs of the present invention will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

In eukaryotic systems, the terminator region may also comprise specific DNA sequences that permit site-specific cleavage of the new transcript so as to expose a polyadenylation site. This signals a specialized endogenous polymerase to add a stretch of about 200 A residues (polyA) to the 3' end of the transcript. RNA molecules modified with this polyA tail appear to more stable and are translated more efficiently. Thus, in other embodiments involving eukaryotes, it is preferred that that terminator comprises a signal for the cleavage of the RNA, and it is more preferred that the terminator signal promotes polyadenylation of the message. The terminator and/or polyadenylation site elements can serve to enhance message levels and/or to minimize read through from the cassette into other sequences.

Terminators contemplated for use in the invention include any known terminator of transcription described herein or known to one of ordinary skill in the art, including but not limited to, for example, the termination sequences of genes, such as for example the bovine growth hormone terminator or viral termination sequences, such as for example the SV40 terminator. In certain embodiments, the termination signal may be a lack of transcribable or translatable sequence, such as due to a sequence truncation.

f. Polyadenylation Signals

For expression, particularly eukaryotic expression, one will typically include a polyadenylation signal to effect proper polyadenylation of the transcript. The nature of the polyadenylation signal is not believed to be crucial to the successful practice of the invention, and/or any such sequence may be employed. Preferred embodiments include the SV40 polyadenylation signal and/or the bovine growth hormone polyadenylation signal, convenient and/or known to function well in various target cells. Polyadenylation may increase the stability of the transcript or may facilitate cytoplasmic transport.

g. Origins of Replication

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

h. Selectable and Screenable Markers

In certain embodiments of the invention, the cells containing a nucleic acid construct of the present invention may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

3. Host Cells

As used herein, the terms "cell," "cell line," and "cell culture" may be used interchangeably. All of these terms also include their progeny, which refers to any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organisms that is capable of replicating a vector and/or expressing a heterologous gene encoded by a vector. A host cell can, and has been, used as a recipient for vectors. A host cell may be "transfected" or "transformed," which refers to a process by which exogenous nucleic acid is transferred or introduced into the host cell. A transformed cell includes the primary subject cell and its progeny.

Characterization of PBMC subsets identified the CD4+ T cells as the cells supporting GBV-C replication. Although early studies suggested that GBV-C replicates in the liver, most reported studies indicate that GBV-C is not hepatotropic (Kiyosawa and Tanaka, 1999; Laskus et al., 1998). The inability to demonstrate infection of HepG2 cells is consistent with this, although the inventors were also unable to demonstrate persistent replication in the CD4+ T cell line (MOLT-4). Thus, host cell factors in primary cells may be necessary for replication. Studies are underway with primary hepatocyte cultures to test this hypothesis. Nevertheless, several studies have found GBV-C replication in PBMC's, and the concentration of virus in plasma relative to liver tissues suggests that the hepatocyte is not a prominent source of virus (Kobayashi et al., 1999). Taken together, these data suggest that GBV-C may be lymphotropic. As such, any lymphocyte-derived cell or cell line, particularly a CD4+ cell, is preferred for use with the present invention, however, any other cell line that permits transfection and/or propagation of an infectious GBV-C nucleic acid molecule is contemplated for use with the present invention. In other embodiments, the CD4+ cell may be infected with HIV, and such cells are contemplated to be targets for treatment to prevent or inhibit the progression of AIDS.

Nonetheless, host cells may be derived from prokaryotes or eukaryotes, depending upon whether the desired result is replication of the vector, expression of part or all of the vector-encoded nucleic acid sequences, or production of infectious viral particles. Numerous cell lines and cultures are available for use as a host cell, and they can be obtained through the American Type Culture Collection (ATCC), which is an organization that serves as an archive for living cultures and genetic materials (see the world wide web at atcc.org). An appropriate host can be determined by one of skill in the art based on the vector backbone and the desired result. A plasmid or cosmid, for example, can be introduced into a prokaryote host cell for replication of many vectors. Bacterial cells used as host cells for vector replication and/or expression include DH5α, JM109, and KC8, as well as a number of commercially available bacterial hosts such as SURE® Competent Cells and SOLOPACK™ Gold Cells (STRATAGENE®, La Jolla). Alternatively, bacterial cells such as *E. coli* LE392 could be used as host cells for phage viruses.

Examples of eukaryotic host cells for replication and/or expression of a vector include HeLa, NIH3T3, Jurkat, 293, Cos, CHO, Saos, and PC12. Many host cells from various cell types and organisms are available and would be known to one of skill in the art. Similarly, a viral vector may be used in conjunction with either an eukaryotic or prokaryotic host cell, particularly one that is permissive for replication or expression of the vector.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

4. Expression Systems

Numerous expression systems exist that comprise at least a part or all of the compositions discussed above. Prokaryote- and/or eukaryote-based systems can be employed for use with the present invention to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986 and 4,879,236, which can be bought, for example, under the name MAXBAC® 2.0 from INVITROGEN® and BACPACK™ BACULOVIRUS EXPRESSION SYSTEM from CLONTECH®.

Other examples of expression systems include STRATAGENE®'S COMPLETE CONTROL™ Inducible Mammalian Expression System, which involves a synthetic ecdysone-inducible receptor, or its pET Expression System, an *E. coli* expression system. Another example of an inducible expression system is available from INVITROGEN®, which carries the T-REX™ (tetracycline-regulated expression) System, an inducible mammalian expression system that uses the full-length CMV promoter. The Tet-On™ and Tet-Off™ systems from CLONTECH® can be used to regulate expression in a mammalian host using tetracycline or its derivatives. The implementation of these systems is described in Gossen et al., 1992 and Gossen et al., 1995, and U.S. Pat. No. 5,650,298.

INVITROGEN® also provides a yeast expression system called the *Pichia methanolica* Expression System, which is designed for high-level production of recombinant proteins in the methylotrophic yeast *Pichia methanolica*. One of skill in the art would know how to express a vector, such as an expression construct, to produce a nucleic acid sequence or its cognate polypeptide, protein, or peptide.

5. Non-Translated Nucleic Acid Sequences

In some embodiments of the present invention, a GBV-C clone or infectious GBV-C nucleic acid molecule encodes a heterologous nucleic acid sequence that is transcribed into RNA but that is not translated. Examples of this type of heterologous nucleic acid sequence include antisense molecules or sequences and ribozymes.

a. Antisense Constructs

Antisense methodology takes advantage of the fact that nucleic acids tend to pair with "complementary" sequences. By complementary, it is meant that polynucleotides are those which are capable of base-pairing according to the standard Watson-Crick complementarity rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

Targeting double-stranded (ds) DNA with polynucleotides leads to triple-helix formation; targeting RNA will lead to double-helix formation. Antisense polynucleotides, when introduced into a target cell, specifically bind to their target polynucleotide and interfere with transcription, RNA processing, transport, translation and/or stability. Antisense RNA constructs, or DNA encoding such antisense RNA's, may be employed to inhibit gene transcription or translation or both within a host cell, either in vitro or in vivo, such as within a host animal, including a human subject.

Antisense constructs may be designed to bind to the promoter and other control regions, exons, introns or even exon-intron boundaries of a gene. It is contemplated that the most effective antisense constructs will include regions complementary to intron/exon splice junctions. Thus, it is proposed that a preferred embodiment includes an antisense construct with complementarity to regions within 50-200 bases of an intron-exon splice junction. It has been observed that some exon sequences can be included in the construct without seriously affecting the target selectivity thereof. The amount of exonic material included will vary depending on the particular exon and intron sequences used. One can readily test whether too much exon DNA is included simply by testing the constructs in vitro to determine whether normal cellular function is affected or whether the expression of related genes having complementary sequences is altered.

As stated above, "complementary" or "antisense" means polynucleotide sequences that are substantially complementary over their entire length and have very few base mismatches. For example, sequences of fifteen bases in length may be termed complementary when they have complementary nucleotides at thirteen or fourteen positions. Naturally, sequences that are completely complementary will be sequences which are entirely complementary throughout their entire length and have no base mismatches. Other sequences with lower degrees of homology also are contemplated. For example, an antisense construct that has limited regions of high homology, but also contains a non-homologous region (e.g., ribozyme; see below) could be designed. These molecules, though having less than 50% homology, would bind to target sequences under appropriate conditions.

It may be advantageous to combine portions of genomic DNA with cDNA or synthetic sequences to generate specific constructs. For example, where an intron is desired in the ultimate construct, a genomic clone will need to be used. The cDNA or a synthesized polynucleotide may provide more convenient restriction sites for the remaining portion of the construct and, therefore, would be used for the rest of the sequence.

Particular oncogenes that are targets for antisense constructs are ras, myc, neu, raf erb, src, fms, jun, trk, ret, hst, gsp, bcl-2, and abl. Also contemplated to be useful are anti-apoptotic genes and angiogenesis promoters. Other antisense constructs can be directed at genes encoding viral or microbial genes to reduce or eliminate pathogenicity, such as HCV or HIV genes. Specific constructs target genes such as viral env, pol, gag, rev, tat, taf or coat or capsid genes, or microbial endotoxin, recombination, replication, or transcription genes.

b. Ribozymes

Although proteins traditionally have been used for catalysis of nucleic acids, another class of macromolecules has emerged as useful in this endeavor. Ribozymes are RNA-protein complexes that cleave nucleic acids in a site-specific fashion. Ribozymes have specific catalytic domains that possess endonuclease activity (Kim and Cook, 1987; Gerlach et al., 1987; Forster and Symons, 1987). For example, a large number of ribozymes accelerate phosphoester transfer reactions with a high degree of specificity, often cleaving only one of several phosphoesters in an oligonucleotide substrate (Michel and Westhof, 1990; Reinhold-Hurek and Shub, 1992). This specificity has been attributed to the requirement that the substrate bind via specific base-pairing interactions to the internal guide sequence ("IGS") of the ribozyme prior to chemical reaction.

Ribozyme catalysis has primarily been observed as part of sequence-specific cleavage/ligation reactions involving nucleic acids (Joyce, 1989; Cook et al., 1981). For example, U.S. Pat. No. 5,354,855 reports that certain ribozymes can act as endonucleases with a sequence specificity greater than that of known ribonucleases and approaching that of the DNA restriction enzymes. Thus, sequence-specific ribozyme-mediated inhibition of gene expression may be particularly suited to therapeutic applications (Scanlon et al., 1991; Sarver et al., 1990). Recently, it was reported that ribozymes elicited genetic changes in some cells lines to which they were applied; the altered genes included the oncogenes H-ras, c-fos and genes of HIV. Most of this work involved the modification of a target mRNA, based on a specific mutant codon that is cleaved by a specific ribozyme. Targets for this embodiment will include angiogenic genes such as VEGFs and angiopoietins as well as the oncogenes (e.g., ras, myc, neu, raf, erb, src, fms, jun, trk, ret, hst, gsp, bcl-2, EGFR, grb2 and abl). Other constructs will include overexpression of anti-apoptotic genes such as bcl-2, as well as microbial genes directed to viral or bacterial genes.

c. Other Heterologous Sequences

As the present invention is directed in some embodiments to the delivery of a sequence that is heterologous either to the virus or to a transduced cell, a variety of heterologous sequences are envisioned as part of the invention. Nucleic acid molecules that inhibit infection by non-GBV-C viruses are contemplated to be such sequences, for example, nucleotide inhibitors of HIV such as inhibitors of reverse transcriptase or integrase. In addition to encoding nucleic acid molecules, some embodiments of the invention concern the expression of a heterologous sequence as a polypeptide, and this would include proteinaceous inhibitors such as peptidic protease inhibitors, such as inhibitors of proteases associated with viral infection.

6. Introduction of Nucleic Acids into Cells

There are a number of ways in which nucleic acid molecules such as expression vectors may be introduced into cells. In certain embodiments of the invention, the expression vector comprises a GBV-C infectious particle or engineered vector derived from a GBV-C genome. The ability of certain viruses to enter cells via receptor-mediated endocytosis, to integrate into host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986). The first viruses used as gene vectors were DNA viruses including the papovaviruses (simian virus 40, bovine papilloma virus, and polyoma) (Ridgeway, 1988; Baichwal and Sugden, 1986) and adenoviruses (Ridgeway, 1988; Baichwal and Sugden, 1986). These have a relatively low capacity for foreign DNA sequences and have a restricted host spectrum. Furthermore, their oncogenic potential and cytopathic effects in permissive cells raise safety concerns. They can accommodate only up to 8 kb of foreign genetic material but can be readily introduced in a variety of cell lines and laboratory animals (Nicolas and Rubenstein, 1988; Temin, 1986).

"Viral expression vector" is meant to include those vectors containing sequences of that virus sufficient to (a) support packaging of the vector and (b) to express a polynucleotide that has been cloned therein. In this context, expression may require that the gene product be synthesized. The present invention encompasses the use of an infectious GBV-C clone as a viral vector to transport and express a heterologous sequence in a host cell. Alternatively, a viral expression vector could be used to generate RNA transcripts encoding viral packing sequences and a heterologous gene, such that transfection of the transcripts into a host cell yield infectious viral particles containing the heterologous sequence.

A number of such viral vectors have already been thoroughly researched, including adenovirus, adeno-associated viruses, retroviruses, herpesviruses, and vaccinia viruses.

Adenovirus vectors have been used in eukaryotic gene expression (Levrero et al., 1991; Gomez-Foix et al., 1992) and vaccine development (Grunhaus and Horwitz, 1992; Graham and Prevec, 1992). Recently, animal studies suggested that recombinant adenovirus could be used for gene therapy (Stratford-Perricaudet and Perricaudet, 1991; Stratford-Perricaudet et al., 1990; Rich et al., 1993). Studies in administering recombinant adenovirus to different tissues include trachea instillation (Rosenfeld et al., 1991; Rosenfeld et al., 1992), muscle injection (Ragot et al., 1993), peripheral intravenous injections (Herz and Gerard, 1993) and stereotactic inoculation into the brain (Le Gal La Salle et al., 1993).

The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences and also are required for integration in the host cell genome (Coffin, 1990).

In order to construct a retroviral vector, a nucleic acid encoding a gene of interest is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

A novel approach designed to allow specific targeting of retrovirus vectors was recently developed based on the chemical modification of a retrovirus by the chemical addition of lactose residues to the viral envelope. This modification could permit the specific infection of hepatocytes via sialoglycoprotein receptors.

A different approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

Other viral vectors may be employed as expression constructs in the present invention. Vectors derived from viruses such as vaccinia virus (Ridgeway, 1988; Baichwal and Sugden, 1986; Coupar et al., 1988) adeno-associated virus (AAV) (Ridgeway, 1988; Baichwal and Sugden, 1986; Hermonat and Muzycska, 1984) and herpesviruses may be employed. They offer several attractive features for various mammalian cells (Friedmann, 1989; Ridgeway, 1988; Baichwal and Sugden, 1986; Coupar et al., 1988; Horwich et al., 1990).

With the recent recognition of defective hepatitis B viruses (HBV), new insight was gained into the structure-function relationship of different viral sequences. In vitro studies showed that the virus could retain the ability for helper-dependent packaging and reverse transcription despite the deletion of up to 80% of its genome (Horwich et al., 1990). This suggested that large portions of the genome could be replaced with foreign genetic material. The hepatotropism and persistence (integration) were particularly attractive properties for liver-directed gene transfer. Chang et al., recently introduced the chloramphenicol acetyltransferase (CAT) gene into duck hepatitis B virus genome in the place of the polymerase, surface, and pre-surface coding sequences. It was co-transfected with wild-type virus into an avian hepatoma cell line. Culture media containing high titers of the recombinant virus were used to infect primary duckling hepatocytes. Stable CAT gene expression was detected for at least 24 days after transfection (Chang et al., 1991). A GBV-C viral vector may be constructed and propagated in a manner similar to HBV.

7. Methods of Gene Transfer

In order to effect expression of gene constructs, the expression vector or RNA transcripts must be delivered into a cell. This delivery may be accomplished in vitro, as in laboratory procedures for transforming cells lines, or in vivo or ex vivo, as in the treatment of certain disease states. One mechanism for delivery is via viral infection where the expression vector is encapsidated in an infectious viral particle. These methods are described above.

Several non-viral methods for the transfer of expression vectors into cultured mammalian cells also are contemplated by the present invention. These include calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Potter et al., 1984), direct microinjection (Harland and Weintraub, 1985), DNA-loaded liposomes (Nicolau and Sene, 1982; Fraley et al., 1979) and lipofectamine-DNA complexes, cell sonication (Fechheimer et al., 1987), gene bombardment using high velocity microprojectiles (Yang et al., 1990), and receptor-mediated transfection (Wu and Wu, 1987; Wu and Wu, 1988). Some of these techniques may be successfully adapted for in vivo or ex vivo use.

Once the expression vector or RNA transcript has been delivered into the cell the nucleic acid encoding the gene of interest may be positioned and expressed at different sites. In certain embodiments, the nucleic acid encoding a gene or genes may be stably integrated into the genome of the cell. This integration may be in the cognate location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression vector is delivered to a cell and where in the cell the nucleic acid remains is dependent on the type of expression vector employed.

Transfer of a nucleic acid molecule may be performed by any of the methods mentioned above which physically or chemically permeabilize the cell membrane. This is particularly applicable for transfer in vitro but it may be applied to in vivo use as well. Dubensky et al. (1984) successfully injected polyomavirus DNA in the form of calcium phosphate precipitates into liver and spleen of adult and newborn mice demonstrating active viral replication and acute infection. Benvenisty and Neshif (1986) also demonstrated that direct intraperitoneal injection of calcium phosphate-precipitated plasmids results in expression of the transfected genes. It is envisioned that DNA encoding a gene of interest also may be transferred in a similar manner in vivo and express the gene product.

An embodiment of the claimed invention transfers RNA transcripts or a combination of transcripts into cells via perfusion. Continuous perfusion of an expression construct or a viral construct also is contemplated. The amount of construct or peptide delivered in continuous perfusion can be determined by the amount of uptake that is desirable. The present invention discloses an example of perfusion whereby a cell culture with an initial concentration of $10^6$ cells/ml can first be labeled, washed, and then incubated with 100 µg of isolated RNA for two hours.

In still another embodiment of the invention for transferring a nucleic acid molecule into cells may involve particle bombardment. This method depends on the ability to accelerate DNA-coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

Selected organs including the liver, skin, and muscle tissue of rats and mice have been bombarded in vivo (Yang et al., 1990; Zelenin et al., 1991). This may require surgical exposure of the tissue or cells, to eliminate any intervening tissue between the gun and the target organ, i.e., ex vivo treatment. Again, nucleic acid encoding a particular gene such as GBV-C packing polypeptides may be delivered via this method and still be incorporated by the present invention.

In a further embodiment of the invention, the nucleic acid molecule may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated are lipofectamine-nucleic acid complexes.

Liposome-mediated nucleic acid delivery and expression of foreign nucleic acid in vitro has been very successful. Wong et al., (1980) demonstrated the feasibility of liposome-mediated delivery and expression of foreign DNA in cultured chick embryo, HeLa and hepatoma cells. Nicolau et al., (1987) accomplished successful liposome-mediated gene transfer in rats after intravenous injection.

In certain embodiments of the invention, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-1) (Kato et al., 1991). In yet further embodiments, the liposome may be complexed or employed in conjunction with both HVJ and HMG-1. In that such expression vectors have been successfully employed in transfer and expression of nucleic acid in vitro and in vivo, then they are applicable for the present invention. Where a bacterial promoter is employed in the DNA vector, it also will be desirable to include within the liposome an appropriate bacterial polymerase.

Lipid based non-viral formulations provide an alternative to adenoviral gene therapies. Although many cell culture studies have documented lipid based non-viral gene transfer, systemic gene delivery via lipid based formulations has been limited. A major limitation of non-viral lipid based gene delivery is the toxicity of the cationic lipids that comprise the non-viral delivery vehicle. The in vivo toxicity of liposomes partially explains the discrepancy between in vitro and in vivo gene transfer results. Another factor contributing to this contradictory data is the difference in lipid vehicle stability in the presence and absence of serum proteins. The interaction between lipid vehicles and serum proteins has a dramatic impact on the stability characteristics of lipid vehicles (Yang and Huang, 1997). Cationic lipids attract and bind negatively charged serum proteins. Lipid vehicles associated with serum proteins are either dissolved or taken up by macrophages leading to their removal from circulation. Current in vivo lipid delivery methods use subcutaneous, intradermal, intratumoral, or intracranial injection to avoid the toxicity and stability problems associated with cationic lipids in the circulation. The interaction of lipid vehicles and plasma proteins is responsible for the disparity between the efficiency of in vitro (Felgner et al., 1987) and in vivo gene transfer (Zhu et al., 1993; Philip et al., 1993; Solodin et al., 1995; Liu et al., 1995; Thierry et al., 1995; Tsukamoto et al., 1995; Aksentijevich et al., 1996).

Recent advances in lipid formulations have improved the efficiency of gene transfer in vivo (Smyth-Templeton et al. 1997; WO 98/07408). A novel lipid formulation composed of an equimolar ratio of 1,2-bis(oleoyloxy)-3-(trimethyl ammonio)propane (DOTAP) and cholesterol significantly enhances systemic in vivo gene transfer, approximately 150 fold. The DOTAP:cholesterol lipid formulation is said to form a unique structure termed a "sandwich liposome." This formulation is reported to "sandwich" DNA between an invaginated bi-layer or 'vase' structure. Beneficial characteristics of these lipid structures include a positive ρ, colloidal stabilization by cholesterol, two dimensional DNA packing and increased serum stability.

The production of lipid formulations often is accomplished by sonication or serial extrusion of liposomal mixtures after (I) reverse phase evaporation (II) dehydration-rehydration (III) detergent dialysis and (IV) thin film hydration. Once manufactured, lipid structures can be used to encapsulate compounds that are toxic (chemotherapeutics) or labile (nucleic acids) when in circulation. Lipid encapsulation has resulted in a lower toxicity and a longer serum half-life for such compounds (Gabizon et al., 1990). Numerous disease treatments are using lipid based gene transfer strategies to enhance conventional or establish novel therapies.

In certain embodiments of the invention, the lipid vehicle may be complexed with a hemagglutinating virus (HVJ). This has been shown to facilitate fusion with the cell membrane and promote cell entry of lipid-encapsulated DNA (Kaneda et al., 1989). In other embodiments, the lipid vehicle may be complexed or employed in conjunction with nuclear non-histone chromosomal proteins (HMG-1) (Kato et al., 1991). In yet further embodiments, the lipid vehicle may be complexed or employed in conjunction with both HVJ and HMG-1.

Protamine may also be used to form a complex with an expression construct. Such complexes may then be formulated with the lipid compositions described above for administration to a cell. Protamines are small highly basic nucleoproteins associated with DNA. Their use in the delivery of nucleic acids is described in U.S. Pat. No. 5,187,260.

Other expression vectors that can be employed to deliver a nucleic acid encoding a particular gene into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu, 1993).

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987) and transferrin (Wagner et al., 1990). A synthetic neoglycoprotein, which recognizes the same receptor as ASOR, has been used as a gene delivery vehicle (Ferkol et al., 1993; Perales et al., 1994) and epidermal growth factor (EGF) also has been used to deliver genes to squamous carcinoma cells (Myers, EPO 0273085).

In other embodiments, the delivery vehicle may comprise a ligand and a liposome. For example, Nicolau et al., (1987) employed lactosyl-ceramide, a galactose-terminal asialganglioside, incorporated into liposomes and observed an increase in the uptake of the insulin gene by hepatocytes. Thus, it is feasible that a nucleic acid encoding a particular gene also may be specifically delivered into a cell type such as lung, epithelial or tumor cells, by any number of receptor-ligand systems with or without liposomes. For example, epidermal growth factor (EGF) may be used as the receptor for mediated delivery of a nucleic acid encoding a gene in many tumor cells that exhibit upregulation of EGF receptor. Mannose can be used to target the mannose receptor on liver cells. Also, antibodies to CD5 (CLL), CD22 (lymphoma), CD25 (T-cell leukemia) and MAA (melanoma) can similarly be used as targeting moieties.

In certain embodiments, gene transfer may more easily be performed under ex vivo conditions. Ex vivo gene therapy refers to the isolation of cells from an animal, the delivery of a nucleic acid into the cells in vitro, and then the return of the modified cells back into an animal. This may involve the surgical removal of tissue/organs from an animal or the primary culture of cells and tissues.

Continuous perfusion of an expression vector or a viral vector also is contemplated. The amount of vector or peptide delivered in continuous perfusion can be determined by the amount of uptake that is desirable.

Primary mammalian cell cultures may be prepared in various ways. In order for the cells to be kept viable while in vitro and in contact with the nucleic acid molecule, it is necessary to ensure that the cells maintain contact with the correct ratio of oxygen and carbon dioxide and nutrients but are protected from microbial contamination. Cell culture techniques are well documented and are disclosed herein by reference (Freshner, 1992).

During in vitro culture conditions the expression construct may then deliver and express a nucleic acid encoding GBV-C proteins and/or a heterologous gene(s) into the cells. Finally, the cells may be reintroduced into the original animal, or administered into a distinct animal, in a pharmaceutically acceptable form by any of the means described below. Thus, providing an ex vivo method of treating a mammal with a pathologic condition is within the scope of the invention.

8. Nucleic Acid Detection

In addition to their use in yielding GBV-C proteins, polypeptides and/or peptides, the nucleic acid sequences disclosed herein have a variety of other uses. For example, they have utility as probes or primers for embodiments involving nucleic acid hybridization, such as sequence comparison and detection of infection.

a. Hybridization

The use of a probe or primer of between 13 and 100 nucleotides, preferably between 17 and 100 nucleotides in length, or in some aspects of the invention up to 1-2 kilobases or more in length, allows the formation of a duplex molecule that is both stable and selective. Molecules having complementary sequences over contiguous stretches greater than 20 bases in length are generally preferred, to increase stability and/or selectivity of the hybrid molecules obtained. One will generally prefer to design nucleic acid molecules for hybridization having one or more complementary sequences of 20 to 30 nucleotides, or even longer where desired. Such fragments may be readily prepared, for example, by directly synthesizing the fragment by chemical means or by introducing selected sequences into recombinant vectors for recombinant production.

Accordingly, the nucleotide sequences of the invention may be used for their ability to selectively form duplex molecules with complementary stretches of DNAs and/or RNAs or to provide primers for amplification of DNA or RNA from samples. Depending on the application envisioned, one would desire to employ varying conditions of hybridization to achieve varying degrees of selectivity of the probe or primers for the target sequence.

For applications requiring high selectivity, one will typically desire to employ relatively high stringency conditions to form the hybrids. For example, relatively low salt and/or high temperature conditions, such as provided by about 0.02 M to about 0.10 M NaCl at temperatures of about 50° C. to about 70° C. Such high stringency conditions tolerate little, if any, mismatch between the probe or primers and the template or target strand and would be particularly suitable for isolating specific genes or for detecting specific mRNA transcripts. It is generally appreciated that conditions can be rendered more stringent by the addition of increasing amounts of formamide.

For certain applications, for example, site-directed mutagenesis, it is appreciated that lower stringency conditions are preferred. Under these conditions, hybridization may occur even though the sequences of the hybridizing strands are not perfectly complementary, but are mismatched at one or more positions. Conditions may be rendered less stringent by increasing salt concentration and/or decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Hybridization conditions can be readily manipulated depending on the desired results.

In other embodiments, hybridization may be achieved under conditions of, for example, 50 mM Tris-HCl (pH 8.3), 75 mM KCl, 3 mM $MgCl_2$, 1.0 mM dithiothreitol, at temperatures between approximately 20° C. to about 37° C. Other hybridization conditions utilized could include approximately 10 mM Tris-HCl (pH 8.3), 50 mM KCl, 1.5 mM $MgCl_2$, at temperatures ranging from approximately 40° C. to about 72° C.

In certain embodiments, it will be advantageous to employ nucleic acids of defined sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of being detected. In preferred embodiments, one may desire to employ a fluorescent label or an enzyme tag such as urease, alkaline phosphatase or peroxidase, instead of radioactive or other environmentally undesirable reagents. In the case of enzyme tags, colorimetric indicator substrates are known that can be employed to provide a detection means that is visibly or spectrophotometrically detectable, to identify specific hybridization with complementary nucleic acid containing samples.

In general, it is envisioned that the probes or primers described herein will be useful as reagents in solution hybridization, as in PCR, for detection of expression of corresponding genes, as well as in embodiments employing a solid phase. In embodiments involving a solid phase, the test DNA (or RNA) is adsorbed or otherwise affixed to a selected matrix or surface. This fixed, single-stranded nucleic acid is then subjected to hybridization with selected probes under desired conditions. The conditions selected will depend on the particular circumstances (depending, for example, on the G+C content, type of target nucleic acid, source of nucleic acid, size of hybridization probe, etc.). Optimization of hybridization conditions for the particular application of interest is well known to those of skill in the art. After washing of the hybridized molecules to remove non-specifically bound probe molecules, hybridization is detected, and/or quantified, by determining the amount of bound label. Representative solid phase hybridization methods are disclosed in U.S. Pat. Nos. 5,843,663, 5,900,481 and 5,919,626. Other methods of hybridization that may be used in the practice of the present invention are disclosed in U.S. Pat. Nos. 5,849,481, 5,849,486 and 5,851,772.

b. Amplification of Nucleic Acids

Nucleic acids used as a template for amplification may be isolated from cells, tissues or other samples according to standard methodologies (Sambrook et al., 1989). In certain embodiments, analysis is performed on whole cell or tissue homogenates or biological fluid samples without substantial purification of the template nucleic acid. The nucleic acid may be genomic DNA or fractionated or whole cell RNA. Where RNA is used, it may be desired to first convert the RNA to a complementary DNA.

The term "primer," as used herein, is meant to encompass any nucleic acid that is capable of priming the synthesis of a nascent nucleic acid in a template-dependent process. Typically, primers are oligonucleotides from ten to twenty and/or thirty base pairs in length, but longer sequences can be employed. Primers may be provided in double-stranded and/or single-stranded form, although the single-stranded form is preferred.

Pairs of primers designed to selectively hybridize to nucleic acids corresponding to GBV-C sequences are contacted with the template nucleic acid under conditions that permit selective hybridization. Depending upon the desired application, high stringency hybridization conditions may be selected that will only allow hybridization to sequences that are completely complementary to the primers. In other embodiments, hybridization may occur under reduced stringency to allow for amplification of nucleic acids contain one or more mismatches with the primer sequences. Once hybridized, the template-primer complex is contacted with one or more enzymes that facilitate template-dependent nucleic acid synthesis. Multiple rounds of amplification, also referred to as "cycles," are conducted until a sufficient amount of amplification product is produced.

The amplification product may be detected or quantified. In certain applications, the detection may be performed by visual means. Alternatively, the detection may involve indirect identification of the product via chemiluminescence, radioactive scintigraphy of incorporated radiolabel or fluorescent label or even via a system using electrical and/or thermal impulse signals (Affymax technology; Bellus, 1994).

A number of template dependent processes are available to amplify the oligonucleotide sequences present in a given template sample. One of the best known amplification methods is the polymerase chain reaction (referred to as PCR) which is described in detail in U.S. Pat. Nos. 4,683,195, 4,683,202 and 4,800,159, and in Innis et al., 1990.

A reverse transcriptase PCR amplification procedure may be performed to quantify the amount of mRNA amplified. Methods of reverse transcribing RNA into cDNA are well known and described in Sambrook et al., 1989. Alternative methods for reverse transcription utilize thermostable DNA polymerases. These methods are described in WO 90/07641. Polymerase chain reaction methodologies are well known in the art. Representative methods of RT-PCR are described in U.S. Pat. No. 5,882,864.

Another method for amplification is ligase chain reaction ("LCR"), disclosed in European Application No. 320 308. U.S. Pat. No. 4,883,750 describes a method similar to LCR for binding probe pairs to a target sequence. A method based on PCR and oligonucleotide ligase assay (OLA), disclosed in U.S. Pat. No. 5,912,148, may also be used.

Alternative methods for amplification of target nucleic acid sequences that may be used in the practice of the present invention are disclosed in U.S. Pat. Nos. 5,843,650, 5,846,709, 5,846,783, 5,849,546, 5,849,497, 5,849,547, 5,858,652, 5,866,366, 5,916,776, 5,922,574, 5,928,905, 5,928,906, 5,932,451, 5,935,825, 5,939,291 and 5,942,391, GB Application No. 2 202 328, and in PCT Application No. PCT/US89/01025.

Qbeta Replicase, described in PCT Application No. PCT/US87/00880, may also be used as an amplification method in the present invention. In this method, a replicative sequence of RNA that has a region complementary to that of a target is added to a sample in the presence of an RNA polymerase. The polymerase will copy the replicative sequence which may then be detected.

An isothermal amplification method, in which restriction endonucleases and ligases are used to achieve the amplification of target molecules that contain nucleotide 5'-[alpha-thio]-triphosphates in one strand of a restriction site may also be useful in the amplification of nucleic acids in the present invention (Walker et al., 1992). Strand Displacement Amplification (SDA), disclosed in U.S. Pat. No. 5,916,779, is another method of carrying out isothermal amplification of nucleic acids which involves multiple rounds of strand displacement and synthesis, i.e., nick translation.

Other nucleic acid amplification procedures include transcription-based amplification systems (TAS), including nucleic acid sequence based amplification (NASBA) and 3SR (Kwoh et al., 1989; Gingeras et al., PCT Application WO 88/10315). Davey et al., European Application No. 329 822 disclose a nucleic acid amplification process involving cyclically synthesizing single-stranded RNA ("ssRNA"), ssDNA, and double-stranded DNA (dsDNA), which may be used in accordance with the present invention.

Miller et al., PCT Application WO 89/06700 disclose a nucleic acid sequence amplification scheme based on the hybridization of a promoter region/primer sequence to a target single-stranded DNA ("ssDNA") followed by transcription of many RNA copies of the sequence. This scheme is not cyclic, i.e., new templates are not produced from the resultant RNA transcripts. Other amplification methods include "race" and "one-sided PCR" (Frohman, 1990; Ohara et al., 1989a).

c. Detection of Nucleic Acids

Following any amplification, it may be desirable to separate the amplification product from the template and/or the excess primer. In one embodiment, amplification products are separated by agarose, agarose-acrylamide or polyacrylamide gel electrophoresis using standard methods (Sambrook et al., 1989). Separated amplification products may be cut out and eluted from the gel for further manipulation. Using low melting point agarose gels, the separated band may be removed by heating the gel, followed by extraction of the nucleic acid.

Separation of nucleic acids may also be effected by chromatographic techniques known in art. There are many kinds of chromatography that may be used in the practice of the present invention, including adsorption, partition, ion-exchange, hydroxylapatite, molecular sieve, reverse-phase, column, paper, thin-layer, and gas chromatography as well as HPLC.

In certain embodiments, the amplification products are visualized. A typical visualization method involves staining of a gel with ethidium bromide and visualization of bands under UV light. Alternatively, if the amplification products are integrally labeled with radio- or fluorometrically-labeled nucleotides, the separated amplification products can be exposed to x-ray film or visualized under the appropriate excitatory spectra.

In one embodiment, following separation of amplification products, a labeled nucleic acid probe is brought into contact with the amplified marker sequence. The probe preferably is conjugated to a chromophore but may be radiolabeled. In another embodiment, the probe is conjugated to a binding partner, such as an antibody or biotin, or another binding partner carrying a detectable moiety.

In particular embodiments, detection is by Southern blotting and hybridization with a labeled probe. The techniques involved in Southern blotting are well known to those of skill in the art. See Sambrook et al., 1989. One example of the foregoing is described in U.S. Pat. No. 5,279,721, which discloses an apparatus and method for the automated electrophoresis and transfer of nucleic acids. The apparatus permits electrophoresis and blotting without external manipulation of the gel and is ideally suited to carrying out methods according to the present invention.

Other methods of nucleic acid detection that may be used in the practice of the instant invention are disclosed in U.S. Pat. Nos. 5,840,873, 5,843,640, 5,843,651, 5,846,708, 5,846,717, 5,846,726, 5,846,729, 5,849,487, 5,853,990, 5,853,992, 5,853,993, 5,856,092, 5,861,244, 5,863,732, 5,863,753, 5,866,331, 5,905,024, 5,910,407, 5,912,124, 5,912,145, 5,919,630, 5,925,517, 5,928,862, 5,928,869, 5,929,227, 5,932,413 and 5,935,791.

d. Other Assays

Other methods for genetic screening may be used within the scope of the present invention, for example, to detect mutations in genomic DNA, cDNA and/or RNA samples. Methods used to detect point mutations include denaturing gradient gel electrophoresis ("DGGE"), restriction fragment length polymorphism analysis ("RFLP"), chemical or enzymatic cleavage methods, direct sequencing of target regions amplified by PCR, single-strand conformation polymorphism analysis ("SSCP") and other methods well known in the art.

One method of screening for point mutations is based on RNase cleavage of base pair mismatches in RNA/DNA or RNA/RNA heteroduplexes. As used herein, the term "mismatch" is defined as a region of one or more unpaired or mispaired nucleotides in a double-stranded RNA/RNA, RNA/DNA or DNA/DNA molecule. This definition thus includes mismatches due to insertion/deletion mutations, as well as single or multiple base point mutations.

U.S. Pat. No. 4,946,773 describes an RNase A mismatch cleavage assay that involves annealing single-stranded DNA or RNA test samples to an RNA probe, and subsequent treatment of the nucleic acid duplexes with RNase A. For the detection of mismatches, the single-stranded products of the RNase A treatment, electrophoretically separated according to size, are compared to similarly treated control duplexes. Samples containing smaller fragments (cleavage products) not seen in the control duplex are scored as positive.

Other investigators have described the use of RNase I in mismatch assays. The use of RNase I for mismatch detection is described in literature from Promega Biotech. Promega markets a kit containing RNase I that is reported to cleave three out of four known mismatches. Others have described using the MutS protein or other DNA-repair enzymes for detection of single-base mismatches.

Alternative methods for detection of deletion, insertion or substitution mutations that may be used in the practice of the present invention are disclosed in U.S. Pat. Nos. 5,849,483, 5,851,770, 5,866,337, 5,925,525 and 5,928,870.

B. Polypeptides

The present application is directed to the function or activity of an infectious GBV-C, which indicates it has the ability to propagate itself in a cell to produce an infectious GBV-C virus particle; expression of certain GBV-C polypeptides are required for virus activity, including replication, processing, and infection. The translated product of SEQ ID NO:1 is provided by SEQ ID NO:2. It is contemplated that the compositions and methods disclosed herein may be utilized to express part or all of SEQ ID NO:2. Determination of which molecules possess this ability may be achieved using functional assays measuring infectivity familiar to those of skill in the art. In other embodiments of the invention, heterologous polypeptides may be encoded by a sequence that also contains GBV-C sequences. "Heterologous" polypeptide indicates the polypeptide is not a GBV-C polypeptide. An endogenous GBV-C polypeptide refers to a polypeptide encoded by GBV-C viral RNA. Such a polypeptide would possess the same or similar sequence as SEQ ID NO:2.

1. Variants of Polypeptides

Amino acid sequence variants of the polypeptide can be substitutional, insertional or deletion variants. Deletion variants lack one or more residues of the native protein that are not essential for function or immunogenic activity, and are exemplified by the variants lacking a transmembrane sequence described above. Another common type of deletion variant is one lacking secretory signal sequences or signal sequences directing a protein to bind to a particular part of a cell. Insertional mutants typically involve the addition of material at a non-terminal point in the polypeptide. This may include the insertion of an immunoreactive epitope or simply a single residue. Terminal additions, called fusion proteins, are discussed below.

Substitutional variants typically contain the exchange of one amino acid for another at one or more sites within the protein, and may be designed to modulate one or more properties of the polypeptide, such as stability against proteolytic cleavage, without the loss of other functions or properties. Substitutions of this kind preferably are conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

The term "biologically functional equivalent" is well understood in the art and is further defined in detail herein. Accordingly, sequences that have between about 70% and about 80%; or more preferably, between about 81% and about 90%; or even more preferably, between about 91% and about 99%; of amino acids that are identical or functionally equivalent to the amino acids of GBV-C polypeptides, for example SEQ ID NO:2, provided the biological activity of the protein is maintained.

The term "functionally equivalent codon" is used herein to refer to codons that encode the same amino acid, such as the six codons for arginine or serine, and also refers to codons that encode biologically equivalent amino acids (see Table 3, below).

TABLE 3

CODON TABLE

| Amino Acids | | | Codons | | | | | |
|---|---|---|---|---|---|---|---|---|
| Alanine | Ala | A | GCA | GCC | GCG | GCU | | |
| Cysteine | Cys | C | UGC | UGU | | | | |
| Aspartic acid | Asp | D | GAC | GAU | | | | |
| Glutamic acid | Glu | E | GAA | GAG | | | | |
| Phenylalanine | Phe | F | UUC | UUU | | | | |
| Glycine | Gly | G | GGA | GGC | GGG | GGU | | |
| Histidine | His | H | CAC | CAU | | | | |
| Isoleucine | Ile | I | AUA | AUC | AUU | | | |
| Lysine | Lys | K | AAA | AAG | | | | |
| Leucine | Leu | L | UUA | UUG | CUA | CUC | CUG | CUU |
| Methionine | Met | M | AUG | | | | | |

TABLE 3-continued

CODON TABLE

| Amino Acids | | | Codons | | | | |
|---|---|---|---|---|---|---|---|
| Asparagine | Asn | N | AAC | AAU | | | |
| Proline | Pro | P | CCA | CCC | CCG | CCU | |
| Glutamine | Gln | Q | CAA | CAG | | | |
| Arginine | Arg | R | AGA | AGG | CGA | CGC | CGG CGU |
| Serine | Ser | S | AGC | AGU | UCA | UCC | UCG UCU |
| Threonine | Thr | T | ACA | ACC | ACG | ACU | |
| Valine | Val | V | GUA | GUC | GUG | GUU | |
| Tryptophan | Trp | W | UGG | | | | |
| Tyrosine | Tyr | Y | UAC | UAU | | | |

It also will be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences that may, for example, include various non-coding sequences flanking either of the 5' or 3' portions of the coding region or may include various internal sequences, i.e., introns, which are known to occur within genes.

The following is a discussion based upon changing of the amino acids of a protein to create an equivalent, or even an improved, second-generation molecule. For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid substitutions can be made in a protein sequence, and in its underlying DNA coding sequence, and nevertheless produce a protein with like properties. It is thus contemplated by the inventors that various changes may be made in the DNA sequences of genes without appreciable loss of their biological utility or activity, as discussed below. Table 3 shows the codons that encode particular amino acids.

In making such changes, the hydropathic index of amino acids may be considered. The importance of the hydropathic amino acid index in conferring interactive biologic function on a protein is generally understood in the art (Kyte & Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It also is understood in the art that the substitution of like amino acids can be made effectively on the basis of hydrophilicity. U.S. Pat. No. 4,554,101 states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine *−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still produce a biologically equivalent and immunologically equivalent protein. In such changes, the substitution of amino acids whose hydrophilicity values are within ±2 is preferred, those that are within ±1 are particularly preferred, and those within ±0.5 are even more particularly preferred.

As outlined above, amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known to those of skill in the art and include: arginine and lysine; glutamate and aspartate; serine and threonine; glutamine and asparagine; and valine, leucine and isoleucine.

The amino acid sequence of the variant GBV-C polypeptide corresponds essentially to the native GBV-C amino acid sequence. As used herein "correspond essentially to" refers to a polypeptide sequence that will elicit a protective immunological response substantially the same as the response generated by native GBV-C. Such a response may be at least 60% of the level generated by native GBV-C, and may even be at least 80% of the level generated by native GBV-C. An immunological response to a composition or vaccine is the development in the host of a cellular and/or antibody-mediated immune response to the polypeptide or vaccine of interest. Usually, such a response consists of the subject producing antibodies, B cell, helper T cells, suppressor T cells, and/or cytotoxic T cells directed specifically to an antigen or antigens included in the composition or vaccine of interest.

A variant of the invention may include amino acid residues not present in the corresponding native GBV-C or deletions relative to the corresponding native GBV-C. A variant may also be a truncated "fragment" as compared to the corresponding native GBV-C, i.e., only a portion of a full-length protein. GBV-C variants also include peptides having at least one D-amino acid.

2. Fusion Proteins

A specialized kind of insertional variant is the fusion protein. This molecule generally has all or a substantial portion of the native molecule, linked at the N- or C-terminus, to all or a portion of a second polypeptide. For example, fusions typically employ leader sequences from other species to permit the recombinant expression of a protein in a heterologous host. Another useful fusion includes the addition of an immunologically active domain, such as an antibody epitope, to facilitate purification of the fusion protein. Inclusion of a cleavage site at or near the fusion junction will facilitate removal of the extraneous polypeptide after purification. Other useful fusions include linking of functional domains, such as active sites from enzymes such as a hydrolase, glycosylation domains, cellular targeting signals or transmembrane regions.

3. In Vitro Protein Production

Following transduction with a vector according to some embodiments of the present invention, primary mammalian cell cultures may be prepared in various ways. A host cell strain may be chosen that modulates the expression of the inserted sequences, or that modifies and processes the gene product in the manner desired. Such modifications (e.g., glycosylation) and processing (e.g., cleavage) of protein products may be important for the function of the protein. Different host cells have characteristic and specific mechanisms for the post-translational processing and modification of proteins. Appropriate cell lines or host systems can be chosen to insure the correct modification and processing of the foreign protein expressed. In order for the cells to be kept viable while in vitro and in contact with the expression construct, it is necessary to ensure that the cells maintain contact with the correct ratio of oxygen and carbon dioxide and nutrients but are protected from microbial contamination. Cell culture techniques are well documented and are disclosed herein by reference (Freshner, 1992).

One embodiment of the foregoing involves the use of gene transfer to immortalize cells for the production and/or presentation of proteins. The gene for the protein of interest may be transferred as described above into appropriate host cells followed by culture of cells under the appropriate conditions. The gene for virtually any polypeptide may be employed in this manner. The generation of recombinant expression vectors, and the elements included therein, are discussed above. Alternatively, the protein to be produced may be an endogenous protein normally synthesized by the cell in question.

A number of selection systems may be used including, but not limited to, HSV thymidine kinase, hypoxanthine-guanine phosphoribosyltransferase and adenine phosphoribosyltransferase genes, in tk-, hgprt- or aprt-cells, respectively. Also, anti-metabolite resistance can be used as the basis of selection: for dhfr, which confers resistance to; gpt, which confers resistance to mycophenolic acid; neo, which confers resistance to the aminoglycoside G418; and hygro, which confers resistance to hygromycin.

Animal cells can be propagated in vitro in two modes: as non-anchorage-dependent cells growing in suspension throughout the bulk of the culture or as anchorage-dependent cells requiring attachment to a solid substrate for their propagation (i.e., a monolayer type of cell growth).

Non-anchorage dependent or suspension cultures from continuous established cell lines are the most widely used means of large scale production of cells and cell products. However, suspension cultured cells have limitations, such as tumorigenic potential and lower protein production than adherent cells.

4. Protein Purification

It may be desirable to purify GBV-C polypeptides, heterologous peptides and polypeptides, or variants thereof. Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. A particularly efficient method of purifying peptides is fast protein liquid chromatography or even HPLC.

Certain aspects of the present invention concern the purification, and in particular embodiments, the substantial purification, of an encoded protein or peptide. The term "purified protein or peptide" as used herein, is intended to refer to a composition, isolatable from other components, wherein the protein or peptide is purified to any degree relative to its naturally-obtainable state. A purified protein or peptide therefore also refers to a protein or peptide, free from the environment in which it may naturally occur.

Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number." The actual units used to represent the amount of activity will, of course, be dependent upon the particular assay technique chosen to follow the purification and whether or not the expressed protein or peptide exhibits a detectable activity.

Various techniques suitable for use in protein purification will be well known to those of skill in the art. These include, for example, precipitation with ammonium sulphate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

High Performance Liquid Chromatography (HPLC) is characterized by a very rapid separation with extraordinary resolution of peaks. This is achieved by the use of very fine particles and high pressure to maintain an adequate flow rate. Separation can be accomplished in a matter of minutes, or at most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Gel chromatography, or molecular sieve chromatography, is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size. Hence, molecules are eluted from the column in decreasing size, so long as the shape is relatively constant. Gel chromatography is unsurpassed for separating molecules of different size because separation is independent of all other factors such as pH, ionic strength, temperature, etc. There also is virtually no adsorption, less zone spreading and the elution volume is related in a simple matter to molecular weight.

Affinity Chromatography is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (e.g., alter pH, ionic strength, and temperature.).

A particular type of affinity chromatography useful in the purification of carbohydrate containing compounds is lectin affinity chromatography. Lectins are a class of substances that bind to a variety of polysaccharides and glycoproteins. Lectins are usually coupled to agarose by cyanogen bromide. Conconavalin A coupled to Sepharose was the first material of this sort to be used and has been widely used in the isolation of polysaccharides and glycoproteins other lectins that have been include lentil lectin, wheat germ agglutinin which has been useful in the purification of N-acetyl glucosaminyl residues and *Helix pomatia* lectin. Lectins themselves are purified using affinity chromatography with carbohydrate ligands. Lactose has been used to purify lectins from castor bean and peanuts; maltose has been useful in extracting lectins from lentils and jack bean; N-acetyl-D galactosamine is used for purifying lectins from soybean; N-acetyl glucosaminyl binds to lectins from wheat germ; D-galactosamine has been used in obtaining lectins from clams and L-fucose will bind to lectins from lotus.

The matrix should be a substance that itself does not adsorb molecules to any significant extent and that has a broad range of chemical, physical and thermal stability. The ligand should be coupled in such a way as to not affect its binding properties. The ligand also should provide relatively tight binding. And it should be possible to elute the substance without destroying the sample or the ligand. One of the most common forms of affinity chromatography is immunoaffinity chromatography. The generation of antibodies that would be suitable for use in accord with the present invention is discussed below.

II. Therapies

A. Treatment with a Heterologous Sequence

Some of the therapeutic embodiments contemplated by the present invention involve administering or supplying an infectious GBV-C nucleic acid molecule. Heterologous sequences, such as a gene or genes, may be included in the molecule such that these sequences are provided to and expressed within a cell via an infectious GBV-C virus, transcripts, or viral vector. The heterologous sequences may be from a prokaryote, eukaryote, or non-GBV-C virus. In some embodiments the infectious GBV-C nucleic acid molecule is employed simply as an effective vehicle for transporting heterologous sequences to a cell. In some cases, the heterologous gene is a wild-type copy, which will be provided to a cell lacking the wild-type gene. In addition to encoding non-expressed sequences such as ribozymes and antisense sequences, heterologous sequences could encode, but are not limited to, the following classes of gene products: cytokines, tumor suppressors, protein kinases, protein phosphorylases, proteases, protease inhibitors, receptors, transcription factors, ion channels, neurotransmitters, hormones and chemokines, toxins, transporters, ligands, cell cycle proteins, adhesion proteins, structural proteins, proteins involved in post-translational modification; chaperones; proteins that provokes an immune response (antigen); proteins involved in cell division; repair enzymes; proteins involved in replication, transcription, or translation; proteins involved in apoptosis; scavenger proteins; and housekeeping proteins. Some of these are discussed in more detail below. The compositions and methods of the present invention may be used with any of the genes or proteins, or with a combination of these genes and proteins.

1. Tumor Suppressors p53 currently is recognized as a tumor suppressor gene. High levels of mutant p53 have been found in many cells transformed by chemical carcinogenesis, ultraviolet radiation, and several viruses. The p53 gene is a frequent target of mutational inactivation in a wide variety of human tumors and is already documented to be the most frequently-mutated gene in common human cancers. It is mutated in over 50% of human NSCLC (Hollstein et al., 1991) and in a wide spectrum of other tumors.

Wild-type p53 is recognized as an important growth regulator in many cell types. Missense mutations are common for the p53 gene and are essential for the transforming ability of the oncogene. A single genetic change prompted by point mutations can create carcinogenic p53, in as much as mutations in p53 are known to abrogate the tumor suppressor capability of wild-type p53. Casey and colleagues have reported that transfection of DNA encoding wild-type p53 into two human breast cancer cell lines restores growth suppression control in such cells (Casey et al., 1991). A similar effect also has been demonstrated on transfection of wild-type, but not mutant, p53 into human lung cancer cell lines (Takahasi et al., 1992). p53 appears dominant over the mutant gene and will select against proliferation when transfected into cells with the mutant gene. Normal expression of the transfected p53 does not affect the growth of normal or non-malignant cells with endogenous p53. Thus, such constructs might be taken up by normal cells without adverse effects. It is thus proposed that the treatment of p53-associated cancers with wild-type p53 will reduce the number of malignant cells or their growth rate.

The major transitions of the eukaryotic cell cycle are triggered by cyclin-dependent kinases, or CDK's. One CDK, cyclin-dependent kinase 4 (CDK4), regulates progression through the $G_1$. The activity of this enzyme may be to phosphorylate Rb at late $G_1$. The activity of CDK4 is controlled by an activating subunit, D-type cyclin, and by an inhibitory subunit p16$^{INK4}$. The p16$^{INK4}$ has been biochemically characterized as a protein that specifically binds to and inhibits CDK4, and thus may regulate Rb phosphorylation (Serrano et al., 1993; Serrano et al., 1995). Since the p16$^{INK4}$ protein is a CDK4 inhibitor (Serrano, 1993), deletion of this gene may increase the activity of CDK4, resulting in hyperphosphorylation of the Rb protein. p16 also is known to regulate the function of CDK6.

p16$^{INK4}$ belongs to a newly described class of CDK-inhibitory proteins that also includes p15$^{INK4B}$, p21$^{WAF1}$ and p27$^{KIP1}$. The p16$^{INK4}$ gene maps to 9p21, a chromosome region frequently deleted in many tumor types. Homozygous deletions and mutations of the p16$^{INK4}$ gene are frequent in human tumor cell lines. This evidence suggests that the p16$^{INK4}$ gene is a tumor suppressor gene. This interpretation has been challenged, however, by the observation that the frequency of the p16$^{INK4}$ gene alterations is much lower in primary uncultured tumors than in cultured cell lines (Caldas et al., 1994; Cheng et al., 1994; Hussussian et al., 1994; Kamb et al., 1994; Kamb et al., 1994; Mori et al., 1994; Okamoto et al., 1994; Nobori et al., 1995; Orlow et al., 1994; Arap et al., 1995). However, it was later shown that while the p16 gene was intact in many primary tumors, there were other mechanisms that prevented p16 protein expression in a large percentage of some tumor types. p16 promoter hypermethylation is one of these mechanisms (Merlo et al., 1995; Herman, 1995; Gonzalez-Zulueta, 1995). Restoration of wild-type p16$^{INK4}$ function by transfection with a plasmid expression vector reduced colony formation by some human cancer cell lines (Okamoto, 1994; Arap, 1995). Delivery of p16 with adenovirus vectors inhibits proliferation of some human cancer lines and reduces the growth of human tumor xenografts.

C-CAM is expressed in virtually all epithelial cells (Odin and Obrink, 1987). C-CAM, with an apparent molecular weight of 105 kD, was originally isolated from the plasma membrane of the rat hepatocyte by its reaction with specific antibodies that neutralize cell aggregation (Obrink, 1991). Recent studies indicate that, structurally, C-CAM belongs to the immunoglobulin (Ig) superfamily and its sequence is highly homologous to carcinoembryonic antigen (CEA) (Lin and Guidotti, 1989). Using a baculovirus expression system, Cheung et al. (1993) demonstrated that the first Ig domain of C-CAM is critical for cell adhesive activity.

Cell adhesion molecules, or CAM's are known to be involved in a complex network of molecular interactions that regulate organ development and cell differentiation (Edelman, 1985). Recent data indicate that aberrant expression of CAM's maybe involved in the tumorigenesis of several neoplasms; for example, decreased expression of E-cadherin, which is predominantly expressed in epithelial cells, is associated with the progression of several kinds of neoplasms (Edelman and Crossin, 1991; Frixen et al., 1991; Bussemakers et al., 1992; Matsura et al., 1992; Umbas et al., 1992). Also, Giancotti and Ruoslahti (1990) demonstrated that increasing expression of $\alpha_5\beta_1$ integrin by gene transfer can reduce tumorigenicity of Chinese hamster ovary cells in vivo. C-CAM now has been shown to suppress tumor growth in vitro and in vivo.

Other tumor suppressors that may be employed according to the present invention include p21, p15, BRCA1, BRCA2, IRF-1, PTEN (MMAC1), RB, APC, DCC, NF-1, NF-2, WT-1, MEN-I, MEN-II, zac1, p73, VHL, FCC, MCC, DBCCR1, DCP4, and p57.

2. Inducers of Apoptosis

Inducers of apoptosis, such as Bax, Bak, Bcl-X$_s$, Bad, Bim, Bik, Bid, Harakiri, E1B, Bad, ICE-CED3 proteases, TRAIL, SARP-2, and apoptin, similarly could find use according to the present invention.

3. Enzymes

Various enzyme genes are of interest according to the present invention. Such enzymes include cytosine deaminase, adenosine deaminase, hypoxanthine-guanine phosphoribosyltransferase, galactose-1-phosphate uridyltransferase, phenylalanine hydroxylase, glucocerbrosidase, sphingomyelinase, α-L-iduronidase, glucose-6-phosphate dehydrogenase, HSV thymidine kinase, and human thymidine kinase, and extracellular proteins such as collagenase, matrix metalloprotease, RSKB, RSK1, RSK2, RSK3, thrombospondin, fibronectin, and plasminogen. In other embodiments of the present invention, the use of anti-angiogenic factors are contemplated.

4. Cytokines

Another class of genes that is contemplated to be inserted into the nucleic acid molecules of the present invention include interleukins and cytokines. Interleukin 1 (IL-1), IL-2, IL-3, IL-4, IL-5, IL-6, IL-7, IL-8, IL-9, IL-10, IL-11, IL-12, IL-13, IL-14, IL-15, β-interferon, α-interferon, γ-interferon, angiostatin, thrombospondin, endostatin, METH-1, METH-2, GM-CSF, G-CSF, M-CSF, and tumor necrosis factor.

5. Toxins

Various toxins are also contemplated to be useful as part of the expression vectors of the present invention, these toxins include bacterial toxins such as ricin A-chain (Burbage, 1997), diphtheria toxin A (Massuda et al., 1997; Lidor, 1997), pertussis toxin A subunit, *E. coli* enterotoxin toxin A subunit, cholera toxin A subunit, and pseudomonas toxin c-terminal. Recently, it was demonstrated that transfection of a plasmid containing the fusion protein regulatable diphtheria toxin A chain gene was cytotoxic for cancer cells. Thus, gene transfer of regulated toxin genes might also be applied to the treatment of cancers (Massuda et al., 1997).

6. Single Chain Antibodies

In yet another embodiment, one gene may comprise a single-chain antibody. Methods for the production of single-chain antibodies are well known to those of skill in the art. The skilled artisan is referred to U.S. Pat. No. 5,359,046 for such methods. A single chain antibody is created by fusing together the variable domains of the heavy and light chains using a short peptide linker, thereby reconstituting an antigen binding site on a single molecule.

Single-chain antibody variable fragments (scFvs) in which the C-terminus of one variable domain is tethered to the N-terminus of the other via a 15 to 25 amino acid peptide or linker, have been developed without significantly disrupting antigen binding or specificity of the binding (Bedzyk et al., 1990; Chaudhary et al., 1990). These Fvs lack the constant regions (Fc) present in the heavy and light chains of the native antibody.

Antibodies to a wide variety of molecules are contemplated, such as oncogenes, growth factors, hormones, enzymes, transcription factors or receptors. Also contemplated are secreted antibodies, targeted to serum, against angiogenic factors (VEGF/VSP; βFGF; αFGF; and others) and endothelial antigens necessary for angiogenesis (i.e., V3 integrin). Specifically contemplated are growth factors such as transforming growth factor, and platelet derived growth factor (PDGF).

7. Transcription Factors and Regulators

Another class of genes that can be applied in an advantageous combination are transcription factors. Examples include C/EBPα, IκB, NFκB, Par-4, Sp1, TBP, TBP-binding proteins, and CREB.

8. Cell Cycle Regulators

Cell cycle regulators provide possible advantages, when combined with other genes. Such cell cycle regulators include p27, p16, p21, p57, p18, p73, p19, p15, E2F-1, E2F-2, E2F-3, p107, p130, and E2F-4. Other cell cycle regulators include anti-angiogenic proteins, such as soluble Flt1 (dominant negative soluble VEGF receptor, soluble Wnt receptors, soluble Tie2/Tek receptor, soluble hemopexin domain of matrix metalloprotease 2, and soluble receptors of other angiogenic cytokines (e.g. VEGFR1/KDR, VEGFR3/Flt4—both VEGF receptors).

9. Chemokines

Genes that code for chemokines also may be used in the present invention. Chemokines generally act as chemoattractants to recruit immune effector cells to the site of chemokine expression. It may be advantageous to express a particular chemokine gene in combination with, for example, a cytokine gene, to enhance the recruitment of other immune system components to the site of treatment. Such chemokines include RANTES, MCAF, MIP1-alpha, MIP1-Beta, and IP-10. The skilled artisan will recognize that certain cytokines are also known to have chemoattractant effects and could also be classified under the term chemokines.

B. Treatment by Infection with GBV-C

In other embodiments GBV-C infection comprises a therapeutic or preventative treatment for AIDS. As a therapeutic measure, an infectious GBV-C nucleic acid molecule can be used to reduce the severity or progression of AIDS, including the prevention of AIDS in HIV-infected individuals. A reduction in severity or progression of AIDS includes, but is not limited to prevention of or a reduction in the severity, duration, or discomfort associated with the following conditions: prolonged and unexplained fatigue; swollen glands; prolonged fever; chills; excessive sweating; swollen gums and mouth lesions; sore throat; cough; shortness of breath; constipation; diarrhea; symptoms of well-known opportunistic infections; Kaposi sarcomas; skin rashes or lesions; loss of appetite or weight loss; malaise; headaches; speech impairment; muscle atrophy; memory loss; reduced cognitive functioning; swelling of the joints; joint stiffness or pain; cold intolerance; pain or tenderness in bones; energy level; anxiety, stress, and tension; groin lump; pruritus; genital sores; blurred or decreased vision; diplopia; light sensitivity; pain in chest, sides, back, muscle or stomach; and seizures. As a preventative measure, infection of CD4+ T cells with GBV-C or a recombinant version of GBV-C can be used to inhibit infection of these cells by HIV. Alternatively, treatment with the GBV-C compositions of the present invention may effect a combination of preventative and therapeutic treatments insofar as infection of other cells in an HIV-infected subject's body is prevented.

Alternatively, inhibition of AIDS progression may be demonstrated by reduction of detectable HIV in the HIV-infected subject; maintaining a CD4 count above 200 for a longer than average period of time; maintaining a normal T cell count; or maintaining normal p24 antigen. The term "therapeutic benefit" used throughout this application refers to anything that promotes or enhances the well-being of the subject with respect to the medical treatment of his condition, which includes treatment of HIV-infection (before the onset of AIDS), AIDS, as well as treatment of Hepatitis C. A list of nonexhaustive examples of this includes extension of the subject's life by any period of time; decrease or delay in the progression of AIDS (HIV, as described above) or Hepatitis C; decrease in viral load of HIV or HCV; decrease in HIV replicationclearance of HIV or HCV viremiareduced transmission of HCV or HIV; decrease in liver damage or complications; and a decrease in pain to the subject that can be attributed to the subject's condition.

A. Pharmaceutical Compositions and Routes of Administration

The present invention contemplates infectious GBV-C nucleic acid molecules as well as infectious nucleic acid molecules encoding, in some embodiments, a heterologous sequence. In some embodiments, pharmaceutical compositions are administered to a subject. Different aspects of the present invention involve administering an effective amount of an aqueous composition. In another embodiment of the present invention, infectious GBV-C is administered to a subject to either prevent the infection by HIV or prevent the progression of HIV infection to development of AIDS. Additionally, such compounds can be administered in combination with treatment by HAART or by administration of AZT, or both. Though typically, infectious GBV-C will be administered separately from medication. Such compositions will generally be dissolved or dispersed in a pharmaceutically acceptable carrier or aqueous medium.

Those of skill in the art are well aware of how to apply gene delivery to in vivo and ex vivo situations. For viral vectors, one generally will prepare a viral vector stock. Depending on the kind of virus and the titer attainable, one will deliver 1 to 100, 10 to 50, 100-1000, or up to $1\times10^4$, $1\times10^5$, $1\times10^6$, $1\times10^7$, $1\times10^8$, $1\times10^9$, $1\times10^{10}$, $1\times10^{11}$, or $1\times10^{12}$ infectious particles to the patient. Similar figures may be extrapolated for liposomal or other non-viral formulations by comparing relative uptake efficiencies. Formulation as a pharmaceutically acceptable composition is discussed below.

The phrases "pharmaceutically acceptable" or "pharmacologically acceptable" refer to molecular entities and compositions that do not produce an adverse, allergic, or other untoward reaction when administered to an animal, or human, as appropriate. As used herein, "pharmaceutically acceptable carrier" includes any and all solvents, dispersion media, coatings, antibacterial and antifungal agents, isotonic and absorption delaying agents, and the like. The use of such media and agents for pharmaceutical active substances is well known in the art. Except insofar as any conventional media or agent is incompatible with the active ingredients, its use in the therapeutic compositions is contemplated. Supplementary active ingredients, such as other anti-cancer agents, can also be incorporated into the compositions.

In addition to the compounds formulated for parenteral administration, such as those for intravenous or intramuscular injection, other pharmaceutically acceptable forms include, e.g., tablets or other solids for oral administration; time release capsules; and any other form currently used, including cremes, lotions, mouthwashes, inhalants and the like.

The active compounds of the present invention can be formulated for parenteral administration, e.g., formulated for injection via the intravenous, intramuscular, intrathoracic, sub-cutaneous, or even intraperitoneal routes. Administration by i.v. or i.m. are specifically contemplated to achieve infection. The preparation of an aqueous composition that contains a compound or compounds that increase the expression of an MHC class I molecule will be known to those of skill in the art in light of the present disclosure.

Typically, such compositions can be prepared as injectables, either as liquid solutions or suspensions; solid forms suitable for use to prepare solutions or suspensions upon the addition of a liquid prior to injection can also be prepared; and, the preparations can also be emulsified.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions; formulations including sesame oil, peanut oil, or aqueous propylene glycol; and sterile powders for the extemporaneous preparation of sterile injectable solutions or dispersions. In all cases the form must be sterile and must be fluid to the extent that it may be easily injected. It also should be stable under the conditions of manufacture and storage and must be preserved against the contaminating action of microorganisms, such as bacteria and fingi.

The active compounds may be formulated into a composition in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier also can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion, and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques, which yield a powder of the active ingredient, plus any additional desired ingredient from a previously sterile-filtered solution thereof.

In certain cases, the therapeutic formulations of the invention also may be prepared in forms suitable for topical administration, such as in cremes and lotions. These forms may be used for treating skin-associated diseases, such as various sarcomas.

Administration of therapeutic compositions according to the present invention will be via any common route so long as the target tissue is available via that route. In cases where the present invention is used as a viral vector, a primary consideration will be the desired location for the heterologous sequences carried by the vector. Routes of administration include oral, nasal, buccal, rectal, vaginal or topical. For example, topical administration would be particularly advantageous for treatment of AIDS- or HCV-related skin conditions, or where a heterologous gene useful in treating a skin condition is carried by a viral vector. Alternatively, administration will be by orthotopic, intradermal subcutaneous, intramuscular, intraperitoneal or intravenous injection. Such compositions would normally be administered as pharmaceutically acceptable compositions that include physiologically acceptable carriers, buffers or other excipients. For treatment of conditions of the lungs, aerosol delivery to the lung is contemplated. Volume of the aerosol is between about 0.01 ml and 0.5 ml. Similarly, a preferred method for treatment of colon-associated disease would be via enema. Volume of the enema is between about 1 ml and 100 ml. Direct intratumoral injection is the preferred mode, with continuous intratumoral perfusion a more specific embodiment.

In certain embodiments, it may be desirable to provide a continuous supply of therapeutic compositions to the patient. For intravenous or intraarterial routes, this is accomplished by drip system. For topical applications, repeated application would be employed. For various approaches, delayed release formulations could be used that provided limited but constant amounts of the therapeutic agent over and extended period of time. For internal application, continuous perfusion, for example with a GBV-C viral vector carrying a heterologous nucleic acid segment, of the region of interest may be preferred. This could be accomplished by catheterization, post-operatively in some cases, followed by continuous administration of the therapeutic agent. The time period for perfusion would be selected by the clinician for the particular patient and situation, but times could range from about 1-2 hours, to 2-6 hours, to about 6-10 hours, to about 10-24 hours, to about 1-2 days, to about 1-2 weeks or longer. Generally, the dose of the therapeutic composition via continuous perfusion will be equivalent to that given by single or multiple injections, adjusted for the period of time over which the injections are administered. It is believed that higher doses may be achieved via perfusion, however.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media that can be employed will be known to those of skill in the art in light of the present disclosure. For example, one dosage could be dissolved in 1 mL of isotonic NaCl solution and either added to 1000 mL of hypodermoclysis fluid or injected at the proposed site of infusion, (see for example, Remington's Pharmaceutical Sciences, 1990). Some variation in dosage will necessarily occur depending on the condition of the subject being treated. The person responsible for administration will, in any event, determine the appropriate dose for the individual subject.

An effective amount of the therapeutic composition is determined based on the intended goal. The term "unit dose" or "dosage" refers to physically discrete units suitable for use in a subject, each unit containing a predetermined-quantity of the therapeutic composition calculated to produce the desired responses, discussed above, in association with its administration, i.e., the appropriate route and treatment regimen. The quantity to be administered, both according to number of treatments and unit dose, depends on the protection desired.

Precise amounts of the therapeutic composition also depend on the judgment of the practitioner and are peculiar to each individual. Factors affecting dose include physical and clinical state of the patient, the route of administration, the intended goal of treatment (alleviation of symptoms versus cure) and the potency, stability, and toxicity of the particular therapeutic substance.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

As used herein, the term in vitro administration refers to manipulations performed on cells removed from an animal, including, but not limited to, cells in culture. The term ex vivo administration refers to cells that have been manipulated in vitro, and are subsequently administered to a living animal. The term in vivo administration includes all manipulations performed on cells within an animal.

In certain aspects of the present invention, the compositions may be administered either in vitro, ex vivo, or in vivo. In certain in vitro embodiments, transcribed RNA from a GBV-C clone is transfected into PBMC using DEAE-dextran. The transduced cells can then be used for in vitro analysis, or alternatively for in vivo administration.

U.S. Pat. Nos. 4,690,915 and 5,199,942 disclose methods for ex vivo manipulation of blood mononuclear cells and bone marrow cells for use in therapeutic applications.

In vivo administration of the compositions of the present invention are also contemplated. Examples include, but are not limited to, transduction of bladder epithelium by administration of the transducing compositions of the present invention through intravesicle catheterization into the bladder (Bass, 1995), and transduction of liver cells by infusion of appropriate transducing compositions through the portal vein via a catheter (Bao, 1996). Additional examples include direct injection of tumors with the instant transducing compositions, and either intranasal or intratracheal (Dong, 1996) instillation of transducing compositions to effect transduction of lung cells.

1. Vaccines

The present invention includes methods for preventing the development of AIDS in both infected and uninfected persons, as well as the elicitation of an immune response to a heterologous polypeptide. As such, the invention contemplates vaccines for use in both active and passive immunization embodiments. Immunogenic compositions, proposed to be suitable for use as a vaccine, may be prepared most readily directly from infectious GBV-C nucleic acid molecules prepared in a manner disclosed herein. Preferably the antigenic material is extensively dialyzed to remove undesired small molecular weight molecules and/or lyophilized for more ready formulation into a desired vehicle.

The preparation of vaccines that contain GBV-C sequences as active ingredients is generally well understood in the art by analogy, as exemplified by U.S. Pat. Nos. 5,958,895, 6,004,799, and 5,620,896. Typically, such vaccines are prepared as injectables either as liquid solutions or suspensions: solid forms suitable for solution in or suspension in liquid prior to injection may also be prepared. The preparation may also be emulsified. The active immunogenic ingredient is often mixed with excipients that are pharmaceutically acceptable and compatible with the active ingredient. Suitable excipients are, for example, water, saline, dextrose, glycerol, ethanol, or the like and combinations thereof. In addition, if desired, the vaccine may contain minor amounts of auxiliary substances such as wetting or emulsifying agents, pH buffering agents, or adjuvants that enhance the effectiveness of the vaccines.

Vaccines may be conventionally administered parenterally, by injection, for example, either subcutaneously or intramuscularly. Additional formulations which are suitable for other modes of administration include suppositories and, in some cases, oral formulations. For suppositories, traditional binders and carriers may include, for example, polyalkalene glycols or triglycerides: such suppositories may be formed from mixtures containing the active ingredient in the range of about 0.5% to about 10%, preferably about 1% to about 2%. Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders and contain about 10% to about 95% of active ingredient, preferably about 25% to about 70%.

The GBV-C infectious nucleic acids and GBV-C expressed heterologous proteins of the present invention may be formulated into the vaccine as neutral or salt forms. Pharmaceutically-acceptable salts include the acid addition salts (formed with the free amino groups of the peptide) and those that are formed with inorganic acids such as, for example, hydrochloric or phosphoric acids, or such organic acids as acetic, oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The vaccines are administered in a manner compatible with the dosage formulation, and in such amount as will be therapeutically effective and immunogenic. The quantity to be administered depends on the subject to be treated, including, e.g., the capacity of the individual's immune system to synthesize antibodies and the degree of protection desired. Precise amounts of active ingredient required to be administered depend on the judgment of the practitioner. However, suitable dosage ranges are of the order of several hundred micrograms active ingredient per vaccination. Suitable regimes for initial administration and booster shots are also variable, but are typified by an initial administration followed by subsequent inoculations or other administrations.

The manner of application may be varied widely. Any of the conventional methods for administration of a vaccine are applicable. These are believed to include oral application on a solid physiologically acceptable base or in a physiologically acceptable dispersion, parenterally, by injection or the like. The dosage of the vaccine will depend on the route of administration and will vary according to the size of the host.

Various methods of achieving adjuvant effect for the vaccine includes use of agents such as aluminum hydroxide or phosphate (alum), commonly used as about 0.05 to about 0.1% solution in phosphate buffered saline, admixture with synthetic polymers of sugars (Carbopol®) used as an about 0.25% solution, aggregation of the protein in the vaccine by heat treatment with temperatures ranging between about 700 to about 101° C. for a 30-second to 2-minute period, respectively. Aggregation by reactivating with pepsin-treated (Fab) antibodies to albumin, mixture with bacterial cells such as *C. parvum* or endotoxins or lipopolysaccharide components of Gram-negative bacteria, emulsion in physiologically acceptable oil vehicles such as mannide monooleate (Aracel A), or emulsion with a 20% solution of a perfluorocarbon (Fluosol-DA®) used as a block substitute may also be employed.

In many instances, it will be desirable to have multiple administrations of the vaccine, usually not exceeding six vaccinations, more usually not exceeding four vaccinations and preferably one or more, usually at least about three vaccinations. The vaccinations will normally be at from two to twelve week intervals, more usually from three to five week intervals. Periodic boosters at intervals of 1-5 years, usually three years, will be desirable to maintain protective levels of the antibodies. The course of the immunization may be followed by assays for antibodies for the supernatant antigens. The assays may be performed by labeling with conventional labels, such as radionuclides, enzymes, fluorescents, and the like. These techniques are well known and may be found in a wide variety of patents, such as U.S. Pat. Nos. 3,791,932; 4,174,384 and 3,949,064, as illustrative of these types of assays.

2. Viruses as Therapeutic Compositions

The engineered viruses of the present invention may be administered directly into animals, or alternatively, administered to cells that are subsequently administered to animals. The viruses can be combined with the various β-interferon inhibiting formulations to produce transducing formulations with greater transduction efficiencies. A discussion of suitable viruses is presented above.

3. Treatment Additives a. Carrier Molecules

As is well known in the art, a given composition may vary in its immunogenicity. It is often necessary therefore to boost the host immune system, as may be achieved by coupling the heterologous polypeptide immunogen or GVH-C infectious nucleic acid to a carrier. Exemplary and preferred carriers are keyhole limpet hemocyanin (KLH) and bovine serum albumin (BSA). Other albumins such as ovalbumin, mouse serum albumin, or rabbit serum albumin can also be used as carriers. Means for conjugating a polypeptide to a carrier protein are well known in the art and include glutaraldehyde, m-maleimidobencoyl-N-hydroxysuccinimide ester, carbodiimyde, and bis-biazotized benzidine.

b. Adjuvants

As is also well known in the art, the immunogenicity of a polypeptide or peptide composition can be enhanced by the use of non-specific stimulators of the immune response, known as adjuvants. Suitable adjuvants include all acceptable immunostimulatory compounds, such as cytokines, toxins, or synthetic compositions.

Adjuvants that may be used include IL-1, IL-2, IL-4, IL-7, IL-12, γ-interferon, GMCSP, BCG, aluminum hydroxide, MDP compounds, such as thur-MDP and nor-MDP, CGP (MTP-PE), lipid A, and monophosphoryl lipid A (MPL). RIBI, which contains three components extracted from bacteria, MPL, trehalose dimycolate (TDM) and cell wall skeleton (CWS) in a 2% squalene/Tween 80 emulsion. MHC antigens may even be used.

Exemplary, often preferred adjuvants include complete Freund's adjuvant (a non-specific stimulator of the immune response containing killed *Mycobacterium tuberculosis*), incomplete Freund's adjuvants and aluminum hydroxide adjuvant.

In addition to adjuvants, it may be desirable to coadminister biologic response modifiers (BRM), which have been shown to upregulate T cell immunity or downregulate suppresser cell activity. Such BRMs include, but are not limited to, Cimetidine (CIM; 1200 mg/d) (Smith/Kline, PA); or low-dose Cyclophosphamide (CYP; 300 mg/m$^2$) (Johnson/Mead, NJ) and cytokines such as γ-interferon, IL-2, or IL-12 or genes encoding proteins involved in immune helper functions, such as B-7.

B. Combination Therapies

Of course it is understood that the method of the present invention, particularly administration of infectious GBV-C nucleic acid molecules as treatment for an HIV-infected subject, may also be used in combination with the administration of traditional therapies. Alternatively, the compositions of the present invention may be given in combination with treatment or prevention of hepatitis C, such as alpha interferon. Some such therapies are described below.

1. AZT

A well-known, traditional therapy for the treatment of AIDS involves zovidovudine (AZT™ available from Burroughs Wellcome). This is one of a class of nucleoside analogues known as dideoxynucleosides which block HIV replication by inhibiting HIV reverse transcriptase. The anti-AIDS drug zidovudine (also known as AZT) may also be used in limited circumstances, mostly in combination with rifampin, as described by Burger et al. (1993).

The compositions and methods disclosed herein will be particularly effective in conjunction with other forms of therapy, such as AZT and/or protease inhibitors that are designed to inhibit viral replication, by maintaining desirable levels of white blood cells. This, in effect, buys the patient the time necessary for the anti-viral therapies to work.

2. HAART

New combination drug therapy has shown promising results in the treatment of HIV-infected patients. Treatment with potent anti-HIV drug combinations is referred to as "highly active antiretroviral therapy" (HAART), and it has provided clinical improvement, longer survival, and improved quality of life for people infected with HIV during all four stages of HIV disease. Examples of HAART include a protease inhibitor (indinavir, nelfinavir, ritonavir, ritonavir/saquinavir, or saquinavir) combined with two nucleoside analogs (AZT/ddI, d4T/ddI, AZT/ddC, AZT/3TC, or d4T/3TC).

III. EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments

Example 1

Materials and Methods

Isolation and Preparation of Cells

Peripheral blood mononuclear cells (PBMCs) from healthy blood donors (HCV RNA and antibody negative, HGV RNA negative, and HBV surface antigen negative) were isolated from heparinized blood by centrifugation on Ficoll-Hypaque gradients, washed twice with phosphate-buffered saline (PBS), and suspended in RPMI 1640 medium (Sigma, St. Louis, Mo.) supplemented with 10% fetal calf serum (FCS) and antibiotics as previously described (Cook et al., 1997). PBMC ($2 \times 10^6$ cells/ml) were maintained at 36° C. in 5% $CO_2$. Phytohemagglutin (PHA, 10 µg/ml; DIFCO, Detroit, Mich.) and *Escherichia coli* lipopolysaccharide (LPS, 10 µg/ml; Sigma) were added to the medium for 48 hours, following which, $10^7$ cells/ml were maintained in RPMI supplemented with 5% of interleukin-2 (IL-2) (Cellular Products Inc., Buffalo, N.Y.) and 5 µg/ml of PHA.

GBV-C RNA Preparation and RT-PCR

A previously described GBV-C RNA positive patient with a diagnosis of chronic liver disease was selected for this study (Xiang et al., 1998). This patient did not have detectable HCV antibody (Abbott EIA 2.0, North Chicago, Ill.) or RNA. RNA was prepared from plasma using a previously described guanidinium isothiocyanate (GITC) RNA extraction method (Schmidt et al., 1995). GBV-C RNA was detected using nested oligonucleotide primers from the 5' non-translated region as previously described (Xiang et al., 1998). Primers used for producing the full-length clone are described below. All RT-PCR reactions utilized MMLV RT (40 units) as previously described (Stapleton et al., 1999), followed by 35 cycles of PCR™ (94° C. for 30 s, 55° C. for 30 s, and 72° C. for 45 s). Three microliters of the first round served as the template for 35 cycles of second round PCR using nested primers and the same time and temperature settings (Schmidt et al., 1995).

Cloning and Sequencing of PCR Products

PCR™ products were separated by agarose gel electrophoresis, visualized by ethidium bromide staining, excised and purified using the Promega DNA purification system kit (Promega Co., Madison, Wis.). Amplicons were ligated into PCR 2.1 (Original TA Cloning® Kit, Invitrogen, Carlsbad, Calif.), and plasmid DNA was sequenced in both directions using primers complementary to the T7 polymerase or the M13 universal primer sequences present in the vector as previously described (Stampleton et al., 1999). Automated fluorescent dye terminator cycle sequencing was performed by the University of Iowa DNA Core Facility (Applied Biosystems automated DNA sequencer 373A, Foster City, Calif.).

Construction of Full-Length GBV-C cDNA

Based on conserved sequences throughout the GBV-C genome, a series of primers were designed which contained suitable restriction sites in their overlapping sequences. Primer sets that generated products were used to prepare the full-length clone. FIG. 1 demonstrates the 6 primer sets and fragments generated in this study. The rapid amplification of cDNA ends (RACE) method was used to prepare the 5' and 3' terminal RNA (GIBCO BRL, Rockville, Md.). The eight DNA fragments were ligated into a full-length clone by using the restriction enzymes in either the overlapping sequences or in the vector DNA.

RNA Transcription and Transfection

10 µg GBV-C full-length DNA in pCR 2.1 was digested into linear DNA by Spe I and transcribed using T7 RNA polymerase (Promega) for 1 h at 37° C. An infectious HCV clone (Kolykhalov et al., 1997) was obtained (Genbank accession #AF009606). This clone was digested with Spe I, and RNA transcription was carried out in the same fashion. To eliminate plasmid DNA sequences, RQI Rnase-Free DNase (IU/µg) digestion of template DNA was completed for 15 min at 37° C. RNA transcripts were purified by chloroform extraction and ethanol precipitation. RNA from transcription reactions was denatured with formamide and formaldehyde, and analyzed on a 1% agarose-formaldehyde gel. Transcribed RNA in DEAE-dextran (1 mg/ml in HBSS) was added to washed PHA and LPS stimulated PBMC ($1 \times 10^6$), and the cells were incubated for 30 min at 36° C. in 5% $CO_2$ RPMI supplemented with 10% FCS was added, and the cells were incubated at 36° C. for 6 h with gentle rocking. After 6 h the medium was removed, the cells were washed twice, and incubated in RPM1 (10% FCS) at 36° C. in 5% $CO_2$. Fresh PHA, IL-2 stimulated donor cells were added each week to the cultured cells at a ratio of 4:1. After 4 weeks, cell culture supernatant from the transfected cells was used to inoculate fresh cells ($2 \times 10^6$/ml) for at least four consecutive passages.

Negative Strand GBV-C RT-PCR

For detection of GBV-C antisense RNA, cDNA synthesis was performed with an oligonucleotide primer containing a sequence unrelated to GBV-C (5'TCATGGTGGC-GAATAAAAGCCCCAGAAACCGACGCC 3' (SEQ ID NO:3)) as described by others (Laskus et al., 1998). cDNA synthesis was stopped by heating at 99° C. for 1 h, and samples were treated with 50 µg/ml RNase A at 37° C. for 30 min. Subsequent amplification of plus-sense RNA by Taq polymerase used only the tag sequence (5'TCATGGTGGC-GAATAA, Tag (SEQ ID NO:4)) for both first round of amplification and for the nested PCR reaction.

CD4 Staining and Flow Cytometry

Seventy two hours post infection, PMBC's ($2 \times 10^7$) were pelleted, resuspended in PBS containing 10% normal goat serum for 30 min at 4° C. prior to incubation with mouse anti-CD4 antibody (10 µg/ml, Molecular Probes) for 45 min at 4° C. Anti-CD4 binding was detected using Texas-Red-conjugated goat anti-mouse antibody (10 µg/ml, Molecular Probes, Eugene, Oreg.) for 45 min at 4° C. Between each step, cells were washed two times with PBS. CD4 positive and CD4 negative cells were sorted by Flow Cytometry (FACScan, Becton Dickinson, San Jose, Calif.), and the two populations were collected for analysis.

Immunofluorescence

Indirect immunofluorescence was performed using a mouse monoclonal antibody against GBV-C E2 protein (Biodesign, Saco, Me.). Forty-eight hours post-infection, PBMCs were fixed with 10% formalin for 15 min, then permeabilized in acetone at −20° C. for 5 min. Following blocking with 10% normal goat sera, the cells were incubated for 1 hour at room temperature with the anti-GBV-C E2 antibody (10 µg/ml). After being washed, cells were incubated for 1 hour (5 µg/ml fluorescein Texas-red-labeled goat anti-mouse IgG, Molecular Probes). Images were recorded using confocal microscopy (519 nm, Zeiss, Jena, Germany) as previously described (Wünschmann and Stapleton, 2000).

Equilibrium Centrifugation in Sucrose

500 µl of either infected cell culture supernatant fluid or the infected cell lysates were layered onto 10 ml of a 20% to 60% sucrose gradient, and centrifugation was performed using a Beckman SW41 rotor at 156 000×g for 16 h at 4° C. as previously described (Xiang et al., 1999). Fourteen fractions (750 µl each) were collected, RNA extracted as above, and GBV-C RNA was detected by RT-PCR.

Immuno-Electron Microscopy

Cell culture supernatants were collected 96 h post infection, and then concentrated by centrifugation at 80 000×g for 16 h at 4° C. in a SW 28 rotor (Beckman). The pellet was resuspended in 200 µl PBS. GBV-C E2 monoclonal antibody (5 µg/ml, Biodesign) was added to 50 µl of the virus pellet for 2 h at 37° C. Virus-IgG complexes were pelleted by centrifugation at 17,115×g for 15 min (Rotor 220.88 V01 Hermle). Gold-labeled goat anti-mouse monoclonal antibody (1:100 dilution, Aurlon, Netherlands) was used to detect GBV-C particles. The resuspended pellet was applied to a carbon coated copper grid, and was negatively stained with 1 uranyl acetate (pH 7.0). Particles were visualized by an H7000 Hitachi transmission electron microscope (75 V accelerating voltage).

Example 2

Construction of GBV-C Clone

Figure 1A:
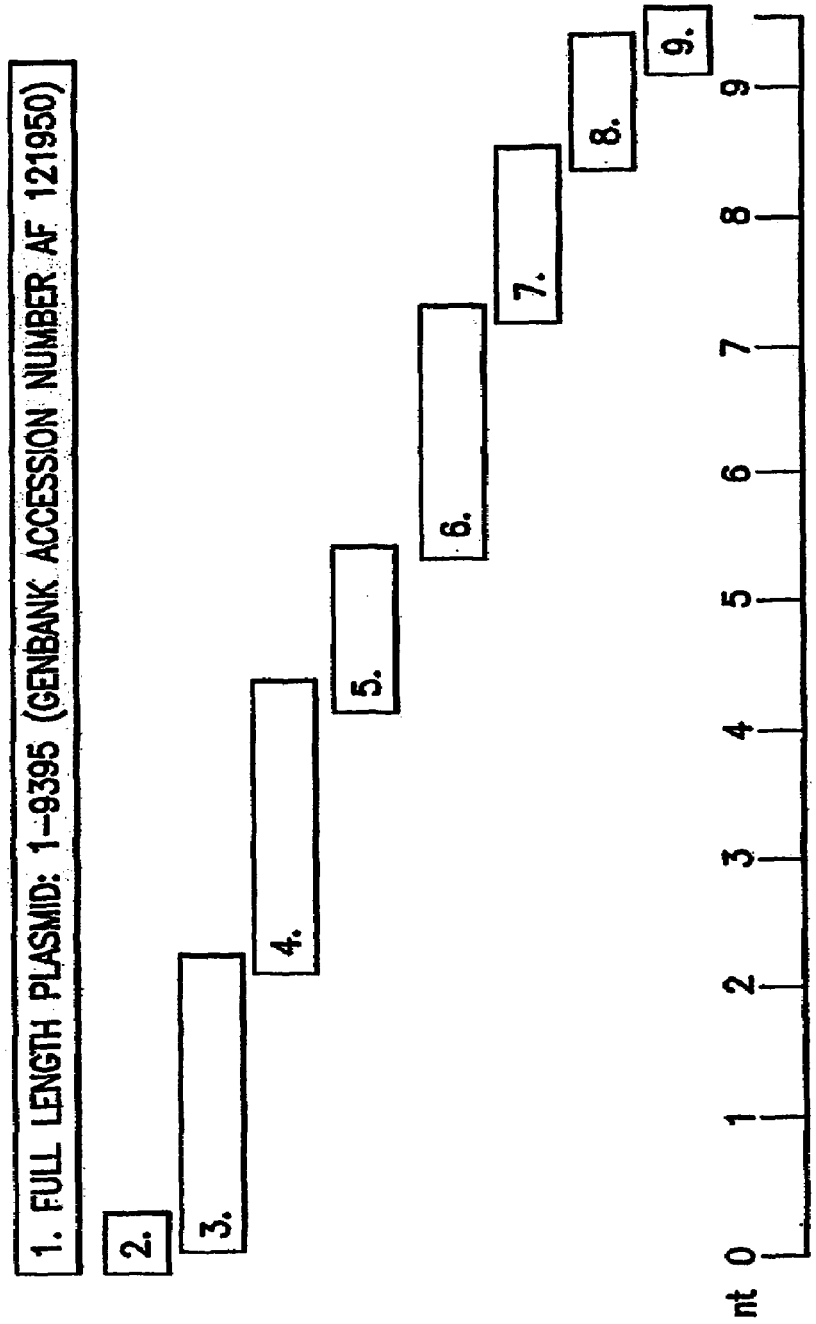
FIG. 1A-B Cloning strategy for GBV-C full length clone. FIG. A. This schematically presents the full-length GBV-C cDNA sequences at the top. Each box beneath the full-length sequence represent the cDNAs amplified by RT-PCR used to make the full length clone. The 5' and 3' ends were generated using the RACE methods. The specific primer sets used for RT-PCR are shown in Table 4. FIG. B. This demonstrates RNA transcripts from GBV-C and HCV full-length cDNA. HCV and GBV-C RNA transcripts are indicated, and the RNA size marker is depicted.

To construct full-length GBV-C cDNA, nested RT-PCR was performed on plasma RNA obtained from a GBV-C infected individual using a variety of oligonucleotide sets spanning the entire genome. Six primer sets were identified which generated overlapping products containing restriction sites useful for ligation (Table 4). These six fragments started at nucleotide 25 and ended at nucleotide 9340. To identify the 5' and 3' ends of the genome, the 5' and 3' RACE methods were used. Primers used for these reactions were located from nt 284 to nt 305 (antisense) for 5' RACE and 9085 to 9106 (positive sense) for the 3' RACE. Each of these eight PCR amplification products was cloned into the pCR 2.1 vector and the nucleotide sequence was determined (FIG. 1A, Genbank accession # AF 121950). Following ligation of the 8 fragments shown in FIG. 1A, a clone containing the full length GBV-C sequence of the GBV-C isolate was obtained. All cloning sites were again sequenced to exclude the possibility of cloning artifacts. Restriction digests of this full-length cDNA in the pCR 2.1 vector were consistent with the sequence data.

TABLE 4

Synthetic Oligonucleotide Primers Used to Construct a Full-Length GBV-C cDNA

| Clone Number | POSITIVE SENSE | | NEGATIVE SENSE | |
|---|---|---|---|---|
| | Outer | Inner | Outer | INNER |
| 2 | NA | NA | NA | 284-305* |
| 3 | 25-45 | 66-87 | 2550-2572 | 2543-2564 |
| 4 | 2224-2245 | 2250-2271 | 4464-4485 | 4358-4379 |
| 5 | 4275-4296 | 4281-4302 | 5547-5568 | 5538-5559 |
| 6 | 5328-5349 | 5334-5355 | 7491-7512 | 7483-7504 |
| 7 | 7380-7401 | 7389-7410 | 8644-8665 | 8638-8659 |

TABLE 4-continued

Synthetic Oligonucleotide Primers Used to Construct a Full-Length GBV-C cDNA

| Clone Number | POSITIVE SENSE | | NEGATIVE SENSE | |
|---|---|---|---|---|
| | Outer | Inner | Outer | INNER |
| 8 | 8475-8496 | 8483-8504 | 9417-9438 | 9319-9340 |
| 9 | NA | 9085-9106* | NA | NA |

*The 5' and 3' ends were generated using the RACE method. The numbers represent the nucleotide sequence numbers based on this isolate (GenBank AF 121950).

Example 3

GBV-C Sequence Analysis and Comparison with GBV-B and HCV

Figure 2:
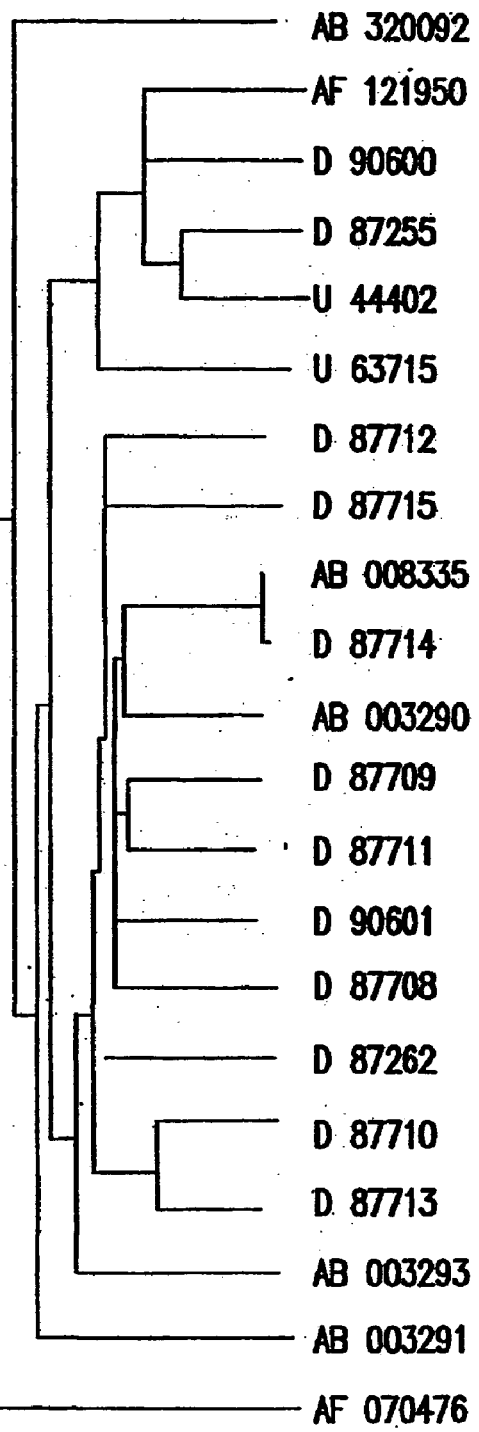
FIG. 2 Phylogenetic relationship between 20 full length human GBV-C isolates including the full-length clone described in this report (AF121950), and a chimpanzee full-length isolate (AF 070476) (Birkenmeyer et al., 1998). The GenBank accession number of each isolate is shown.

The GBV-C sequence the inventors obtained (AF121950) contained an open reading frame (ORF) beginning at nucleotide (nt) 351 and extending to nt 9080. This ORF is predicted to encode a 2910 amino acid long polyprotein with a molecular weight of 314,548 daltons. The complete GBV-C sequence of this isolate was compared with 19 additional human isolates and one chimpanzee isolate obtained by searching Genbank for complete GBV-C sequences. Nucleotide sequences were aligned, and the evolutionary distance between sequences was determined using the Jukes-Canter method (DNAMAN software; Lynnon BioSoft Inc, Quebec, Canada). Computed distances were used to construct phylogenetic trees by using the neighbor joining method (DNAMAN). FIG. 2 demonstrates that except for the chimpanzee isolate (AF 070476, GBV-Ctro), there were close phylogenetic relationships between the isolate and all published GBV-C isolates. Twelve of these sequences contain the complete 5' ntr and 3' ntr. Comparison of these 12 revealed 92.79% homology at the nucleotide level. The isolate is most closely related to a Japanese isolate D 90600 (FIG. 2) (Okamoto et al., 1997). A list of the sequence accession numbers is displayed in FIG. 2.

Based on in vitro translation studies, the 5' nontranslated region (ntr) was shown to direct translation from the AUG starting at nt 554 of the isolate (Okamoto et al., 1997; Simons et al., 1996). There are three upstream AUG sequences in isolate AF 121950 that are in frame with the polyprotein, and 2 additional AUG's upstream of 554 which are not in frame. Thus, there are an additional 68 amino acids upstream of AUG-554 in the isolate. Fourteen of the 21 isolates studied provided complete 5' ntr sequence data. Comparison of potential translational start codons in frame with the polyprotem of these isolates revealed that 10 of the 14 contained only one AUG upstream of the AUG-554. This ORF would encode 31 amino acids upstream of the putative start site. Three of the 14 isolates had no AUG's upstream of AUG-554 in frame, although isolate D90600 had 5 AUG's in frame (which if translated, would encode 144 amino acids upstream of the proposed translational start site). The isolate and 3 additional isolates contained a single nt insertion at position 376 of the 5' ntr. If the remaining 10 isolates contained this insertion, all would include an in-frame AUG at position 381.

Evaluation of the predicted amino acid composition of the 21 GBV-C polyproteins intiating translation at 554 revealed them to be highly conserved with the exception of the chimpanzee isolate, AF 070476 (Birkenmeyer et al., 1998). The E1 and E2 coding regions displayed the most heterogeneity. The isolate (AF 121950) contained 9 amino acids that were not present in any of the complete sequences studied (E1: 117R. 122L; 127K; E2: 281 P; NS2: 157 1; NS3: 179K, 1848; NS5b: 2091, 522R). Comparison of the 20 human isolates for amino acid insertions and deletions revealed a single 12 amino acid insertion in the NS5a protein in isolate AB003291, and a single amino acid deletion found in NS5b of isolates D87710 and D87711. The chimpanzee isolate contained a 12 amino acid insertion in NS5a, which was very similar to the insertion in AB003291. In addition, the chimpanzee isolate contained a single amino acid insertion in E1 and E2 and several deletions that were not present in any of the human isolates (2 isolated deletions in E2, a 6 amino acid deletion in NS2, a 4 amino acid deletion in NS4, a 10 amino acid deletion in NS5a, a two amino acid deletion in NS5b, and a truncated carboxy-terminus with 15 amino acids fewer than AF121950 and 10 other isolates).

The complete 3' nontranslated region (ntr) from 11 of the 21 full-length isolates studied were available. There was 96.46% homology among these sequences, with AF121950 containing no unique nucleotide sequences. Of the 312 nucleotides present in the 3' ntr, there was only a single nt difference between AF121950 and D 90600. In both HCV and GBV-B, additional 3' ntr sequences were found at the 3' terminus subsequent to the original publication of the sequence (Bukh et al., 1999; Kolykhalov et al., 1996). Because of this, the inventors were concerned that there may be additional sequences on the 3' end of GBV-C. Consequently, the inventors performed 3' RACE studies eight times, and also carried out RT-PCR across 5'-to-3'-end-ligated viral RNA four times in an attempt to identify additional sequences downstream of the previously published 3' terminus. However, no additional nucleotide sequences were identified.

Figure 3A:
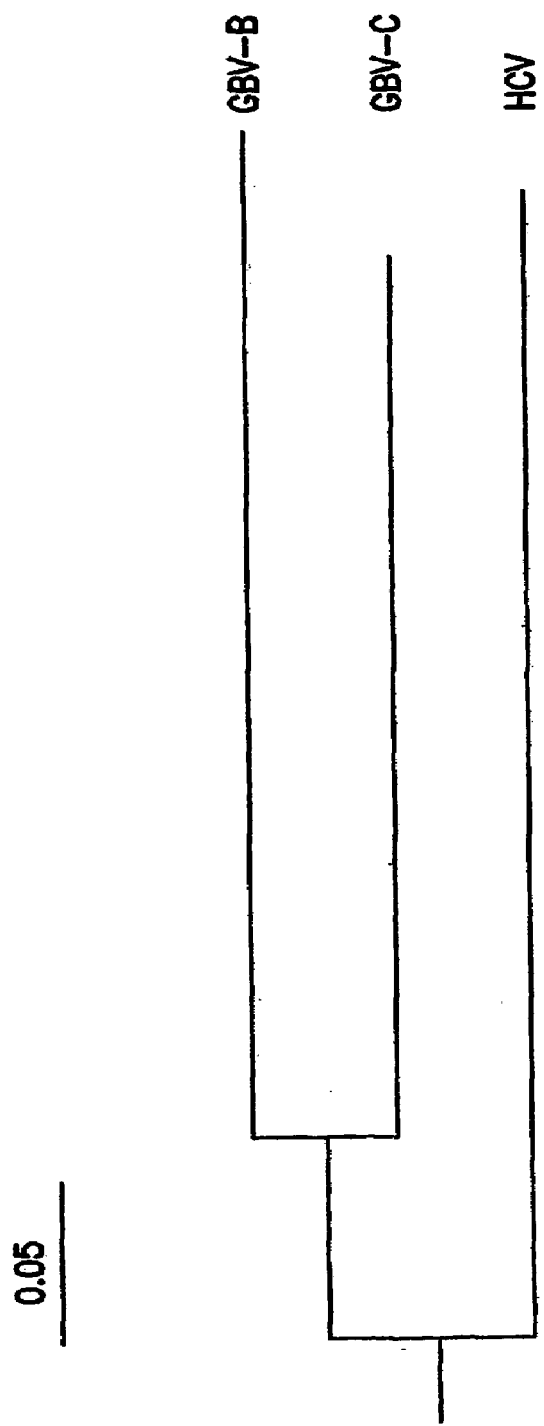
Figure 3B:
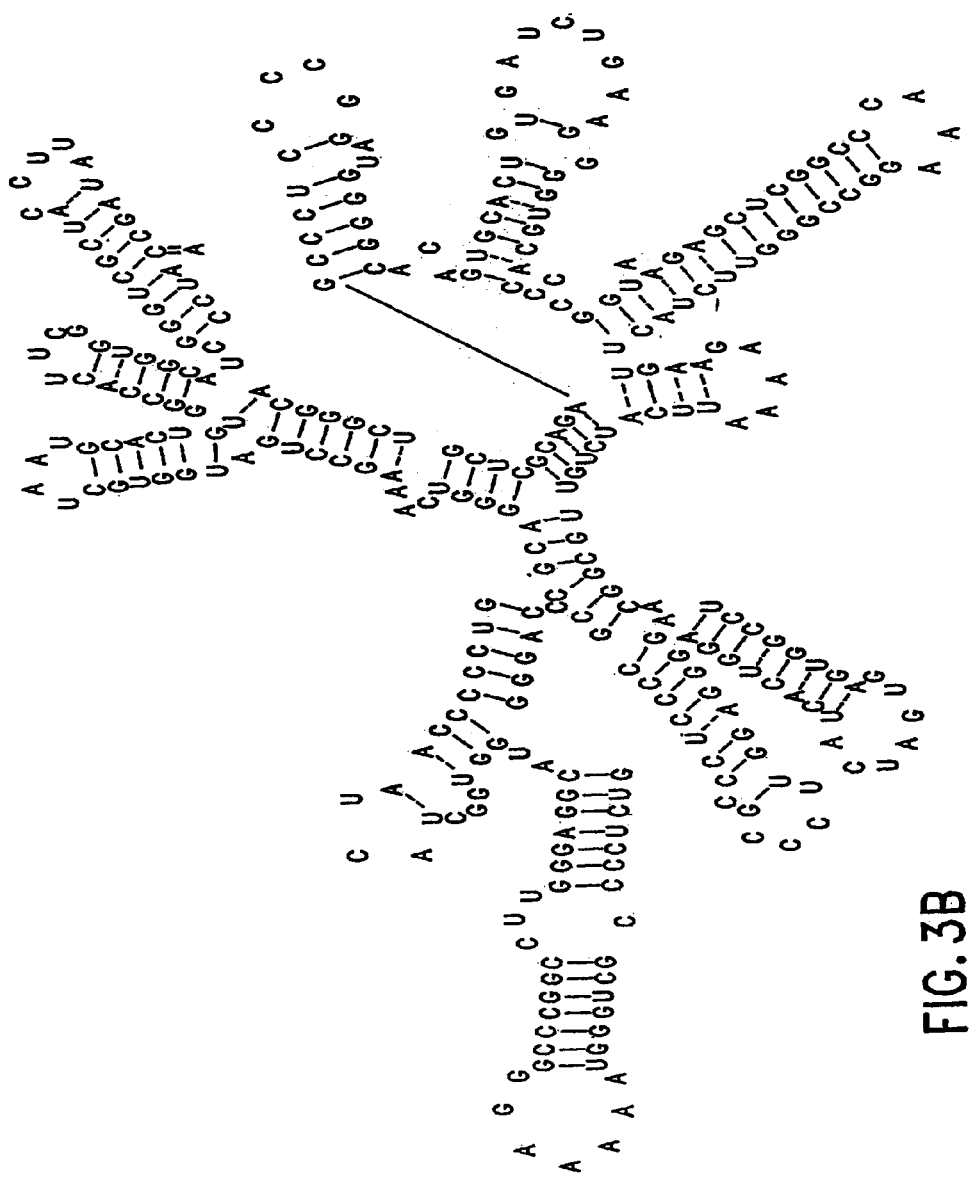
Figure 3D:
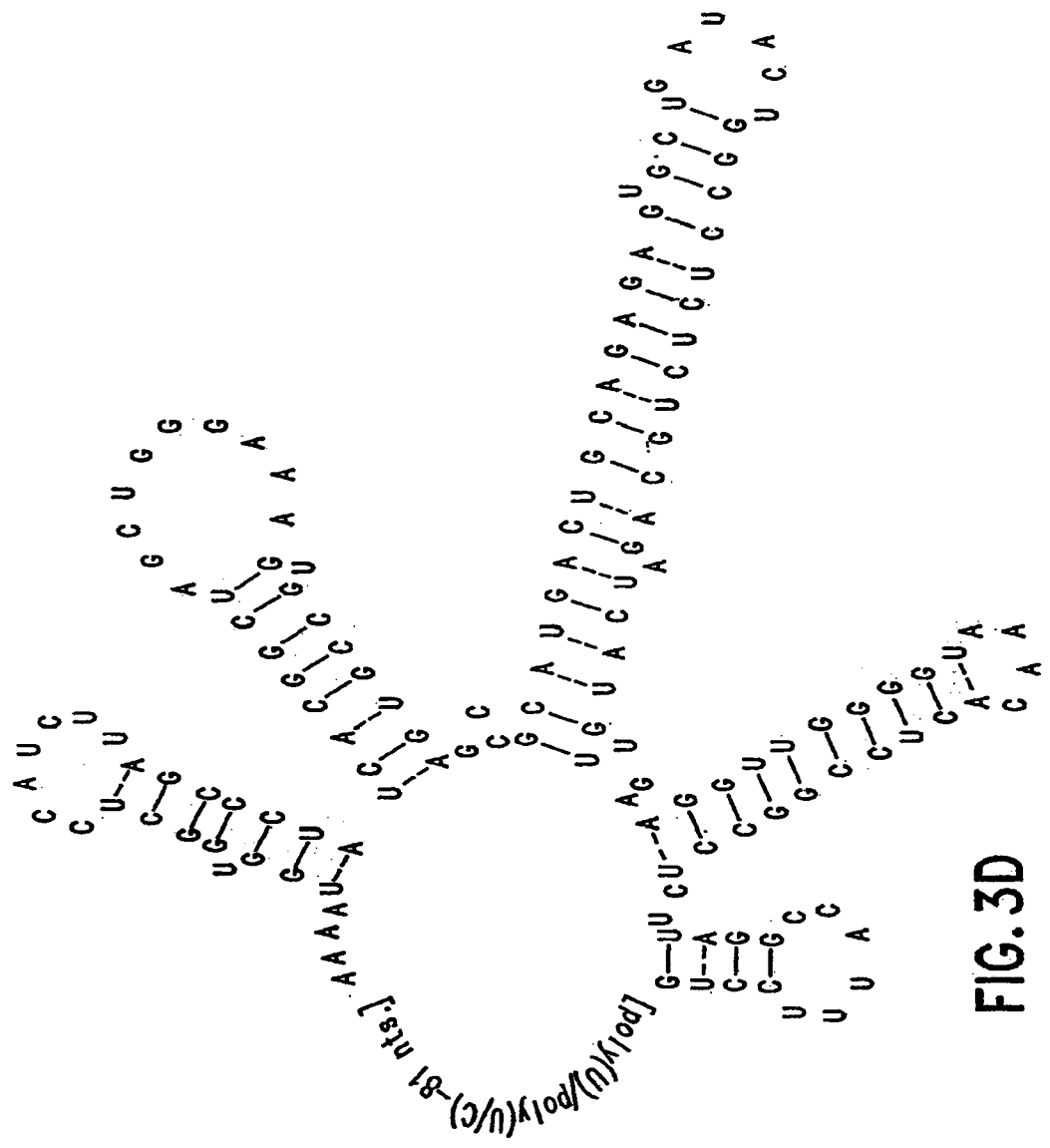

Not surprisingly, comparison of the 3' ntr of GBV-C with the 3' ntr of an infectious GBV-B clone and the infectious HCV clone used as a control demonstrated only 45.69% homology among the three sequences. GBV-C was more closely related to GBV-B than HCV, and of the two GB-hepatitis agents, GBV-C was more closely related to HCV than was GBV-B (FIG. 3A). Although there was little sequence homology of this region, analysis of the predicted secondary structures demonstrated several similarities (FIG. 3B-D), particularly at the extreme 3' end (RNAdraw: an integrated program for RNA secondary structure calculation and analysis under 32-bit Microsoft Windows) Matzura and Wennborg, 1996). Although GBV-C does not have a polypyrimidine tract, the 3' end has three stem-loop structures closely resembling the HCV and GBV-B 3' end (FIG. 3B, FIG. 3C, and FIG. 3D, respectively. In addition, the 5' end of this region bears remarkable structural resemblance to GBV-B (FIG. 3B and FIG. 3C). The predicted free energy of the GBV-C, GBV-B, and HCV 3'ntr RNA structures (37° C.) were −92.98 kCal, −109.01 kCal, and −55.08 kCal, respectively (Matzura and Wennborg, 1996).

Example 4

Full-Length GBV-C RNA is Infectious in Cell Culture

Figure 1B:
Figure 4A:
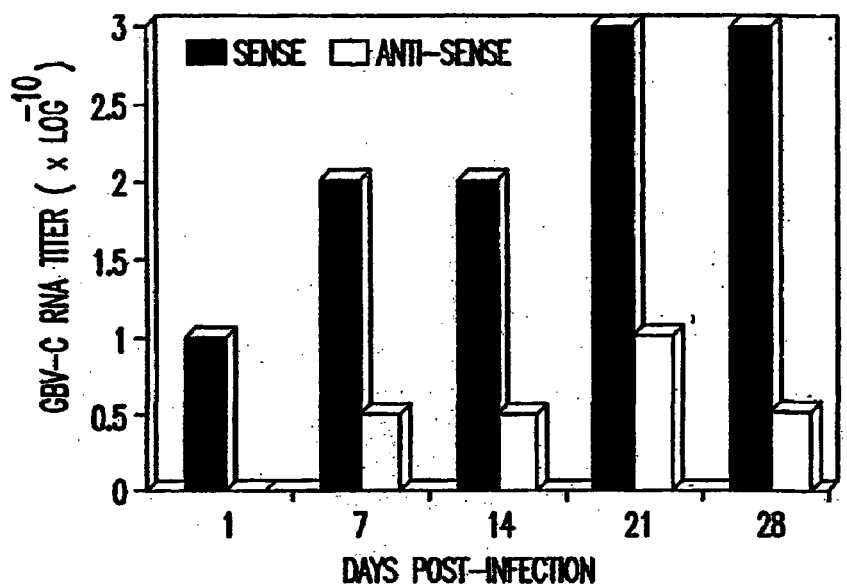
FIG. 4A-B Detection of GBV-C RNA in cell culture supernatants (FIG. 4A) and cell lysates (FIG. 4B). Results are expressed as the relative GBV-C RNA end point dilution titer. GBV-C RNA was detected 1 day following infection, and after 7, 14, 21, and 28 days of culture.
Figure 4B:
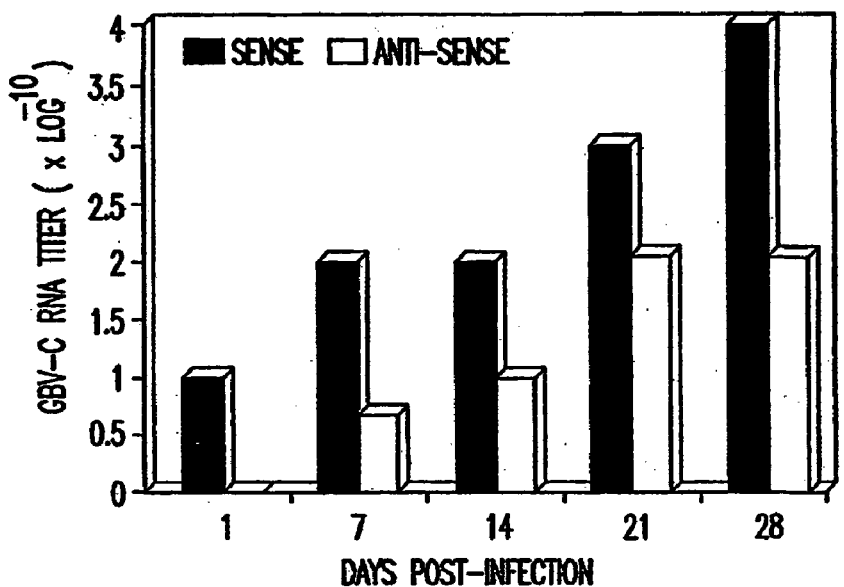

Full-length GBV-C transcripts were generated using T7 polymerase. For comparison, full length HCV RNA was also transcribed from an infectious cDNA clone using T7 polymerase (Kolykhalov et al., 1997). RNA from the transcription reactions was denatured with formamide and analyzed on a 1% agarose formaldehyde gel (FIG. 1B). The GBV-C transcript was approximately 9.4 kb, whereas the HCV transcript was approximately 9.7 kb. GBV-C and HCV RNA transcripts were transfected into PBMCs, Molt4 and HepG-2 cell lines. Following transfection, PBMC's were supplemented with fresh, PHA-IL2 stimulated PBMC's weekly for four weeks. Culture supernatants and cell lysates were evaluated for GBV-C and HCV RNA, and GBV-C RNA was detected in all PBMC lysates and culture supernatants (Table 2). In contrast, HCV RNA was not detected in PBMCs cell lysates or culture supernatants after three weeks in culture (Table 5). GBV-C and HCV RNA were detected in MOLT-4 cell lysates for three or fewer weeks, and were detected in the culture supernatants for only the week of transfection (Table 5). GBV-C and HCV RNA were not detected in HepG2 cells within one week of transfection. Cell lysates and cell culture supernatants from the GBV-C transfected cells were used to infect fresh PHA-IL2 stimulated PBMC cultures for four passages, and persistent GBV-C infection was demonstrated (Table 5). All studies were performed in duplicate or triplicate, and transfections were repeated twice. To ensure that the GBV-C RNA detected in PBMC cell lysates and culture supernatants did not represent amplification of residual plasmid DNA, the cell lysate and supernatant fluids from which GBV-C RNA was detected were amplified in PCR reactions not containing MMLV RT. These reactions did not produce PCR products. In addition, the relative concentration of GBV-C positive and negative sense RNA in culture supernatants and cell lysates was determined by terminal dilution. FIG. 4 demonstrates that a low concentration of negative strand RNA was present in culture supernatants following 7 days of infection (pass 5 virus), concomitantly with an increase in positive strand RNA. Negative strand RNA was detected 14 days post-infection in the cell lysates, and increased on day 21 and 28.

To determine the immunophenotype of the PBMCs that supported GBV-C replication, cells were infected with passage 4 supernatant and five days later, CD4 positive and CD4 negative cells were sorted by flow cytometry. RNA was extracted from $1.5 \times 10^5$ CD4 positive and $2 \times 10^5$ CD4 negative cells respectively, and GBV-C RNA was evaluated by RT-PCR in each cell population. The relative concentration of both positive and negative strand viral RNA was 100-fold higher in CD4 positive cells than in CD4 negative cells, indicating that ≧99% of viral replication in PBMCs occurred in the CD4+ subset (FIG. 5).

To further confirm that GBV-C RNA detection in cells represented viral replication, the $5^{th}$ passage of GBV-C infection cells was evaluated by indirect immunofluorescence. Two and 4 days post-infection, PBMCs were fixed and GBV-C E2 expression was assessed using a commercial anti-E2 monoclonal antibody. FIG. 6 demonstrates E2 expression in the cytoplasm of cells from pass 5 (FIG. 6A, B) but not uninfected cells (FIG. 6D). Panel C shows infected cells evaluated as in A; however, an isotype control monoclonal antibody was used in place of the GBV-C E2 specific monoclonal antibody.

TABLE 5

Passage history of in vitro transfection of GBV-C and HCV full length RNA's and subsequent infection of primary peripheral blood mononuclear cells (PBMC) and MOLT-4 cells.

| Cells | Viruses | 0 | 1 | 2 | 3 | 4 | 5 | 6 | 7 | 8 |
|---|---|---|---|---|---|---|---|---|---|---|
| | | | | | Cells | | | | | |
| PBMC | GBV-C T | | + | + | + | + | + | + | + | + |
| | HCV T | | + | + | + | − | − | − | − | − |
| MOLT-4 | GBV-C T | | + | + | + | − | − | − | − | − |
| | HCV T | | + | + | − | − | − | − | − | − |
| | | | | Culture Supernatant | | | | | | |
| PBMC | GBV-C | + | + | + | + | + | + | + | + | + |
| | HCV | + | − | − | − | − | − | − | − | − |
| MOLT-4 | GBV-C | + | − | − | − | − | − | − | − | − |
| | HCV | + | − | − | − | − | − | − | − | − |
| | | | | ** Generation | | | | | | |
| | | 0 | Ia | Ib | Ic | Id | II | III | IV | V |

T = DEAE transfection of cells with full length RNA transcripts;
+ = Viral RNA detected by RT-PCR;
− = Viral RNA not detected by RT-PCR.
*The number of weeks in culture as shown on top.
** The passage generation for PBMC's is shown. Following transfection, fresh PHA-IL2 stimulated PBMC's were added to the cells weekly for 4 weeks (generation Ia, Ib, Ic, and Id). Following this, cell culture supernatant was used to infect fresh cells (generation II, III, IV, V) MOLT-4 cells were passed weekly.

Example 5

GBV-C Particle Characterization

Figure 7A:
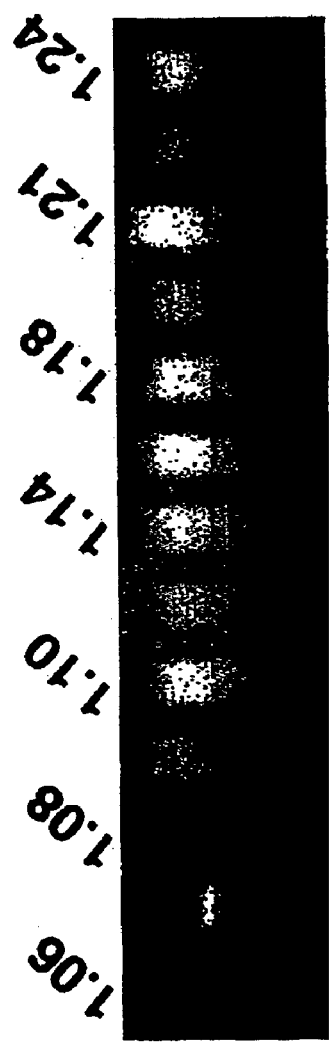
FIG. 7A-B Cell lysate and concentrated cell culture supernatant from the fourth passage of GBV-C in PBMCs were separated on a 20 to 60% (wt/wt) sucrose equilibrium gradient. The sucrose density of each fraction is shown on top in gram per milliliter. GBV-C RNA was extracted from each fraction, and detected by RT-PCR.
Figure 7B:
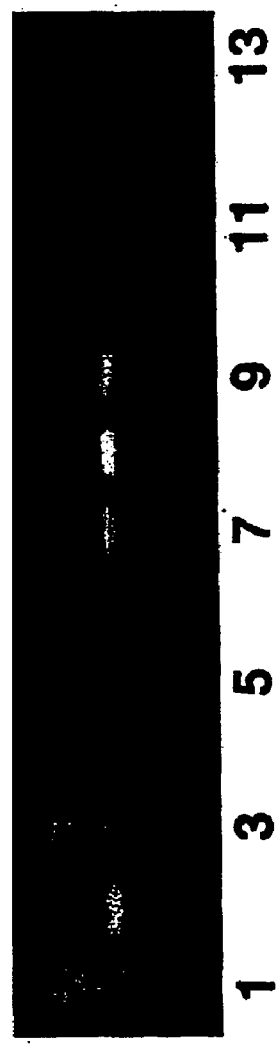
Figure 8A:
FIG. 8A-C Electron micrographs of GBV-C particles precipitated with an anti-GBV-C E2 antibody (FIG. 8A). Immuno-gold labeling of particles with (FIG. 8B) and without (FIG. 8C) the E2 antibody are shown. The arrow indicates an immuno-gold labeled particle.
Figure 8B:

In order to determine the biophysical properties of GBV-C particles generated by the infectious clone, concentrated supernatants and cell lysates from infected PBMCs (5$^{th}$ passage) were characterized by sucrose gradient centrifugation (FIG. 7). RNA was extracted from each fraction, and GBV-C RNA was detected by RT-PCR. Similar to GBV-C particles found in plasma (Xiang et al., 1998), a very low density particle type was identified with a density of 1.06 g/ml in cell lysates (FIG. 8A). This particle type, and an intermediate density particle were identified in supernatant samples (buoyant densities of 1.06 g/ml and 1.12 to 1.17 g/ml, respectively) (FIG. 8B).

Figure 8C:
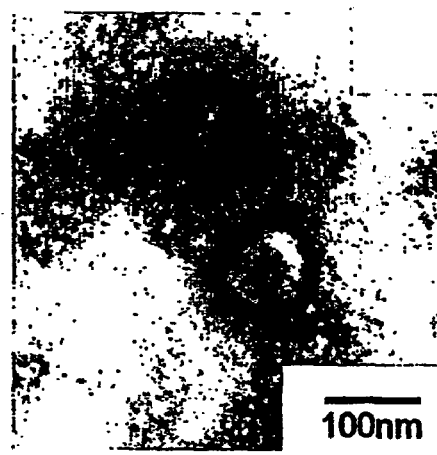

To visualize GBV-C particles, culture supernatants were concentrated from the 5$^{th}$ passage and incubated with the anti-E2 MAb. Polymorphic virus-like particles, 60-70 nm in diameter, were seen which appeared to be enveloped (FIG. 8A and FIG. 8C). Many of these particles had electron-dense structures in the center suggestive of nucleocapsids. Gold-labeled anti-mouse IgG was applied to GBV-C containing grids with (B) or without (C) the anti-E2 MAb. Immunogold labeled particles were observed only in the grids first incubated with anti-E2 antibody.

Example 6

GBV-C Inhibits HIV Replication and Delays Aids

Materials and Methods

Clinical Evaluation

All serum and plasma specimens were prepared within 2 hours of blood sampling, and were stored at −80° C. until use. Patient demographics and CD4$^+$ T cell counts were prospectively entered onto a relational database (Paradox, Borland Scientific), and surivival statistics were obtained from state health department records. To identify GBV-C viremia, RNA was extracted from serum or plasma (200 μl) using a GITX extraction methods previously described (Xiang et al. 1998). One-fourth of the RNA preparation was used as the template in a nested RT-PCR reaction to amplify GBV-C RNA using primers from the 5'ntr region (Xiang et al., 1988; Xiang et al., 1999). PCT products were separated by agarose gel electrophoresis and visualized by ethidium bromide staining. Negative control samples and positive control samples were evaluated with each PCT reaction. To be considered positive, the sample was positive on two separate occasions, or two samples from differents dates were positive. A chi-square or Fisher's exact test was used for the comparison of categorical variables, and a two-samples t-test was used for the comparison of continuous variables. A cod proportional hazards model was used to compare survival between GBV-C infected and non-infected individuals, controlling for age, baseline CD4 count, gender, race, HCV antibody status, and HIV transmission category. Statistical analysis was performed using SPSS version 8.0 (Chicago, Ill.).

Cells and Viruses

PBMCs from healthy blood donors (HCV RNA and antibody negative, HGV RNA negative, and HBV surface antigen negative) were prepared and incubated in RPMI 1640 media containing phytohemagglutinin (PHA 10 μg/ml; DIFCO, Detroit, Mich.), and 5% interleukin-2 (IL-2; Cellular Products Inc., Buffalo, N.Y.) at 35° C. in 5% CO for 48 hours prior to infection as previously described (Xiang et al., 2000). Cell viability was measured by trypan blue exclusion microscopy. Protein synthesis in mock- and GBV-C-infected PBMC's was determined by metabolically lavelling cellular proteins with $^{35}$S-methionine and determining the counts per minute of incoporation by acid precipitation as previously described (Wunschmann et al., 2000). The GBV-C isolate used in this study was derived from cell culture supernatant fluids previously transfected with full-length GBV-C RNA transcripts and passed 3 to 6 times in PBMC cultures as previously described (Xiang et al., 2000). The HIV isolate used in these studies was an NSI strain (NIH AIDS Research and Reference Reagent Program strain 92UG031; Catalog #1741). HIV stock preparations were propagated as previously described Wunschmann and Stapleton, 2000). Following activation in PHA/IL-2 for two days 1×10$^6$ PBMC's were washed, re-suspended in 100 μl of virus preparation containing HIV, GBV-C or both viruses (multiplicity of infection approximately 0.1). Co-infection was also done varying the timing of HIV or GBV-C infection. Cells were incubated for 4 hours at 37° C. prior to the addition of 2 ml fresh media, and cells were incubated overnight. The next morning, cells were washed and culture supernatant sampes were immediately collected (time 0), and twice weekly thereafter. HIV replication was determined by measuring positive RNA in culture supernatants (Wunschmnann and Stapleton, 2000; Cook et al., 1997), and GBV-C replication was determined by measuring positive sense RNA in culture supernatants and positive and negative sense RNA in cell lysates as described (Xiang et al., 2000).

Flow Cytometry

HIV receptor (CD4) and major co-receptor (CXCR4 and CCR5) expression on PBMC's following infection with GBV-C was determined by flow cytometry (FACScan, Becton Dickinson, San Jose, Calif.) (Xiang et al., 2000; Wunschmann and Stapleton, 2000). Cells were infected for varying lengths of time with GBV-C or mock-infected culture supernatants. Cells were pelleted, re-suspended in 10 µg/ml murine anti-CD4 (IgG1 conjugated with FITC), biotinylated anti-CXCR4 (IgG2a), anti-CCR5 antibodies (IgG 2a, R-PE conjugated) (Pharmingen, Inc., San Diego, Calif.) or murine isotype control antibodies (murine IgG1-FITC, IgG2a-biotin, and IgG2s R-PE, respectively) for 30 min at 4° C. CXCR4 and the appropriate isotype control-stained cells were incubated with streptavidin conjugated CyChrome for 30 min (Pharmingen, Inc.). Between each steps, cells were washed two times with PBS.

Results

Figure 9:
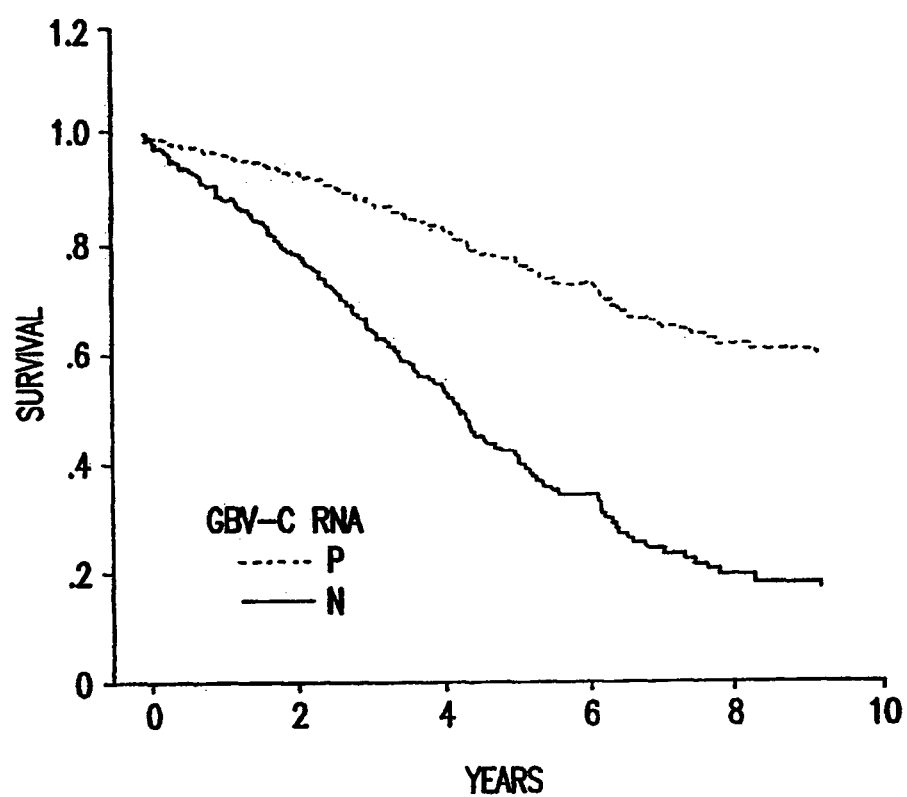
FIG. 9 Survival curves for HIV-infected individuals with and without GBV-C viremia from a Cox proportional hazards analysis. P=GBV-C RNA positive (144 subjects) and N=GBV-C RNA negative (218 subjects).

To determine if GBV-C infection prolonged survival in a large population of HIV-1 infected people with a variety of modes of HIV transmission, frozen serum and plasma samples from 362 HIV-positive individuals were studied. Samples were tested for the presence of GBV-C RNA using a previously described RT-PCR method (Xiang et al., 1998). One hundred forty-four (39.7%) of our patients were viremic on replicate samples. The baseline clinical and demographic variables for the GBV-C RNA positive and negative groups were very similar, except for the baseline CD4+ T cell count and HCV antibody status (Table 6). The mean CD4 count was higher in the GBV-C RNA positive group, although the difference was not statistically significant (Table 6). Using a Cox proportional hazards analysis, controlling for baseline CD4 count, age, race, gender, HIV transmission category, and HCV antibody status, the adjusted relative risk of mortality among GBV-C negative individuals was 3.41 (p<0.001; confidence intervals 2.37-4.91) compared to the GBV-C viremic group. FIG. 9 demonstrates the survival curve for GBV-C RNA positive and GBV-C RNA negative HIV-positive patients. A significant mortality difference between the two groups was seen in individuals with CD4+ T cell counts of 0 to 50 per mm$^3$, 51 to 200 cells per mm$^3$, and 201 to 500 cells per mm$^3$. The number of deaths among people with more than 500 CD4+ T cells/mm$^3$ was lower in the GBV-C viremic group, although the numbers were too small to achieve statistical significance (Table 7). By Cox regression analysis, the likelihood of survival at 9 years was approximately 62% in the GBV-C RNA positive group compared to only 18% in the GBV-C negative group.

TABLE 6

Baseline demographics and mortality among human GB virus (GBV-C) RNA positive and negative individuals

| Variable | GBV-C RNA status: Positive (N = 144) | Negative (N = 218) | Two tailed p-value* |
|---|---|---|---|
| Age (mean yrs) | 34.5 | 35.1 | 0.48 |
| Gender: N (%) female | 17 (11.8) | 26 (11.9) | 1.0 |
| Race: N (%) caucasian | 128 (88.9) | 189 (86.7) | 0.626 |
| Baseline CD4+ T cell count (mean) | 313.5 | 263.5 | 0.07 |
| HCV antibody positive: N (%) | 35 (24.3) | 97 (44.5) | <0.001 |

TABLE 6-continued

Baseline demographics and mortality among human GB virus (GBV-C) RNA positive and negative individuals

| Variable | GBV-C RNA status: Positive (N = 144) | Negative (N = 218) | Two tailed p-value* |
|---|---|---|---|
| Transmission category: | | | |
| Intravenous drug use: N (%) | 23 (16.0) | 36 (16.5) | 1.0 |
| Sexual**: N (%) | 113 (78.4) | 162 (74.3) | 0.365 |
| Blood or blood products: N (%) | 8 (5.6) | 20 (9.2) | 0.2 |
| Died during follow up period: N (%) | 41 (28.5) | 123 (56.4) | <0.001 |

*Pearson's Chi-square or Fisher's Exact test for categorical variables, t-test for continuous variables.
**80% of the sexual transmission was in men having sex with men, and the remaining 20% was heterosexual. There was no difference in the distribution of sexual transmission category by GBV-C RNA status.

TABLE 7

Mortality rates among GBV-C RNA positive and negative individuals stratified by baseline CD4+ T cell count

| Baseline CD4 count | N | HGV (GB Virus C) RNA status: Positive (N = 144) | Negative (N = 218) | two tailed p-value |
|---|---|---|---|---|
| ≤50 cells/mm$^3$ | 73 | 11/25 (44.0%) | 36/48 (75.0%) | 0.01 |
| 51-200 cells/mm$^3$ | 98 | 14/32 (43.8%) | 50/66 (75.8%) | 0.003 |
| 201-500 cells/mm$^3$ | 122 | 13/56 (23.2%) | 29/66 (43.9%) | 0.022 |
| >500 cells/mm$^3$ | 69 | 3/31 (6.5%) | 8/38 (21.1%) | 0.322 |

Figure 11:
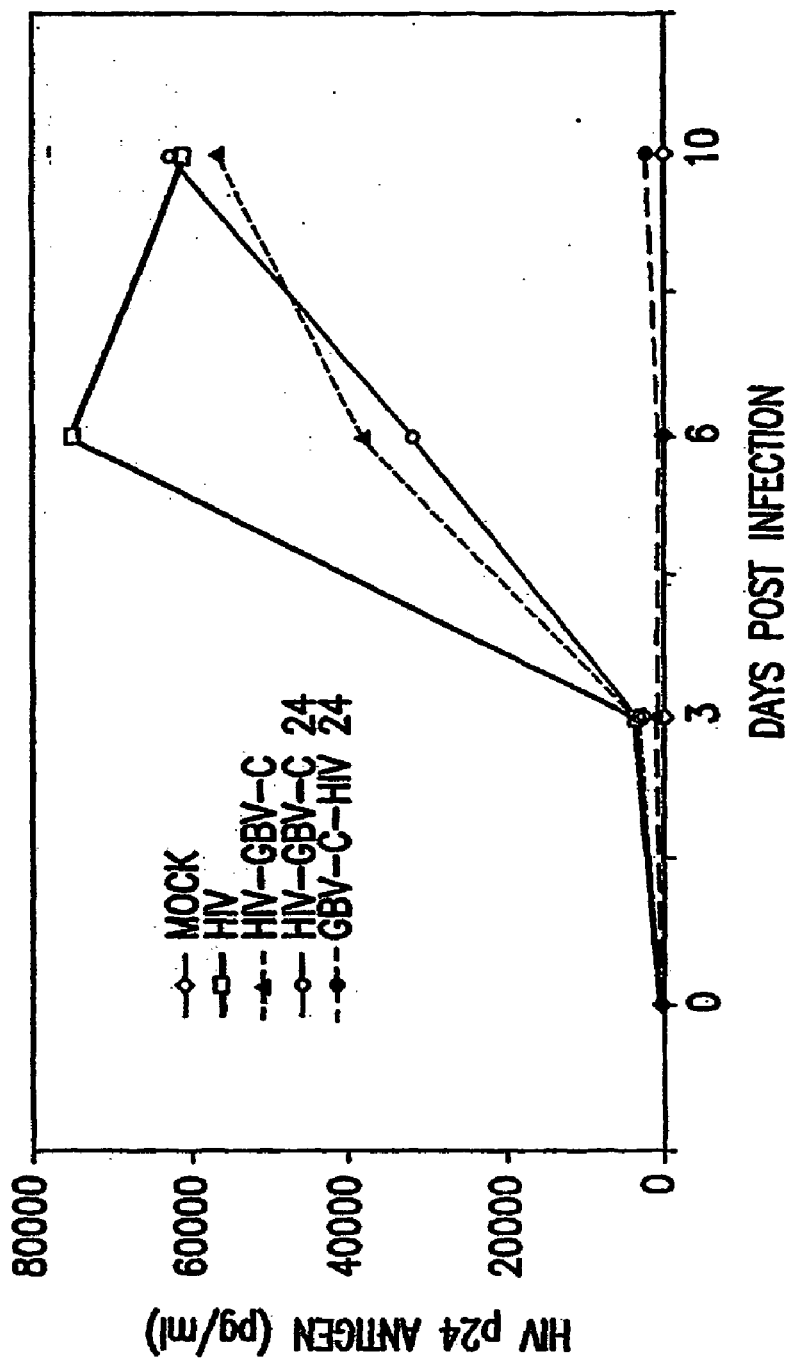
FIG. 11 GBV-C infection of PBMCs inhibits HIV replication. PHA-IL-2-stimulated PBMCs were mock infected (mock) or infected with HIV alone (HIV), HIV and GBV-C simultaneously (HIV-GB), HIV followed by GBV-C 24 hours later (HIV-GBV 24), or GBV-C followed by HIV 24 hours later (GB-HIV 24). HIV replication was measured by determining the concentration of HIV p24 antigen in culture supernatants immediately post infection, and 3, 6 and 10 days later.

To examine potential mechanisms to explain why HIV-GBV-C co-infected subjects live longer than patients infected only with HIV, the effects of GBV-C on HIV infection was examined in vitro. To determine if GVB-C infection altered HIV replication in vitro, replicate PBMC cultures were infected with HIV alone, GBV-C alone, or with HIV and GBV-C. Mock-infected PBMC's served as the negative controls. In vitro, HIV replication was diminished in cells infected with both GBV-C and HIV compared to control cells infected with HIV alone, although the inhibition was not complete. Since the inhibitory effect of GBV-C replication on HIV growth in cell culture occurred when HIV infection preceded GBV-C, and since GBV-C did not decrease the expression of CD4, CXCR4 or CCR5, the mechanism of inhibition does not appear to involve an HIV cell receptor. GBV-C isolates were obtained from culture supernatants following transfection of PBMCs with full-length RNA transcripts from our infectious GBV-C clone (Xiang, et al. 2000; three separate GBV-C isolates with different passage histories were used in these studies and all demonstrated inhibition activity. The NSI HIV isolate used in these studies was obtained from the NIH AIDS Repository as previously described (Wünschmann and Stapleton, 2000). PBMCs were stimulated with PHA and IL-2 as previously described (Xiang et al., 2000), and replicate cultures were infected with HIV alone, GBV-C alone, HIV and GBV-C simultaneously, HIV for 24 hours followed by GBV-C, or GBV-C for 24 hours followed by HIV or the mock control. FIG. 11 demonstrates that HIV replication, demonstrated by the production of p24 antigen in the cell culture supernatant fluid, was inhibited by 31.6% after 3 days in culture, and further inhibited by 49.4% following 6 days in culture when GBV-C and HIV were used to infect cells simultaneously. Similarly, HIV replication decreased 23% (3 days) and 58.1% (6 days) post-infection when the HIV infection was initiated 24 hours prior to GBV-C infection. However, HIV replication was almost completely abrogated 3 and 6 days post-infection if GBV-C infection was initiated 24 hours prior to HIV infection (87.4% and 100% reduction at day 3 and 6 respectively). If the cultures were fed with fresh, PHA-IL2-stimulated PBMCs on Day 6 post-infection, the extent of inhibition in the co-infected cells diminished (FIG. 11). GBV-C was detected in cell culture supernatants by RT-PCR and replication was confirmed by detecting negative strand GBV-C RNA. These experiments have been repeated a total of seven times using three GBV-C virus preparations with different passage history, and with two different HIV virus preparations with similar results. In most experiments, HIV replication increased over time, even in cells initially infected with GBV-C. Thus, the inhibitory effect of GBV-C infection was not completely protective.

Figure 10:
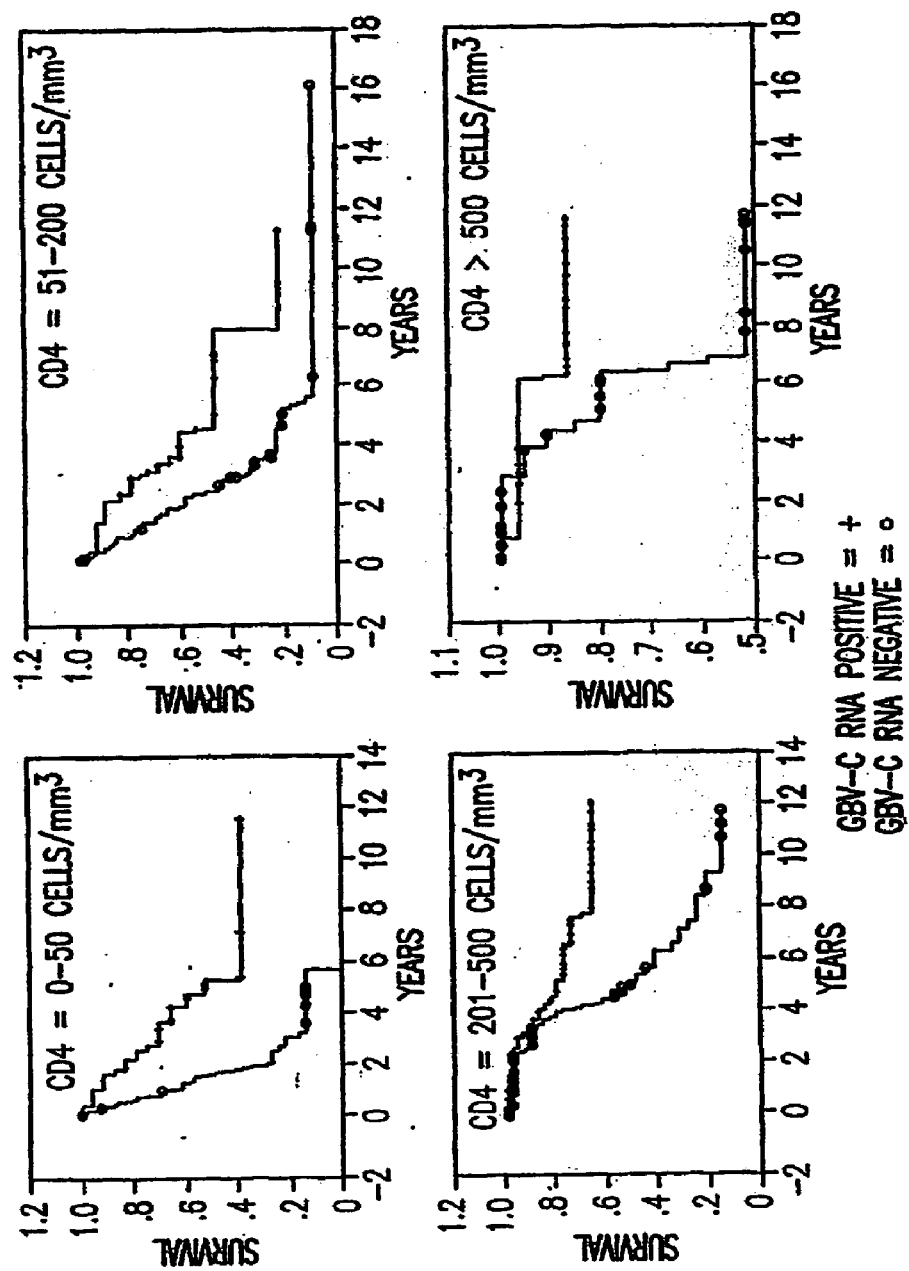
FIG. 10 Survival in HIV-infected people with and without GBV-C viremia stratigied by baseline CD4+ T cell counts. Survival rates among people with more than 500 CD4+ T cells/mm$^3$ were much higher in both groups (note different scale).

The difference in mortality between HIV and HIV-GBV-C co-infected people was observed in all CD4+ T cell count strata (Table 7). FIG. 10 demonstrates the Kaplan-Meier survival curves for the HIV-GBV-C co-infected and HIV only groups based on their baseline CD4+ T cell count. Examiner subjects who entered our clinic prior to 1990, 6 years prior to the availability of highly active antiretroviral therapy (HAART), 9 of 27 GBV-C RNA positive patients died compared to 48 of 67 GBV-C RNA negative individuals ($p<0.001$). Of the 47 HIV-infected people in our study who entered our clinic after 1995, one died prior to Jul. 1, 2000, the time data collection ceased.

HIV-related mortality was significantly lower among GBV-C-viremic individuals, independent of baseline CD4 count, age, race, gender, transmission category and HCV antibody status. GBV-C does not completely prevent CD4 T cell depletion, as at baseline, there were 25 individuals with HIV-GBV-C co-infection who had fewer than 50 CD4+ T cells/mm$^3$, 32 with 51 to 200 CD+ T cells/mm$^3$ and 56 with 201 to 500 CD4+ T cells/mm$^3$ (Table 7). However, even these patients demonstrated a significant decreased mortality rate compared to HIV infected people without GBV-C infection. Thus, the effect of GBV-C infection on mortality is more pronounced than the effect on CD4 count. Decreased mortality was observed even when controlled for variables known to be associated with rapid HIV disease progression (e.g., age and baseline CD4).

Figure 12:
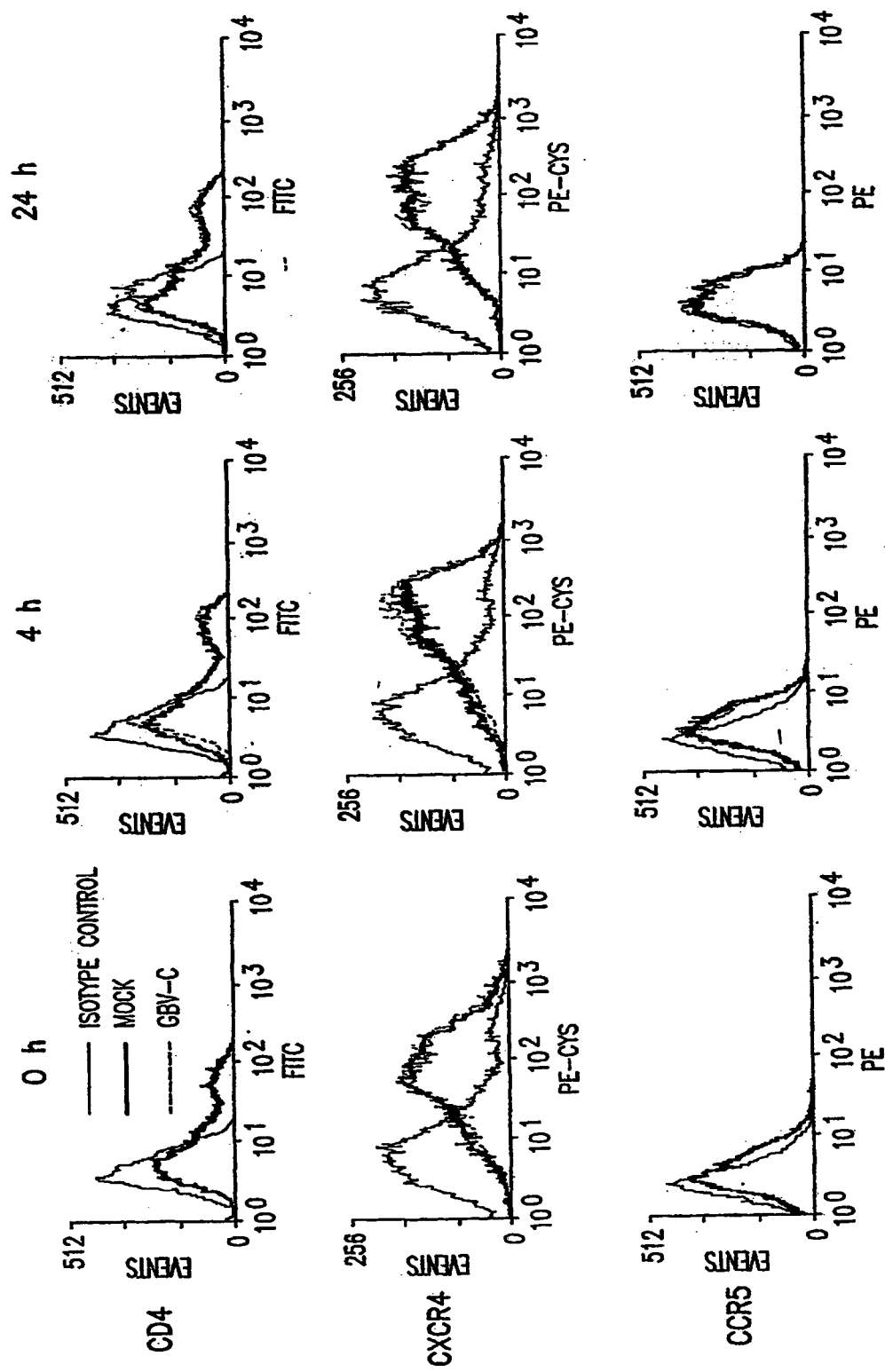
FIG. 12 GBV-C infection does not alter surface expression of HIV receptors. PHA-IL-2-stimulated normal donor PBMCs were infected with GBV-C or mock infected, and cells were evaluated by FACS immediately (0 hr), 4 and 24 hours later. CD4 expression, CXCR4 expression and CCR5 expression are demonstrated in the top, middle and lower panels respectively. FITC, PE-Cy5 and PE conjugated antibodies were used to quantify receptor expression, and the isotype controls are shown as previously described (Wünschmann et al., 2000). There were no difference between mock-infected and GBV-C-infected cell surface expression of any of these HIV receptors.

To determine if GBV-C infection led to a change in the expression of HIV cell receptors, thus decreasing HIV entry, the surface expression of CD4, CXCR4 and CCR5 on GBV-C- and mock-infected PBMC cultures was measured using flow activated cell sorting (FACS) analysis (Xiang et al., 2000). The antibodies used in FACS analysis were obtained from Pharmingen, Inc., San Diego, Calif. There were no differences between mock- and GBV-C-infected cells in the expression of either the major HIV receptor (CD4) or the co-receptors (CXCR4 or CCR5) immediately after infection, and 5, 20, 60, 240 and 1440 minutes after GBV-C infection. FIG. 12 demonstrates data obtained from selected time points. Thus, the inhibitory effect that GBV-C infection had on HIV replication appears to involve a step in HIV replication which occurs after receptor binding.

Example 7

Further Characterization of GBV-C in PBMCs

Figure 13:
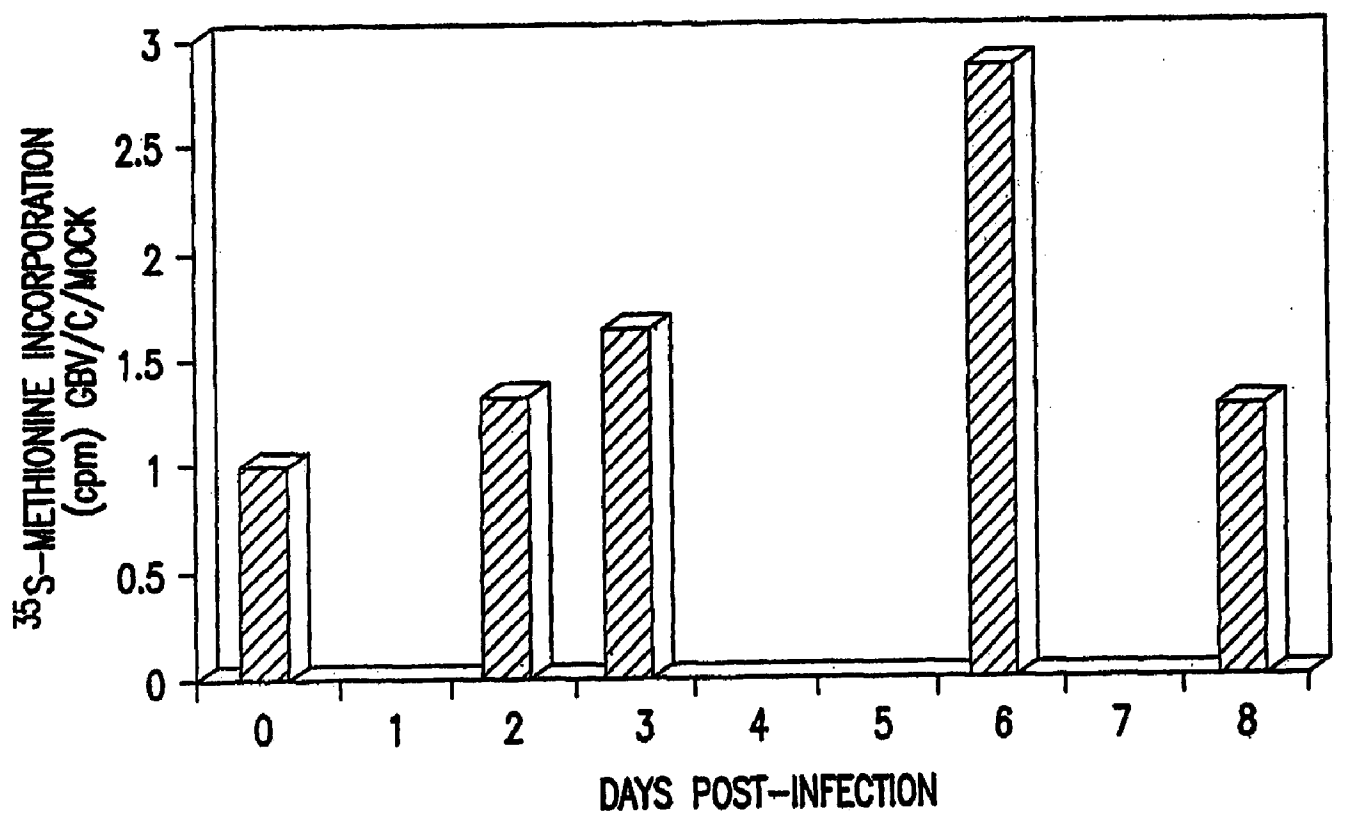

The effect of GBV-C infection on the metabolic activity of IL-2-, PHA-activated peripheral blood mononuclear cells (PBMC's) was investigated. Equal volumes of culture supernatants from GBV-C- or mock-infected PBMCs were used to infect replicate cultures of activated PBMC's ($1\times10^6$). Immediately following (day 0) and 2, 3, 6 and 8 days later, cells in culture wells were washed, placed in methionine-free media and incubated with $^{35}$S-methionine-cysteine (trans-label) for 15 minutes. Mock- and GBV-C-infected cells were again washed, lysed and incorporated $^{35}$S-methionine was determined by acid-precipitation and counted as previously described (Wünschmann et al., 2000). Data are shown as the ratio of incorporated $^{35}$S-methionine counts per minute (cpm) in GBV-C infected cells divided by cpm in mock-infected cells. The data indicate that GBV-C increases metabolic activity of PBMCs following infection (FIG. 13), thus the effect on HIV is not related to toxicity of GBV-C infection. In addition, GBV-C may influence cellular factors that increase either proliferation, protein synthesis, or prevent apoptosis relative to mock-infected cells.

Figure 14:
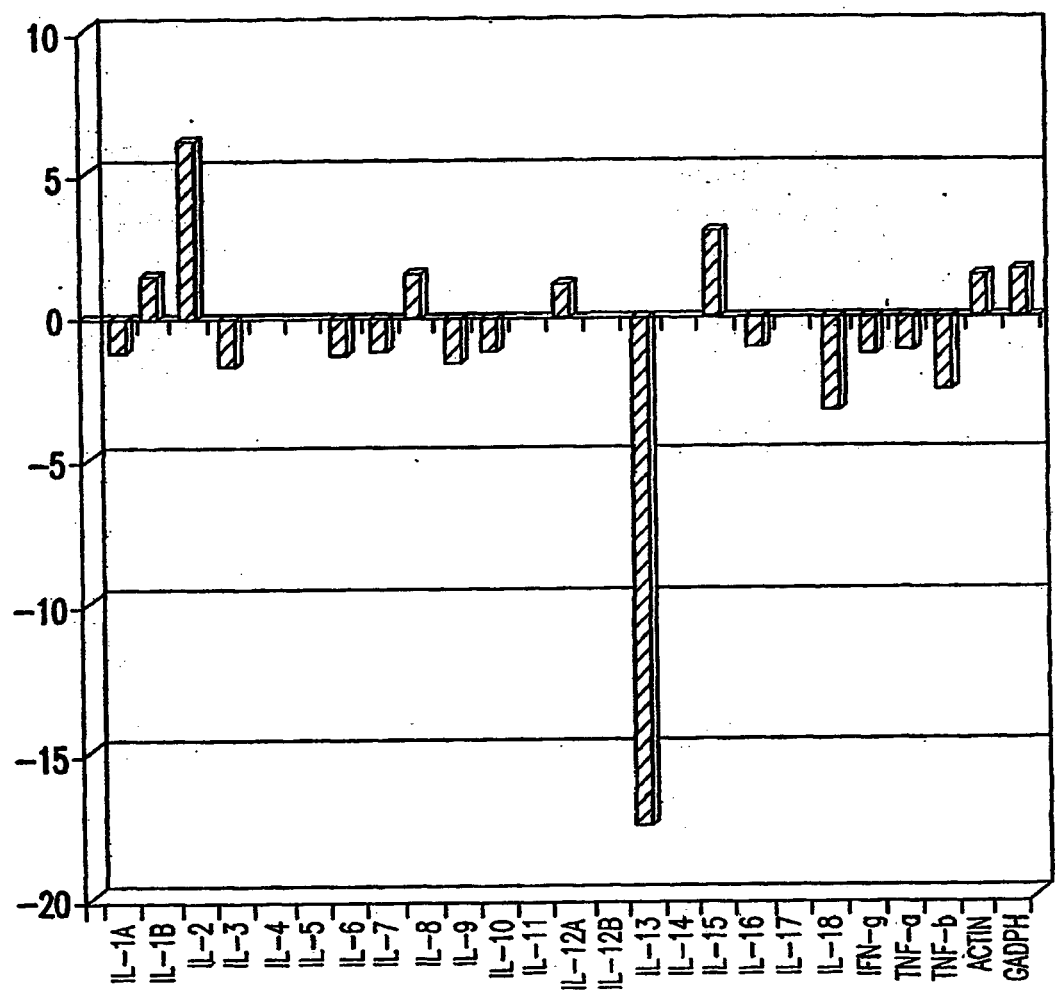
FIG. 14 Alteration of Cytokine Expression with GBV-C Infection. A cytokine array assay on GBV-C-infected PBMCs is shown.

Using the "Cytokine Array" (SuperArray, Inc.), the effect of GBV-C infection on induction of cytokines in PBMC's was compared with Mock-infected PBMCs. Cells were infected with GBV-C or mock-infected culture supernatants, and 24 hrs. later RNA was prepared using the Trizol RNA extraction methodology. RNA was used to generate $^{32}$P-dCTP labeled probes, and these were hybridized to nitrocellulose membranes containing cytokine genes, and actin and GADPH controls. Hybridization intensity was determined by counting $^{32}$P counts per minute (cpm) with a phosphoimager. Data represent the cpm for each gene (shown on the X axis) in the GBV-C-infected cells divided by the mock-infected cells (FIG. 14). IL-2 was increased more than 5-fold and IL-13 decreased more than 20-fold. In addition, IL-1B, IL-8, IL-15 were increased relative to control, and all other cytokines were decreased relative to controls.

Figure 15:
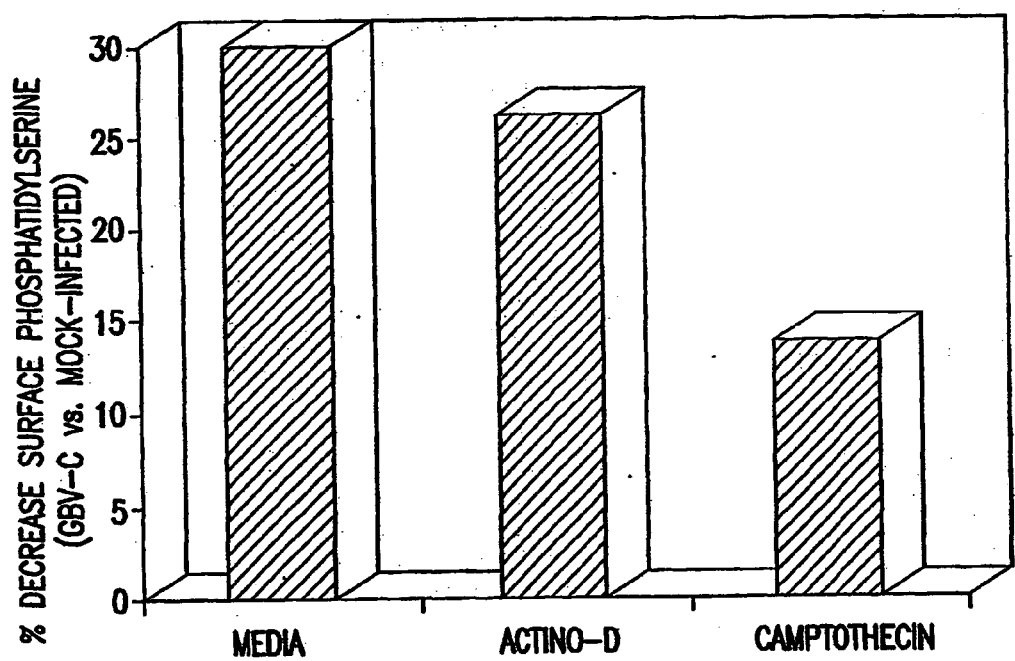
FIG. 15 Annexin binding to phosphatidylserine on surface of cells is a marker of apoptosis. GBV-C-infected and mock-infected PBMCs were evaluated for apoptosis.

GVB-C was also evaluated for its ability to induce apoptosis. Annexin binding to phosphatidylserine on surface of cells is a marker of apoptosis. PBMCs were stimulated for 48 h in PHA, LPS/IL-2 medium, infected with GBV-C (pass3 JX and pass $4_{pb}$) for 48 h. To determine if GBV-C inhibits apoptosis, mock-infected and GBV-C-infected cells were incubated in either media, or in the presence of inducers of apoptosis for 5 h (actinomycin-D or Camptothecin). AnnexinV staining of phosphatidylserine on the outer leaflet of the cell plasma membrane (a marker of apoptosis) was done according to manufacturer's instructions (Vybrant Apoptosis Assay Kit 2—Molecular Probes). AnnexinV staining was done according to manufacturer's instructions (Vybrant Apoptosis Assay Kit 2—Molecular Probes) and annexin labeling was accomplished by flow cytometry. Both actinomycin-D and media treated cells demonstrated reduced apoptosis in GBV-C-infected cells compared to mock-infected cells (FIG. 15). Thus, GBV-C did not induce apoptosis, but instead reduced or inhibited it.

Example 8

Introduction

Human infection with GB Virus type C (GBV-C) is common; approximately 2% of healthy blood donors, 15% of HCV positive individuals, and up to 40% of HIV-infected people have GBV-C RNA detected in serum. In HIV clinic populations, up to 40% of patients test positive for GBV-C RNA. GBV-C is the most closely related human virus to Hepatitis C virus (HCV). Both viruses produce persistent infection in healthy people associated with prolonged viremia. However, HCV infection results in liver disease in 20% of infected people, whereas GBV-C infection has not been convincingly associated with any disease (Alter).

Several studies found that people coinfected with GBV-C and human immunodeficiency virus (HIV) appear to have longer AIDS free survival than HIV-infected people without GBV-C (7 studies). GBV-C infection was associated with higher baseline CD4+T cell counts, lower baseline plasma HIV concentration, better response to anti-retroviral therapy (Tillmann, Ledermen), and lower mortality, although two studies did not show this effect (Sabin, Fauci). This benefit was independent of baseline CD4+ T cell count, age, race, gender, HCV antibody status, CCR5 polymorphisms, HIV transmission category, and administration of antiretroviral therapy and PCP prophylaxis. The survival benefit of GBV-C coinfection on infection with HIV was most consistently demonstrated in people with GBV-C viremia; however, people with antibodies to the GBV-C E2 protein and who cleared viral RNA may also have improved survival compared with HIV-infected people without any exposure to GBV-C (Yeo, Heringlake). The mechanism of the effect of GBV-C on HIV is unknown, but has been shown not to be dependent on down-regulation of HIV receptors or cell protein syntheses.

Tillmann et al reported an inverse correlation between HIV viral load and GBV-C viral load, suggesting an antagonistic effect of GBV-C on HIV replication (Tillmann). Coinfection studies demonstrated suppression of HIV replication in human peripheral blood mononuclear cells (PBMC's) coinfected with GBV-C. GBV-C replicated in the CD4+ subset of cultured PBMC's, and inhibition of HIV replication occurred when the two viruses were added to PBMC's simultaneously and when HIV infection preceded GBV-C, suggesting that the inhibition is not due to competition for HIV cell receptor(s). GBV-C infection 24 hrs prior to HIV infection resulted in more dramatic reduction of HIV levels, suggesting the induction of a cellular factor or factors which inhibit HIV replication.

Fogeda et al used GBV-C in plasma from a patient without HIV to infect human PBMC's. In these infections distinct quasispecies of GBV-C were selected over 30 days in culture. The predominant quasispecies in supernatant following growth in cell culture was distinct from the predominant quasispecies in the source plasma. In this study, we sought to determine if GBV-C isolates from individual patients differ in their ability to replicate in vitro, and to characterize GBV-C replication in human PBMC's.

Methods

Study participants: Individuals attending the University of Iowa HIV clinic were invited to participate in a study of GBV-C infection, and one additional person infected with GBV-C but not HIV participated. Informed consent was obtained from all participants and the study was approved by the University of Iowa Institutional Review Board. Participants were asked to allow testing of blood samples for GBV-C viremia; 12 participants testing positive for GBV-C on at least two samples from separate days were asked to give an additional 60 cc of blood for isolation and culturing of PBMCs. Review of medical records confirmed HIV infection by HIV-ELISA and western blot testing, and all subjects received HAART and *Pneumocystis carinii* (PCP) prophylaxis as prescribed by their primary care provider without reference to GBV-C status. Demographic and clinical data were obtained from patient's medical records, including age, gender, race, HIV-RNA, CD4+T cell count, HCV serologies, and alanine aminotransferase (ALT) levels. Testing of HIV-RNA, CD4+T and CD8+ T cell counts were done within 30 days of the date samples were collected for culture, and ALT levels were obtained within 90 days. HCV antibody testing was performed at the time of the patients initial clinic visit. Serum HIV RNA levels of <400, <50, and >750,000 copies/mL were treated as 399, 49, and 750,001 copies/mL for statistical purposes. All statistics were performed using SigmaStat software V2.03S (Jandel Scientific, Chicago, Ill.).

Sample collection and GBV-C Characterization: To screen for GBV-C viremia, blood samples were anticoagulated with acid-citrate-dextrose anticoagulant (Becton-Dickinson, Franklin Lakes, N.J.) and processed within 2 hours of collection. Aliquots of whole blood (200 µl) were added to 500 µl of GITC solution and stored at −80° C. as previously described. Plasma was prepared (600×g 15 minutes at 4° C.) prior to storage at −80° C. RNA was extracted from 200 µl whole blood or 200 µl plasma as previously described. One fourth of the final RNA preparation was used as template in each RT-PCR reaction, representing 50 µl of the original plasma sample. Primers from the GBV-C 5' non-translated region (ntr) of GBV-C (nt #s 23-330) were used in nested RT-PCR reactions as previously described. In addition, primers from the GBV-C NS5A region (nt#s 6651-6877) homologous to the putative Hepatitis C interferon-sensitivity determining region were used to amplify viral RNA: (outer antisense: TACTGCARTCYTCCATGATGACAT (SEQ ID NO:5); outer sense: ATGGTYTAYGGYCCTGGV-CAAA (SEQ ID NO:6); nest antisense: TTCAAGAATC-CTCGCAGCATTCT (SEQ ID NO:7); nest sense: CTGGV-CAAAGYGTYACCATT) (SEQ ID NO:8)). All sequence numbers are based on the sequence of the infectious GBV-C clone, GenBank Accession #AF 121950. At least 2 negative and positive control samples were processed in duplicate with each PCR reaction, and all samples were tested in duplicate. Detection of GBV-C RNA in culture supernatants used RNA extracted from 50 µl of superatant as the template in nested RT-PCR reactions as described above, and detection of GBV-C RNA in cultured PBMC's was done under identical conditions using RNA extracted from $5 \times 10^5$ cells.

To determine the GBV-C genotypes of each isolate, first round products from 5'ntr RT-PCR were re-amplified in nested PCR using primers specific for GBV-C genotypes I-IV under conditions described by Naito et al. PCR products were separated by agarose gel electrophoresis and visualized by ethidium bromide staining. GBV-C PCR products were purified (Wizard PCR purification kit, Promega, Madison, Wis.) and ligated into the pTA vector (Original TA cloning kit; Invitrogen, Carlsbad, Calif.) as previously described. Plasmid DNA was sequenced using an ABI automatic sequencer (University of Iowa DNA Core facility).

PBMC preparation and Infection protocols: Three methods of infection were analyzed: culture of patient PBMC's alone, culture of patient PBMC's maintained in co-culture with healthy donor PBMC's, and infecting healthy donor PBMC's with patient plasma. PBMCs from GBV-C/HIV coinfected people and healthy donors were prepared by layering 60 cc of acid-citrate-dextrose anticoagulated whole blood onto an equal volume of Ficoll-Hypaque followed by centrifugation at 600×g 45 minutes at 4° C. The PBMC layer was removed and washed twice in RPMI 1640 media containing 10% FCS. One×$10^7$ washed PBMC's were cultured either alone or cocultured with 1×$10^7$ pooled PBMC's from healthy HIV, HCV, and GBV-C negative donors for 48 hours in RPMI 1640 media supplemented with 10% FCS, 5% recombinant human IL-2, 10 mcg/mL PHA, and LPS at a final concentration of 2×$10^6$ PBMC's/mL. The same pool of donors was used for each infection. After 48 hours, PBMC's were pelleted and resuspended in RPMI supplemented with 10% FCS, 5% recombinant human IL-2, and 5 mcg/mL PHA at a concentration of 2×$10^6$/mL, and cells were maintained for up to 21 days. Fresh donor PBMC's and media were added weekly to the PBMC cocultures; media alone was added weekly to patient PBMC's. Aliquots of 5×$10^5$ PBMC's and 500 µl culture supernatant were removed at twice weekly intervals and stored in GITC at −80° C. until use. Mock control infections of donor PBMC's were maintained under identical conditions.

For plasma infections 20 µl plasma obtained from patients on the same date as PBMC's used for culture above was used to infect 2×$10^6$ PHA, IL-2 stimulated pooled donor PBMC's (4 hours at 37° C.). Infected PBMC's were washed ×3 and supplemented weekly with fresh donor PBMC's and media for 21 days. All of the plasma infections were done in duplicate using the same donor pool of PBMC's. Five×$10^5$ PBMC's and 500 µl supernatant were removed at twice weekly intervals and stored in GITC solution at −80° C. In addition, plasma from a GBV-C positive, HIV-negative subject and a full-length infectious GBV-C clone were used to infect PHA, IL-2 stimulated donor PBMC's and maintained under identical conditions. Serial passages of GBV-C was accomplished using 20 µl of GBV-C positive culture supernatant fluid to infect PHA, IL-2 stimulated donor PBMC's. Culture supernatant fluid from the last day PBMC cultures had detectable GBV-C RNA in supernatant were used in these infections. All cultures were infected in duplicate using the same pool of stimulated donor PBMC's and with mock controls. Cultures were maintained for 2 weeks and supplemented with donor cells and media at 7 days as described above. Cultures were monitored daily and cell viability was evaluated with trypan blue staining.

GBV-C E2 antibody assay: 10 µl plasma samples were tested in duplicate for anti-GBV-C E2 antibody using the Roche microplate Anti-HGenv kits (Roche Diagnostics) according to the manufacturer's instructions. Duplicate positive and negative controls were performed with each assay, and plasma samples which tested in the borderline range for GBV-C E2 were retested in a confirmatory assay according to the manufacturer's instructions. Absorbance cut-off values for positive and negative were determined in each assay according to manufacturer's instructions.

GBV-C plasma quantitation: GBV-C RNA purified from patient plasma obtained on the day of donation of PBMC's was quantitated by nested TaqMan real-time PCR reactions (Perkin-Elmer) and confirmed by plasma endpoint dilution using nested RT-PCR.

TaqMan Real-time PCR: RNA from 100 µl plasma was used as template for duplicate RT-PCR reactions using primers from the 5'ntr region as described above. Six µl (20%) of the RT-PCR reaction product was then used as template for nested TaqMan PCR using primers from the 5'ntr region (sense primer at nt 211: TACCGGTGT-GAATAAGGGCC (SEQ ID NO:9); antisense primer at nt 283: CGTCGTTTGCCCAGGTG) (SEQ ID NO:10) and a 6-FAM labeled probe corresponding to nt # 241-265 (CTCGTCGTTAAACCGAGCCCGTCAC) (SEQ ID NO:11)). Real-time PCR conditions were: 1 hold at 50° C. for 2 minutes, then 1 hold at 95° C. for 10 minutes, followed by 40 cycles consisting of 50° C. for 15 seconds and 60° C. for 1 minute on an ABI Prism 7700 sequence detector. Duplicate positive and negative controls were performed with each reaction. To convert real-time PCR cycle thresholds to genome equivalents of GBV-C RNA, end-terminal dilution RT-PCR was performed on a plasma sample of high GBV-C titer. PCR products were then used as template for real-time PCR reactions and Sigmastat software was used to determine a standard curve correlating cycle thresholds and genome equivalents as determined by terminal dilution (Adjusted $R^2$=0.985; p<0.001); this equation was used to convert cycle thresholds to GBV-C RNA genome equivalents per mL of plasma. Plasma samples of known GBV-C RNA concentration were run as controls with each real-time PCR reaction. To confirm the genome equivalents calculated from real-time PCR, nested end-terminal dilutions of plasma were used as templates for duplicate RT-PCR reactions performed using 5'ntr and NS5A primers as described above. Products were visualized using agarose gels stained with ethidium bromide as described above. End-terminal dilutions of template plasma were performed using 10-fold dilutions, thus a band visualized at an end-terminal dilution of 250,000 genome equivalents/mL plasma would indicate a titer between 250,000 and 2.5×$10^6$ genome equivalents/mL.

HIV p24 antigen assay: 450 µl aliquots of culture supernatants obtained at two weeks were analyzed in duplicate for HIV replication using Retro-Tek HIV-1 p24 antigen ELISA kits (Zeptometrix, Buffalo, N.Y.) in accordance with the manufacturer's instructions. Duplicate positive, negative, and substrate controls were run with each assay and a p24 antigen standard curve from 0 to 125.0 pg/mL was prepared in accordance with the manufacturers instructions. Optical densities were determined using BioRad's microplate reader and microplate manager software version 4.01 (BioRad, Hercules, Calif.) and a p24 antigen standard curve was calculated for each assay using Sigmastat software.

Results

GBV-C infection in HIV-positive patients: One hundred and ninety-three HIV-infected patients attending the University of Iowa HIV clinic agreed to participate in this study. Sixty-nine patients (35.8%) tested positive for GBV-C RNA on at least two separate dates, similar to our previous findings. Twelve patients' GBV-C isolates were analyzed in the in vitro infectivity experiments. Clinical features of 12 HIV/GBV-C coinfected people whose GBV-C isolates were characterized.

TABLE 8

Clinical features of GBV-C/HIV coinfected PBMC donors

| Patient | CD4 Cells* | CD8 cells* | HIV RNA** | HCV antibody*** | ALT (u/L) |
|---|---|---|---|---|---|
| 1 | 251 | 1086 | <400 | Pos | 57 |
| 2 | 161 | 540 | <400 | Neg | 22 |
| 3 | 64 | 654 | 233,000 | Neg | 48 |
| 4 | 127 | 928 | 69,000 | Pos | 147 |
| 5 | 197 | 1942 | <400 | Neg | 19 |
| 6 | 443 | 1894 | <400 | Neg | 23 |
| 7 | 254 | 1129 | <400 | Neg | 16 |
| 8 | 701 | 1336 | <400 | Neg | 19 |
| 9 | 885 | 2588 | <400 | Pos | 30 |
| 10 | 113 | 1806 | 20,000 | Neg | 25 |

TABLE 8-continued

Clinical features of GBV-C/HIV coinfected PBMC donors

| Patient | CD4 Cells* | CD8 cells* | HIV RNA** | HCV antibody*** | ALT (u/L) |
|---|---|---|---|---|---|
| 11 | 222 | 1126 | <400 | Neg | 11 |
| 12 | 247 | 856 | 500 | Neg | 10 |

*CD4 and CD8 cells = number of cells/mm$^3$
**HIV RNA = Genome equivalents/mm$^3$
***Pos. = positive, Neg. = negative CD4+ cell counts (column 1), CD8+ T cell counts (column 2), and HIV RNA (column 3) were all obtained on the day PBMC's were collected or within 30 days. Alanine aminotransferase (ALT) data (column 5) were obtained within 90 days of PBMC collection. Hepatitis C(HCV) antibody status was determined at the time of the patient's initial clinic visit (column 4).

The 12 GBV-C/HIV coinfected patients had a mean CD4+ T cell count of 305 cells/mm$^3$ (range 64-885 cells/mm$^3$), mean CD8+ T cell count of 1324 cells/mm$^3$ (range 540-2588 cells/mm$^3$), and a mean ALT of 35.6 U/L (range: 10-147 U/L).

Four of the 12 patients had HIV RNA>400 copies/mL in serum at the time of PBMC collection: patients 3,4,10, and 12 (233,000 copies/mL, 69,000 copies/mL, 20,000 copies/mL, and 500 copies/mL, respectively). Three patients had antibodies to HCV: 1, 4, and 9. The mean age was 45 years (range 28-60 years), 10 patients were male, 1 patient was African-American, 11 patients were Caucasian (data not shown). Ten patients reported sexual risk factors for HIV transmission; two reported IV drug use (data not shown). These 12 patients were representative of our overall clinic population.

Plasma GBV-C quantification and characterization: All 12 patients had GBV-C RNA detected in plasma by nested PCR reactions on the day of PBMC donation.

GBV-C data on the 12 HIV/GBV-C coinfected people whose GBV-C isolates were characterized are shown in Table 9.

TABLE 9

Characteristics of GBV-C in the 12 HIV coinfected patients.

| | Plasma GBV-C titer | | | |
|---|---|---|---|---|
| Patient | Real-time PCR | Semi-quantitative PCR | GBV-C E2 antibody | GBV-C Genotype |
| 1 | 297,950 | 250,000 | + | 2 |
| 2 | 950,550 | 250,000 | − | 2 |
| 3 | 2,250,930 | 2.5 × 10$^6$ | − | 1, 2 |
| 4 | 5,858,700 | 2.5 × 10$^6$ | − | 2 |
| 5 | 22,950 | | − | 2 |
| 6 | 926,150 | | + | 2 |
| 7 | 565,400 | | + | 2 |
| 8 | >10,000,000 | 2.5 × 10$^8$ | − | 2 |
| 9 | >10,000,000 | 2.5 × 10$^8$ | − | 2 |
| 10 | 119,000 | 250,000 | − | 2 |
| 11 | 1,598,000 | 250,000 | − | 2 |
| 12 | >10,000,000 | 2.5 × 10$^8$ | − | 2 |

GE/mL = genome equivalents per mL of plasma detected in nested RT-PCR reactions.

Plasma was obtained at the time of PBMC collection, and used as template for nested RT-PCR reactions using TaqMan (real-time) PCR (Column 1). Plasma examples of known concentration of GBV-C RNA determined using endpoint dilutions were used as controls. Calculated genome equivalents of GBV-C RNA per mL of plasma are given. To confirm the plasma GBV-C titers determined using real-time PCR in column 1, plasma obtained on the day of collection of PBMC's was used as template for nested RT-PCR reactions in endpoint dilutions (semi-quantitative PCR) (Column 2). The terminal dilution of template for which a band was seen is shown. All dilutions were 1:10, thus a band seen at a dilution of 2×10$^6$ would indicate an endpoint dilution between 2×10$^6$ and 2×10$^7$. Plasma obtained on the day of collection of PBMC's was tested for presence of GBV-C E2 antibody using the Roche assay (Column 3). Detection of E2 antibody is indicated by a "+". Plasma GBV-C genotype was determined using genotype-specific primers in nested RT-PCR reactions (Naito et al.) (Column 4).

Genome equivalents (GE) of GBV-C RNA detected in plasma using real-time PCR ranged from 22,950 GE/mL to >10,000,000 GE/mL.

Plasma GBV-C titers in patients 8, 9, and 12 were too high to be quantified in real-time PCR without dilution; serial dilution of these patient's plasma samples followed by nested RT-PCR reactions gave GBV-C RNA titers of 2.5× 10$^8$ GE/mL. Semiquantitative nested RT-PCR reactions using serial dilutions of patient plasma as template confirmed the titers measured by real-time PCR within an order of magnitude. Eleven of 12 patients were infected exclusively with GBV-C genotype 2; patient 3 was coinfected with genotypes 1 and 2. Three patients (1, 6, and 7) had detectable GBV-C E2 antibody in the same plasma sample used to quantitate RNA and perform infectivity studies (Table 9).

PBMC and Plasma Cultures: GBV-C RNA was detected in both supernatant and cultured PBMC's from all 12 patients, however persistence of GBV-C RNA in culture varied significantly between patients (FIG. 16). PBMC cultures from patients 8 through 12 had detectable GBV-C RNA in supernatant and PBMCs for at least 7 days, while patients 1-6 did not have detectable GBV-C RNA in cultured PBMC's or supernatant after day 5 (FIG. 16A). Patient 7 had GBV-C RNA in detected in culture supernatant at day 7 in only in PBMC's not cocultured with donor PBMC's (FIG. 16A). GBV-C persistence in culture was not enhanced by coculture with donor PBMC's (FIG. 16B). Patients #1, #2, #3, and #7 did not have GBV-C RNA detectable in PBMC cell lysates after day 1, whereas patients 8 through 12 had detectable GBV-C RNA in PBMC cell lysates for at least 7 days and up to 21 days (FIG. 16C). No difference is cell viability was noted between different patients' PBMC cultures compared with PBMC's cocultured with donor PBMC's with the exception of patient 3, whose cultured PBMC's were no longer viable after day 7.

Figure 17:
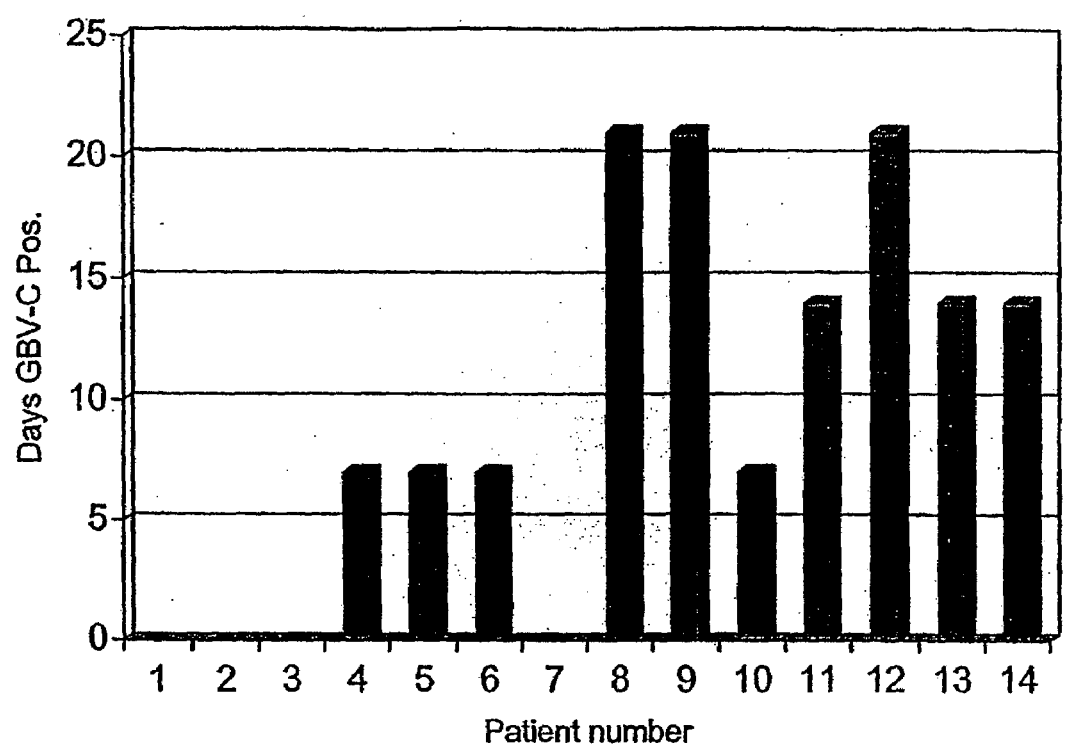
FIG. 17 Plasma aliquots from HIV/GBV-C coinfected patients were infected into donor PBMC's. All cultures were set up simultaneously and the same donor pool was used for each culture. Total days GBV-C RNA was detected in culture supernatant is shown for each patient. Patient 13 is an HIV-negative, GBV-C infected donor and isolate 14 is the GBV-C infectious clone AF121950.

When pooled stimulated donor PBMC's were infected simultaneously with 20 µl patient plasma, patients 8-9 and 11-12 had GBV-C RNA detectable in supernatants for 14 days or longer (FIG. 17). Patients 4-6 and 10 had no detectable GBV-C RNA in supernatants after day 7, and patients 1-3 and 7 had no detectable GBV-C RNA in supernatants at one week. Pooled donor PBMC's infected with plasma from the non-HIV infected, GBV-C positive subject (patient 13) and the GBV-C infectious clone AF121950 (isolate 14) had detectable GBV-C RNA in supernatants for 14 days but none thereafter (FIG. 17). PBMC viability in all cultures was identical until the final day evaluated (day 21).

Figure 18:
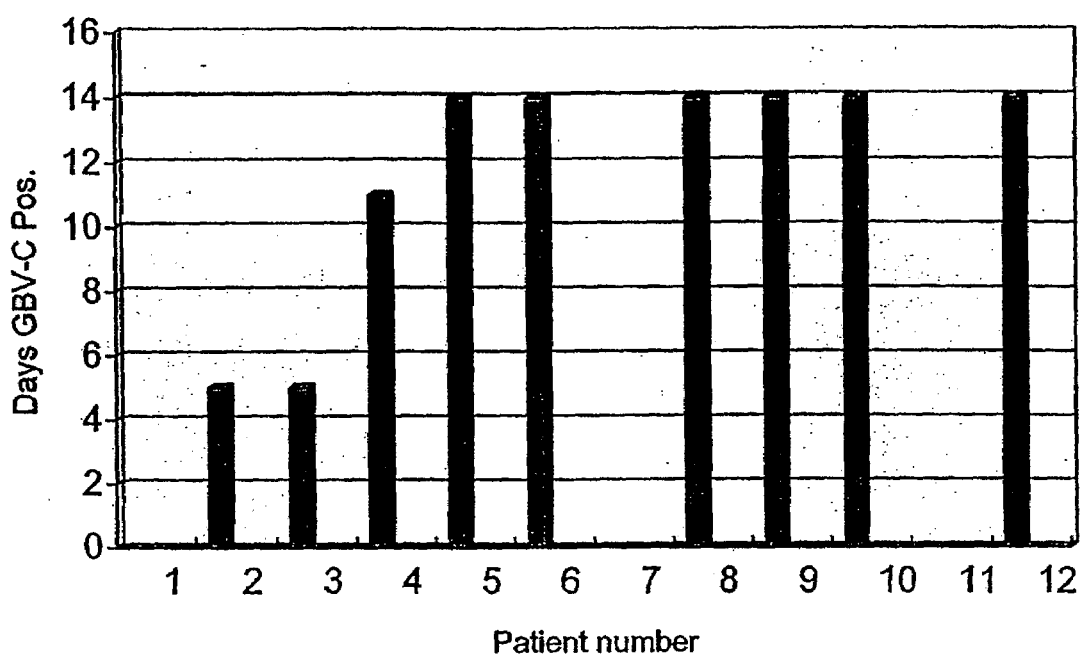
FIG. 18 Serial passage of GBV-C from PBMC coculture supernatant into donor PBMC's. The same pool of donors was used for each passage. All cultures were maintained for 14 days. Supernatant from patients 1, 7, and 11 were not available for passage. Total days GBV-C RNA was detected in culture supernatant is shown for each patient.

To determine if GBV-C isolates could be serially passaged into donor PBMC's, 20 µl aliquots of supernatants obtained on the last day GBV-C RNA was detected in PBMC culture supernatant was used to infected stimulated pooled donor PBMC's. PBMC cultures were maintained for 2 weeks, and serially passed 4 times. Passages of supernatants from PBMC cultures of patients 1, 7, and 11 were not done due to insufficient culture supernatant. All 9 patients who had supernatant available for passage demonstrated ability to replicate in PBMC culture at the end of 4 passages. Replication was improved when compared with GBV-C replication in their initial PBMC or plasma cultures (FIG. 18). PBMC culture supernatants from patients 2 and 3 had GBV-C RNA detected in supernatant from passage culture for 5 days, increased from 2 days in the original PBMC culture; and supernatant from patient 4 had GBV-C RNA detected in supernatant from passage culture for 11 days, increased from 5 days in the original PBMC culture. Supernatants from the 6 remaining patients remained positive for GBV-C RNA in passage culture for the 14 days evaluated.

HIV replication in PBMC cultures: To determine if HIV replication occurred in cocultured patient PBMC's or in infected donor PBMC's HIV p24 antigen was assayed in duplicate samples of supernatant obtained on day 14. No HIV p24 antigen was detected in supernatant of infected donor PBMC's at day 14, however HIV replication was detected in supernatants from PBMC cocultures of patients 4, 6, and 10 (data not shown). Both patients 4 and 10 had detectable HIV in plasma on the day of PBMC collection (Table 8).

Selection of GBV-C quasispecies in PBMC culture: Partial NS5A sequences were determined from both the initial plasma sample and from the last coculture supernatant sample with detectable GBV-C RNA from patients 2, 4, 5, and 8. Five clones from each sample were sequenced. Culture supernatants from patients 2, 4, and 5 did not demonstrate evidence of GBV-C replication after day 5, whereas supernatant from patient 8 demonstrated presence of GBV-C RNA in supernatant for 14 days (FIG. 16A). No sequence difference was found between plasma in patients 2, 4, and 5. In contrast, patient 8 demonstrated selection of a distinct quasispecies containing 14 mutations in the 200 bp region in all 5 clones sequenced.

Discussion

GBV-C replication has been correlated with decreased HIV replication both in vitro and in vivo. Currently, GBV-C in vitro replication methods are inefficient, inadequately reproducible, and often require mixed populations of primary cells (PBMC's). Improved GBV-C in vitro replication systems are needed. To better characterize GBV-C in vitro replication, we employed three different methods: fresh PBMC's were cultured with PHA/IL-2 alone or cocultured with stimulated donor PBMC's, and patient plasma was used to infect stimulated donor PBMC's. Cultured PBMC lysates were tested for the presence of GBV-C RNA, and supernatant from PBMC culture was passages a total of 4 times in stimulated donor PBMC's Both patient PBMC's and donor PBMC's infected with plasma from patients 1-7 had no detectable GBV-C RNA in culture supernatants or cell lysates following 7 days in culture. In contrast, supernatant from cultured patient PBMC's, donor PBMC's infected with patient plasma, and PBMC cell lysates from patients 8-12 had detectable GBV-C RNA for at least 7 days in culture and more commonly 14 to 21 days. Thus, the ability of these clinical GBV-C isolates to replicate in vitro was consistent in the three PBMC-based culture methods, and GBV-C from patients 8-12 demonstrated prolongation of in vitro replication compared with GBV-C from patients 1-7. Plasma from an HIV-negative GBV-C RNA positive person infected into donor PBMC's replicated in culture for 2 weeks, as did an infectious GBV-C clone. GBV-C isolates from patients 8-12 demonstrated both longer replication capacity in vitro compared with both the isolate from the HIV negative person and the infectious clone.

Replication of GBV-C in these 3 culture systems was not associated with cell toxicity, as significant cell death was noted only in PBMC cultures from patient 3 at one week. HIV p24 antigen was not found in supernatant of PBMC cultures infected with patient plasma at 14 days and was present in only 3 of 12 patient PBMC cocultures.

GBV-C replication capacity was independent of the source patient's CD4+T cell count, CD8+T cell count, hepatitis C antibody status, gender, age, or HIV acquisition mode. The high HIV RNA levels in patients 3, 4 and 10 on the day of PBMC collection may have played a role in the relatively poor replication noted in GBV-C isolates from patients 3 and 4, but does not explain the improved replication capacity noted in GBV-C from patient 10. When plasma from patients 3, 4, and 10 was used to infect donor PBMC's, no GBV-C RNA was found in supernatant after 7 days, indicating a possible inhibitory effect of HIV on GBV-C infection. The same PBMC donors were used for each infection to eliminate variability in permissiveness of donor PBMC's, as has been described by others. Addition of fresh donor PBMC's did not increase or prolong GBV-C replication in culture, compared to culture of patient PBMC's without supplementation with donor PBMC's.

GBV-C replication in culture was also independent of plasma GBV-C RNA titer as measured by real-time RT-PCR and serial dilution. Patient 4, with 5,858,700 GBV-C GE/mL demonstrated poor replication capacity in the three culture methodologies studied whereas patient 10, with 119,000 GBV-C GE/mL consistently demonstrated prolonged replication both in the three culture methodologies studies and after 4 serial passages. GBV-C RNA plasma titers in our patients varied from 22,950 GE/mL to $2.5 \times 10^8$ GE/mL. Tillmann et al reported plasma GBV-C viral loads ranging from 67,000 copies/mL to $1.43 \times 10^8$ copies/mL in 162 plasma samples collected from 72 GBV-C/HIV coinfected patients, similar to our own data. These data confirm that the range of GBV-C RNA concentrations in patient plasma varies far more widely than either HIV or HCV.

Serial passage of culture supernatant fluids into donor PBMC's demonstrated prolongation of replication of GBV-C isolates in culture from all 9 patients studied, though the effect was less pronounced in isolates from patients 2 and 3. Improved replication of GBV-C passed from PBMC culture supernatants into donor PBMC's did not represent increased concentrations of infectious virus in culture supernatant relative to plasma and PBMC's, as GBV-C titers in supernatant as measured by real-time PCR were consistently several orders of magnitude lower than those measured in the source plasma (data not shown). Improved replication of GBV-C passed from culture supernatant fluids into donor PBMC's more likely represents selection of viral quasispecies more adapted for in vitro replication. Fogeda et al. noted selection of a viral quasispecies not identified in the source plasma following 30 days in PBMC culture. Similarly, we isolated a distinct viral quasispecies in culture supernatants from patient 8 that was not present in patient plasma. The nucleotide substitutions noted in this quasispecies did not alter the predicted amino acid sequence of this 200 bp region, but they may alter the RNA secondary structure such that viral replication is enhanced. No quasispecies selection was found in clones amplified from 3 patients whose isolates did not persist in patient PBMC coculture beyond one week.

GBV-C replication in culture did not appear to be associated with presence or absence of GBV-C E2 antibody in plasma, nor was there an association between GBV-C plasma viral titer and detection of E2 antibody in plasma. In normal hosts, appearance of GBV-C E2 antibody in plasma is usually associated with clearance of GBV-C from blood. However, we found co-existence of infectious GBV-C RNA and E2 antibody in 3 of our 12 subjects (25%).

In summary, different isolates of GBV-C obtained from individuals coinfected with HIV demonstrated different replication capacity in vitro. Replication of the 12 clinical isolates was consistent using 3 different culture methodologies and serial passage. No improvement in viral replication was noted when cultures were supplemented with donor PBMC's. In addition, no correlation with clinical factors in the source patient or GBV-C plasma titer or presence of E2 antibody was noted. Specific nucleotide sequence mutations were identified following two weeks in culture in one isolate, suggesting that specific GBV-C nucleotide sequence mutations may influence GBV-C replication capacity in PBMC cultures.

Example 9

Introduction: GB Virus C (GBV-C) is closely related to hepatitis C virus (HCV), and coinfection with GBV-C and HIV has been associated with improved survival compared with HIV infection without GBV-C. GBV-C replicates in cultured peripheral blood mononuclear cells (PBMCs), and unique quasispecies have been found following in vitro cultivation. We previously described unique GBV-C sequence mutations in people treated with α-interferon (IFN) in the NS5A coding region with structural homology with the HCV interferon-sensitivity determining region (ISDR). GBV-C replication in vitro remains inefficient and poorly characterized, for example, sequence polymorphisms related to in vitro replication have not been described.

Methods: GBV-C isolates from 12 HIV-GBV-C coinfected people were tested for replication in cultured PBMCs. Marked variability in replication between isolates was demonstrated. GBV-C RNA was amplified by RT-PCR from the plasma of an HIV-coinfected patient (patient 12) whose isolate replicated in PBMCs for 72 days, and which was capable of serially passage in PBMC's (isolate # 765). Primers spanning the entire GBV-C genome were designed based on published sequences and sequences generated from previous PCR products. PCR products were ligated into the pTA vector (Invitrogen), sequenced in both directions, and homology was determined for 21 full-length GBV-C sequences (DNAMAN software; Lynnon Biosoft), including the infectious GBV-C clone.

Results: The full-length sequence of GBV-C isolate 765 was obtained, and unique amino acid mutations in the polyprotein were identified. Compared to 21 published full-length GBV-C sequences, there were 16 unique amino acids identified. Mutations occurred predominantly in the region encoding the serine protease/helicase (NS3 region; 4 mutations), the NS5A coding region (corresponding to the HCV ISDR; 3 mutations), and the RNA-dependent, RNA polymerase NS5B coding region (4 mutations).

Conclusions: The complete sequence of a GBV-C isolate that replicates well in PBMC culture was determined. Unique amino acid polymorphisms were identified, primarily in the NS5A and NS5B proteins. These regions have been shown to influence HCV RNA replication, thus they may be involved in GBV-C in vitro replication. In contrast, only 6 unique amino acids were identified in the envelope, protease, and helicase regions. Development of chimeric infectious clones should determine the importance of these amino acid polymorphisms in replication and IFN sensitivity.

Background

Figure 19A:
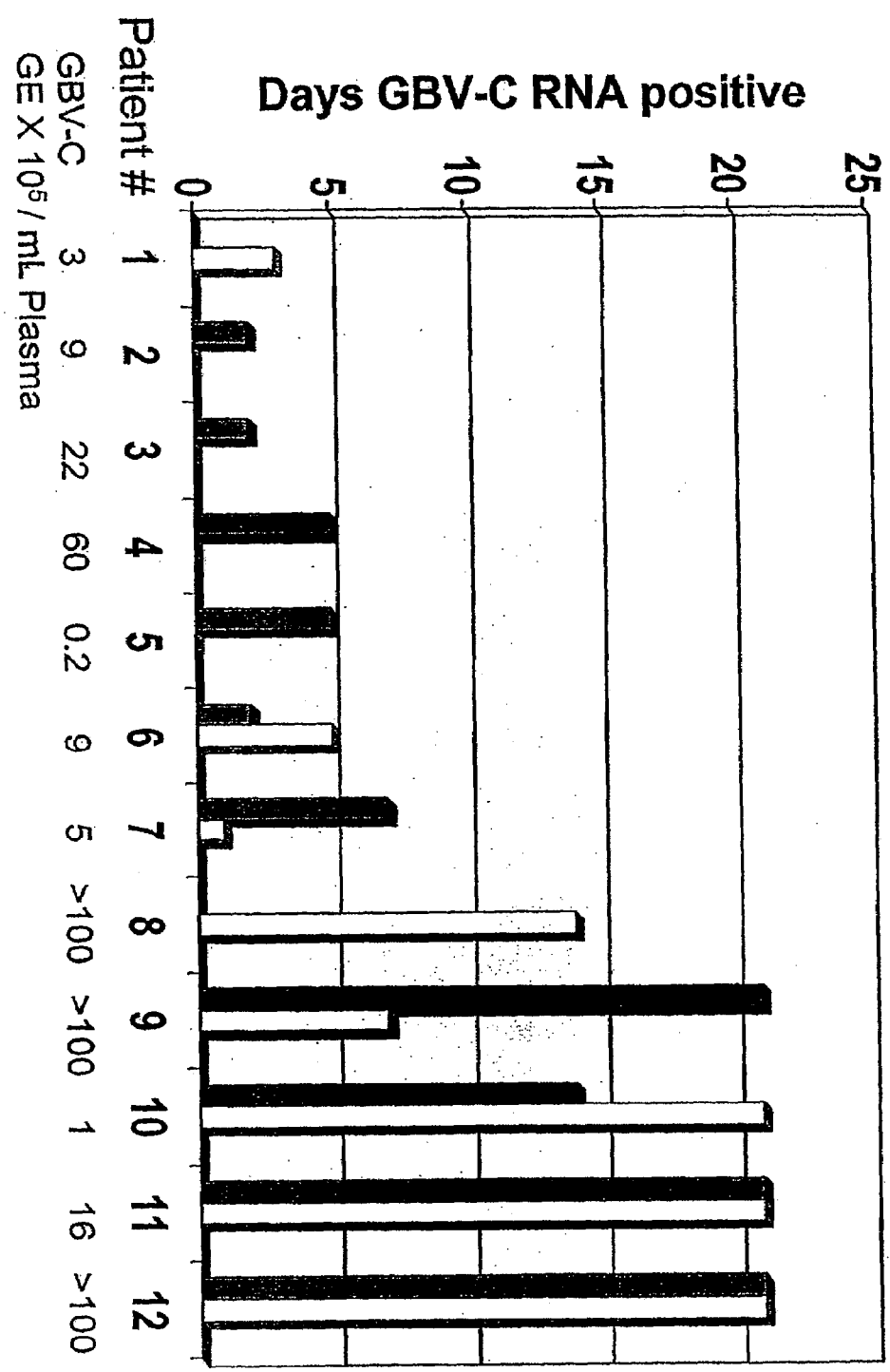
FIG. 19A PBMC's obtained from 12 HIV/GBV-C coinfected people were cultured for 3 weeks with (white) and without (gray) supplementation with pooled donor PBMC's. Last day of detection of GBV-C RNA in culture supernatant is given. Quantification of GBV-C viral genomes in patient plasma was performed using real-time PCR; the number of genome equivalents ($\times 10^5$) per mL plasma is given.
Figure 19B:
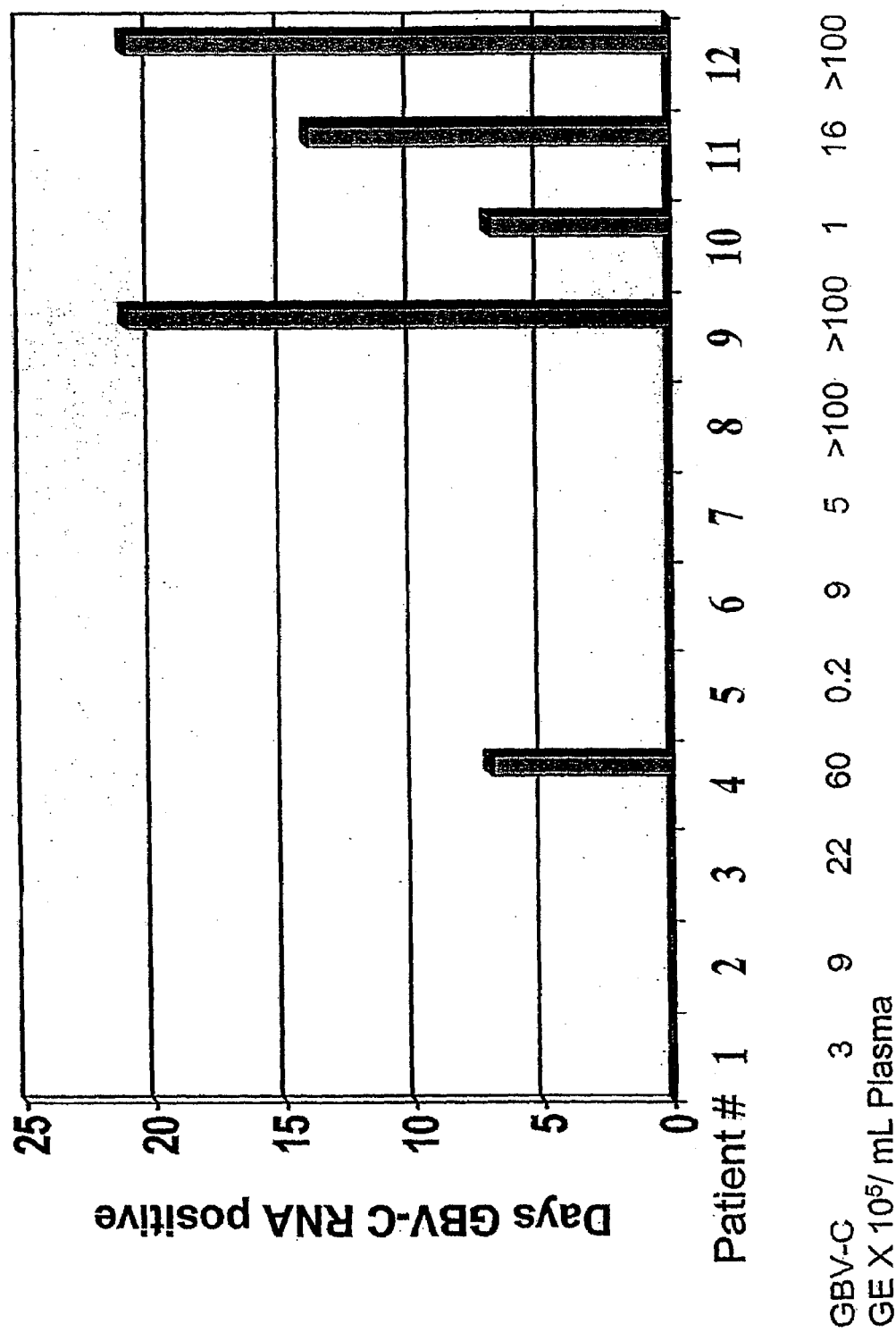
FIG. 19B Plasma obtained from 12 HIV/GBV-C coinfected people was infected into pooled donor PBMC's. 50 uL aliquots of plasma was infected into $2 \times 10^6$ PBMC's for 4 hours; after which PBMC's were washed 3 times. Absence of GBV-C from $3^{rd}$ wash supernatant was confirmed with RT-PCR. PBMC cultures were maintained for 3 weeks and supplemented weekly with fresh donor PBMC's. All cultures were maintained in duplicate. Last day of detection of GBV-C RNA (blue) in culture supernatant is given. Quantification of GBV-C viral genomes in patient plasma was performed using real-time PCR; the number of genome equivalents$\times 10^5$ per mL plasma is given.
Figure 20:
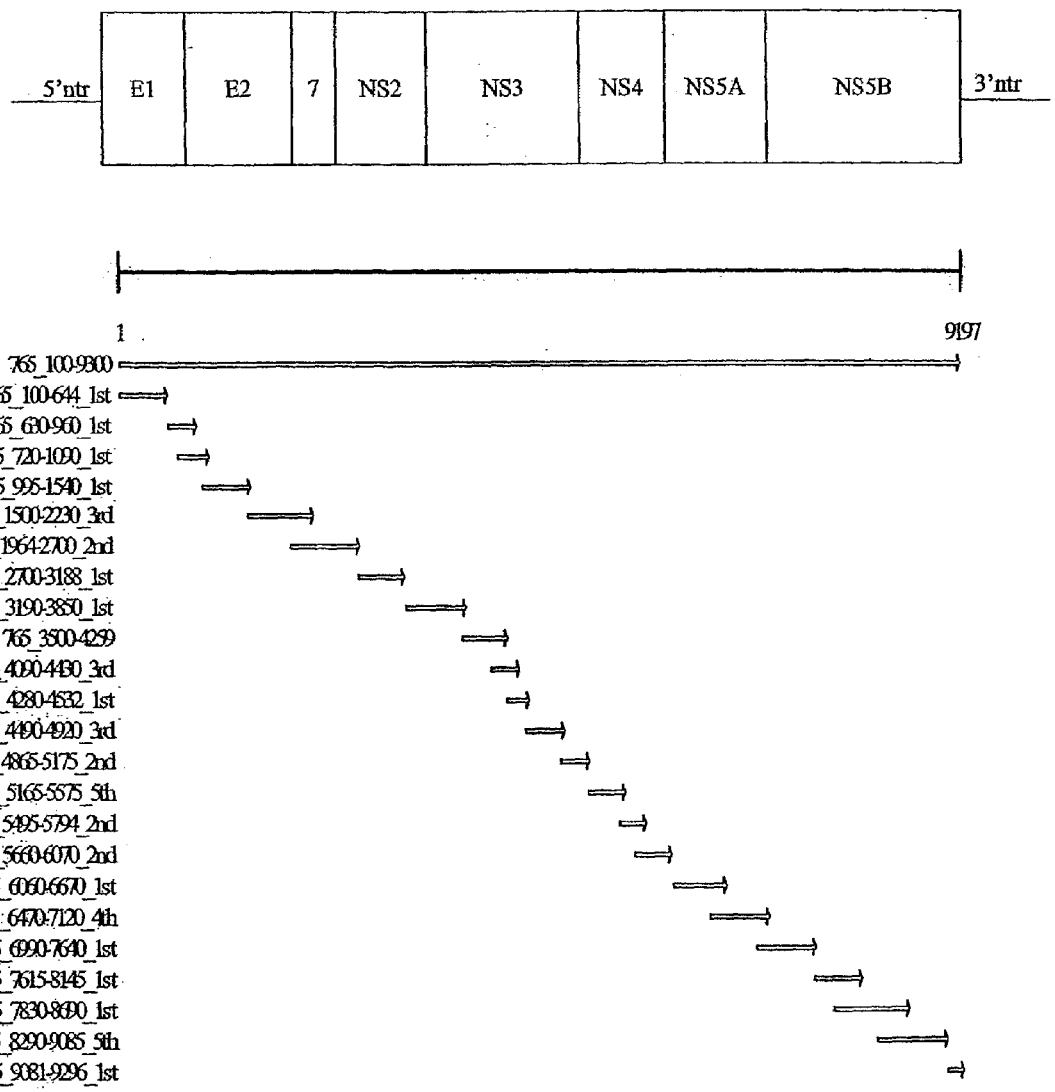
FIG. 20 GBV-C sequence (nucleotides 100-9300) was assembled using GBV-C RNA from plasma obtained from patient 12 as described in the methods section. This isolate was selected based on its prolonged replication time in PBMC culture and was designated #765. RT-PCR products used to assemble the full-length sequence are shown.
Figure 21:
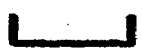
FIG. 21 Comparison of the nucleotide sequence of GBV-C isolate 765 (patient 12) with 21 full-length GBV-C sequences from GenBank. Phylogenetic relationships (using the Kimura method) are shown. Sequence AF121950 is the full-length GBV-C infectious clone, sequence HGU 63715 and sequence U44402 represent the original hepatitis G and GB Virus C sequences respectively.
Figure 22:
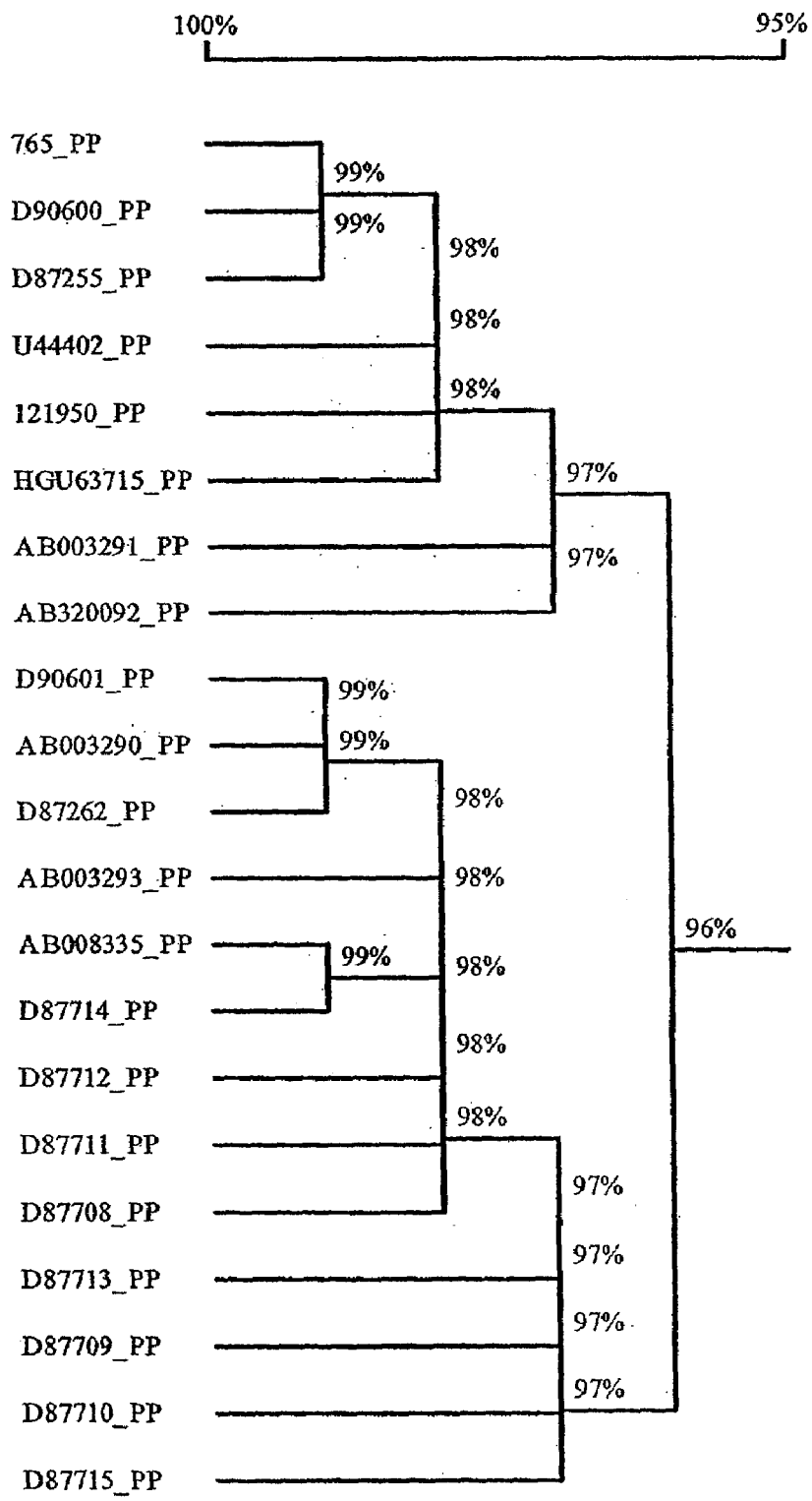
FIG. 22 Comparison of the polyprotein sequence of GBV-C isolate 765 (patient 12) with 21 GBV-C polyprotein sequences from GenBank. Percent homology between isolates by Kimura method is shown.
Figure 24:
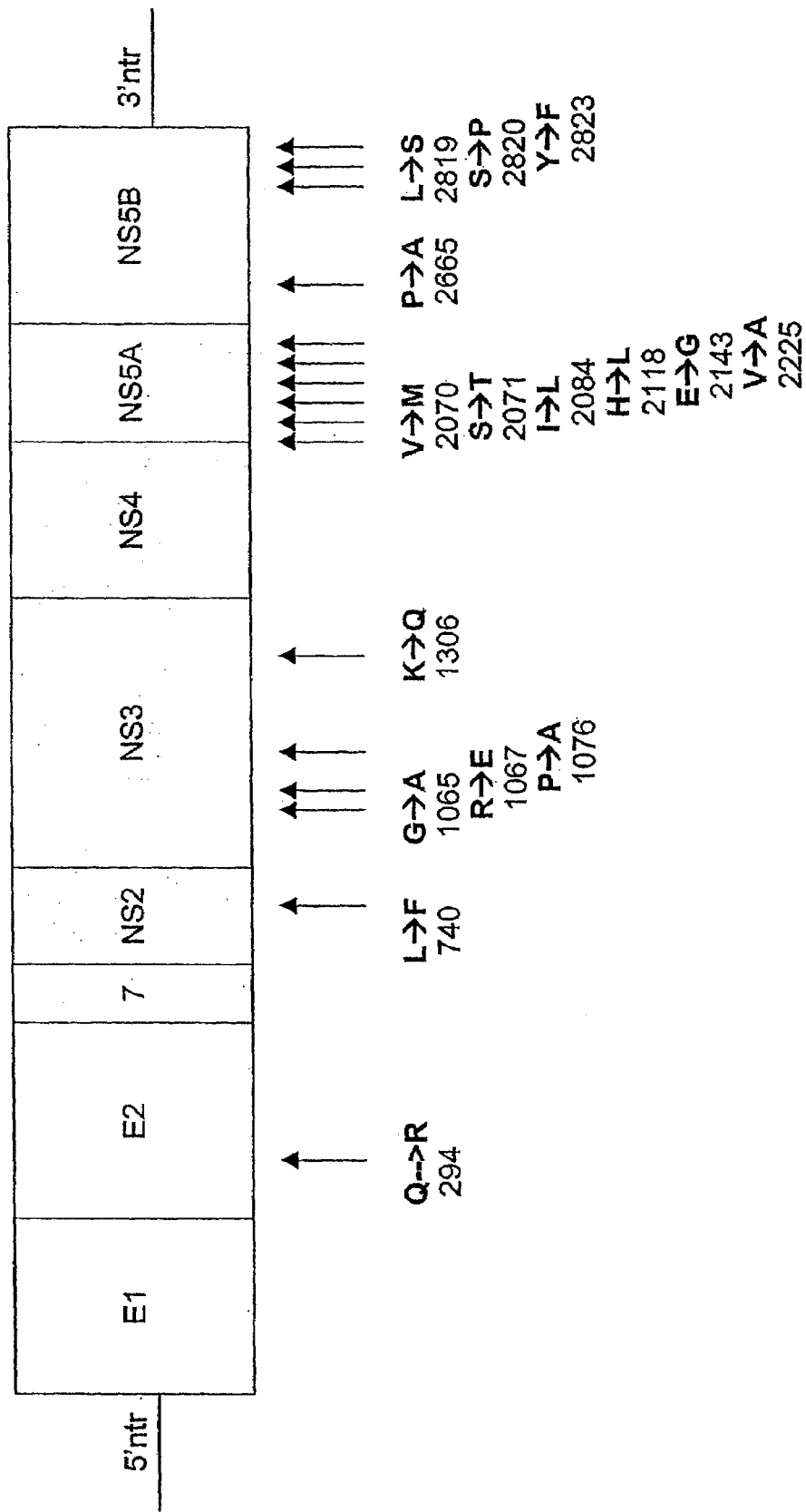
FIG. 24 Unique mutations in isolate 765 compared with 21 full-length GBV-C sequences from GenBank. None of the mutations shown were found in any other sequence. Mutations at aa 2070, 2071, and 2084 are in the region homologous to the interferon-sensitivity determining region of HCV.

GB Virus type C (GBV-C) is a human flavivirus closely related to hepatitis C virus (HCV). No disease state has been found to be associated with GBV-C infection, and persistent viremia is detected in ~2% of healthy blood donors, ~15% of HCV positive individuals, and up to 40% of HIV-infected people. Since 1998, 6 independent studies found that HIV-positive individuals co-infected with GBV-C demonstrated a decreased mortality rate compared with HIV-infected people without GBV-C co-infection (Xiang et al., 2001, reviewed by George et al., 2002). In addition, co-infection of human peripheral blood mononuclear cells (PBMC's) with GBV-C and HIV resulted in decreased HIV replication (Xiang et al., 2001). Inhibition of HIV replication occurred when the two viruses were added to cells simultaneously and when HIV infection preceded GBV-C, suggesting that the inhibition is not due to competition for the cell receptor(s) for HIV. GBV-C infection 24 hrs prior to HIV resulted in more dramatic inhibition of HIV, suggesting the induction of a cellular factor(s) which decreased HIV replication. Using 3 culture methods and serial passage, we previously demonstrated that GBV-C isolates derived from HIV and GBV-C coinfected hosts differ in their in vitro replication phenotype in PBMC's; a summary of this data is presented in FIG. 19. GBV-C replication phenotype did not correlate with plasma GBV-C RNA titer, host CD4 count, HIVRNA or HCV coinfection, and was reasonably consistent throughout the 3 culture methodologies.

The goal of this project was to obtain the full-length sequence of a GBV-C isolate that demonstrated high-level in vitro replication, and that inhibited HIV replication in the co-infection model. Ultimately, the goal is to produce a full-length infectious clone of this isolate (Xiang et al., 2000) and to identify critical amino acid mutations involved in viral replication by creating chimeric viruses.

Methods

Sequence determination: RNA prepared from plasma obtained from patient 12 (designated ioslate # 765) served as template in nested RT-PCR reactions as previously described (Xiang et al., 2000). Primers were designed that spanned the entire genome based on published sequences, and based on sequence generated from isolate 765. PCR products were visualized using ethidium bromide gels and ligated into the pTA cloning vector (Invitrogen). Inserts were sequenced using an ABI automatic sequencer and assembled using DNAMAN software (Lynnon Biosoft). At least 5 clones from each PCR product were sequenced.

Sequence analysis: Twenty-one full-length GBV-C genomes were identified in GenBank including the infectious clone developed in our laboratory (Xiang et al., 2000; AF121950). Sequences of all 4 GBV-C genotypes were utilized in comparisons. Both nucleotide and amino acid sequence homology was determined using DNAMAN software. Homology within individual coding regions for the E1, E2, NS2, NS3, NS4, NS5A, and NS5B were also determined.

Comparison of GBV-C isolates of differing in vitro replication phenotype: Previous studies demonstrated that GBV-C isolate 765 demonstrated prolonged high-level replication in PBMC culture up to 72 days, while 121950 did not replicate beyond 7 days. Comparison was made of the predicted amino acid sequences of the NS5A and NS5B regions of these two isolates, and amino acid substitutions were identified.

Summary

1. GBV-C isolates from HIV/GBV-C coinfected people differed in their ability to replicate in PBMC cultures. This was not correlated with plasma GBV-C RNA titer, host CD4 count, HIV RNA, or HCV coinfection, and was reproducible and reasonably consistent in 3 different culture methodologies.
2. The full-length sequence of a GBV-C isolate (765) that replicated well in PBMC's was determined. This isolate demonstrated prolonged high-level replication in PBMC cultures, and inhibited HIV replication in vitro (data not shown).
3. Phylogenetic comparison of this isolate and 21 published full-length GBV-C sequences demonstrated this efficiently replicating isolate has 16 unique amino acid mutations.
4. These unique mutations occured predominantly in the non-structural regions of the GBV-C polyprotein, particularly in the NS5A region and the RNA-dependent RNA polymerase NS5B coding region. Additional mutations were found in the serine protease and helicase coding region (NS3).
5. Sequence comparsion between AF121950 (a poorly growing isolate) and 765 demonstrated that most mutations occurred in NS5A and NS5B.
6. The NS5A region of HCV has been shown to be involved in PKR interactions, response to interferon therapy, and RNA replication.

CONCLUSIONS

The complete RNA sequence of a GBV-C isolate (765) derived from an HIV/GBV-C coinfected host was determined. Previous experiments demonstrated that this isolate replicated efficiently in PBMC cultures, and that it inhibited HIV replication in coinfection studies. Comparison of the predicted amino acid sequence of isolate 765 with 21 GBV-C isolates in GenBank demonstrated several unique mutations, predominantly located in the non-structural coding regions of the GBV-C genome. Ten of these mutations were in the NS5A and NS5B regions. In HCV, these regions have been shown to be critical in viral replication and to play a role in response to interferon treatment. In addition, single amino acid substitutions in the NS5A region of HCV have been shown to increase colony-forming units 100-fold in a cell-based RNA replication system (replicon; Lohman et al., 2001). Comparison of the NS5A region of GBV-C isolate 765 with the infectious clone (AF121950) demonstrated 7 amino acid substitutions in NS5A and NS5B that may contribute to the observed high level replication in PBMC culture.

TABLE 10

GBV-C genome 765 compared with 22 full-length GBV-C sequences: Predicted amino acid homology

| REGION | Length (aa) | Predicted Function | Homology % | Mutations # (%) | Mutations present in >2 isolates (%) |
|---|---|---|---|---|---|
| Complete polyprotein | 2910 | | 95.2–98.8 | 411 (14.1%) | 60 (2.1%) |
| E1 | 189 | Receptor Binding | 93.2–98.9 | 47 (24.9%) | 4 (2.1%) |
| E2 | 388 | Receptor Binding | 89.9–98.4 | 45 (25.8%) | 18 (3.6%) |
| NS2 | 283 | Viral Protease | 92.2–98.9 | 52 (18.4%) | 6 (2.1%) |
| NS3 | 678 | Serine Protease; Helicase | 97.0–99.3 | 82 (12.1%) | 5 (0.7%) |
| NS4 | 317 | Co-factor Serine Protease | 93.4–99.4 | 57 (18.0%) | 7 (2.2%) |
| NS5A | 413 | Replicase Component? | 94.2–98.6 | 53 (12.8%) | 13 (3.1%) |
| NS5B | 562 | RNA Polymerase | 95.6–99.1 | 75 (13.3%) | 7 (1.2%) |

Example 10

Clinical Isolates of GB Virus Type C Vary in their Ability to Persist and Replicate in Peripheral Blood Mononuclear Cell Cultures GB virus C/hepatitis G virus (GBV-C) replication in vitro is inefficient and inconsistent. In this study, clinical isolates of GBV-C were evaluated using peripheral blood mononuclear cell (PBMC) based culture methods. Isolates varied consistently in their ability to persistently replicate, and yield increased in cells grown without PHA/IL-2 stimulation. The deduced polyprotein sequence of an isolate that replicated well was determined (GenBank AY196904) and compared to 20 full-length GBV-C sequences. Fourteen of the sixteen unique amino acid polymorphisms identified were in the coding regions for non-structural proteins associated with interferon resistance and RNA replication. These data indicate that clinical GBV-C isolates vary in their ability to persist in culture, do not require PHA/IL-2 stimulation, and that sequence variability in key regulatory regions may affect growth in PBMC cultures. Since GBV-C appears to inhibit HIV replication in a co-infection model, these studies should facilitate determination of the mechanism of this interaction.

Introduction

GB Virus type C/hepatitis G virus (GBV-C) infection of humans is common; approximately 2% of healthy blood donors, 15% of HCV positive individuals, and 25% to 40% of HIV-infected people have GBV-C RNA in their serum (Alter et al. 1997; Dawson et al. 1996; Feucht et al. 1997; Gutierrez et al. 1997; Linnen et al. 1996; Tacke et al. 1997). GBV-C is the most closely related human virus to hepatitis C virus (HCV), and infection with either GBV-C or HCV may result in persistent infection and prolonged viremia. Approximately 25% of HCV infections are spontaneously cleared by the host immune system (reviewed in Hoofnagle, 1997). In contrast, an estimated 50% to 75% of GBV-C infections are cleared (reviewed in Alter, 1997). HCV infection frequently results in chronic, progressive liver disease.

However, GBV-C infection has not been convincingly associated with any disease (Alter 1997; Alter, et al. 1997).

Several studies have found that people coinfected with GBV-C and human immunodeficiency virus (HIV) appear to have longer AIDS free survival than HIV-infected people without GBV-C (reviewed in George et al. 2002b). In addition, GBV-C infection in HIV-positive people was associated with higher baseline CD4+ T cell counts, lower plasma HIV RNA concentration, and better response to anti-retroviral therapy (Tillmann et al. 2001; Xiang et al. 2001; Yeo et al. 2000). The survival benefit of GBV-C infection in HIV-positive people was most consistently demonstrated in individuals with GBV-C viremia; however, people with antibodies to the GBV-C envelope glycoprotein (E2) and who cleared GBV-C RNA also had improved survival when compared with HIV-infected people without evidence of prior or active infection with GBV-C (Tillmann, et al. 2001; Yeo, et al. 2000).

The mechanism by which GBV-C infection alters HIV disease progression is not established. Tillmann et al. reported an inverse correlation between HIV viral load and GBV-C plasma RNA concentration, suggesting an antagonistic effect of GBV-C on HIV replication. GBV-C was shown to replicate in vitro in peripheral blood mononuclear cells (PBMCs) (Fogeda et al. 1999), and a GBV-C infectious clone replicated in vitro in the CD4+ T cell subset of cultured PBMCs (Xiang et al. 2000). In vitro coinfection of PBMCs with GBV-C and HIV demonstrated diminished HIV replication (Xiang, et al. 2001), suggesting a direct inhibitory effect of GBV-C on HIV replication. GBV-C infection of PBMCs did not result in altered expression of the HIV receptors CD4, CCR5, or CXCR4 in the first 48 hrs post-infection, nor in decreased PBMC viability or protein syntheses during the first week post-infection when compared to mock-infected controls (Xiang, et al. 2001). Thus GBV-C did not appear to alter HIV entry or lead to decreased HIV replication due to cellular toxicity. Furthermore, the amount of inhibition of HIV replication was similar when the two viruses were added to PBMCs simultaneously or when the HIV infection preceded GBV-C (Xiang, et al. 2001). The inhibitory effect of GBV-C infection was more pronounced when GBV-C infection preceded HIV, suggesting that GBV-C replication may induce a cellular factor or factors that inhibited HIV replication (Xiang, et al. 2001).

Fogeda et al used plasma from a person with GBV-C viremia to infect human PBMCs (Fogeda, et al. 1999). Distinct quasispecies of GBV-C were identified in culture supernatant fluids following 30 days in culture that differed from the predominant quasispecies present in the plasma used to initiate infection, suggesting selection of a culture-adapted species (Fogeda et al. 2000). In this study, clinical isolates of GBV-C were evaluated to determine if they differed in their ability to replicate in vitro, and to further characterize GBV-C replication and persistence in human PBMC cultures. Considerable variation in the persistence and amount of GBV-C replication was found in PBMCs, suggesting that both viral determinants and donor cell variability were important in GBV-C replication. In addition, the nucleotide sequence of the entire coding region of a clinical GBV-C isolate that replicated for ≧60 days in PBMC cultures was determined. The sequence of this isolate was compared to the sequence of the isolate used to prepare the GBV-C infectious clone, which did not replicate in PBMC cultures beyond 14 days, and to 20 full-length GBV-C sequences in GenBank.

Methods

Study participants: Individuals attending the University of Iowa HIV clinic between 1999 and 2002 were invited to participate in a study of GBV-C infection. In addition, an HIV-negative, GBV-C RNA positive person and several healthy individuals (who were negative for HIV, HCV and GBV-C) participated in these studies. Informed consent was obtained from all participants and the study was approved by the University of Iowa Institutional Review Board. Medical records were reviewed to confirm HIV results and related clinical information. HIV-RNA and CD4+T cell counts were obtained within 30 days of blood collection for these studies, and ALT levels were obtained within 90 days. HCV antibody testing was performed during the initial clinic visit. All statistics were performed using SigmaStat software V2.03S (Jandel Scientific, Chicago, Ill.).

GBV-C RNA Detection and Sequence Determination: Blood samples were anticoagulated (acid-citrate-dextrose; Becton-Dickinson, Franklin Lakes, N.J.) and processed within 2 hours of collection. Whole blood or plasma (200 µl) was added to 500 µl GITC solution and stored at −80° C. as previously described (Schmidt et al. 1995; Xiang et al. 1998). RNA was extracted as previously described (George et al. 2002a), and the final RNA quantity used as template in each RT-PCR reaction represented 50 µl of the original sample. Primers from the GBV-C5' non-translated region (5'ntr) of GBV-C (nt #s 23-330) were used in nested RT-PCR reactions as previously described (Schmidt et al. 1997b; Schmidt et al. 1997a; Stapleton et al. 1999; Xiang, et al. 1998). In addition, primers from the GBV-C NS5A region (nt#s 6651-6877) were used to amplify viral RNA: (outer antisense: TACTGCARTCYTCCATGATGACAT (SEQ ID NO:12); outer sense: ATGGTYTAYGGYCCTGGVCAAA (SEQ ID NO:13); nest antisense: TTCAAGAATCCTCG-CAGCATTCT (SEQ ID NO:14); nest sense: CTGGV-CAAAGYGTYACCATT (SEQ ID NO:15)). All sequence numbers are based on the sequence of the infectious GBV-C clone, GenBank Accession #AF121950 (Xiang, et al. 2000). At least 2 negative and positive control samples were evaluated with each PCR reaction, and all samples and controls were tested in duplicate. Where noted, RNA extracted from culture supernatant fluids (50 µl) and PBMCs ($5 \times 10^5$) was tested for GBV-C RNA in nested RT-PCR reactions as previously described (George, et al. 2002a; Xiang, et al. 2000). To determine GBV-C genotype, first round products from 5'ntr RT-PCR were amplified using primers specific for GBV-C genotypes I-IV as described by Naito et al (Naito & Abe 2001). PCR products were separated by agarose gel electrophoresis and visualized by ethidium bromide staining.

GBV-C PCR products were purified (Wizard PCR purification kit, Promega, Madison, Wis.) and ligated into the pTA vector (Original TA cloning kit; Invitrogen, Carlsbad, Calif.) as previously described (Stapleton, et al. 1999). Plasmid DNA was sequenced using an ABI automatic sequencer (University of Iowa DNA Core facility; (George, et al. 2002a). Sequences were analyzed using DNAMAN software (DNAMAN software, Lynnon BioSoft Inc, Quebec, Canada).

Culture Methods and Infectivity Assays: PBMCs from GBV-C/HIV coinfected people and healthy donors (HD PBMCs) who were HIV, HCV, GBV-C negative were prepared by Ficoll-Hypaque followed by centrifugation as previously described (Cook et al. 1997). PBMCs obtained from GBV-C infected donors were maintained in stimulation media (RPMI 1640 media supplemented with 10% FCS, 5% recombinant human IL-2 (Cellular Products Inc., Buffalo, N.Y.), 10 mcg/mL phytohemagglutinin (PHA, Difco, Detroit, Mich.), and 10 mcg/mL lipopolysaccharide (*Escherichia coli* LPS, Sigma) at a concentration of $2\times10^6$ PBMCs/mL for 48 hrs. (Xiang, et al. 2000). PBMCs were then incubated in RPMI 1640 media supplemented with 10% FCS, 5% recombinant human IL-2, and 5 mcg/mL PHA at a concentration of $2\times10^6$ PBMCs/mL, and media was changed weekly. For co-culture experiments, an equal number of PHA-IL-2 stimulated HD PBMCs were added when PBMCs from GBV-C infected donors were obtained and weekly thereafter. For infectivity experiments, HD PBMCs were stimulated for 48 hours prior to infection with GBV-C or mock serum, and maintained as above.

Figure 26:
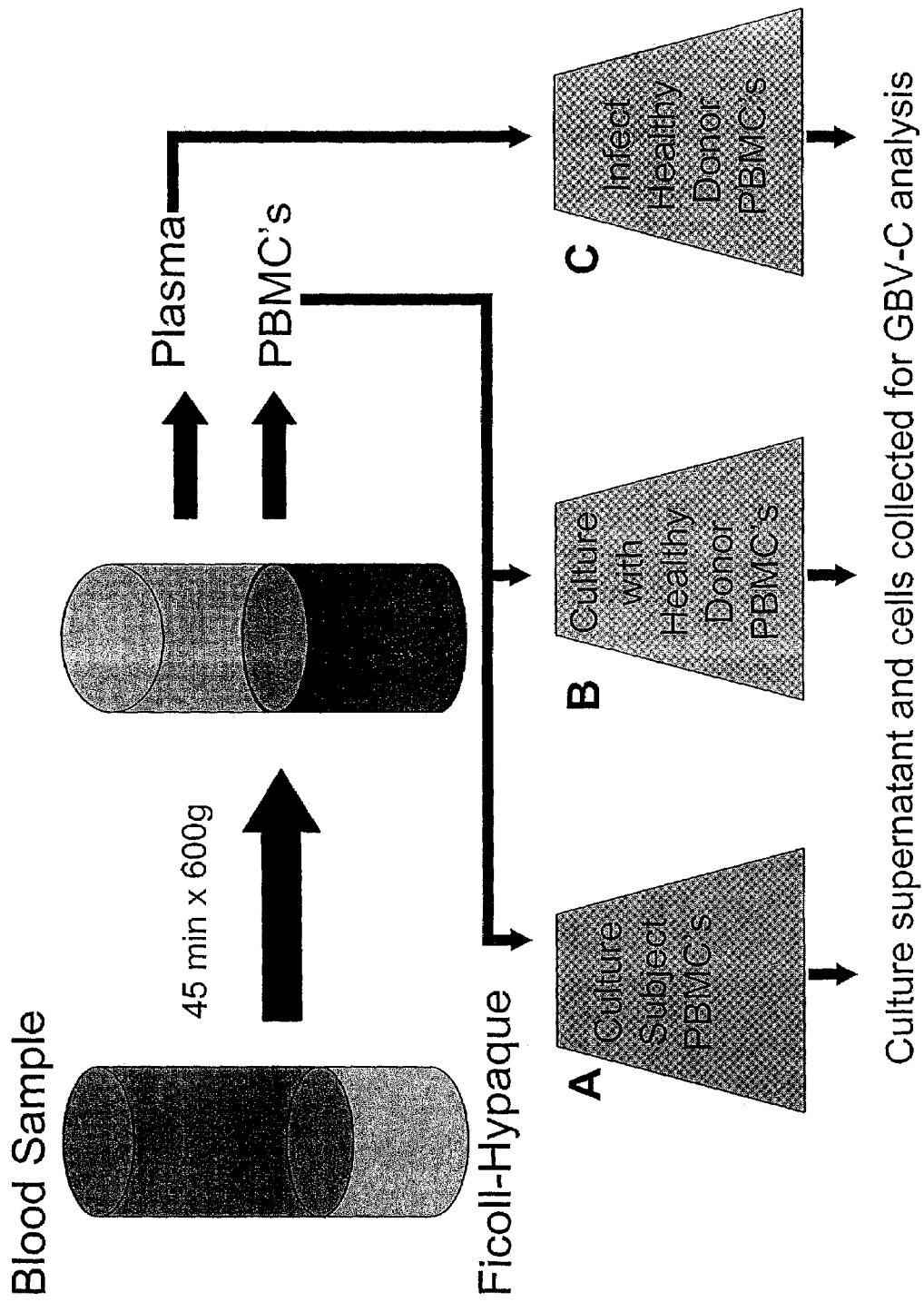
FIG. 26 Illustrates the culture methods used to characterize GBV-C replication. Plasma and PBMCs were isolated from GBV-C/HIV infected people by standard methods and PBMCs were cultured alone (A) or supplemented with an equal number of healthy donor PBMCs (B). Alternatively, GBV-C positive plasma was used to infect healthy donor PBMCs (C). Culture supernatants and cells were collected for GBV-C RNA analysis.

GBV-C replication and persistence were studied in three ways (FIG. 26). First, PBMCs from GBV-C/HIV coinfected people were cultured without donor cells. Secondly, PBMCs from the same people were cultured with the addition of an equal number of HD PBMCs and fresh HD PBMCs were added weekly. The same PBMC donor pool was used for each culture and each weekly supplementation. Finally, plasma from the same GBV-C RNA/HIV coinfected people was used to infect PHA, IL-2 stimulated donor PBMCs. The same PBMC donor pool was used for each infection, and plasma infections of all 12 clinical isolates were done simultaneously. PBMCs ($5\times10^5$) were removed weekly and stored in GITC at $-80°$ C. until use, and culture supernatants (500 µl) were removed twice weekly and stored at $-80°$ C. Mock control infections of donor PBMCs were maintained under identical conditions.

GBV-C RNA quantitation: GBV-C RNA was purified from plasma, PBMCs or culture supernatant and quantified using both real-time PCR (Perkin-Elmer, Branchburg, N.J.) and endpoint dilution using nested RT-PCR. RNA from 100 µl plasma was used as the template for RT-PCR using primers from the 5'ntr region described above. The product of the RT-PCR was used as the template for real-time PCR with primers from the 5'ntr region (sense primer at nt 211: TACCGGTGTGAATAAGGGCC (SEQ ID NO:16); antisense primer at nt 283: CGTCGTTTGCCCAGGTG (SEQ ID NO:17)), a 6-FAM/TAMRA labeled probe corresponding to nt # 241-265 (CTCGTCGTTAAACCGAGCCCGTCAC (SEQ ID NO:18)), and TaqMan Universal PCR Master Mix (Perkin-Elmer, Branchburg, N.J.). Samples were incubated at $50°$ C. for 2 minutes, followed by $95°$ C. for 10 minutes, then amplified in 40 cycles ($50°$ C. for 15 seconds and $60°$ C. for 1 minute) in an ABI Prism 7700 sequence detector. Duplicate positive and negative controls were performed with each reaction. A standard curve was determined using terminal dilution PCR to relate cycle threshholds (Ct) and genome equivalents (GE) of GBV-C RNA per mL of plasma or supernatant (adjusted $R^2=0.985$; $p<0.001$; SigmaStat). Real-time PCR results were compared with terminal dilution experiments using RT-PCR. Terminal dilution experiments utilized $\log_{10}$ serial dilutions of RNA as the template for RT-PCR, and PCR was performed using primers from two regions of the genome (5'ntr and NS5A).

HIV p24 antigen assay: Culture supernatants fluids obtained two weeks post-infection (450 µl) were analyzed in duplicate for HIV replication using Retro-Tek HIV-1 p24 antigen ELISA kits (Zeptometrix, Buffalo, N.Y.) as previously described (Wuenschmann & Stapleton 2000; Xiang, et al. 2001). Duplicate positive, negative, and substrate controls were run with each assay and a p24 antigen standard curve from 0 to 125.0 pg/mL was prepared in accordance with the manufacturers instructions.

Results

GBV-C isolates from 12 HIV-positive people who had GBV-C RNA detected in blood on at least two prior occasions were analyzed in infectivity experiments. These GBV-C-HIV coinfected people had a mean CD4+ T cell count of 305 cells/mm$^3$ (range 64-885 cells/mm$^3$), mean CD8+ T cell count of 1324 cells/mm$^3$ (range 540-2588 cells/mm$^3$), and mean ALT values of 36 U/L (range: 10-147 U/L) (Table 11). Four of the patients had detectable HIV RNA in plasma at the time of PBMC collection, and 3 patients were HCV antibody positive. The mean age was 45 years (range 28-60 years); 10 patients were male, 1 patient was African-American, and 11 patients were Caucasian (data not shown). Ten patients reported sexual risk factors for HIV transmission and two reported IV drug use (data not shown). These 12 patients were representative of our clinic population.

Plasma GBV-C quantification and characterization: All 12 patients had GBV-C RNA detected in plasma on the day of PBMC collection, ranging from 22,950 genome equivalents (GE)/mL to $5.6\times10^8$ GE/mL using real-time PCR (Table 12). Semiquantitative nested RT-PCR reactions performed using serial dilutions of patient plasma RNA as template confirmed the GBV-C RNA concentrations within an order of magnitude (Table 12). Eleven of 12 patients were infected exclusively with GBV-C genotype 2; whereas patient 3 had PCR products using primers specific for both genotypes 1 and 2. As described by others, 3 patients (1, 6, and 7) had detectable GBV-C E2 antibody in the same plasma sample used to quantitate RNA and perform infectivity studies (data not shown; Tillmann, et al. 2001).

Figure 27A:
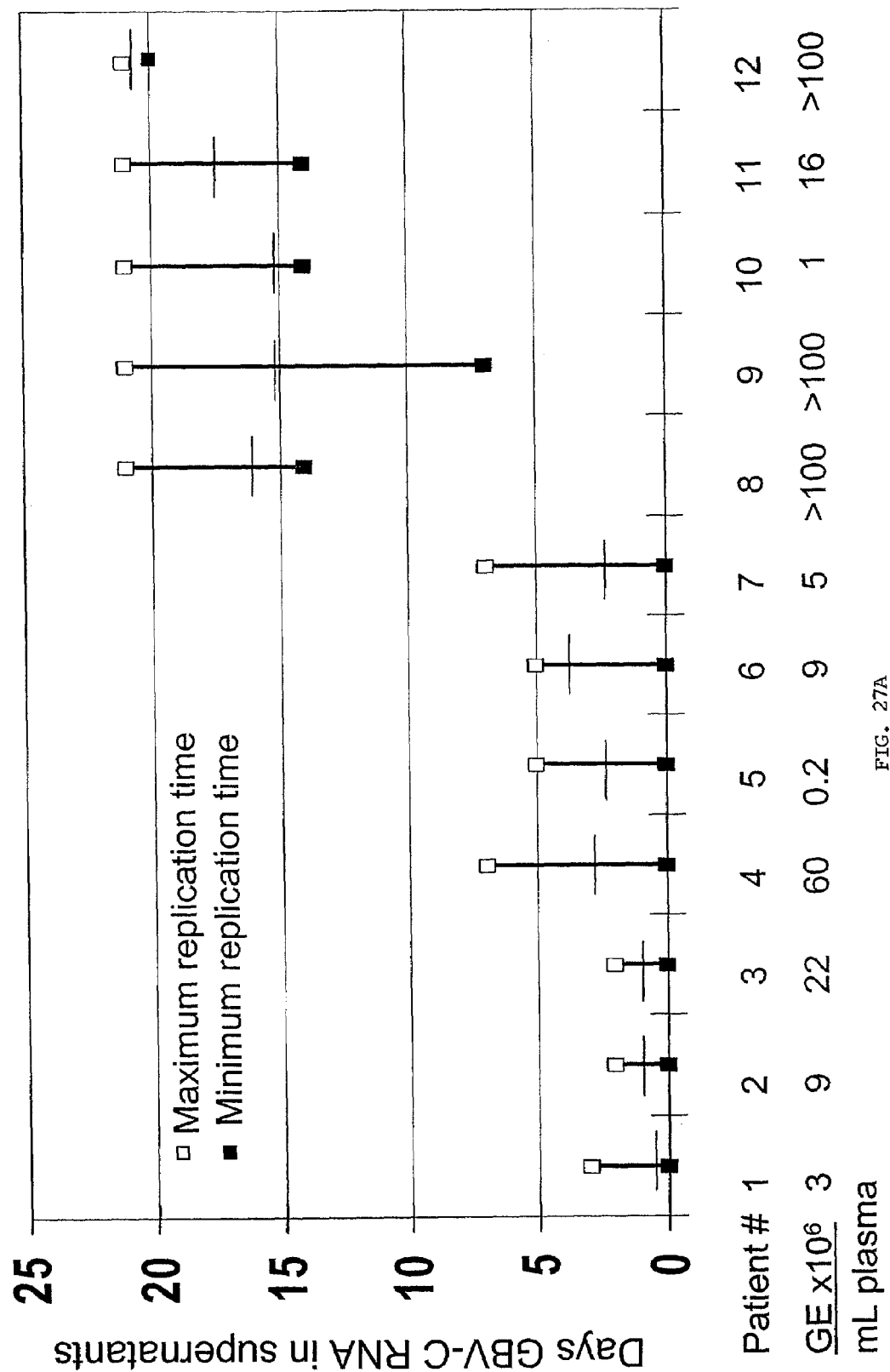
FIG. 27 GBV-C clinical isolates were analyzed for infectivity using three modalties. The mean duration of persistence for all expereiments is shown, along with the minimum (solid boxes) and maximum (open boxes) duration of GBV-C RNA detection in culture supernatants for all three culture modalities (A). PBMCs were cultured without (B) or with (C) supplementation with an equal number of donor PBMCs. Insufficient cells were available for PBMC infection for subject 8. nt=not tested. The GBV-C plasma RNA titer (GE$\times 10^5$/mL plasma) for each patient is shown beneath the X axis.
Figure 27B:
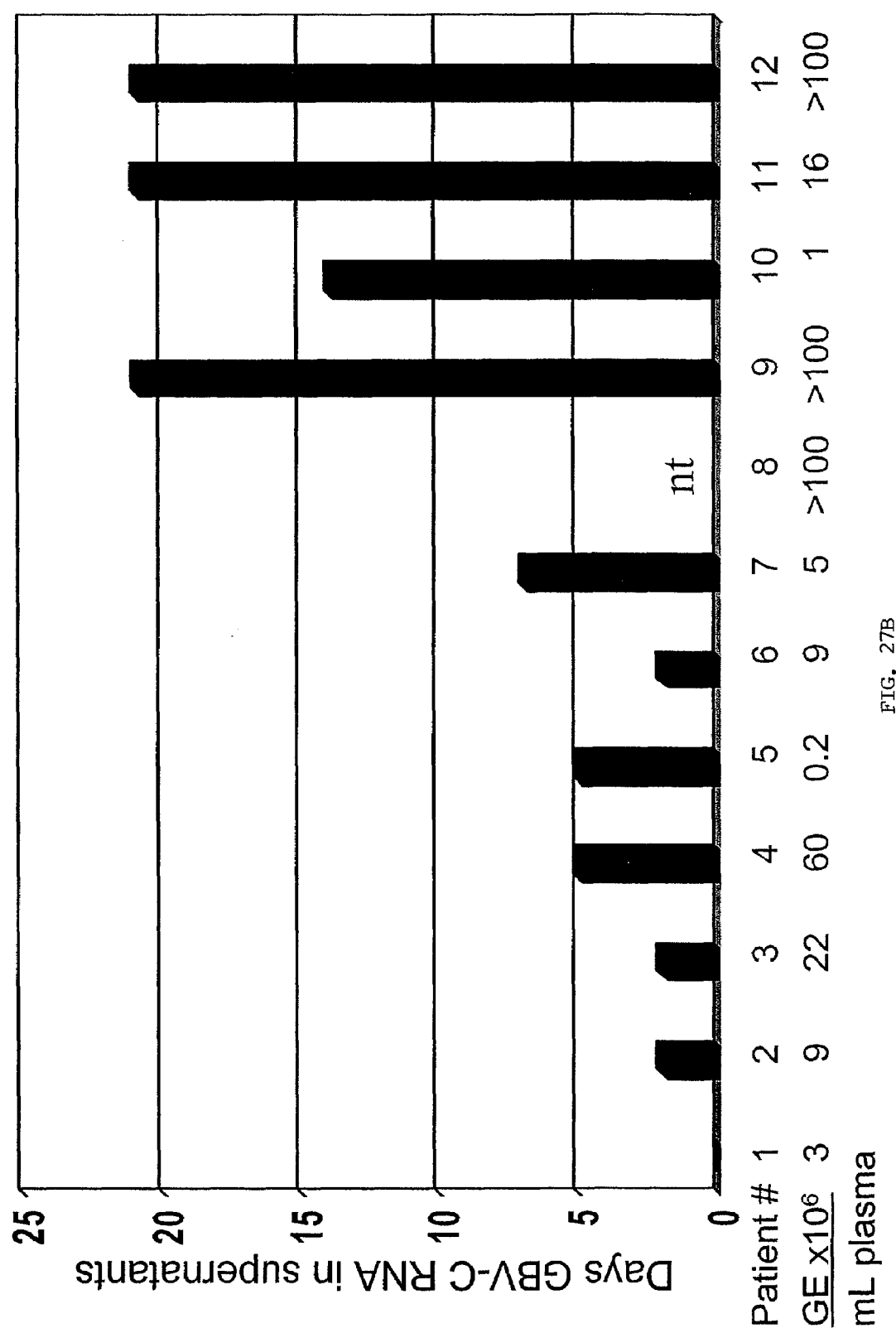

GBV-C Infectivity Studies: Phytohemagluttinen (PHA) and Interleukin-2 (IL-2) stimulated PBMCs from GBV-C/HIV coinfected patients were cultured with and without supplementation with PBMCs obtained from healthy donors (HD), and HD PBMCs were infected with GBV-C RNA-positive plasma (FIG. 26). GBV-C RNA was detected in both supernatant and cultured PBMCs from all 12 patients; however, persistence of GBV-C RNA in culture varied significantly between patients (FIG. 27A). PBMC cultures from patients 8 through 12 consistently had GBV-C RNA detected in culture supernatant and PBMCs for >7 days, while patients 1-6 did not have GBV-C RNA detected in culture after 7 days. GBV-C persistence in culture was not enhanced by coculture with HD PBMCs (FIGS. 27B and C). GBV-C RNA detection in PBMC cell lysates was consistent with culture supernatant findings (data not shown). The concentration of GBV-C RNA in GBV-C RNA-positive donor PBMCs and in healthy donor cells infected with GBV-C isolates was low, ranging from 1 genome equivalent per 1500 to 200,000 PBMCs (data not shown). Studies are underway to develop methods to quantify the percent of PBMCs productively infected with GBV-C. No difference in cell viability was noted between different patients' PBMC cultures or between PBMCs cultured with and without HD PBMCs with the exception of patient 3, whose cultured PBMCs were no longer viable after day 7 (probably due to the high HIV inoculum (Table 11).

TABLE 11

Clinical Features Of Gbv-C/Hiv Coinfected Patients Studied.

| Patient | CD4 Cells* | CD8 cells* | HIV RNA** | HCV antibody*** | ALT |
|---------|-----------|------------|-----------|-----------------|-----|
| 1 | 251 | 1086 | <400 | Pos | 57 |
| 2 | 161 | 540 | <400 | Neg | 22 |

TABLE 11-continued

Clinical Features Of Gbv-C/Hiv Coinfected Patients Studied.

| Patient | CD4 Cells* | CD8 cells* | HIV RNA** | HCV antibody*** | ALT |
|---|---|---|---|---|---|
| 3 | 64 | 654 | 233,000 | Neg | 48 |
| 4 | 127 | 928 | 69,000 | Pos | 147 |
| 5 | 197 | 1942 | <400 | Neg | 19 |
| 6 | 443 | 1894 | <400 | Neg | 23 |
| 7 | 254 | 1129 | <400 | Neg | 16 |
| 8 | 701 | 1336 | <400 | Neg | 19 |
| 9 | 885 | 2588 | <400 | Pos | 30 |
| 10 | 113 | 1806 | 20,000 | Neg | 25 |
| 11 | 222 | 1126 | <400 | Neg | 11 |
| 12 | 247 | 856 | 500 | Neg | 10 |

*CD4 and CD8 cells = number of cells/mm$^3$,
**HIV RNA = Genome equivalents/mm$^3$
***Pos. = positive, Neg. = negative,
ALT = alanine amino transferase, IU/mL.

Figure 28:
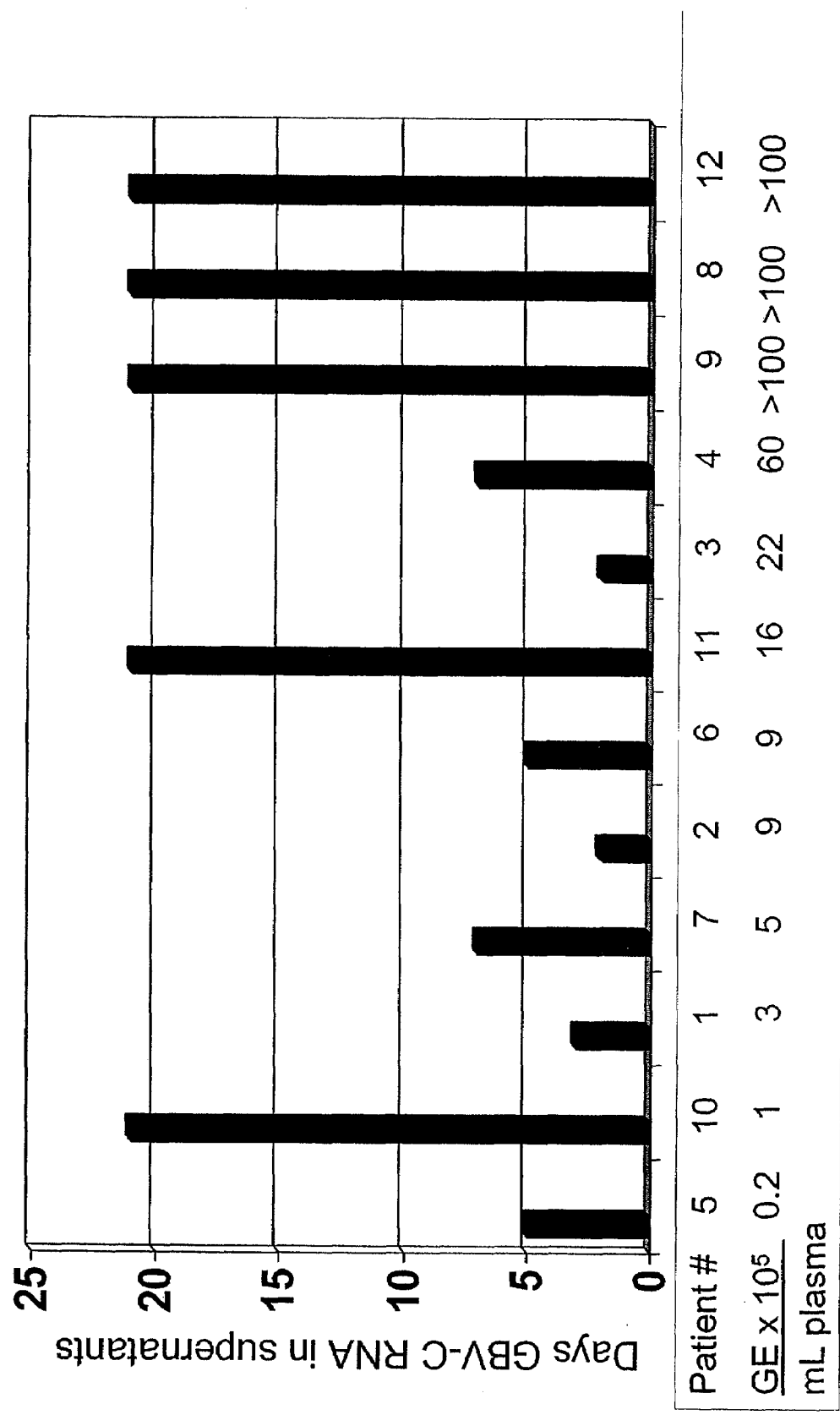
FIG. 28 Correlation between input GBV-C RNA concentration and maximum time of persistent infection. Plasma GBV-C RNA concentration in 20 μL from lowest to highest is presented on the X axis.

When pooled stimulated HD PBMCs were infected simultaneously with 20 μl of each patient's plasma, patients 8 and 10-12 reproducibly had GBV-C RNA detectable in supernatants for 14 days or longer, consistent with the findings of the PBMC cultures (FIG. 27A). These infections utilized a single donor pool, were performed in duplicate, and were repeated with consistent results. PBMCs of all cultures remained viable for 21 days. FIG. 28 illustrates the relationship between persistent infection and input GBV-C concentration. Of note, the amount of input GBV-C RNA did not correlate well with persistent replication, for example patient 10 demonstrated persistent infection despite a plasma GBV-C RNA concentration 60-fold less than that of patient 4, whose GBV-C did not persist in culture (FIG. 28). To determine if the GBV-C replication observed for these 12 isolates in PBMC culture was independent of the input GBV-C RNA, plasma obtained from the 12 GBV-C/HIV coinfected people was normalized and used to infect PHA, IL-2 stimulated HD PBMCs from a single donor in duplicate (MOI=0.01 GBV-C RNA genome equivalents). GBV-C RNA was not identified in culture supernatant fluids 14 days post-infection for patients 1,2,3,6, and 11 (data not shown), generally consistent with the non-normalized infections.

Figure 29:
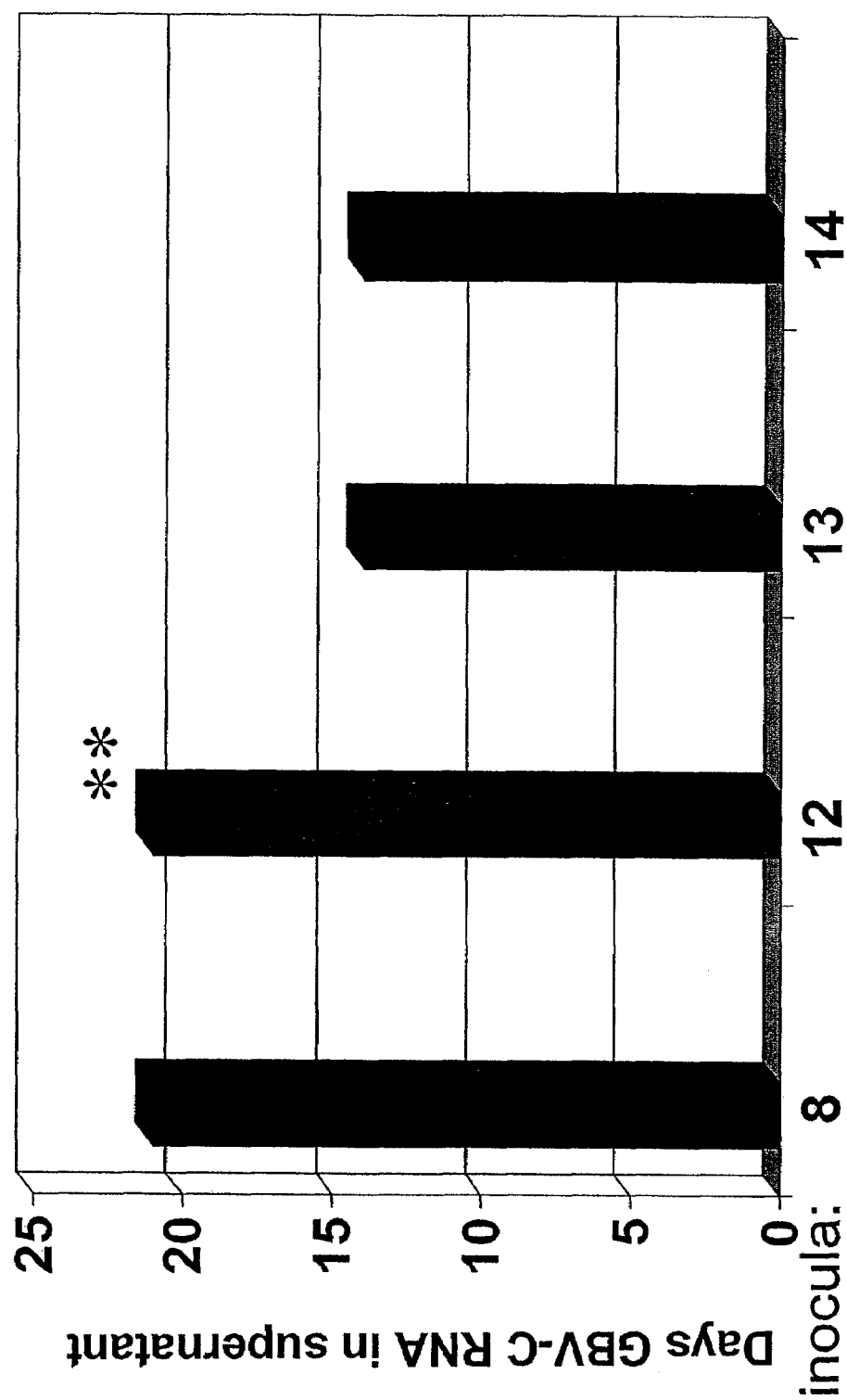
FIG. 29 GBV-C persistence of clinical isolates. GBV-C from an HIV-negative source patient (#13) and from virus derived from the GBV-C infectious clone (#14) were used to infect healthy donor PBMCs and compared with plasma GBV-C from patients 8 and 12. The clone was prepared from patient 13 (GenBank # AF121950). **GBV-C from patient 12 persisted in PBMC cultures for 60 days (data not shown).

Pooled HD PBMCs were also infected with plasma from an HIV-negative, GBV-C RNA positive subject (#13; the source patient used to prepare the infectious clone) and culture supernatants derived from cells initially transfected with RNA transcribed from the infectious clone AF121950. The clinical isolate (#13) and virus derived from the infectious clone (#14) replicated for only ≦14 days (range 3-14; FIG. 29). In contrast, PBMCs from patient 12 demonstrated replication for more than 60 days.

Figure 30:
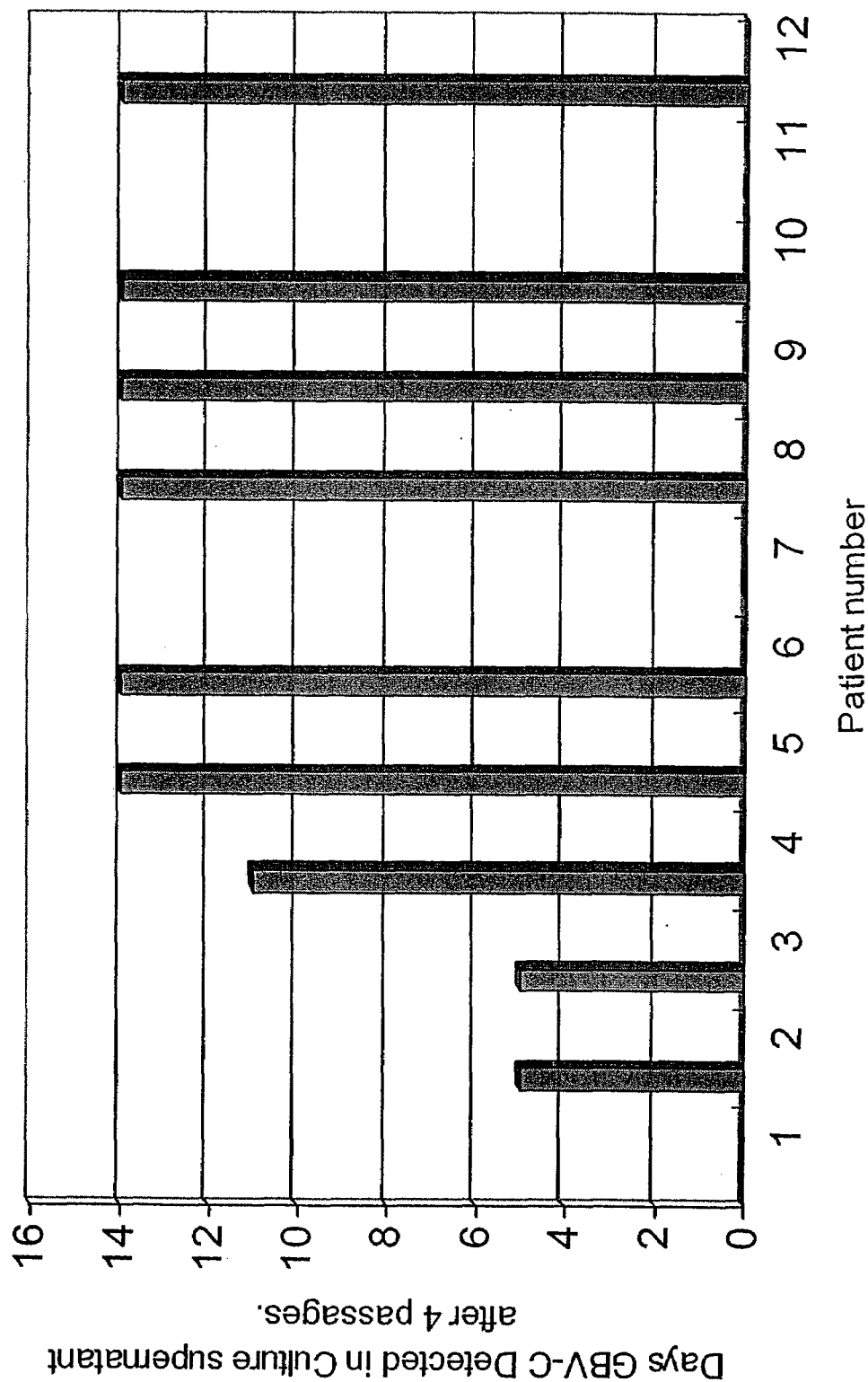
FIG. 30 Serial passage of GBV-C from PBMC coculture supernatant into donor PBMCs. The same donor pool was used for each passage, and all cultures were maintained for 14 days. Supernatant from patients 1, 7, and 11 were not available for testing. Total days GBV-C RNA was detected in culture supernatant after 4 passages is shown for each patient.

GBV-C isolates from culture supernatant fluids (20 μl inocula) were serially passaged 4 times into HD PBMCs. Culture supernatants from each patient's last PBMC culture that tested positive for GBV-C RNA served as the inocula. PBMC cultures were maintained for 2 weeks, with fresh HD PBMCs added 7 days post-infection. Serial passage of GBV-C from patients 1, 7, and 11 was not done due to insufficient culture supernatant material. All 9 patients who had supernatant available for passage demonstrated replication in PBMC cultures at the end of 4 passages, and GBV-C replication and persistence appeared improved when compared with initial PBMC cultures (FIG. 30). For example, patients 5 and 6 had GBV-C RNA in passaged culture supernatant for 14 days, compared to only 5 days in the original PBMC culture.

To determine if selection for specific minor quasispecies in the initial plasma inocula replicated preferentially in PBMC culture, a 194 base-pair segment of the NS5A sequence homologous to the putative interferon-sensitivity determining region of HCV was amplified from both the initial plasma sample and from the last GBV-C RNA-positive coculture supernatant sample from patients 2, 4, 5, and 8. A minimum of five clones from each sample were sequenced. The NS5A sequence of patients 2, 4, and 5 was the same in the plasma-derived GBV-C and in the culture supernatant-derived GBV-C. In contrast, patient 8 demonstrated selection of a distinct quasispecies containing 14 mutations in all 5 clones sequenced (FIG. 31). These mutations did not result in a predicted amino acid change in NS5A; however, the data are consistent with the selective replication of a minor quasispecies in PBMC culture, as has been described previously (Fogeda, et al. 2000).

Figure 32:
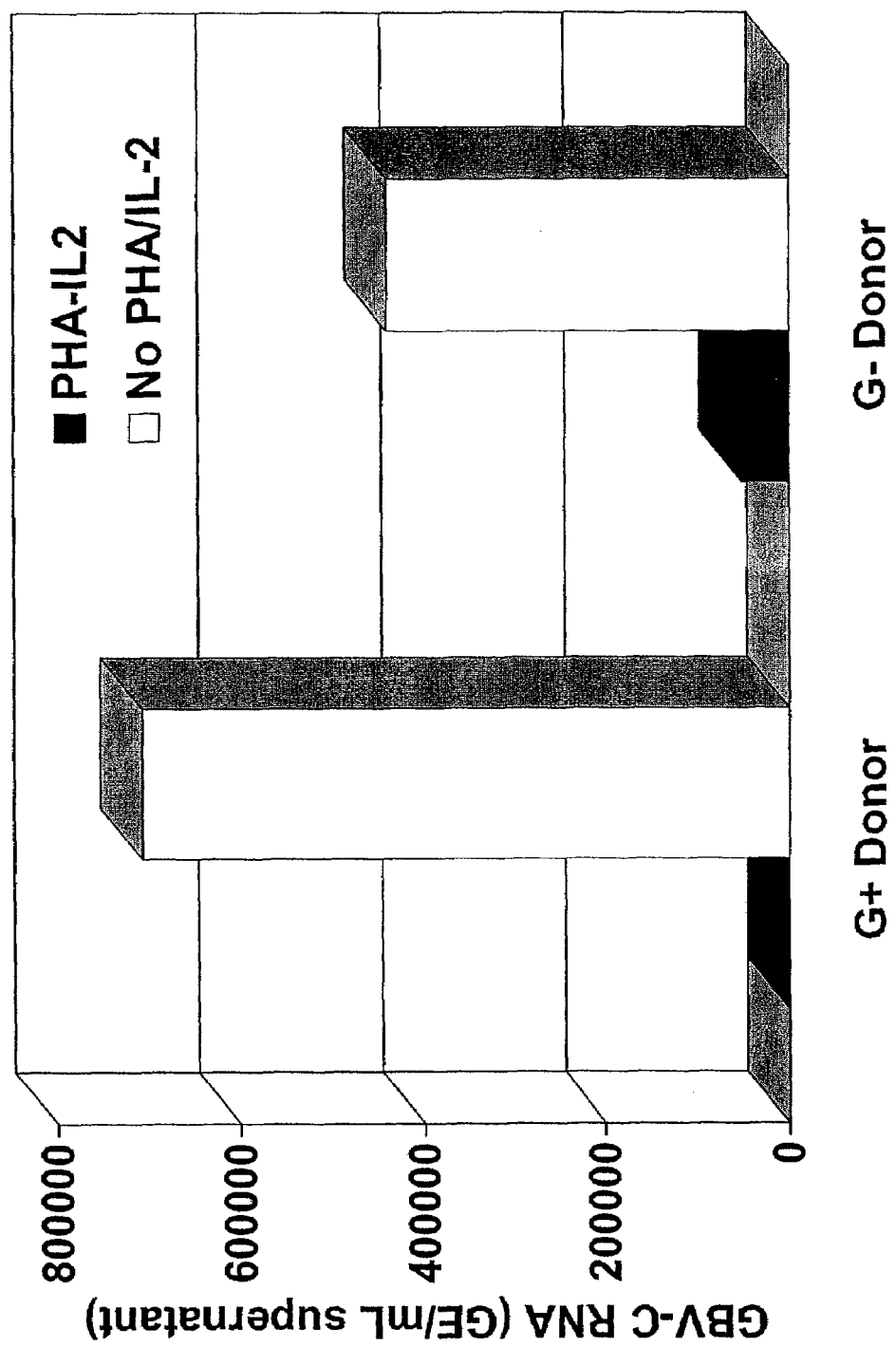
FIG. 32 Peripheral blood mononuclear cells (PBMCs) from a GBV-C/HIV infected patient (patient 12; G+ donor)

To determine if PHA—IL-2 stimulation of PBMCs was required for GBV-C replication in PBMC cultures, PBMCs from patient 12 were cultured with and without IL-2 and PHA. In addition, serum from patient 12 was used to infect HD PBMCs which were then cultured with and without IL-2 and PHA. GBV-C RNA in culture supernatant from day 7 was quantified by real-time PCR. FIG. 32 demonstrates that the amount of GBV-C RNA detected in supernatant was significantly greater in both serum-infected HD cells and infected patient PBMCs when IL-2 and PHA were not added to culture media.

To evaluate HIV replication in the PBMC cultures, HIV p24 antigen was measured in supernatants obtained from cocultured patient PBMCs and infected HD PBMCs on day 14. No HIV p24 antigen was detected in supernatants of infected HD PBMCs, however HIV p24 antigen was detected in supernatants from PBMC cocultures of patients 4, 6, and 10 (data not shown). Patients 4 and 10 both had detectable HIV in plasma on the day of PBMC collection (Table 12).

TABLE 12

Characteristics of GBV-C viremia and E2 antibody in 12 patients with GBV-C - HIV co-infection.

| | Plasma GBV-C titer | | GBV-C |
|---|---|---|---|
| Patient | Real-Time PCR | Quantitative PCR (Td) | Genotype |
| 1 | 2.97 × 10$^5$* | 2.5 × 10$^5$ | 2 |
| 2 | 9.5 × 10$^5$ | 2.5 × 10$^5$ | 2 |
| 3 | 2.25 × 10$^6$ | 2.5 × 10$^6$ | 1, 2 |
| 4 | 5.86 × 10$^6$ | 2.5 × 10$^6$ | 2 |
| 5 | 2.2 × 10$^4$ | 2.5 × 10$^4$ | 2 |
| 6 | 9.26 × 10$^5$ | 2.5 × 10$^5$ | 2 |
| 7 | 5.65 × 10$^5$ | 2.5 × 10$^5$ | 2 |
| 8 | 1.16 × 10$^8$ | 2.5 × 10$^8$ | 2 |
| 9 | 5.6 × 10$^8$ | 2.5 × 10$^8$ | 2 |
| 10 | 1.19 × 10$^5$ | 2.5 × 10$^5$ | 2 |
| 11 | 1.60 × 10$^6$ | 2.5 × 10$^5$ | 2 |
| 12 | 4.26 × 10$^8$ | 2.5 × 10$^8$ | 2 |

All data represent GBV-C RNA genome equivalents/mL of plasma determined in nested RT-PCR reactions.
Td = semi-quantitative PCR determined by terminal dilution of input RNA.

Sequence analysis of a GBV-C isolate that persists in PBMC culture: As GBV-C RNA from patient 12 demonstrated persistent replication in multiple PBMC cultures, we determined the entire nucleotide sequence of this isolate. A series of nested sense and antisense oligonucleotide primers were designed to span the entire open reading frame from nt 41 to 9349 (sequence numbers based on GBV-C isolate #

AF121950; Genbank) using a strategy similar to that previously described (Xiang, et al. 2000). PCR products were purified, ligated into the pTA vector, and the sequence was determined as described above. At least 5 clones of each PCR product were sequenced to determine the consensus sequence (GenBank accession number AY196904).

The sequence contained a long open reading frame (ORF) that began at nt 351 (using sequence numbering of AF121950) and extending to nt 9080. This ORF is predicted to encode a 2,974 amino acid polyprotein with a molecular weight of 313,788 daltons. If translation initiates upstream of the amino terminus of the predicted E1 protein (Simons et al. 1996), the polyprotein would be 2,906 amino acids (MW 312,989 daltons). There are 4 AUG codons in frame with the polyprotein upstream of the putative translational start site of GBV-C in this isolate which could potentially encode a core protein. The complete GBV-C sequence of this isolate was compared with 20 full length human isolates obtained by searching GenBank for complete GBV-C sequences (GenBank accession numbers: AF121950, AB 320090, AB 320091, AB 320092, AB 003293, AB 008335, D90600, D 90601, D 87255, D 87262, D 87708, D 87709, D 87710, D 87711, D 87712, D 87713, D 87714, D 87715, U 44402 and U 63715). Nucleotide and predicted amino acid sequences were aligned, and the evolutionary distance between sequences was determined using the Jukes-Canter method (DNAMAN software, Lynnon BioSoft Inc, Quebec, Canada). Comparison of the polyprotein sequence of these isolates revealed a 96.53% homology in the polyprotein coding sequences (FIG. 33). Sixteen of these sequences (all except AB320090, AB320091, AB320092 and AB320093) contained the complete 5'ntr and 3'ntr sequence, allowing comparison of full-length genome nucleotide sequences. Comparison of these isolates revealed 89.54% homology at the nucleotide level (data not shown).

Figure 34A:
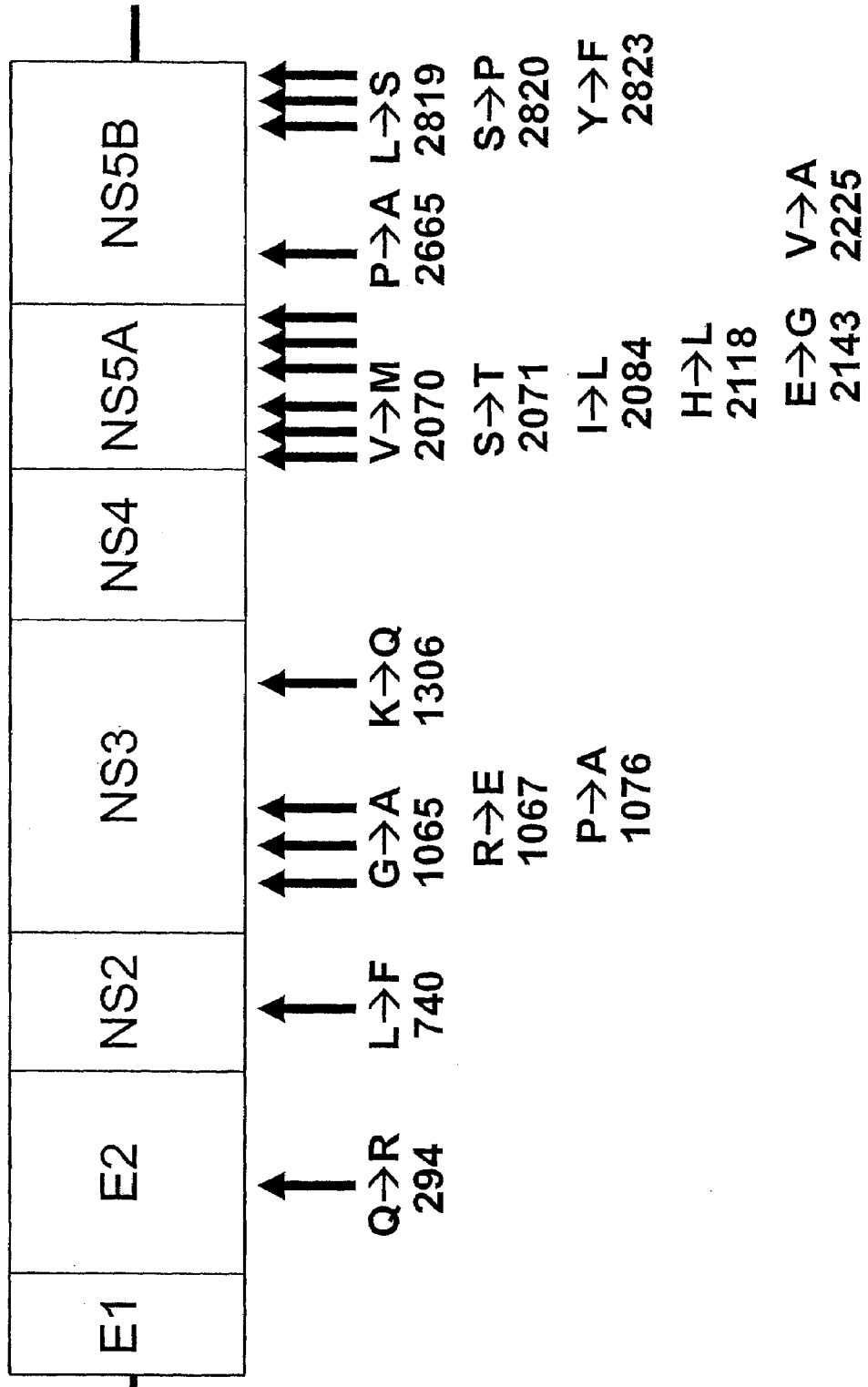

A consensus predicted amino acid sequence was generated from these 21 GBV-C polyproteins (initiating translation at nt 554 of AF121950). There were 62 amino acids differing between our isolate and the consensus sequence (2.9%). Based on the predicted protein encoding regions of the genome, most of the differences between our sequence and the consensus sequence occurred in the NS2 and ES2 coding regions (4.6% and 4.4%, respectively), followed by the NS5A region (3.6%), NS4 (2.5%), NS5B (2.1%), E1 (1.6%), and NS3 (1.2%). There were 16 amino acid polymorphisms identified in our isolate that are not present in any reported GBV-C sequence. Fourteen of these were in nonstructural proteins NS5A, NS5B, and NS3 as seen in FIG. 34A.

Since AY196904 (patient 12) reproducibly demonstrated prolonged replication in PBMC cultures, and AF121950 isolate did not, we compared the predicted amino acid sequence for the polyproteins of these two isolates. There was 97.6% homology between the two isolates, and the region of greatest divergence was E1 (5.3%) followed by E2 (3.6%), NS2 (3.2%), NS4 (1.9%), NS5A (1.7%), NS5B (1.6%), and NS3 (1.3%). Of note, the NS5B substitutions I→V at 2465 and A→G at 2795 are very similar to mutations in HCV NS5B that are associated with increased RNA replication in HCV RNA replicon systems (Lohmann et al. 2001); FIG. 9B). Specifically, HCV substitutions I2442V and R2884G were found to result in a 500-fold increase in RNA replication. In addition, the substitutions 2070-2071 VS→MT and 2074 I→L are found in the region homologous to the putative interferon-sensitivity determining region of HCV (Fujisawa et al. 2000; Kato et al. 1999), and are not found in any other GenBank sequence (FIG. 34C). We previously identified similar substitutions (2069-2071 EVS→KMT) in an interferon-sensitive GBV-C clinical isolate (Xiang et al., manuscript submitted), suggesting that this region may be important in evasion of natural host antiviral defense mechanisms. NS5A is thought to be phosphorylated in HCV (Reed & Rice 1999; Reed, et al. 1997). The mutations noted in FIG. 34C would potentially alter phosphorylation at amino acids 2071 and 2151.

Discussion

Figure 27C:
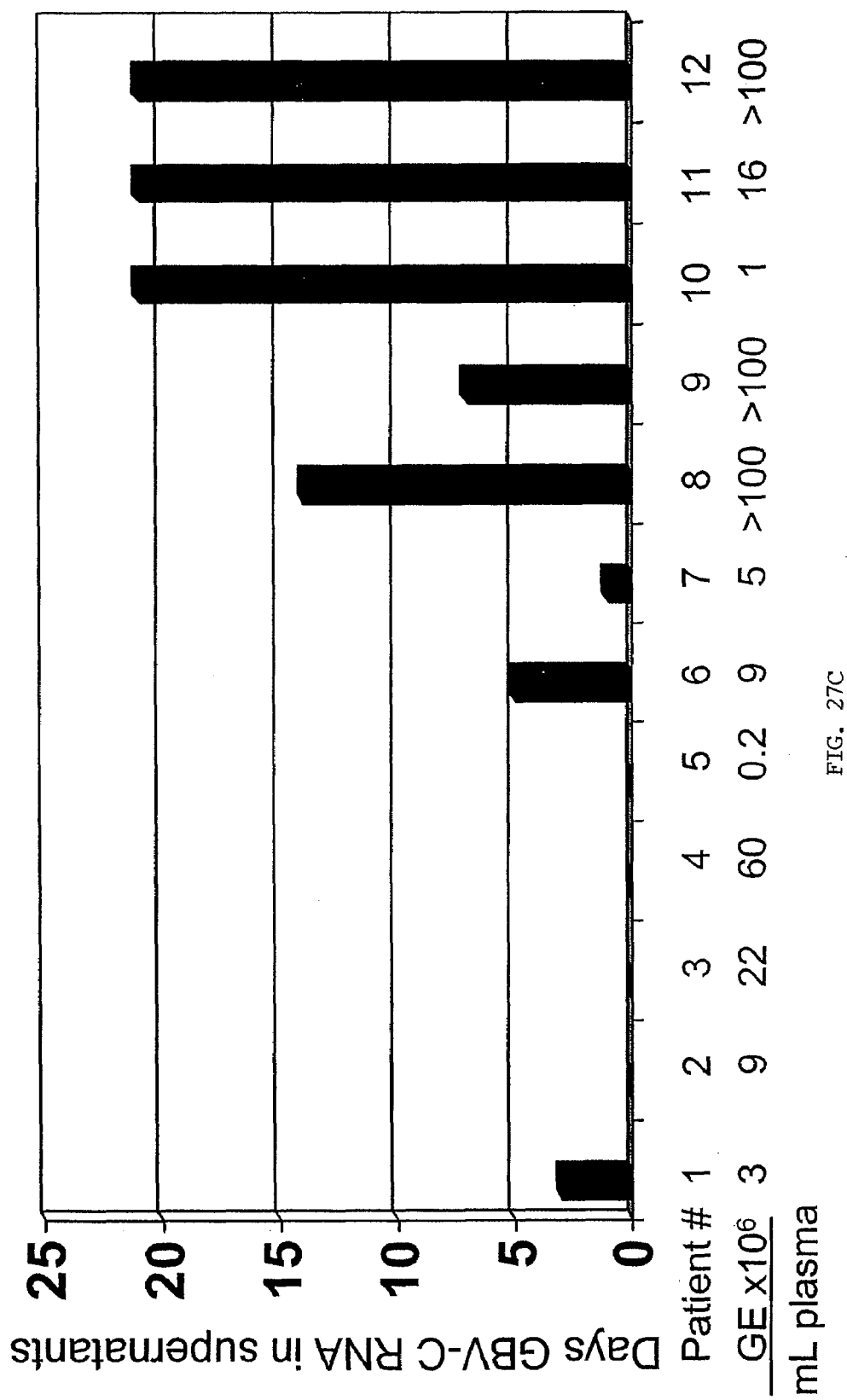

GBV-C replication has been associated with decreased HIV replication in vitro (Xiang, et al. 2001) and in vivo (Tillmann, et al. 2001; Xiang, et al. 2001). GBV-C in vitro replication methods were inefficient and inadequately reproducible, even using an infectious molecular clone. To better characterize GBV-C replication, three different PBMC-based culture methods were employed to measure persistence of GBV-C replication in culture. Clinical isolates propagated either from GBV-C infected patient PBMCs or donor PBMCs infected with GBV-C RNA positive plasma demonstrated two growth patterns. Seven of the 12 clinical isolates demonstrated GBV-C growth in culture supernatants for <7 days, while the other 5 isolates consistently persisted in culture for >14 days (FIG. 27). With two exceptions (patients 4 and 11), the growth pattern was consistent when cultures were normalized for input GBV-C RNA. Coculture of GBV-C positive PBMC's with donor PBMCs did not improve GBV-C persistence, and GBV-C culture in media supplemented with PHA and IL-2 inhibited growth (FIG. 32). Since the 12 GBV-C isolates persisted for similar duration in PBMC cultures from either pooled or single donors on multiple occasions, it appears that the capacity to persist in PBMC cultures is an intrinsic viral characteristic. Nevertheless, host-cell factors may also contribute to this persistence.

Replication of GBV-C in these 3 culture systems was not associated with cell toxicity, as significant cell death was noted in only one patient's PBMC cultures. GBV-C replication was independent of the source patient's CD4+T cell count, CD8+T cell count, hepatitis C antibody status, gender, age, or HIV acquisition mode. High HIV RNA levels in detected in patients 3 and 4 may explain the relatively poor GBV-C replication of these isolates. However, when GBV-C from patient 3 was tested for growth in HD PBMCs at a time with the source patient's HIV RNA was <400, no improvement in GBV-C growth was noted, and GBV-C from patient 10 consistently grew well in culture despite ongoing detectable HIV RNA (data not shown).

GBV-C replication in PBMC culture did not correlate with plasma GBV-C RNA titer (FIG. 28), and growth patterns remained distinctive when GBV-C RNA input was normalized. The twelve patients studied had a broad range of GBV-C RNA concentrations, ranging from $2.3 \times 10^4$ GE/mL to $2.5 \times 10^8$ GE/mL. These data indicate that the range of GBV-C RNA concentrations in patient plasma varies more widely than either HIV or HCV (Tillmann, et al. 2001). The relationship between GBV-C RNA concentration and HIV replication requires further study.

Serial passage of culture supernatant fluids into donor PBMCs appeared to result in prolongation of GBV-C replication in PBMCs (FIG. 30). Improved replication of GBV-C passaged from culture supernatant fluids into donor PBMCs may represent selection of viral quasispecies more adapted for in vitro replication. Consistent with this, distinct GBV-C quasispecies was isolated in culture supernatants from patient 8 that was not identified in patient plasma prior to culture (FIG. 31), as noted by others (Fogeda, et al. 2000). Studies are underway to further adapt GBV-C to growth in cell culture systems.

GBV-C from patient 12 consistently demonstrated prolonged replication in culture. This isolate persisted in PBMC culture longer than GBV-C from an HIV negative patient, and when compared with our previously described infectious clone. The full-length sequence of the polyprotein coding region of this isolate (AY196904) revealed 97.6% homology with the predicted polyprotein consensus sequences of 20 other full-length GBV-C genomes in GenBank. Sixteen unique amino acid substitutions were found, clustered in the key replication nonstructural proteins NS3, NS5A, and NS5B (FIG. 34A). This GBV-C isolate contained amino acid substitutions in both NS5A and NS5B coding regions similar to changes identified in HCV NS5A and NS5B previously found to be involved in interferon sensitivity and enhanced RNA replication (Blight, et al. 2000; Gale et al. 1998; Krieger, et al. 2001). Thus, amino acid substitutions in key GBV-C proteins may play critical roles in viral replication and host immune evasion.

In summary, GBV-C in the plasma of individuals with HIV co-infection demonstrated different replication phenotypes in PBMC-based cultures in vitro. No improvement in GBV-C replication was noted when cultures were supplemented with donor PBMCs, and GBV-C replication was decreased when IL-2 and PHA were added to PBMC cultures. Persistence of GBV-C replication in PBMCs was not correlated with clinical features of the source patient, including plasma GBV-C RNA concentration or the presence of E2 antibody. Specific nucleotide sequence mutations were identified following two weeks in culture in one isolate, suggesting that specific GBV-C nucleotide polymorphisms may influence GBV-C in vitro replication. The full-length polyprotein sequence of a GBV-C isolate that consistently demonstrated prolonged replication in culture also contained unique amino acid substitutions in non-structural proteins involved in viral replication and evasion of the host immune response.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

U.S. Pat. No. 3,949,064, issued Apr. 6, 1976
U.S. Pat. No. 4,174,384, issued Nov. 13, 1979
U.S. Pat. No. 4,554,101, issued Nov. 19, 1985
U.S. Pat. No. 4,683,195, issued Jul. 28, 1987
U.S. Pat. No. 4,683,202, issued Jul. 28, 1987
U.S. Pat. No. 4,690,915, issued Sep. 1, 1987
U.S. Pat. No. 4,800,159, issued Jan. 24, 1989
U.S. Pat. No. 4,879,236, issued Nov. 7, 1989
U.S. Pat. No. 4,883,750, issued Nov. 28, 1989
U.S. Pat. No. 4,946,773, issued Aug. 7, 1990
U.S. Pat. No. 5,187,260, issued Feb. 16, 1993
U.S. Pat. No. 5,199,942, issued Apr. 6, 1993
U.S. Pat. No. 5,279,721, issued Jan. 18, 1994
U.S. Pat. No. 5,354,855, issued Oct. 11, 1994
U.S. Pat. No. 5,359,046, issued Oct. 25, 1994
U.S. Pat. No. 5,620,896, issued Apr. 15, 1997
U.S. Pat. No. 5,650,298, issued Jul. 22, 1997
U.S. Pat. No. 5,840,873, issued Nov. 24, 1998
U.S. Pat. No. 5,843,640, issued Dec. 1, 1998
U.S. Pat. No. 5,843,650, issued Dec. 1, 1998
U.S. Pat. No. 5,843,651, issued Dec. 1, 1998
U.S. Pat. No. 5,843,663, issued Dec. 1, 1998
U.S. Pat. No. 5,846,708, issued Dec. 8, 1998
U.S. Pat. No. 5,846,709, issued Dec. 8, 1998
U.S. Pat. No. 5,846,717, issued Dec. 8, 1998
U.S. Pat. No. 5,846,726, issued Dec. 8, 1998
U.S. Pat. No. 5,846,729, issued Dec. 8, 1998
U.S. Pat. No. 5,846,783, issued Dec. 8, 1998
U.S. Pat. No. 5,849,481, issued Dec. 15, 1998
U.S. Pat. No. 5,849,483, issued Dec. 15, 1998
U.S. Pat. No. 5,849,486, issued Dec. 15, 1998
U.S. Pat. No. 5,849,487, issued Dec. 15, 1998
U.S. Pat. No. 5,849,497, issued Dec. 15, 1998
U.S. Pat. No. 5,849,546, issued Dec. 15, 1998
U.S. Pat. No. 5,849,547, issued Dec. 15, 1998
U.S. Pat. No. 5,851,770, issued Dec. 22, 1998
U.S. Pat. No. 5,851,772, issued Dec. 22, 1988
U.S. Pat. No. 5,853,990, issued Dec. 29, 1998
U.S. Pat. No. 5,853,992, issued Dec. 29, 1998
U.S. Pat. No. 5,853,993, issued Dec. 29, 1998
U.S. Pat. No. 5,856,092, issued Jan. 5, 1999
U.S. Pat. No. 5,858,652, issued Jan. 12, 1999
U.S. Pat. No. 5,861,244, issued Jan. 19, 1999
U.S. Pat. No. 5,863,732, issued Jan. 26, 1999
U.S. Pat. No. 5,863,753, issued Jan. 26, 1999
U.S. Pat. No. 5,866,331, issued Feb. 2, 1999
U.S. Pat. No. 5,866,336, issued Feb. 2, 1999
U.S. Pat. No. 5,866,337, issued Feb. 2, 1999
U.S. Pat. No. 5,866,366, issued Feb. 2, 1999
U.S. Pat. No. 5,871,986, issued Feb. 16, 1999
U.S. Pat. No. 5,874,563, issued Feb. 23, 1999
U.S. Pat. No. 5,882,864, issued Mar. 16, 1999
U.S. Pat. No. 5,900,481, issued May 4, 1999
U.S. Pat. No. 5,905,024, issued May 18, 1999
U.S. Pat. No. 5,910,407, issued Jun. 8, 1999
U.S. Pat. No. 5,912,124, issued Jun. 15, 1999
U.S. Pat. No. 5,912,145, issued Jun. 15, 1999
U.S. Pat. No. 5,912,148, issued Jun. 15, 1999
U.S. Pat. No. 5,916,776, issued Jun. 29, 1999
U.S. Pat. No. 5,916,779, issued Jun. 29, 1999
U.S. Pat. No. 5,919,626, issued Jul. 6, 1999
U.S. Pat. No. 5,919,630, issued Jul. 6, 1999
U.S. Pat. No. 5,922,574, issued Jul. 13, 1999
U.S. Pat. No. 5,925,517, issued Jul. 20, 1999
U.S. Pat. No. 5,925,525, issued Jul. 20, 1999
U.S. Pat. No. 5,925,565, issued Jul. 20, 1999
U.S. Pat. No. 5,928,862, issued Jul. 27, 1999
U.S. Pat. No. 5,928,869, issued Jul. 27, 1999
U.S. Pat. No. 5,928,870, issued, Jul. 27, 1999
U.S. Pat. No. 5,928,905, issued Jul. 27, 1999
U.S. Pat. No. 5,928,906, issued Jul. 27, 1999
U.S. Pat. No. 5,929,227, issued Jul. 27, 1999
U.S. Pat. No. 5,932,413, issued Aug. 3, 1999
U.S. Pat. No. 5,932,451, issued Aug. 3, 1999
U.S. Pat. No. 5,935,791, issued Aug. 10, 1999
U.S. Pat. No. 5,935,819, issued Aug. 10, 1999

U.S. Pat. No. 5,935,825, issued Aug. 10, 1999
U.S. Pat. No. 5,939,291, issued Aug. 17, 1999
U.S. Pat. No. 5,942,391, issued Aug. 24, 1999
U.S. Pat. No. 5,958,895, issued Sep. 28, 1999
U.S. Pat. No. 6,004,799, issued Dec. 21, 1999
European Application No. 0273085
European Application No. 320 308
European Application No. 329 822
GB Application No. 2 202 328
PCT Application No. PCT/US87/00880
PCT Application No. PCT/US89/01025
PCT Application WO 88/10315
PCT Application WO 89/06700
PCT Application WO 90/07641
Agnello et al., *PNAS*, 96:12766-12771, 1999.
Akiyoshi et al., *Am. J. Gastroenterol.*, 94:1627-1631, 1999.
Aksentijevich et al., *Hum. Gene Ther.*, 7(9):1111-22, 1996.
Almendro, et al., *J. Immunol.*, 157(12):5411-21, 1996.
Alter et al., *N. Engl. J. Med.*, 336:741-746. 1997a.
Alter et al., *N. Engl. J. Med.*, 336:747-754. 1997b.
Alter et al., *Transfusion*, 37:569-572, 1997c.
Angel et al., *Cell*, 49:729, 1987b.
Angel et al., *Mol. Cell. Biol.*, 7:2256, 1987a.
Arap et al., *Cancer Res.*, 55:1351-1354, 1995.
Asada et al., *J. Virol.* 73:4019-4028, 1999.
Atchison and Perry, *Cell*, 46:253, 1986.
Atchison and Perry, *Cell*, 48:121, 1987.
Ausubel et al., *Current Protocols in Molecular Biology*, Greene Publishing Associates and Wiley Interscience, N.Y., 1989.
Baichwal and Sugden, In: *Gene Transfer*, Kucherlapati R, ed., New York, Plenum Press, pp. 117-148, 1986.
Banerji et al., *Cell*, 35:729, 1983.
Bao et al., *Hum. Gene Ther.*, 7:355-365, 1996.
Bass et al., *Cancer Gene Ther.*, 2:97-104, 1995.
Beard et al., *Hepatology*, 30:316-324, 1999.
Bedzyk et al., *J. Biol. Chem.*, 265:18615, 1990
Benvenisty and Neshif, *Proc. Nat. Acad. Sci. USA*, 83:9551-9555, 1986.
Berkhout et al., *Cell*, 59:273, 1989.
Birkenmeyer et al., *J. Med. Virol.*, 56:44-51, 1998.
Blanar et al., *EMBO J.*, 8:1139, 1989.
Blight et al., *Science*, 290:1972-1974, 2000.
Bodine and Ley, *EMBO J.*, 6:2997, 1987.
Boshart et al., *Cell*, 41:521, 1985.
Bosze et al., *EMBO J.*, 5:1615, 1986.
Braddock et al., *Cell*, 58:269, 1989.
Bukh et al., *Virol.*, 262:470-478, 1999.
Bukh et al., *J. Inf. Dis.*, 177:855-862, 1998.
Bulla and Siddiqui, *J. Virol.*, 62:1437, 1986.
Burbage et al., *Leuk Res*, 21(7):681-690, 1997.
Burger et al., *Antimicrob Agents Chemother.*, 37(7):1426-31, 1993.
Bussemakers et al., *Cancer Res.*, 52:2916-2922, 1992.
Caldas et al., *Nat. Genet.*, 8:27-32, 1994.
Campbell and Villarreal, *Mol. Cell. Biol.*, 8:1993, 1988.
Campere and Tilghman, *Genes and Dev.*, 3:537, 1989.
Campo et al., *Nature*, 303:77, 1983.
Capaldi et al., *Biochem Biophys. Res. Comm.*, 76:425, 1977.
Carbonell et al., *FEMS Microbiol. Lett.*, 177(1):75-82, 1999.
Casey et al., *Oncogene*, 6:1791-1797, 1991.
Celander and Haseltine, *J. Virology*, 61:269, 1987.
Celander et al., *J. Virology*, 62:1314, 1988.
Chandler et al., *Cell*, 33:489, 1983.
Chandler et al., *Proc Natl. Acad. Sci. USA*, 94(8):3569-601, 1997.
Chang et al., *Hepatology*, 14: 134A, 1991.
Chang et al., *Mol. Cell. Biol.*, 9:2153, 1989.
Chatterjee et al., *Proc. Nat'l Acad. Sci. USA.*, 86:9114, 1989.
Chaudhary et al., *Proc. Nat'l Acad. Sci.*, 87:9491, 1990
Chen and Okayama, *Mol. Cell Biol.*, 7:2745-2752, 1987.
Cheng et al., *Cancer Res.*, 54:5547-5551, 1994.
Cheung et al., *Arch Biochem. Biophys.*, 305(2):563-9, 1993.
Chol et al., *Cell*, 53:519, 1988.
Cocea, *Biotechniques*, 23(5):814-6, 1997.
Coffin, In: *Virology*, ed., New York: Raven Press, pp. 1437-1500, 1990.
Cohen, Hirschhorn, Horowitz, Rubinstein, Polmar, Hong. and Martin, Jr., *Proc. Nat'l Acad. Sci. USA* 75, 472-476, 1978.
Cohen et al., *J. Virol.*, 61:3035-3039, 1987.
Cook et al., *J. Invest. Med.*, 45:265-271, 1997.
Costa et al., *Mol. Cell. Biol.*, 8:81, 1988.
Coupar et al., *Gene*, 68:1-10, 1988.
Cripe et al., *EMBO J.*, 6:3745, 1987.
Culotta and Hamer, *Mol. Cell. Biol.*, 9:1376, 1989.
Dandolo et al., *J. Virology*, 47:55, 1983.
Dawson et al., *J. Med. Virol.* 50:97-103, 1996.
Dawson et al., *J. Med. Virol.*, 50:97-103. 1996.
de Martino et al., *J. Infect. Dis.*, 178:862-865, 1998.
De Villiers et al., *Nature*, 312:242, 1984.
Deacon et al., *Science* 270:988-991, 1995.
Deschamps et al., *Science*, 230:1174, 1985.
Dickens et al., *Hepatology*, 25:1285-1286. 1997.
Dong et al., *Hum. Gene Ther.*, 7:319-331, 1996.
Dubensky et al., *Proc. Nat'l Acad. Sci. USA*, 81:7529-7533, 1984.
Easterbrook, *J. Infect.* 38:71-73, 1999.
Edbrooke et al., *Mol. Cell. Biol.*, 9:1908, 1989.
Edelman and Crossin, *Annu. Rev. Biochem.*, 60:155-190, 1991.
Edelman, *Annu. Rev. Biochem.*, 54:135-169, 1985.
Edlund et al., *Science*, 230:912, 1985.
Elvander et al., *Acta. Vet. Scand.* 39:251-264, 1998.
Emerson et al., *J. Virol.*, 66:6649-6654, 1992.
Fechheimer et al., *Proc. Nat'l Acad. Sci. USA*, 84:8463-8467, 1987.
Felgner et al., *Proc. Nat'l. Acad. Sci. USA*, 84(21):7413-7, 1987.
Feng and Holland, *Nature*, 334:6178, 1988.
Ferkol et al., *FASEB J.*, 7:1081-1091, 1993.
Feucht et al., *Hepatology*, 26:491-494, 1997.
Firak and Subramanian, *Mol. Cell. Biol.*, 6:3667, 1986.
Fogeda et al., *J. Virol.*, 73:4052-4061, 1999.
Forster and Symons, "Self-cleavage of plus and minus RNAs of a virusoid and a structural model for the active sites," *Cell*, 49:211-220, 1987.
Fraley et al., *Proc. Nat'l Acad. Sci. USA*, 76:3348-3352, 1979.
Freshney, R. I. "Animal Cell Culture: a Practical Approach", Second Edition, Oxford/New York, IRL Press, Oxford University Press, 1992.
Friedmann, *Science*, 244:1275-1281, 1989.
Frixen et al., *J. Cell Biol.*, 113:173-185, 1991.
Frohman, In: *PCR Protocols: A Guide To Methods And Applications*, Academic Press, N.Y., 1990.
Fujisawa et al., *J. Gastro. Hepatol.*, 15:632-639, 2000.
Fujita et al., *Cell*, 49:357, 1987.
Gabizon et al., *Cancer Res.*, 50(19):6371-8, 1990.
Gale, Jr. et al., *Mol. Cell. Biol.* 18:5208-5218, 1998.
George et al., *M. Acquir. Immun. Defic. Synd.*, 31:154-162, 2002a.
George et al., *Curr. Infect. Dis. Rep.*, 4:550-558, 2002b.
Gerlach et al., *Nature* (London), 328:802-805, 1987.

Ghosh and Bachhawat, In: Liver diseases, targeted diagnosis and therapy using specific receptors and ligands, (Wu G, Wu C ed.), New York: Marcel Dekker, pp. 87-104, 1991.
Giancotti and Ruoslahti, Cell, 60:849-859, 1990.
Gilles et al., Cell, 33:717, 1983.
Gloss et al., EMBO J., 6:3735, 1987.
Godbout et al., Mol. Cell. Biol., 8:1169, 1988.
Gomez-Foix et al., J. Biol. Chem. 267:25129-25134, 1992.
Gonzalez-Zulueta et al., Cancer Research, 55(20):4531-4535, 1995.
Goodbourn and Maniatis, Proc. Nat'l Acad. Sci. USA, 85:1447, 1988.
Goodman et al., Blood, 84:1492-1500, 1994.
Gopal, Mol. Cell Biol., 5:1188-1190, 1985.
Gossen et al., Proc. Nat'l Acad. Sci. USA, 89:5547-5551, 1992.
Gossen et al., Science, 268:1766-69, 1995.
Graham and Prevec, Biotechnology, 20:363-390, 1992.
Graham and Van Der Eb, Virology, 52:456-467, 1973.
Greene et al., Immunology Today, 10:272, 1989.
Grosschedl and Baltimore, Cell, 41:885, 1985.
Grunhaus and Horwitz, Seminar in Virology, 3:237-252, 1992.
Gutierrez et al., J. Med. Virol., 53:167-173. 1997.
Haslinger and Karin, Proc. Nat'l Acad. Sci. USA., 82:8572, 1985.
Hauber and Cullen, J. Virology, 62:673, 1988.
Hen et al., Nature, 321:249, 1986.
Hensel et al., Lymphokine Res., 8:347, 1989.
Heringlake et al., J. Infect. Dis., 177:1723-26, 1998.
Herman et al., Cancer Research, 55(20):4525-4530, 1995.
Hermonat and Muzyczka, J. Cell Biol., 101:1094-1099, 1985.
Herr and Clarke, Cell, 45:461, 1986.
Herz et al., Proc. Natl. Acad. Sci. USA, 90:2812-2816, 1993.
Hirochika et al., J. Virol., 61:2599, 1987.
Hirsch et al., Mol. Cell. Biol., 10:1959, 1990.
Holbrook et al., Virology, 157:211, 1987.
Hollstein et al., Science, 253:49-53, 1991.
Hong et al., Virology, 256:36-44, 1999.
Horfnagle, Hepatology, 26:155-205, 1997.
Horlick and Benfield, Mol. Cell. Biol., 9:2396, 1989.
Horwich et al., J. Virol., 64:642-650, 1990.
Huang et al., Cell, 27:245, 1981.
Huang et al., Nature Med. 2:1240-1243, 1996.
Hussussian et al., Nature Genetics, 15-21, 1994.
Hwang et al., Mol. Cell. Biol., 10:585, 1990.
Imagawa et al., Cell, 51:251, 1987.
Imbra and Karin, Nature, 323:555, 1986.
Imler et al., Mol. Cell. Biol., 7:2558, 1987.
Imperiale and Nevins, Mol. Cell. Biol., 4:875, 1984.
Jakobovits et al., Mol. Cell. Biol., 8:2555, 1988.
Jameel and Siddiqui, Mol. Cell. Biol., 6:710, 1986.
Jaynes et al., Mol. Cell. Biol., 8:62, 1988.
Johnson et al., Mol. Cell. Biol., 9:3393, 1989.
Joyce, Nature, 338:217-244, 1989.
Kadesch and Berg, Mol. Cell. Biol., 6:2593, 1986.
Kamb et al., Nature Genetics, 8:22-26, 1994.
Kamb et al., Science, 2674:436-440, 1994.
Kaneda et al., Science, 243:375-378, 1989.
Karin et al., Mol. Cell. Biol., 7:606, 1987.
Katinka et al., Cell, 20:393, 1980.
Katinka et al., Nature, 290:720, 1981.
Kato et al., J. Biol. Chem., 266:3361-3364, 1991.
Kato et al., J. Med. Viral., 57:376-382, 1999.
Kawamoto et al., Mol. Cell. Biol., 8:267, 1988.
Kiledjian et al., Mol. Cell. Biol., 8:145, 1988.
Kiyosawa et al., Intervirology, 42:185-195, 1999.
Klamut et al., Mol. Cell. Biol., 10:193, 1990.
Klein et al., Nature, 327:70-73, 1987.
Kobayashi et al., J. Med. Virol., 57:114-121, 1999.
Koch et al., Mol. Cell. Biol., 9:303, 1989.
Kolykhalov et al., Science, 277:570-574, 1997.
Kolykhalov et al., J. Virol., 70:3363-3371, 1996.
Kraus et al., FEBS Lett., 428(3):165-70, 1998.
Krieger et al., J. Viral., 75:4614-4624, 2001.
Kriegler and Botchan, In: Eukaryotic Viral Vectors, Y. Gluzman, ed., Cold Spring Harbor: Cold Spring Harbor Laboratory, NY, 1982.
Kriegler and Botchan, Mol. Cell. Biol., 3:325, 1983.
Kriegler et al., Cell, 38:483, 1984a.
Kriegler et al., Cell, 53:45, 1988.
Kriegler et al., In: Cancer Cells 2/Oncogenes and Viral Genes, Van de Woude et al. eds, Cold Spring Harbor, Cold Spring Harbor Laboratory, 1984b.
Kriegler et al., In: Gene Expression, D. Hamer and M. Rosenberg, eds., New York: Alan R. Liss, 1983.
Kuhl et al., Cell, 50:1057, 1987.
Kunz et al., Nuc. Acids Res., 17:1121, 1989.
Kwoh et al., Proc. Natl. Acad. Sci. USA, 86(4): 1173-1177, 1989.
Kyte and Doolittle, J. Mol. Biol., 157:105-132, 1982.
Lareyre, et al., J. Bio. Chem., 274(12):8282-90, 1999.
Larsen et al., Proc. Nat'l Acad. Sci. USA., 83:8283, 1986.
Laskus et al., J. Virol., 72:3072-3075. 1998.
Laspia et al., Cell, 59:283, 1989.
Latimer et al., Mol. Cell. Biol., 10:760, 1990.
Le Gal La Salle et al., Science, 259:988-990, 1993.
Leary et al., J. Med. Virol., 48:60-67. 1996.
Lee et al., DNA Cell Biol., 16(11):1267-75, 1997.
Lee et al., Mol. Endocrinol., 2: 404-411, 1988.
Lee et al., Nature, 294:228, 1981.
Lefrère et al., J. Infect. Dis. 179:783-789, 1999.
Levenson et al., Hum. Gene Ther., 9(8):1233-6, 1998.
Levinson et al., Nature, 295:79, 1982.
Levrero et al., Gene, 101: 195-202, 1991.
Lin and Guidotti, J. Biol. Chem., 264:14408-14414, 1989.
Lin et al., Mol. Cell. Biol., 10:850, 1990.
Linnen et al., Science, 271:505-508. 1996.
Lohmann et al., J. Virol., 75:1437-1449, 2001.
Luria et al., EMBO J., 6:3307, 1987.
Lusky and Botchan, Proc. Nat'l Acad. Sci. USA., 83:3609, 1986.
Macejak et al., Nature, 353:90-94, 1991.
Majors and Varmus, Proc. Nat'l Acad. Sci. USA., 80:5866, 1983.
Mann et al., Cell, 33:153-159, 1983.
Massuda et al., Proc Natl Acad Sci USA, 94(26):14701-14706, 1997.
Matsura et al., Brit. J. Cancer, 66:1122-1130, 1992.
Matzura et al., Comp. Appl. Biosci., 12:247-249, 1996.
McNeall et al., Gene, 76:81, 1989.
Melvin et al., J. Virol. Methods, 71:147-157, 2000.
Merlo et al., Nat. Med., 1(7):686-92, 1995.
Michel et al., J. Mol. Biol., 216:585-610, 1990.
Miksicek et al., Cell, 46:203, 1986.
Mordacq and Linzer, Genes and Dev., 3:760, 1989.
Moreau et al., Nucl. Acids Res., 9:6047, 1981.
Mori et al., Cancer Res., 54:3396-3397, 1994.
Muesing et al., Cell, 48:691, 1987.
Nagayama et al., J. Med. Virol. 52:156-160, 1997.
Naito and Abe, J. Virol. Methods, 91:3-9, 2001.
Nerurkar et al., J. Med. Virol., 56:123-127, 1998.

Ng et al., *Nuc. Acids Res.*, 17:601, 1989.
Nicolas and Rubenstein, In: *Vectors: A survey of molecular cloning vectors and their uses*, Rodriguez and Denhardt (eds.), Stoneham: Butterworth, pp. 493-513, 1988.
Nicolau and Sene, *Biochim. Biophys. Acta*, 721:185-190, 1982.
Nicolau et al., *Methods Enzymol.*, 149:157-176, 1987.
Nobri et al., *Nature*, 368:753-756, 1995.
Nomoto et al., *Gene*, 236(2):259-271, 1999.
Obrink, *BioEssays*, 13:227-233, 1991.
Odin and Obrink, *Exp. Cell Res.*, 171:1-15, 1987.
Ohara et al., *Proc. Natl. Acad. Sci. USA*, 86(15):5673-5677, 1989a.
Okamoto et al., *Proc. Nat'l Acad. Sci. USA*, 91:11045-11049, 1994.
Okamoto et al., *J. Gen. Virol.*, 78:737-745. 1997.
Ondek et al., *EMBO J.*, 6:1017, 1987.
Orlow et al., *Cancer Res.*, 54:2848-2851, 1994.
Ornitz et al., *Mol. Cell. Biol.*, 7:3466, 1987.
Palmiter et al., *Nature*, 300:611, 1982.
Paskind et al., *Virology*, 67:242-248, 1975.
Pech et al., *Mol. Cell. Biol.*, 9:396, 1989.
Pelletier et al., *Nature*, 334(6180):320-325, 1988.
Perales et al., *Proc. Nat'l Acad. Sci.* 91:4086-4090, 1994.
Perez-Stable and Constantini, *Mol. Cell. Biol.*, 10:1116, 1990.
Pessoa et al., *Hepatol.*, 27:877-880, 1998.
Philip et al., *J. Biol. Chem.*, 268(22):16087-90, 1993.
Picard and Schaffner, *Nature*, 307:83, 1984.
Pinkert et al., *Genes and Dev.*, 1:268, 1987.
Pinto et al., *J. Virol.* 74:4505-4511, 2000.
Ponta et al., *Proc. Nat'l Acad. Sci. USA.*, 82:1020, 1985.
Porton et al., *Mol. Cell. Biol.*, 10:1076, 1990.
Potter et al., *Proc. Nat'l Acad. Sci. USA*, 81:7161-7165, 1984.
Queen and Baltimore, *Cell*, 35:741, 1983.
Quinn et al., *Mol. Cell. Biol.*, 9:4713, 1989.
Ragot et al., *Nature* 361:647-650, 1993.
Redondo et al., *Science*, 247:1225, 1990.
Reed and Rice, *J. Biol. Chem.*, 274:28011-28018, 1999.
Reed and Rice, *J. Virol.*, 71:7187-7197, 1997.
Reinhold-Hurek et al., *Nature*, 357:173-176, 1992.
Reisman and Rotter, *Mol. Cell. Biol.*, 9:3571, 1989.
Resendez Jr. et al., *Mol. Cell. Biol.*, 8:4579, 1988.
Rich et al., *Hum. Gene Ther.*, 4:461-476, 1993.
Ridgeway, In: *Vectors: A survey of molecular cloning vectors and their uses*, Rodriguez R L, Denhardt D T, ed., Stoneham:Butterworth, pp. 467-492, 1988.
Rinaldo, Jr. et al., *Infect. Immun.* 14:660-666, 1976.
Rippe et al., *Mol. Cell Biol.*, 10:689-695, 1990.
Rittling et al., *Nuc. Acids Res.*, 17:1619, 1989.
Robertson et al., *Arch. Virol.*, 143:2493-2503, 1998.
Rosen et al., *Cell*, 41:813, 1988.
Rosenfeld et al., *Cell*, 68:143-155, 1992.
Rosenfeld et al., *Science*, 252:431-434, 1991.
Roux et al., *Proc. Nat'l Acad. Sci. USA*, 86:9079-9083, 1989.
Rowland-Jones, *J. Infect.* 38:67-70, 1999.
Sabin et al., *J. Acquir. Immune Defic. Syndr.* 19:546-547, 1998.
Sakai et al., *Genes and Dev.*, 2:1144, 1988.
Sambrook, Fritsch, Maniatis, In: *Molecular Cloning: A Laboratory Manual*, Vol. 1, Cold Spring Harbor Laboratory Press, Cold Spring Harbor, N.Y., Ch. 7,7,19-17.29, 1989.
Sarver et al., *Science*, 247:1222-1225, 1990.
Satake et al., *J. Virology*, 62:970, 1988.
Scanlon et al., *Proc. Nat'l Acad. Sci. USA*, 88:10591-10595, 1991.
Schaffner et al., *J. Mol. Biol.*, 201:81, 1988.
Schmidt et al., *J. Med. Virol.*, 47:153-160. 1995.
Schmidt et al., *J. Infect. Dis.*, 176:27-33, 1997a.
Schmidt et al., *J. Infect. Dis.*, 176:20-26, 2997b.
Searle et al., *Mol. Cell. Biol.*, 5:1480, 1985.
Seipp et al., *J. Hepatol.*, 30:570-579, 1999.
Serrano et al., *Nature*, 366:704-707, 1993.
Serrano et al., *Science*, 267:249-252, 1995.
Sharp and Marciniak, *Cell*, 59:229, 1989.
Shaul and Ben-Levy, *EMBO J.*, 6:1913, 1987.
Sherman et al., *Mol. Cell. Biol.*, 9:50, 1989.
Shimizu, *J. Virol.*, 73:8411-8414, 1999.
Simons et al., *J. Virol.*, 70:6126-6135. 1996.
Simons et al., *Nature Med.*, 1:564-569, 1995.
Simons et al., *Proc. Natl. Acad. Sci. USA* 92:34013405.
Sleigh and Lockett, *J. EMBO*, 4:3831, 1985.
Solodin et al., *Biochemistry*, 34(41): 13537-44, 1995.
Spalholz et al., *Cell*, 42:183, 1985.
Spandau and Lee, *J. Virology*, 62:427, 1988.
Spandidos and Wilkie, *EMBO J.*, 2:1193, 1983.
Stapleton et al., *J. Clin. Microbiol.*, 37:484-489, 1999.
Stephens and Hentschel, *Biochem. J.*, 248:1, 1987.
Stratford-Perricaudet and Perricaudet, "Gene transfer into animals: the promise of adenovirus," p. 51-61, In: *Human Gene Transfer*, Eds, O. Cohen-Haguenauer and M. Boiron, Editions John Libbey Eurotext, France, 1991.
Stratford-Perricaudet et al., *Hum. Gene Ther.*, 1:241-256, 1990.
Stuart et al., *Nature*, 317:828, 1985.
Sullivan and Peterlin, *Mol. Cell. Biol.*, 7:3315, 1987.
Swartzendruber and Lehman, *J. Cell. Physiology*, 85:179, 1975.
Tacke et al., *Hepatol.*, 26:1626-1633, 1997.
Takahashi et al., *Cancer Res.*, 52:734-736, 1992.
Takebe et al., *Mol. Cell. Biol.*, 8:466, 1988.
Tanaka et al., *J. Hepatol.*, 27:1110-1112, 1997.
Tavernier et al., *Nature*, 301:634, 1983.
Taylor and Kingston, *Mol. Cell. Biol.*, 10:165, 1990a.
Taylor and Kingston, *Mol. Cell. Biol.*, 10:176, 1990b.
Taylor et al., *J. Biol. Chem.*, 264:15160, 1989.
Taylor et al., *Science* 285:107-110, 1999.
Temin, In: *Gene Transfer*, Kucherlapati (ed.), New York: Plenum Press, pp. 149-188, 1986.
Templeton et al., *Nat. Biotechnol.*, 15(7):647-52, 1997.
Thierry et al., *Proc. Natl. Acad. Sci. USA*, 92(21):9742-6, 1995.
Thiesen et al., *J. Virology*, 62:614, 1988.
Thomas et al. *J. Infect. Dis.* 177:539-542. 1998.
Tillmann et al., *N. Engl. J. Med.*, 345:715-724, 2001.
Toyoda et al., *J. Acquir. Immune Defic. Syndr.* 17:209-213, 1998.
Toyoda et al., *J. Med. Virol.* 60:34-38, 2000.
Treisman, *Cell*, 42:889, 1985.
Tronche et al., *Mol. Cell. Biol.*, 9:4759, 1989.
Trudel and Constantini, *Genes and Dev.*, 6:954, 1987.
Tsukamoto et al., *Nat. Genet.*, 9(3):243-8, 1995.
Tur-Kaspa et al., *Mol. Cell Biol.*, 6:716-718, 1986.
Tyndall et al., *Nuc. Acids. Res.*, 9:6231, 1981.
Umbas et al., *Cancer Res.*, 52:5104-5109, 1992.
Vannice and Levinson, *J. Virology*, 62:1305, 1988.
Vasseur et al., *Proc. Nat'l Acad. Sci. USA.*, 77:1068, 1980.
Wagner et al., *Proc. Nat'l Acad. Sci.* 87(9):3410-3414, 1990.
Walker et al. *Proc. Natl. Acad. Sci. USA*, 89(1):392-396, 1992.
Wang and Calame, *Cell*, 47:241, 1986.

Weber et al., *Cell*, 36:983, 1984.
Winoto and Baltimore, *Cell*, 59:649, 1989.
Wolf et al., *Comput. Appl. Biosci.*, 4(1):187-191, 1988.
Wong et al., *Gene*, 10:87-94, 1980.
Wu and Wu, *Adv. Drug Delivery Rev.*, 12:159-167, 1993.
Wu and Wu, *Biochem.*, 27:887-892, 1988.
Wu and Wu, *J. Biol. Chem.*, 262:4429-4432, 1987.
Wu et al., *Biochem. Biophys. Res. Commun.*, 233(1):221-6, 1997.
Wu et al., *J. Med. Virol.*, 52:83-85. 1997.
Wünschmann & Stapleton, *J. Clin. Microbiol.* 38:3055-3060, 2000.
Wünschmann et al., *J. Virol.* 74:10055-10062, 2000.
Xiang et al., *N. Engl. J. Med.*, 345:707-714, 2001.
Xiang et al., *N. Eng., J. Med.*, 345:707-714, 2001.
Xiang et al., *J. Virol.* 74:9125-9133, 2000.
Xiang et al., *J. Viral Hepat.*, 6:S16-S22, 1999.
Xiang et al., *J. Virol.*, 72:2738-2744. 1998.
Yanagi et al., *Proc. Nat'l. Acad. Sci.*, 94:8738-8743, 1997.
Yanagi et al., *Virology*, 244:161-172, 1998.
Yang et al., *Gene Ther.*, 4(9):950-60, 1997.
Yang et al., *Proc. Nat'l Acad. Sci USA*, 87:9568-9572, 1990.
Yeo et al., *Ann. Intern. Med.* 132:959-963, 2000.
Yutzey et al. *Mol. Cell. Biol.*, 9:1397, 1989.
Zelenin et al., *FEBS Lett.*, 280:94-96, 1991.
Zhao-Emonet, et al., *Biochim. Biophys. Acta*, 1442(2-3):109-19, 1998.
Zhu et al., *Science*, 261(5118):209-11, 1993.

All publications, patents and patent applications referred to are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. An isolated and purified nucleic acid molecule encoding an infectious GBV-C, wherein the nucleic acid molecule encodes SEQ ID NO:20, or a variant thereof, wherein said variant is 99% identical to SEQ ID NO:20.

2. The isolated and purified nucleic acid molecule of claim 1, wherein the nucleic acid molecule encodes SEQ ID NO:20.

3. The isolated and purified nucleic acid molecule of claim 1, wherein the nucleic acid is RNA.

4. The isolated and purified nucleic acid molecule of claim 1, wherein the nucleic acid is DNA.

5. The nucleic acid molecule of claim 1, further comprising a heterologous nucleic acid sequence.

6. The nucleic acid molecule of claim 5, wherein the heterologous nucleic acid sequence encodes a polypeptide.

7. The nucleic acid molecule of claim 6, wherein the polypeptide is a mammalian polypeptide.

8. The nucleic acid molecule of claim 1, further comprising a heterologous promoter.

9. A host cell comprising a nucleic acid molecule encoding an infectious GBV-C, wherein the nucleic acid molecule encodes SEQ ID NO:20, or a variant thereof, wherein said variant is 99% identical to SEQ ID NO:20.

10. The host cell of claim 9 comprising a nucleic acid molecule that encodes SEQ ID NO:20.

11. The host cell of claim 10, wherein the cell is a mammalian cell.

12. The host cell of claim 11, wherein the cell is a lymphocyte cell.

13. The host cell of claim 12, wherein the cell is CD4+ lymphocyte cell.

14. An isolated and purified nucleic acid molecule comprising SEQ ID NO:19.

* * * * *